US012636317B2

(12) United States Patent
Saligrama et al.

(10) Patent No.: US 12,636,317 B2
(45) Date of Patent: May 26, 2026

(54) MANIPULATION AND USE OF ANTIGEN-SPECIFIC REGULATORY T CELLS

(71) Applicant: The Board of Trustees of the Leland Stanford Junior University, Stanford, CA (US)

(72) Inventors: Naresha Saligrama, Redwood City, CA (US); Mark M. Davis, Atherton, CA (US); Jing Li, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 309 days.

(21) Appl. No.: 17/630,089

(22) PCT Filed: Aug. 5, 2020

(86) PCT No.: PCT/US2020/045006
§ 371 (c)(1),
(2) Date: Jan. 25, 2022

(87) PCT Pub. No.: WO2021/026233
PCT Pub. Date: Feb. 11, 2021

(65) Prior Publication Data
US 2022/0257657 A1     Aug. 18, 2022

Related U.S. Application Data

(60) Provisional application No. 62/882,810, filed on Aug. 5, 2019.

(51) Int. Cl.
| | |
|---|---|
| *A61K 35/17* | (2025.01) |
| *A61K 40/11* | (2025.01) |
| *A61K 40/22* | (2025.01) |
| *A61K 40/41* | (2025.01) |
| *A61K 40/46* | (2025.01) |
| *A61P 37/02* | (2006.01) |
| *C12N 5/0783* | (2010.01) |

(52) U.S. Cl.
CPC .............. *A61K 35/17* (2013.01); *A61K 40/11* (2025.01); *A61K 40/22* (2025.01); *A61K 40/416* (2025.01); *A61K 40/46* (2025.01); *A61P 37/02* (2018.01); *C12N 5/0637* (2013.01)

(58) Field of Classification Search
None
See application file for complete search history.

(56) References Cited

U.S. PATENT DOCUMENTS

| | | | |
|---|---|---|---|
| 2017/0224732 A1* | 8/2017 | Cantor | A61P 19/02 |
| 2019/0192565 A1* | 6/2019 | Cantor | A61P 35/00 |

FOREIGN PATENT DOCUMENTS

| | | |
|---|---|---|
| JP | 2014502258 | 1/2024 |
| WO | WO2007042573 | 4/2007 |
| WO | WO2012054509 | 4/2012 |
| WO | WO2016196312 | 12/2016 |
| WO | WO2016196912 | 12/2016 |
| WO | WO2018152340 | 8/2018 |

OTHER PUBLICATIONS

Chakraborty et al. (2018) "Providence of the CD25+KIR+CD127+ FOXP3-CD8 Tc ell subset determines the dynamics of tumor immune surveillance," Immunol Cell Bio, vol. 96, No. 10, pp. 1035-1048.

Ortega, et al. "The disease-ameliorating function of autoregulatory CD8 T cells is mediated by targeting of encephalitogenic CD4 T cells in experimental autoimmune encephalomyelitis." *The Journal of Immunology* 191.1 (2013): 117-126.

Menager-Marcq, Ingrid, et al. "CD8+CD28—regulatory T lymphocytes prevent experimental inflammatory bowel disease in mice." *Gastroenterology* 131.6 (2006): 1775-1785.

Brate, et al. "Therapeutic intervention in relapsing autoimmune demyelinating disease through induction of myelin-specific regulatory CD8 T cell responses." *Journal of translational autoimmunity* 2 (2019): 100010.

Zabinska, et al. "CD3+CD8+CD28—T Lymphocytes in Patients, with Lupus Nephritis." *Journal of Immunology Research* (2016), 213, 50-556.

Cunnusamy, et al. "Disease Exacerbation of Multiple Sclerosis is Characterized by Loss of Terminally Differentiated Autoregulatory CD8+ T cells." *NIH Public Access*, (2014): 152(0), 115-126.

Raki, et al. "Tetramer visualization of gut-homing gluten-specific T cells in the peripheral blood of celiac disease patients." *Proceedings of the National Academy of Sciences* 104.8 (2007): 2831-2836.

Li, et al. "Cytotoxic KLRG1 expressing lymphocytes invade portal tracts in primary biliary cholangitis." *Journal of Autoimmunity* 103 (2019): 102293.

Karussis, et al "T Cell Vaccination Benefits Relapsing Progressive Multiple Sclerosis Patients: A Randomized, Double-Blind Clinical Trial." *Research Article* (2012): 7, 12.

(Continued)

*Primary Examiner* — Daniel C Gamett

(74) *Attorney, Agent, or Firm* — Pamela J. Sherwood; Bozicevic, Field & Francis LLP

(57) ABSTRACT

Compositions and methods are provided for isolating, manipulating and using for therapeutic and other purposes, mammalian, MHC Class I restricted, antigen-specific regulatory T cells. The regulatory T cells can be characterized as CD8+ cells that specifically suppress the responses of self-reactive and/or pathogenic CD4+ T cells by cytotoxic mechanisms including, without limitation, perforin, other components of the perforin/granzyme apoptosis pathway, etc. The regulatory T cells are antigen-specific, but are not activated by the same antigen as the self-reactive and/or pathogenic CD4+ T cells. In humans the regulatory T cells express inhibitory KIR proteins, e.g. one or more of KIR2DL2, KIR2DL3, and KIR3DL1.

17 Claims, 50 Drawing Sheets

Specification includes a Sequence Listing.

(56)                    References Cited

OTHER PUBLICATIONS

Crucian, et al. "Alterations in levels of CD28-/CD8+ suppressor cell precursor and CD45RO+/CD4+ memory T lymphocytes in the peripheral blood of multiple sclerosis patients." *Clinical Diagnostic Laboratory Immunology* 2.2 (1995): 249-252.

Zhong, et al. "TGF-β-induced CD8+CD103+ regulatory T cells show potent therapeutic effect on chronic graft-versus-host disease lupus by suppressing B cells." *Frontiers in immunology* 9 (2018): 35.

Kim, et al. "Regulation of self-tolerance by Qa-1-restricted CD8+ regulatory T cells." *Seminars in immunology*. 23.6 (2011): 446-452.

Goods, et al. "Blood handling and leukocyte isolation methods impact the global transcriptome of immune cells." *BMC immunology* 19.1 (2018): 1-12.

Hubbard, et al."[14] Separation of lymphoid cells using immunoadsorbent affinity chromatography." *Methods in enzymology*. 108 (1984): 139-148.

Kurle, et al. "In Vitro Sensitization of T Cells with DC-Associated/Delivered HIV Constructs Can Induce a Polyfunctional CTL Response, Memory T-Cell Response, and Virus Suppression" Viral Immunology 25.1 (2012): 45-54.

Lu et al. (2016) "Suppression of HIV replication by CD8+ regulatory T-cells in elite controllers." *Frontiers in Immunology*, 7, p. 134.

Holderried et al. (2016) "Human CD8+ Treg after Allogeneic Stem-Cell Transplantation." *Blood*, 128(22), p. 2243.

Birnbaum et al. (2014) "Deconstructing the peptide-MHC specificity of T cell recognition." *Cell*, 157(5), p. 1073-1087.

Gee et al. (2017: "Antigen Identification for Orphan T Cell Receptors Expressed on Tumor-Infiltrating Lymphocytes", CELL, 172(3), pp. 549-563.

Kim et al. (2011) "CD8+ T regulatory cells express the Ly49 Class I MHC receptor and are defective in autoimmune prone B6-Yaa mice." *Proceedings of the National Academy of Sciences*, 108(5), pp. 2010-2015.

Saligrama et al. (2019) Opposing T cell responses in experimental autoimmune encephalomyelitis. *Nature*, 572(7770), pp. 481-487.

Li et al. (2022)."KIR+ CD8+ T cells suppress pathogenic T cells and are active in autoimmune diseases and COVID-19". *Science*, 376(6590), p. eabi9591.

Birnbaum et al. (2014) "Deconstructing the peptide-MHC specificity of T cell recognition." *Cell*, 157(5), pp. 1073-1087.

Chakraborty et al. (2018) "Providence of the CD25+ Kir+ CD127—FOXP3—CD8+ T-cell subset determines the dynamics of tumor immune surveillance." Immunology and Cell *Biology*, 96(10), pp. 1035-1048.

Matsumoto et al. (2010) NK cell inhibitory receptors that recognize normal self. *Farumashia*, 46(1), pp. 39-44.

Creticos, (2014) "Advances in synthetic peptide immuno-regulatory epitopes." World Allergy Organization Journal, 7(1): 1-6.

* cited by examiner d e

FACS sorting and single cell paired TCR (α, β, γ, and δ) sequencing on activated CD4+, CD8+, and γδ T cells

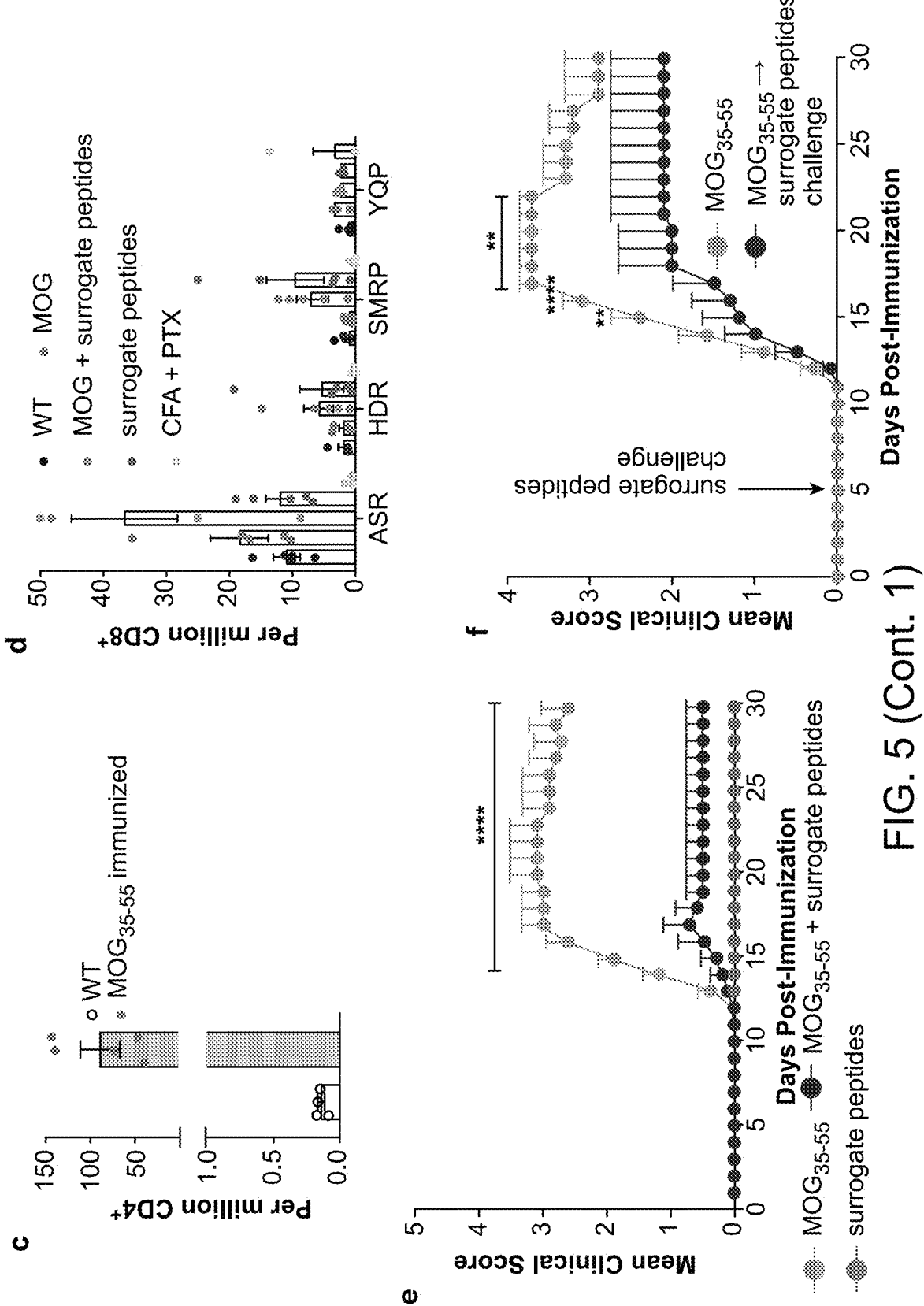
FIG. 5 (Cont. 1)

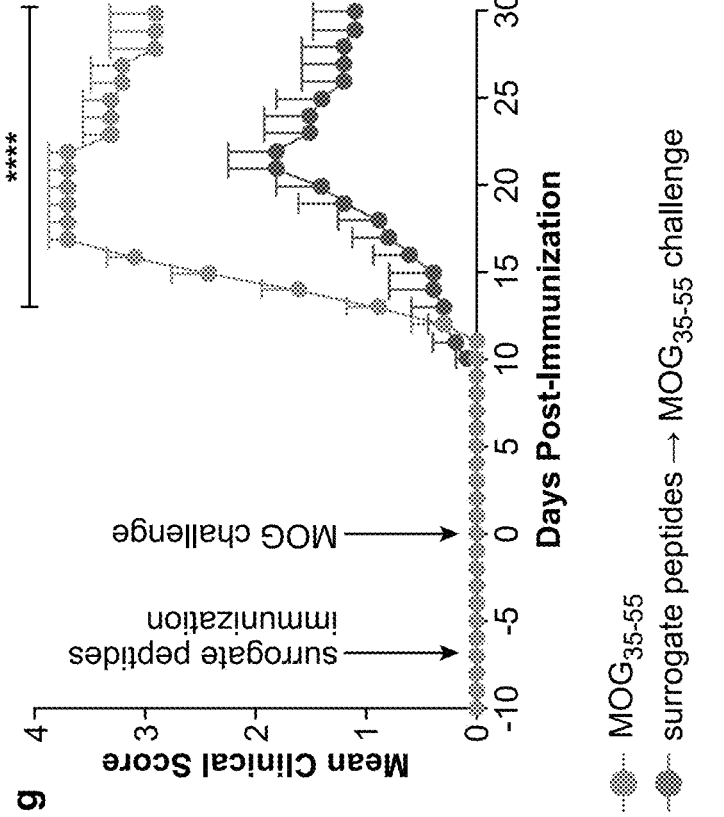
FIG. 5 (Cont. 2)

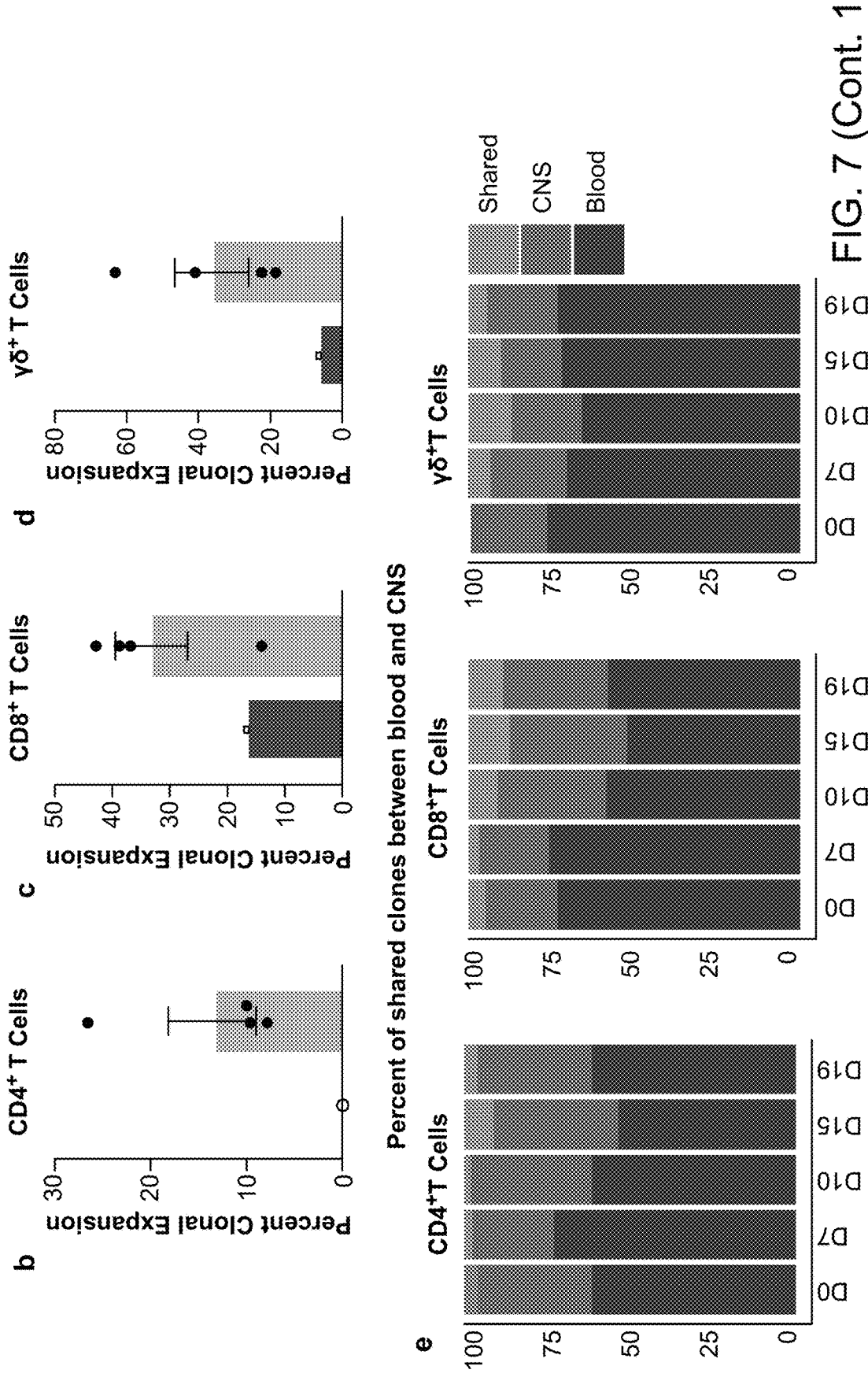
FIG. 7 (Cont. 1)

f

| Blood | Type of nTγδ17 sequences | | | | total nTγδ17 seq | total seq | % of nTγδ17 cells in total γδ T cells |
|---|---|---|---|---|---|---|---|
| PI | Group1 | Group2 | Group3 | Group4 | | | |
| D0 | 0 | 2 | 0 | 5 | 7 | 25 | 28 |
| D7 | 11 | 8 | 16 | 24 | 59 | 379 | 15.6 |
| D10 | 6 | 1 | 1 | 138 | 146 | 365 | 40 |
| D15 | 32 | 1 | 4 | 9 | 46 | 110 | 42 |
| D19 | 1 | 0 | 19 | 9 | 29 | 187 | 15.5 |

| CNS | Type of nTγδ17 sequences | | | | total nTγδ17 seq | total seq | % of nTγδ17 cells in total γδ T cells |
|---|---|---|---|---|---|---|---|
| PI | Group1 | Group2 | Group3 | Group4 | | | |
| D0 | 0 | 0 | 0 | 0 | 0 | 0 | 0 |
| D7 | 16 | 0 | 0 | 5 | 21 | 82 | 25.6 |
| D10 | 3 | 0 | 1 | 73 | 77 | 122 | 63.1 |
| D15 | 65 | 0 | 5 | 29 | 99 | 103 | 95 |
| D19 | 1 | 0 | 0 | 27 | 28 | 53 | 53 | g

| | TCRγ | | TCRδ | |
|---|---|---|---|---|
| Group1 | Vγ6Jγ1 | CACWD-SSGFH | Vδ1Dδ2Jδ2 | CGSD-IGG-SSWDTR |
| Group2 | Vγ4Jγ1 | CSYG-L(Y)-SSGFH | Vδ5Dδ2Jδ1 | CASSGY-IGGIRA-TDKLV |
| Group3 | Vγ4Jγ1 | CSYG-(X)Y-SSGFH | Vδ5Dδ2Jδ1 | CASGY(X)-(I)GGIR(A)-(X)(T)DKLV |
| Group4 | Vγ4Jγ1 | CSYG-(X)Y-SSGFH | Vδ6Dδ2Jδ1 | CALM(ER)(X)-(I)GGIR(A)-(X)(T)DKLV |

FIG. 7 (Cont. 2)

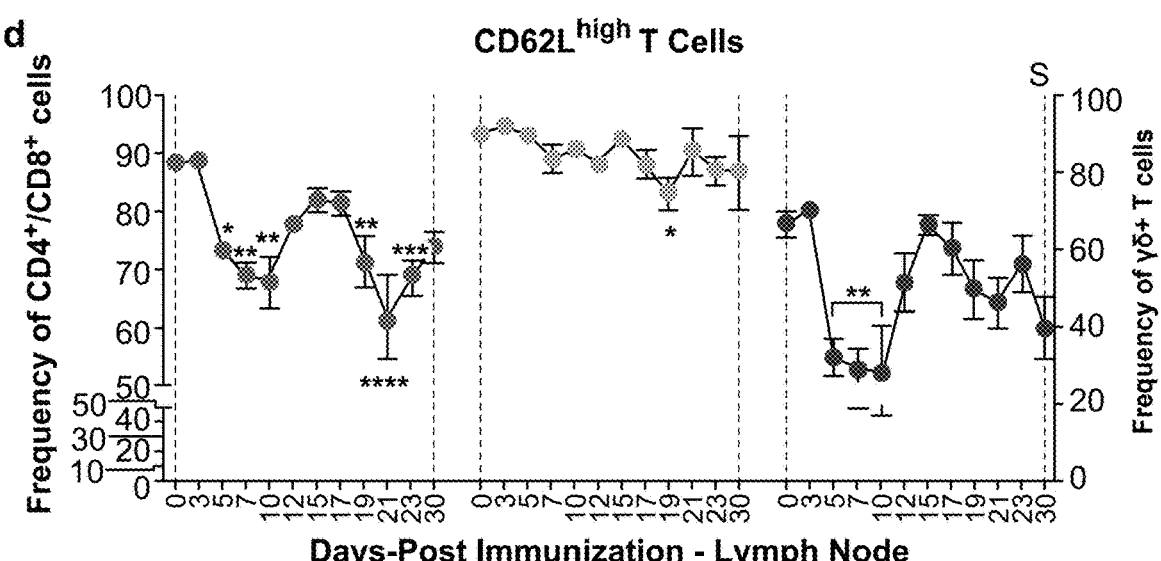
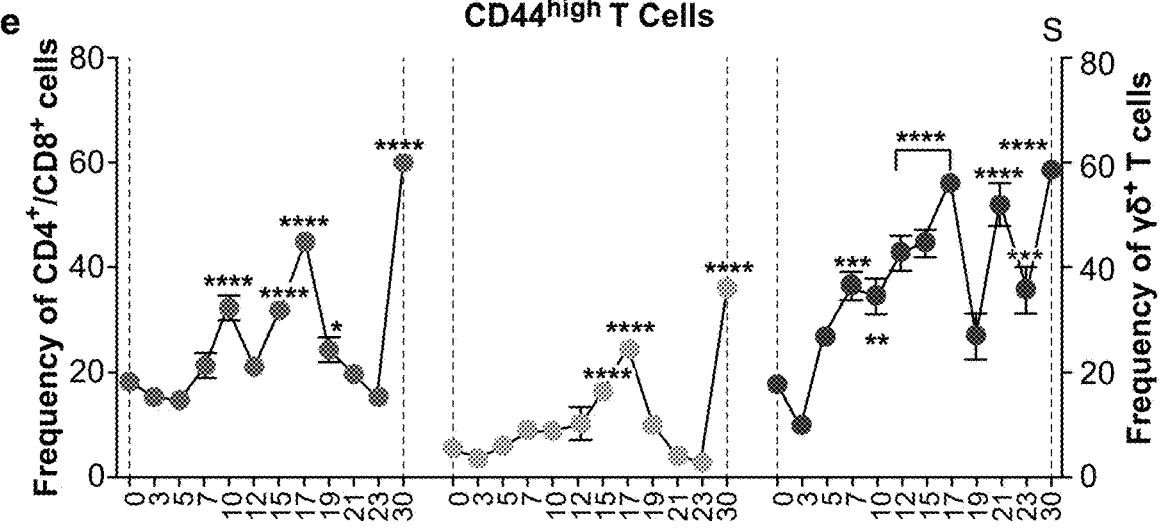
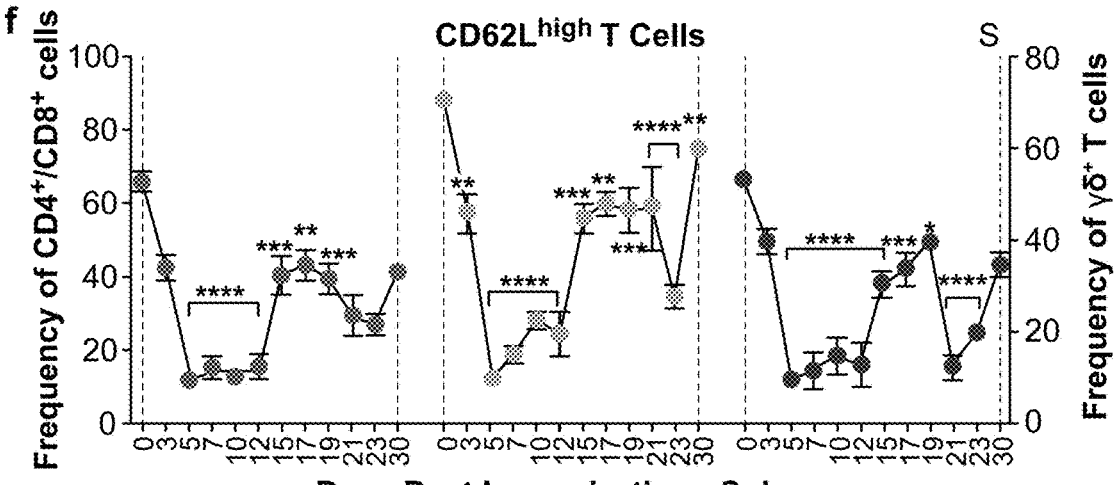
FIG. 8 (Cont. 1)

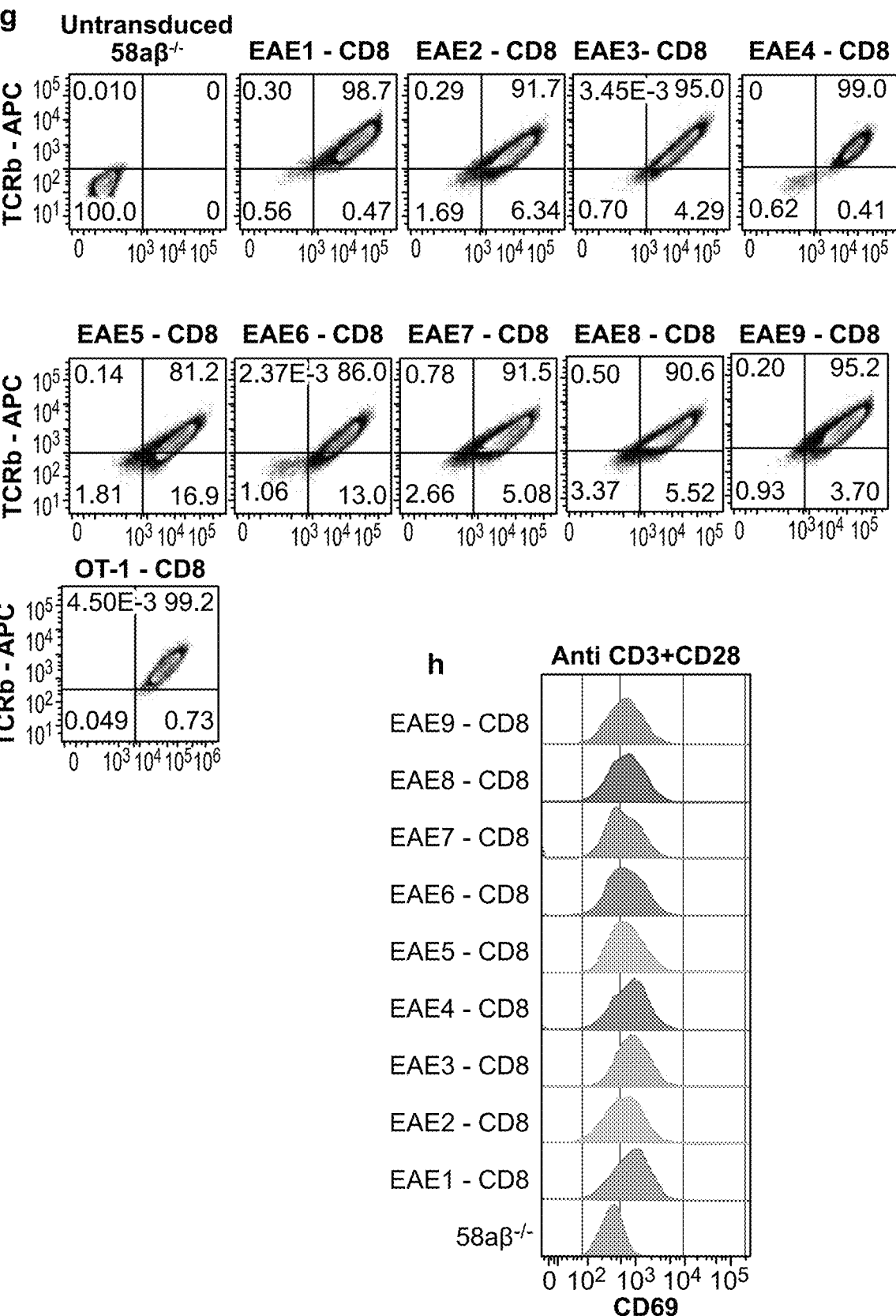
FIG. 8 (Cont. 2)

i
OT-1 TCR
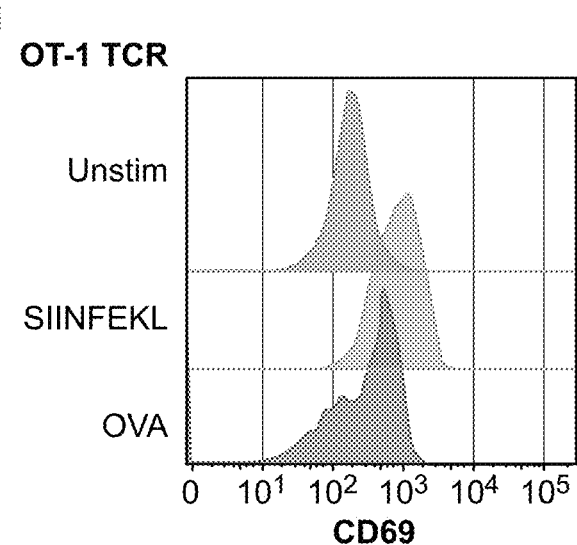
EAE1 - CD8
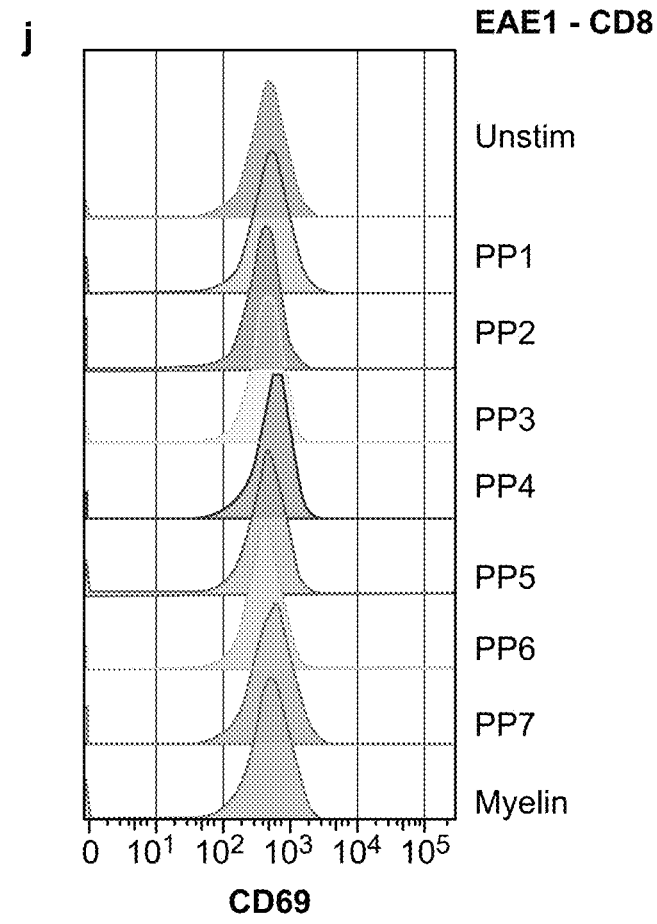
FIG. 8 (Cont. 3)

Mutation Required for function
α2 W131 → α2 G131

α2 W131 →
α2 G131

| Position | 1 | 2 | 3 | 4 | 5 | 6 | 7 | 8 | 9 | 10 |
|---|---|---|---|---|---|---|---|---|---|---|
| Flu Peptide | S | S | L | E | N | F | R | A | Y | V |
| 9 MER Library | X | X | X | X | N | X | X | X | M | M |
| 10 MER Library | X | X | X | X | N | X | X | X | L | L |
| | | | | | | | | | X | L |

■ TCR contact    ■ MHC Anchor
■ Theoretical sequence diversity 1X10^10
Library size 5X10^8

H2-D^b PA_224-233

0.16

6218 TCR

SS | PP | L1 | β2M | L2 | α1+α2+α3 | Myc/HA | L3 | Aga2

H2-D^b

6218 TCRβ

PA_224-233

6218 TCRα

7.68

E4    N5    A8    Y9    V10    R7

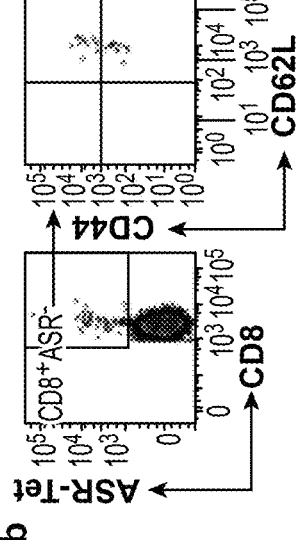
FIG. 10 (Cont. 1)

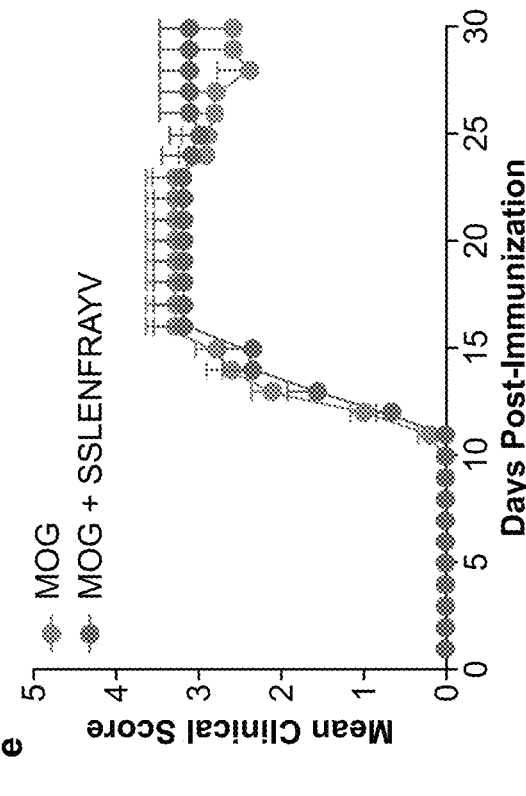
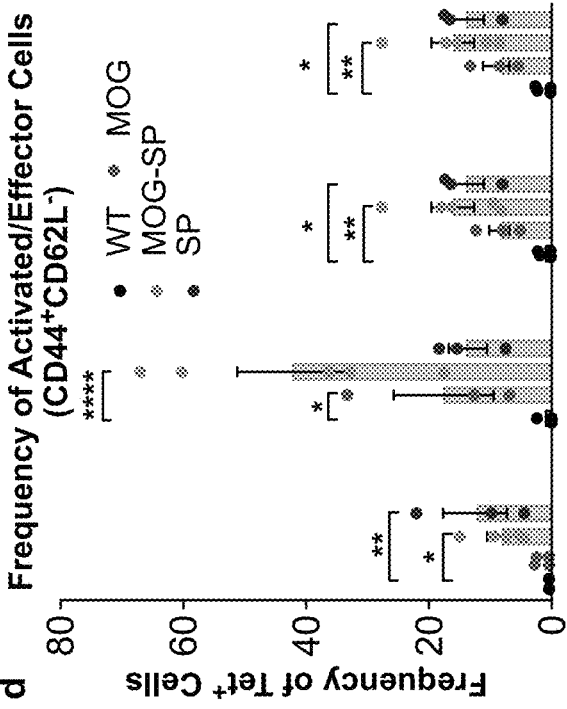
FIG. 10 (Cont. 2)

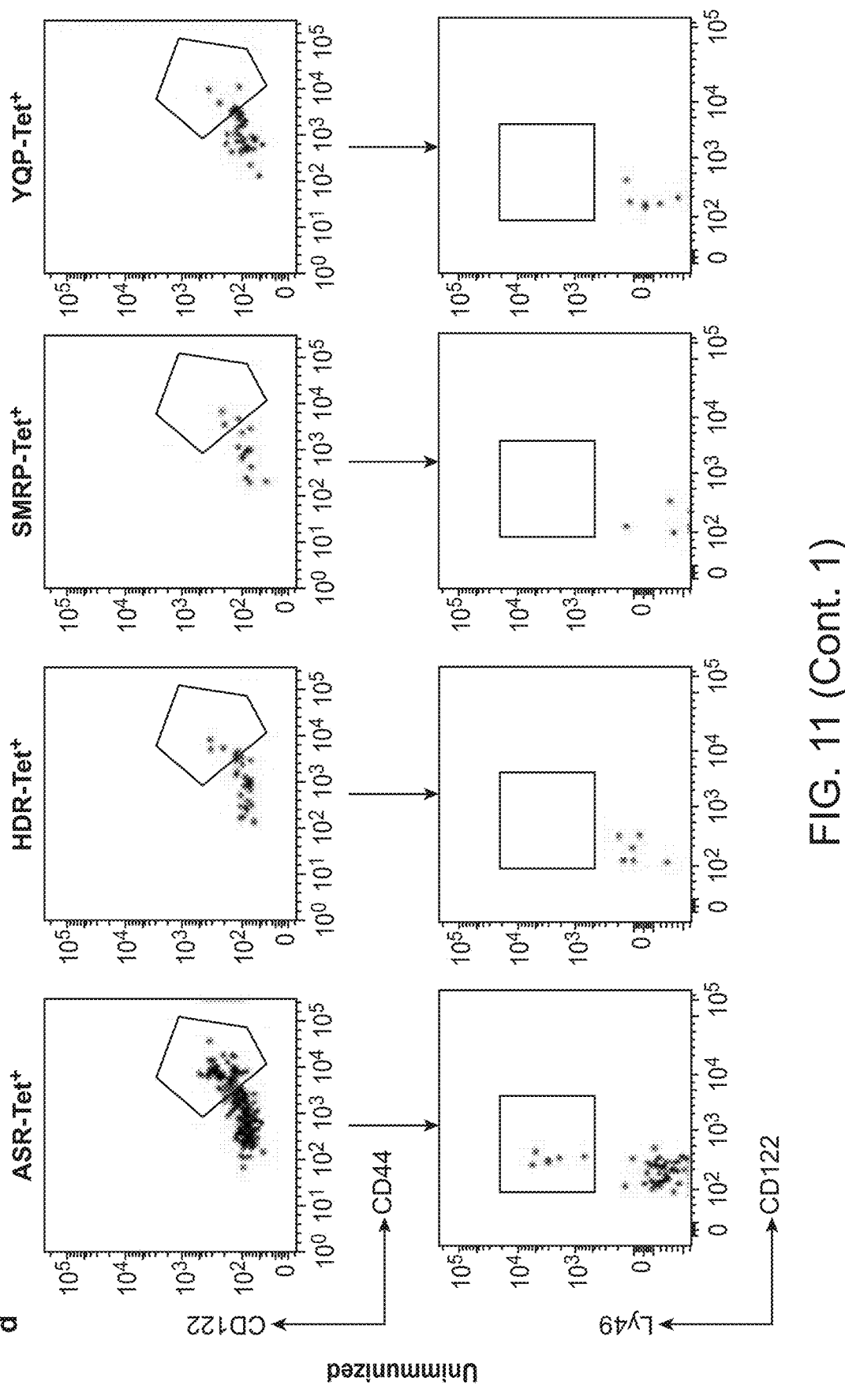
FIG. 11 (Cont. 1)

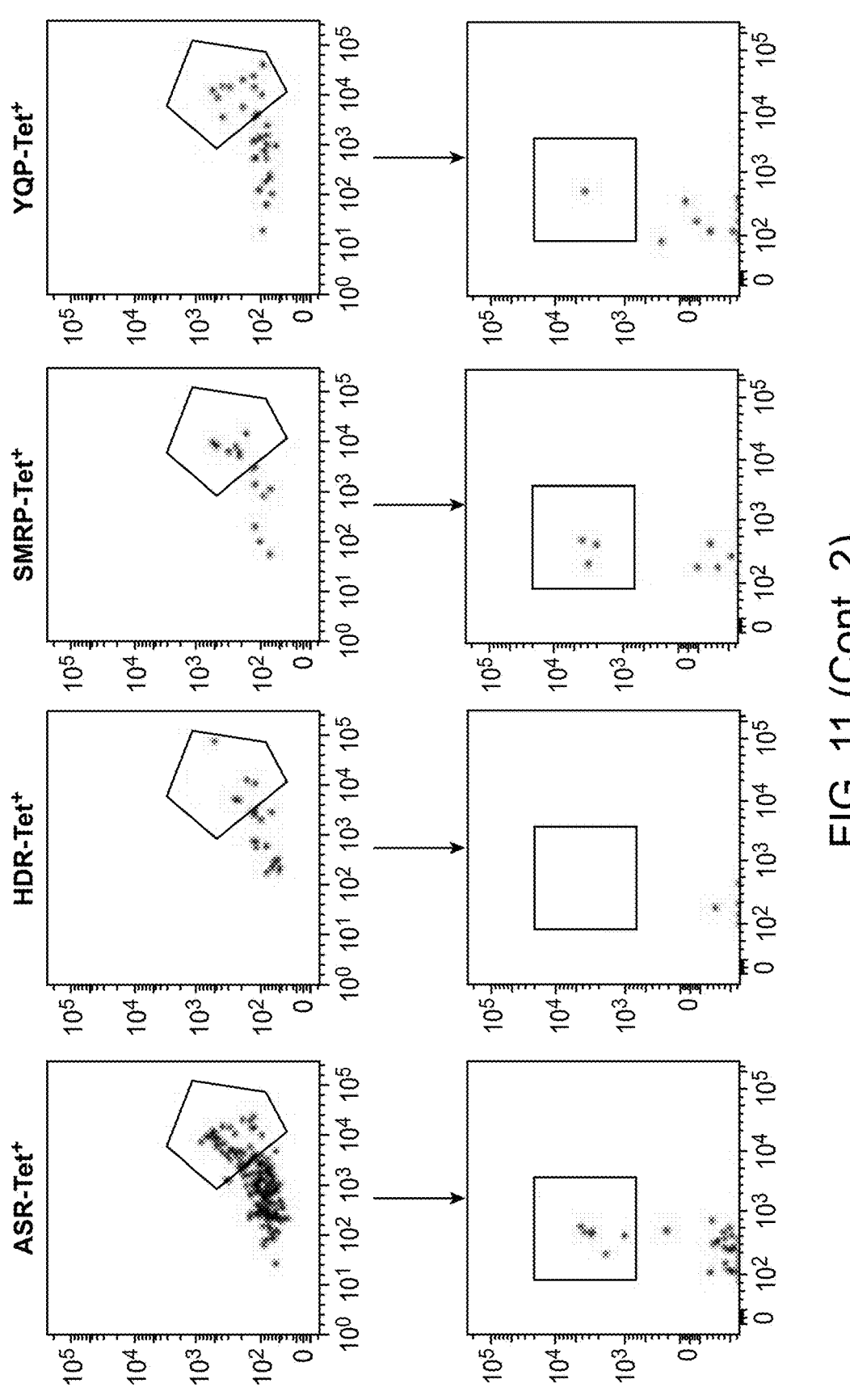
FIG. 11 (Cont. 2)

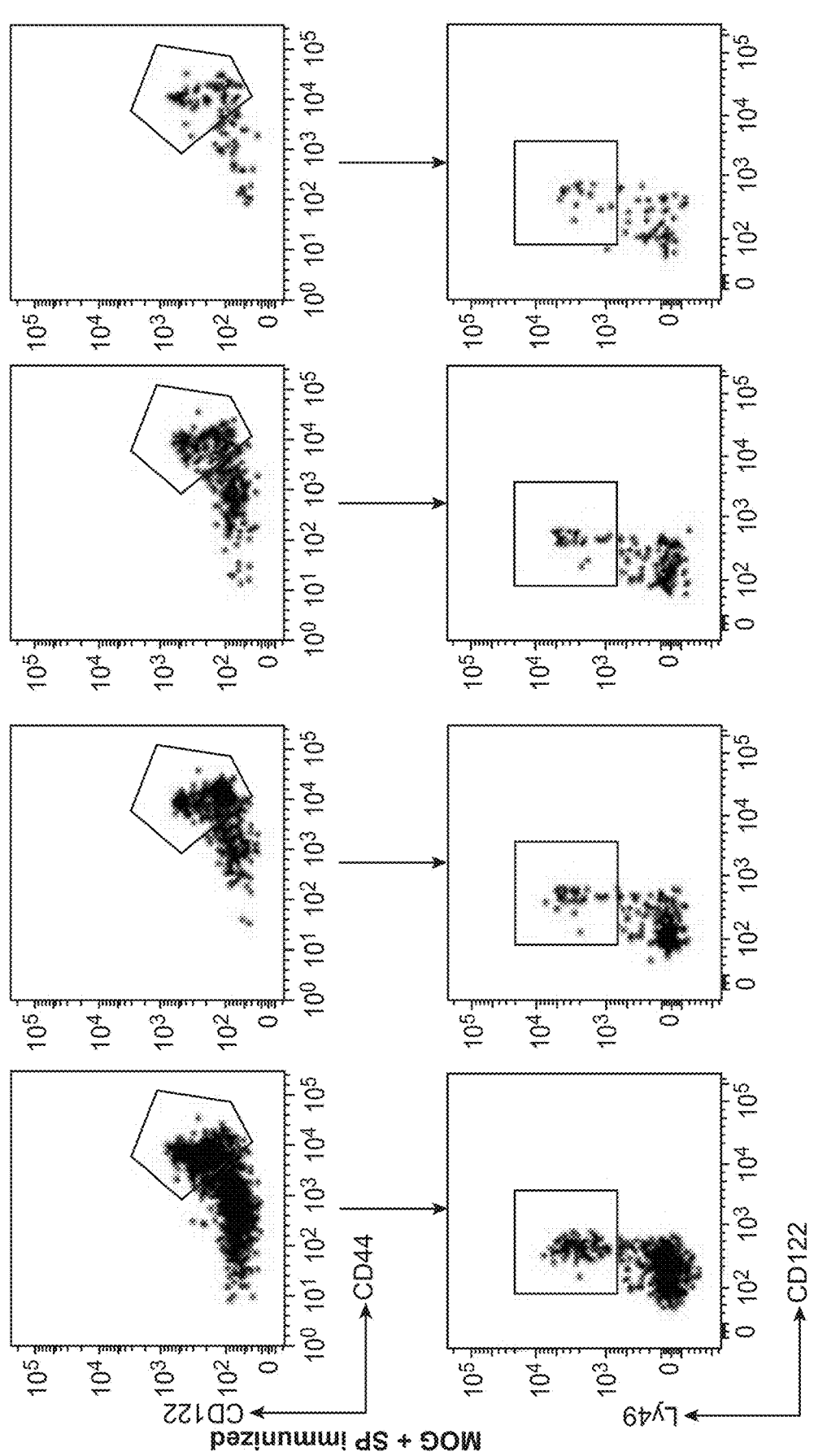
FIG. 11 (Cont. 3)

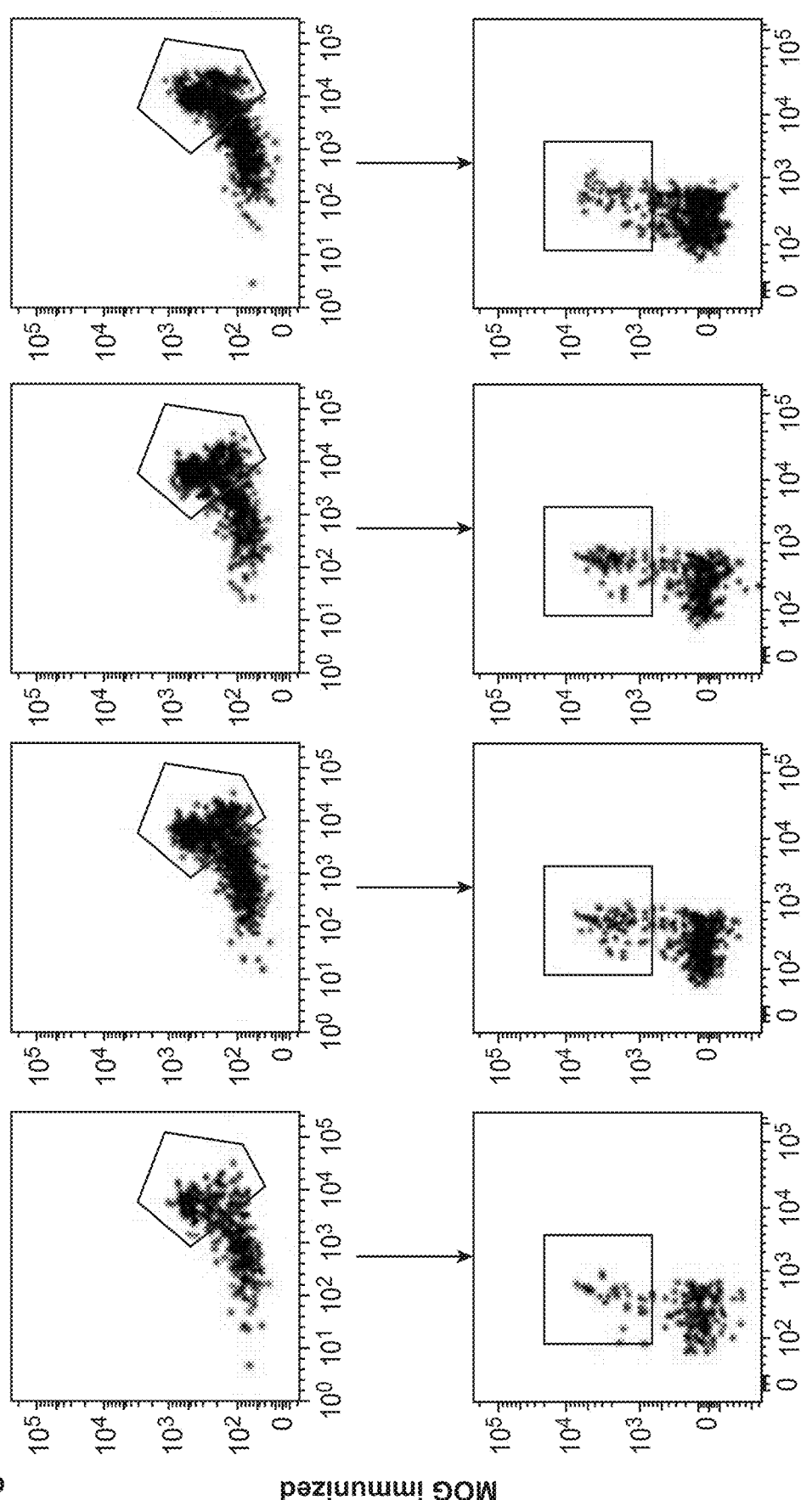
FIG. 11 (Cont. 4)

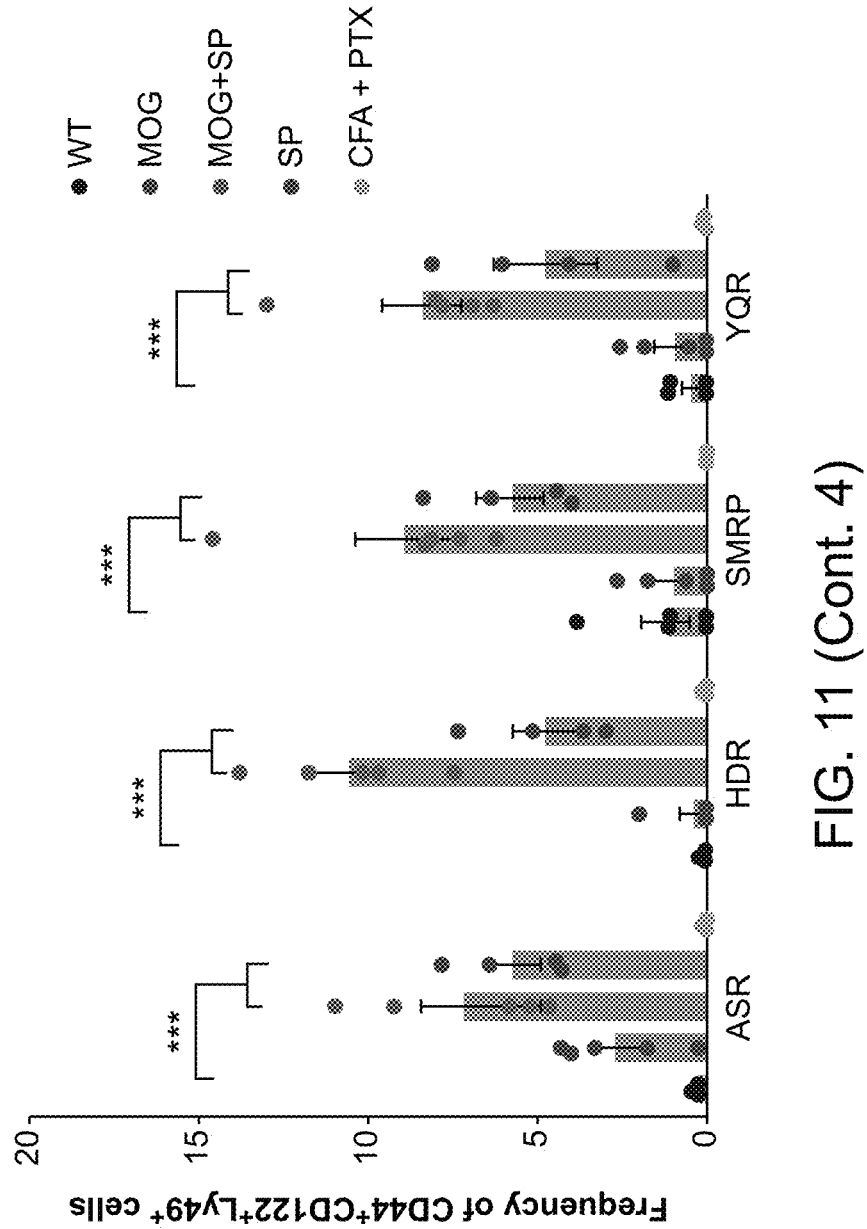
FIG. 11 (Cont. 4)

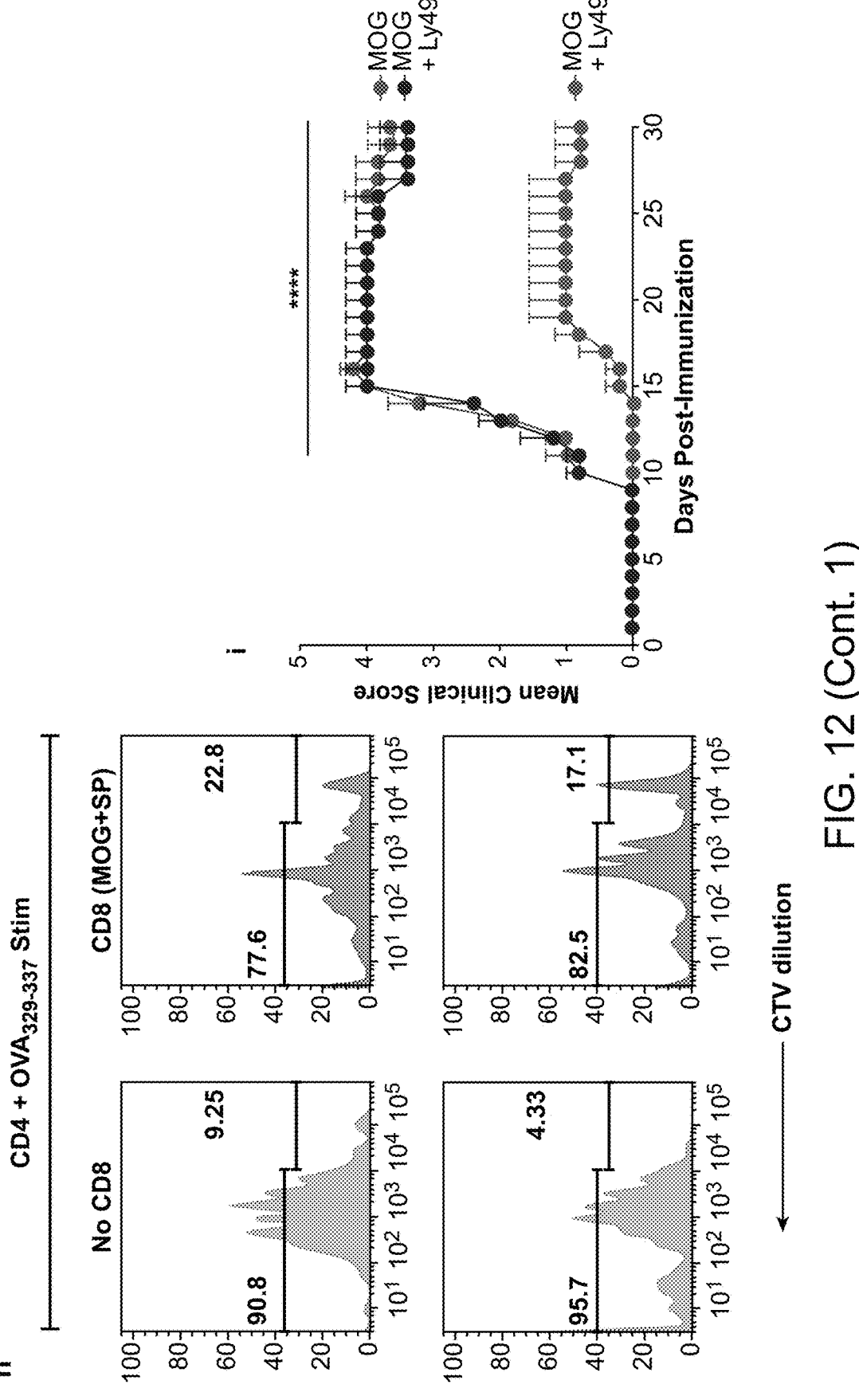
FIG. 12 (Cont. 1)

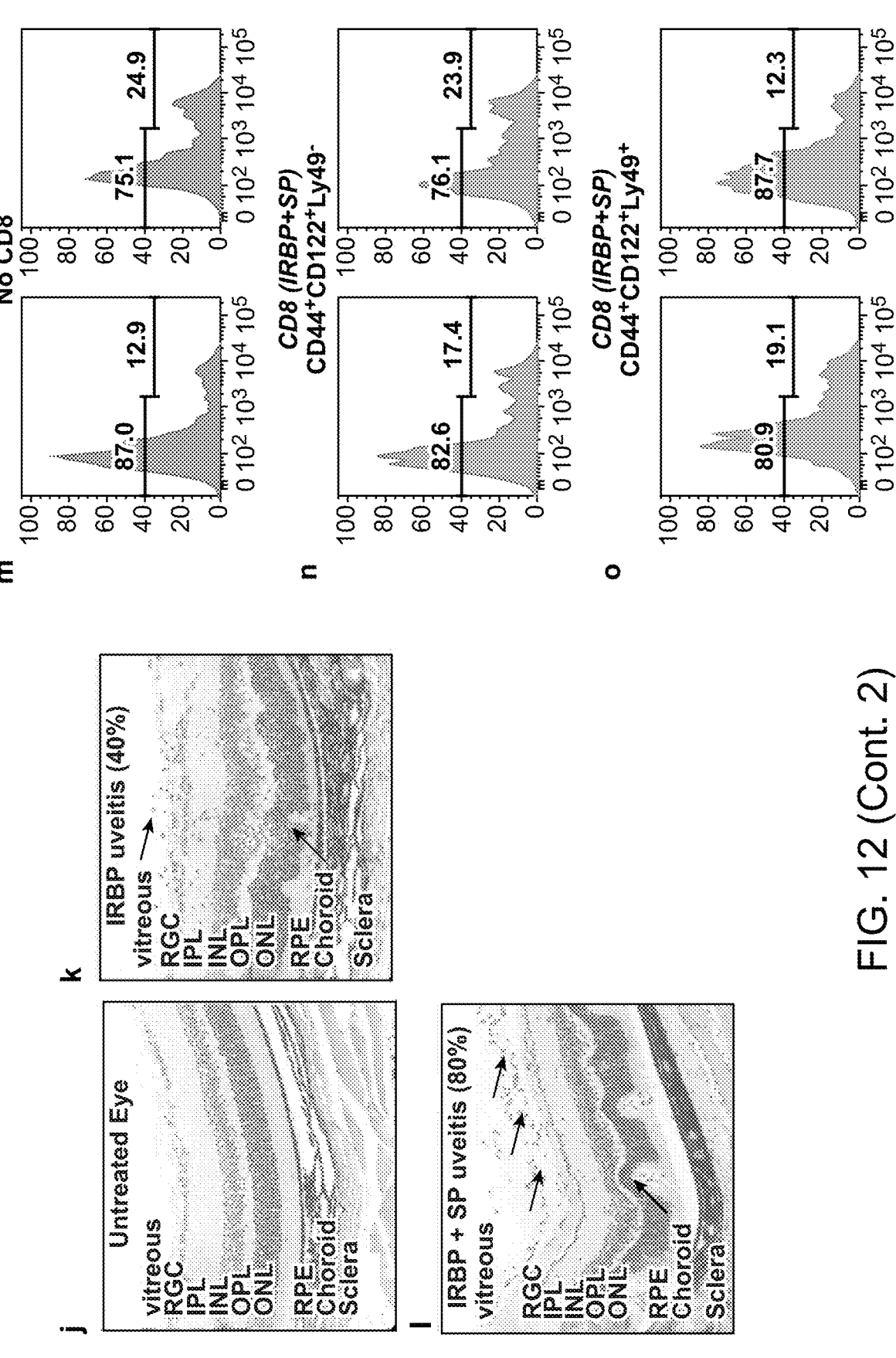
FIG. 12 (Cont. 2)

b
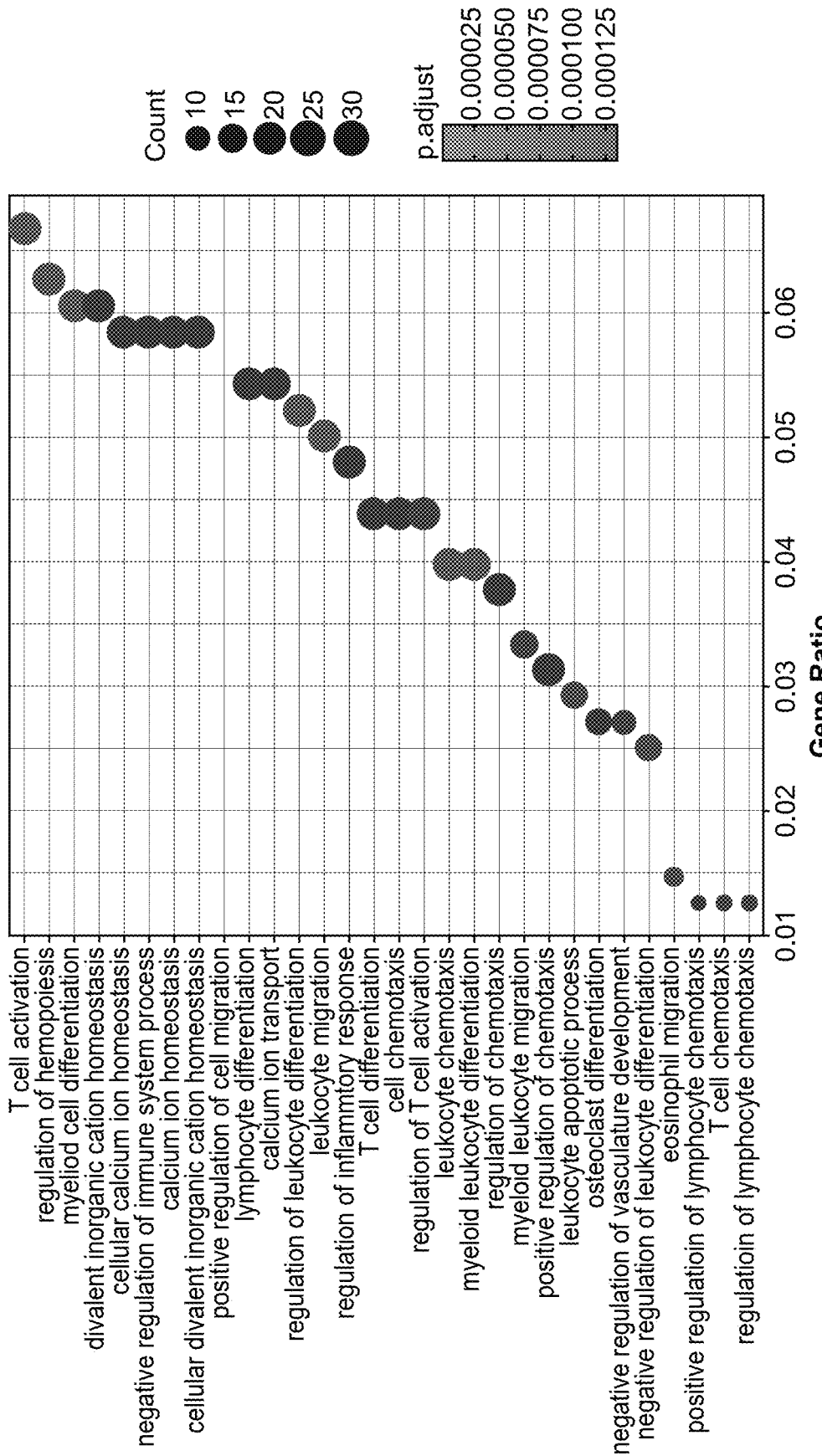
FIG. 13 (Cont. 1)

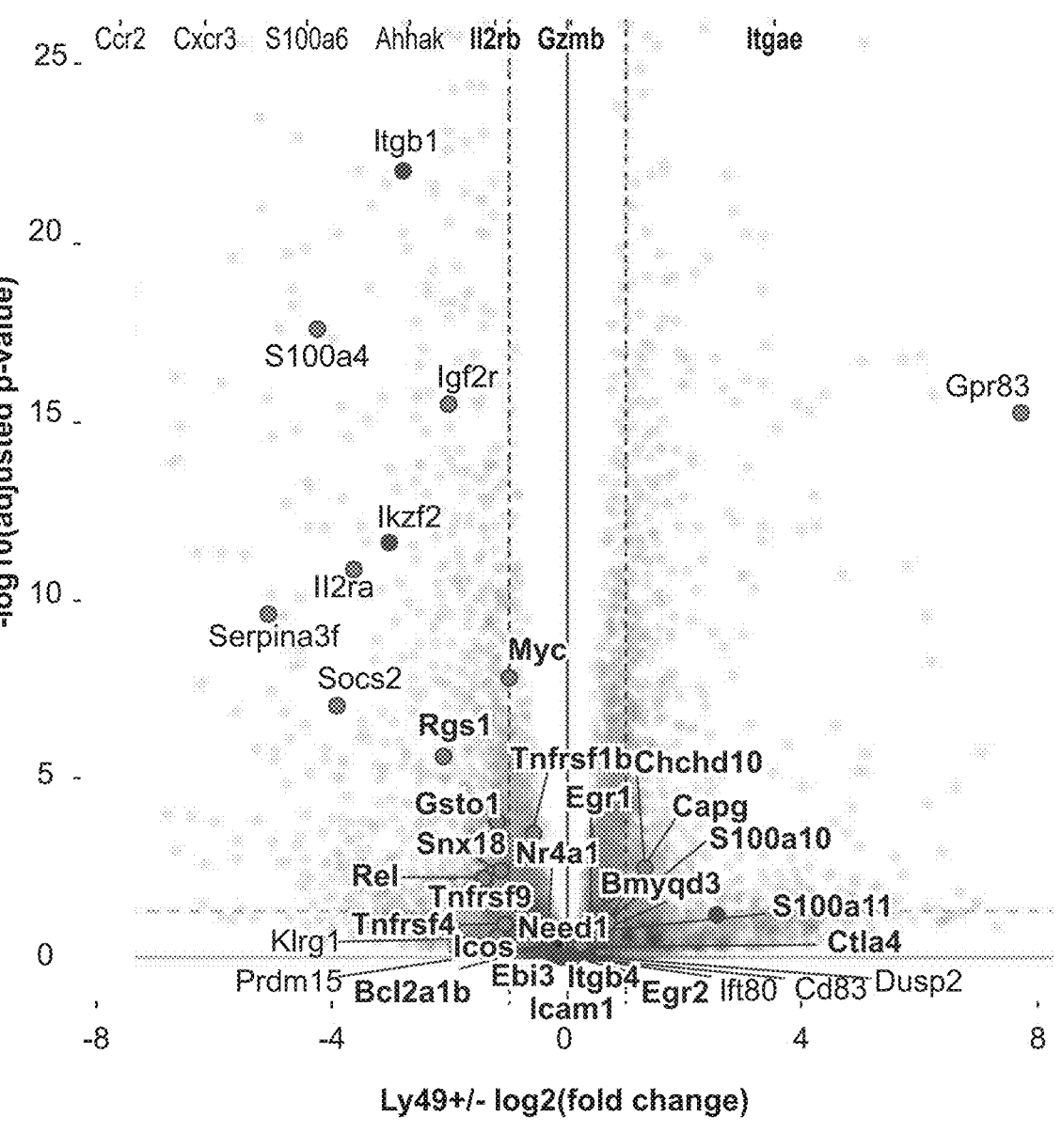
FIG. 13 (Cont. 2)

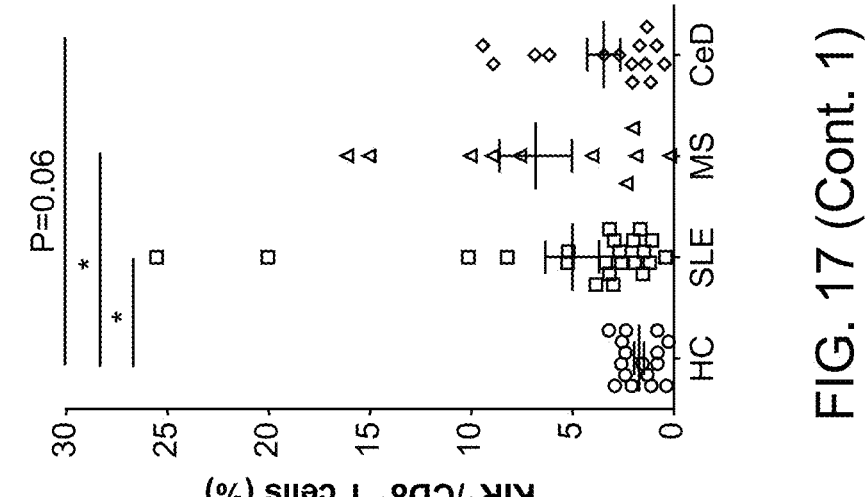
FIG. 17 (Cont. 1)

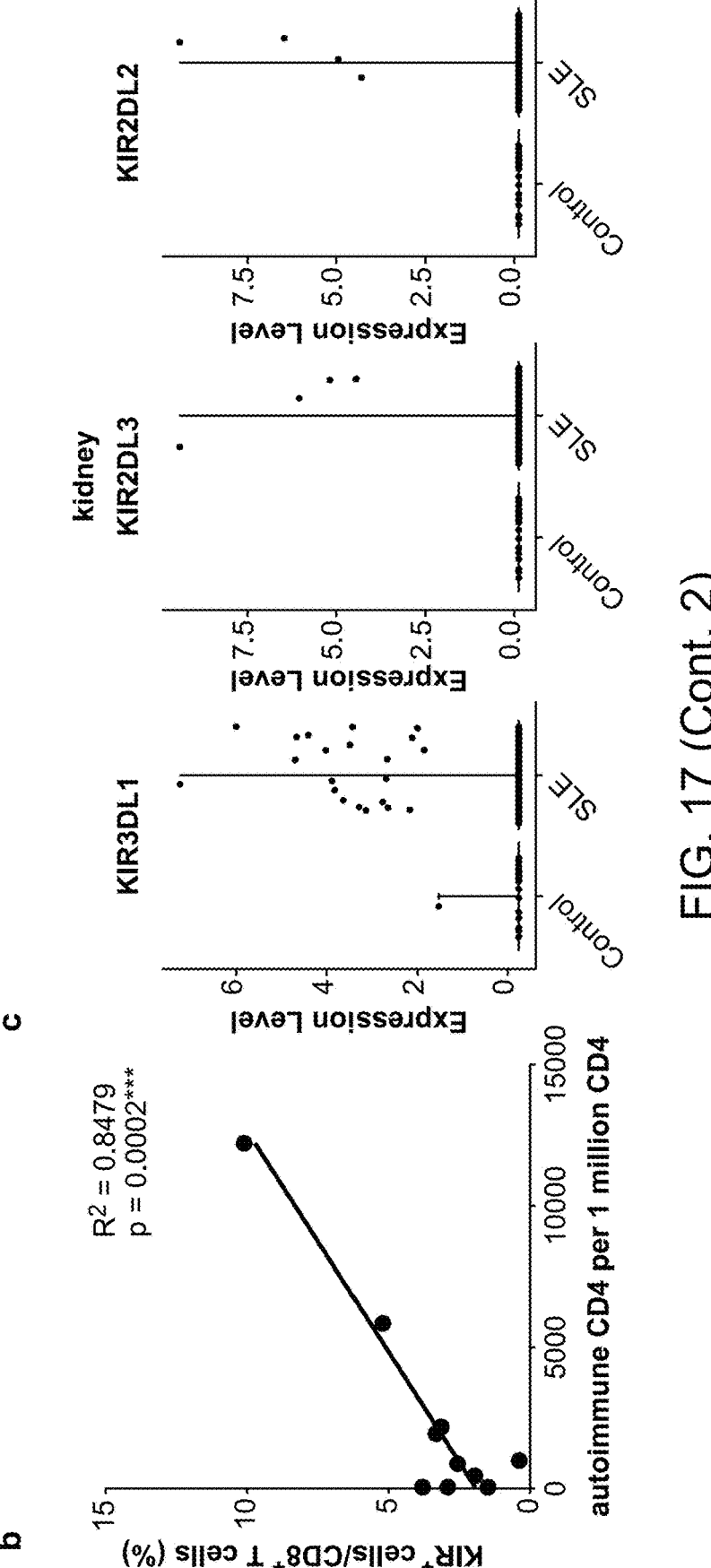
FIG. 17 (Cont. 2)

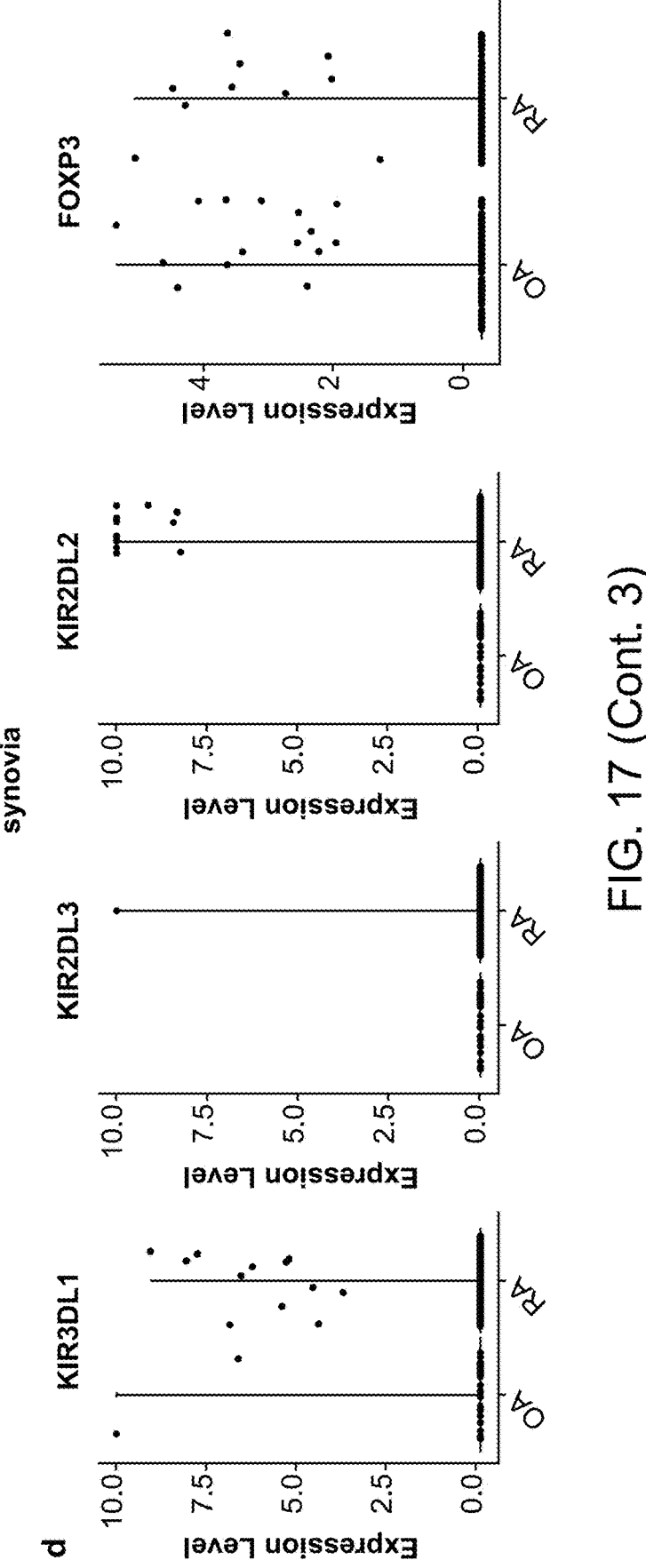
FIG. 17 (Cont. 3)

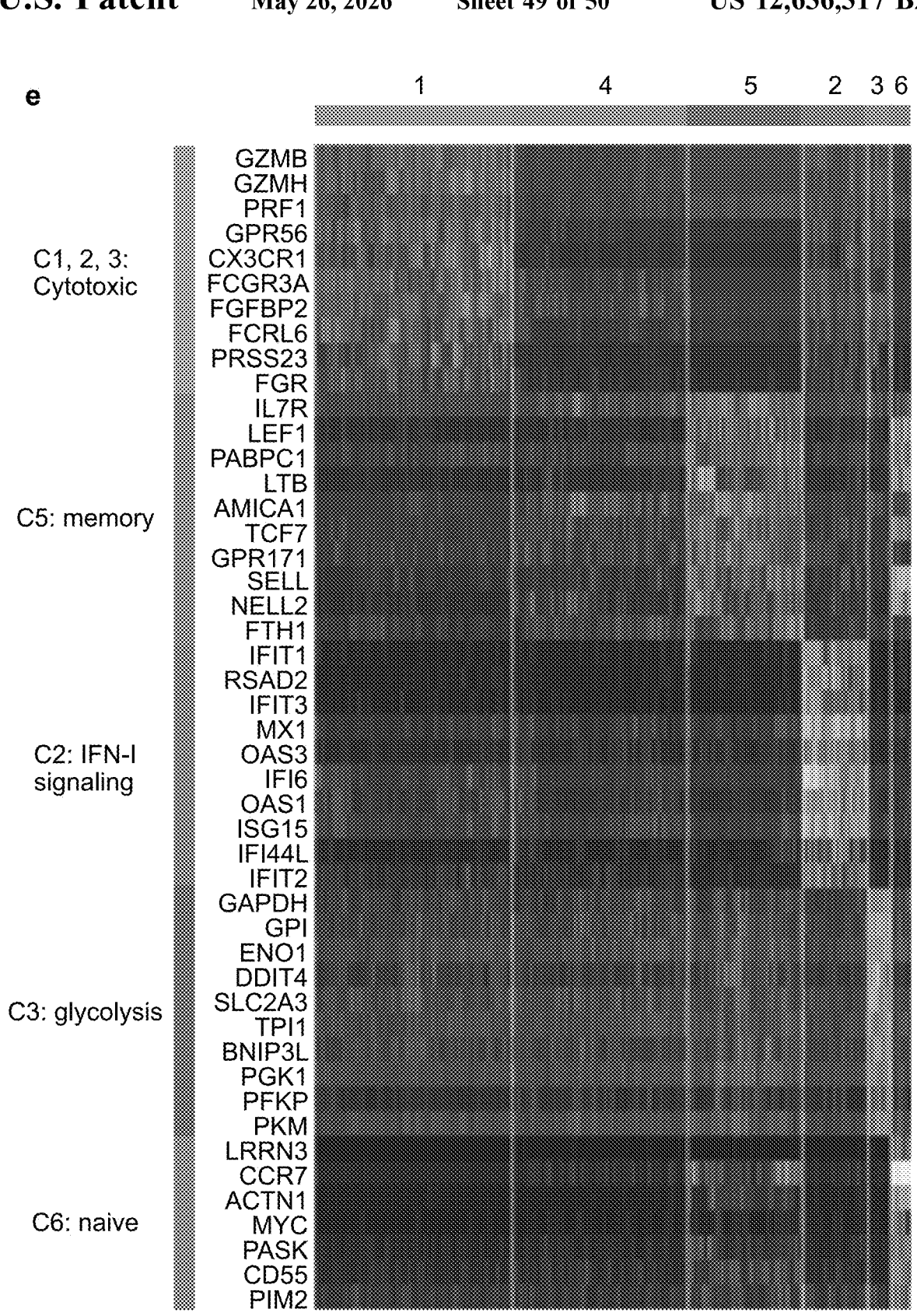
FIG. 20 (Cont. 1)

f
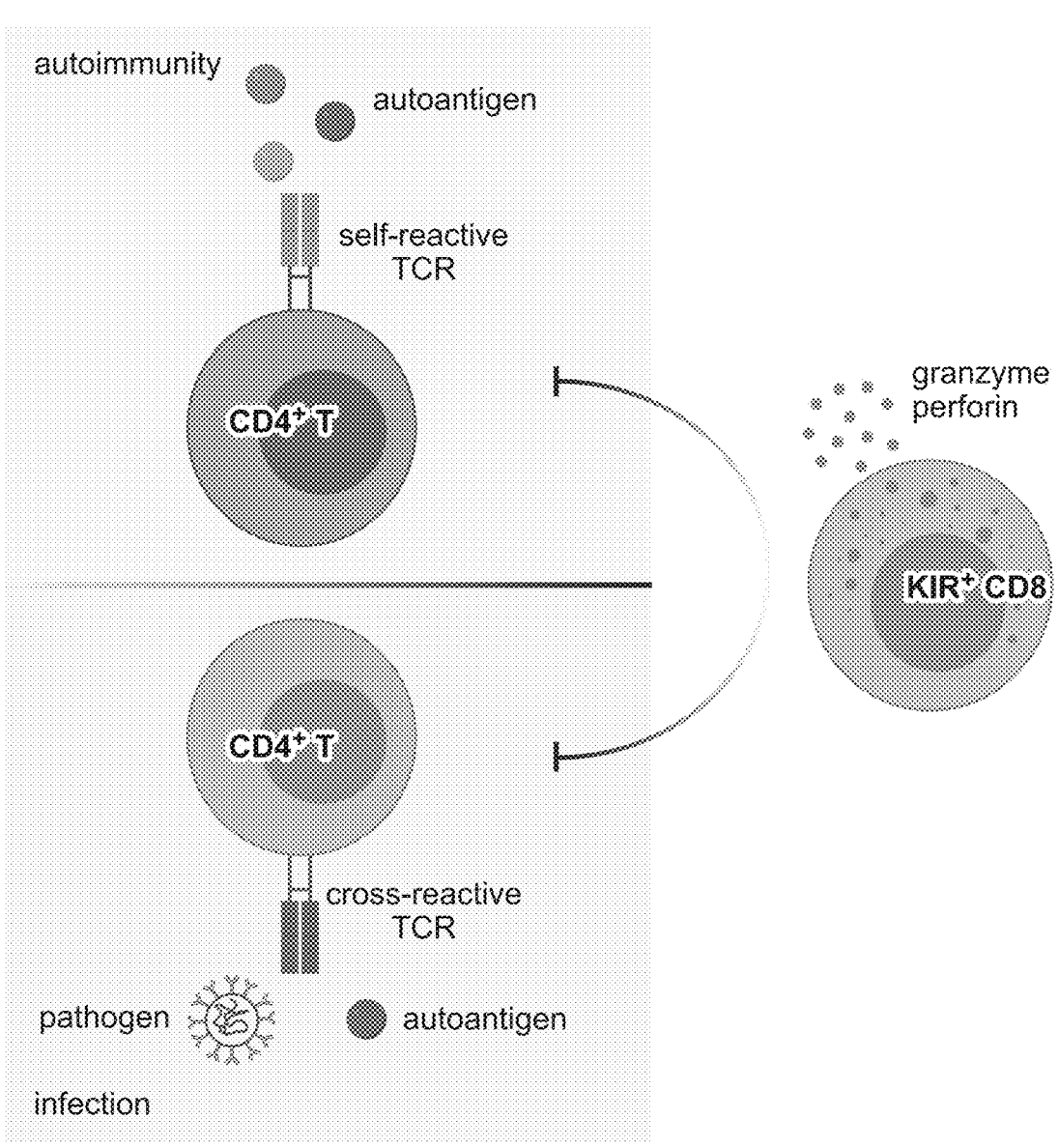
FIG. 20 (Cont. 2)

SEQUENCE LISTING

```
<160> NUMBER OF SEQ ID NOS: 541

<210> SEQ ID NO 1
<211> LENGTH: 10
<212> TYPE: PRT
<213> ORGANISM: Artificial sequence
<220> FEATURE:
<223> OTHER INFORMATION: synthetic sequence

<400> SEQUENCE: 1

Ser Met Arg Pro Asn His Phe Phe Phe Leu
1               5                   10

<210> SEQ ID NO 2
<211> LENGTH: 10
<212> TYPE: PRT
```

<213> ORGANISM: Artificial sequence
<220> FEATURE:
<223> OTHER INFORMATION: synthetic sequence

<400> SEQUENCE: 2

Ala Ser Arg Ser Asn Arg Tyr Phe Trp Leu
1               5                   10

<210> SEQ ID NO 3
<211> LENGTH: 9
<212> TYPE: PRT
<213> ORGANISM: Artificial sequence
<220> FEATURE:
<223> OTHER INFORMATION: synthetic sequence

<400> SEQUENCE: 3

His Asp Arg Val Asn Trp Glu Tyr Ile
1               5

<210> SEQ ID NO 4
<211> LENGTH: 9
<212> TYPE: PRT
<213> ORGANISM: Artificial sequence
<220> FEATURE:
<223> OTHER INFORMATION: synthetic sequence

<400> SEQUENCE: 4

Tyr Gln Pro Gly Asn Trp Glu Tyr Ile
1               5

<210> SEQ ID NO 5
<211> LENGTH: 10
<212> TYPE: PRT
<213> ORGANISM: Artificial sequence
<220> FEATURE:
<223> OTHER INFORMATION: synthetic sequence

<400> SEQUENCE: 5

Ser Ser Leu Glu Asn Phe Arg Ala Tyr Val
1               5                   10

<210> SEQ ID NO 6
<211> LENGTH: 8
<212> TYPE: PRT
<213> ORGANISM: Artificial sequence
<220> FEATURE:
<223> OTHER INFORMATION: synthetic sequence

<400> SEQUENCE: 6

Ser Ile Ile Asn Phe Glu Lys Leu
1               5

<210> SEQ ID NO 7
<211> LENGTH: 5
<212> TYPE: PRT
<213> ORGANISM: Artificial sequence
<220> FEATURE:
<223> OTHER INFORMATION: synthetic sequence

<400> SEQUENCE: 7

Gly Gly Gly Gly Ser
1               5

<210> SEQ ID NO 8
<211> LENGTH: 84
<212> TYPE: DNA
<213> ORGANISM: Artificial sequence -continued
<220> FEATURE:
<223> OTHER INFORMATION: synthetic sequence

<400> SEQUENCE: 8
tgcagttact cgctgtttt tcaatatttt ctgttattgc tagcgtttta gcaagcagcc      60
tggagaactt cagagcctac gtgg                                            84

<210> SEQ ID NO 9
<211> LENGTH: 30
<212> TYPE: DNA
<213> ORGANISM: Artificial sequence
<220> FEATURE:
<223> OTHER INFORMATION: synthetic sequence

<400> SEQUENCE: 9
gaacaaaagc ttatctccga agaagacttg                                      30

<210> SEQ ID NO 10
<211> LENGTH: 76
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 10
tcaatatttt ctgttattgc tagcgtttta gcannknnkn nknnkaacnn knnknnkmts      60
ggtggaggag gttctg                                                     76

<210> SEQ ID NO 11
<211> LENGTH: 51
<212> TYPE: DNA
<213> ORGANISM: Artificial sequence
<220> FEATURE:
<223> OTHER INFORMATION: synthetic sequence

<400> SEQUENCE: 11
tccaccacca ccagcgtagt ctggaacgtc gtatgggtag gatccctccc a              51

<210> SEQ ID NO 12
<211> LENGTH: 67
<212> TYPE: DNA

```
<213> ORGANISM: Artificial sequence
<220> FEATURE:
<223> OTHER INFORMATION: synthetic sequence

<400> SEQUENCE: 12
attttcaatt aagatgcagt tacttcgctg tttttcaata ttttctgtta ttgctagcgt        60
tttagca                                                                  67

<210> SEQ ID NO 13
<211> LENGTH: 15
<212> TYPE: PRT
<213> ORGANISM: Artificial sequence
<220> FEATURE:
<223> OTHER INFORMATION: synthetic sequence

<400> SEQUENCE: 13

Gly Leu Asn Asp Ile Phe Glu Ala Gln Lys Ile Glu Trp His Glu
1               5                   10                  15

<210> SEQ ID NO 14
<211> LENGTH: 11
<212> TYPE: PRT
<213> ORGANISM: Artificial sequence
<220> FEATURE:
<223> OTHER INFORMATION: synthetic sequence

<400> SEQUENCE: 14

Gly Trp Tyr Arg Ser Pro Phe Ser Arg Val Val
1               5                   10

<210> SEQ ID NO 15
<211> LENGTH: 11
<212> TYPE: PRT
<213> ORGANISM: Artificial sequence
<220> FEATURE:
<223> OTHER INFORMATION: synthetic sequence

<400> SEQUENCE: 15

Val His Ala Ala His Ala Glu Ile Asn Glu Ala
1               5                   10

<210> SEQ ID NO 16
<211> LENGTH: 10
<212> TYPE: PRT
<213> ORGANISM: Artificial sequence
<220> FEATURE:
<223> OTHER INFORMATION: synthetic sequence

<400> SEQUENCE: 16

Gln Gly Leu Ser Asn Met Arg Val Arg Leu
1               5                   10

<210> SEQ ID NO 17
<211> LENGTH: 10
<212> TYPE: PRT
<213> ORGANISM: Artificial sequence
<220> FEATURE:
<223> OTHER INFORMATION: synthetic sequence

<400> SEQUENCE: 17

Val Gly Leu Glu Asn Met Arg Val Arg Leu
1               5                   10

<210> SEQ ID NO 18
<211> LENGTH: 10
<212> TYPE: PRT
```

<213> ORGANISM: Artificial sequence
<220> FEATURE:
<223> OTHER INFORMATION: synthetic sequence

<400> SEQUENCE: 18

Val Ser Leu Arg Asn Met Arg Ser Tyr Leu
1               5                   10

<210> SEQ ID NO 19
<211> LENGTH: 8
<212> TYPE: PRT
<213> ORGANISM: Artificial sequence
<220> FEATURE:
<223> OTHER INFORMATION: synthetic sequence

<400> SEQUENCE: 19

Phe Ala Pro Gly Asn Tyr Ala Leu
1               5

<210> SEQ ID NO 20
<211> LENGTH: 24
<212> TYPE: DNA
<213> ORGANISM: Artificial sequence
<220> FEATURE:
<223> OTHER INFORMATION: synthetic sequence

<400> SEQUENCE: 20
gggacaaaga ggtcaaatct cttc                                          24

<210> SEQ ID NO 21
<211> LENGTH: 24
<212> TYPE: DNA
<213> ORGANISM: Artificial sequence
<220> FEATURE:
<223> OTHER INFORMATION: synthetic sequence

<400> SEQUENCE: 21
cctcaagtcg cttccaacct caaa                                          24

<210> SEQ ID NO 22
<211> LENGTH: 26
<212> TYPE: DNA
<213> ORGANISM: Artificial sequence
<220> FEATURE:
<223> OTHER INFORMATION: synthetic sequence

<400> SEQUENCE: 22
gtcatggaga agtctaaact gtttaa                                        26

<210> SEQ ID NO 23
<211> LENGTH: 25
<212> TYPE: DNA
<213> ORGANISM: Artificial sequence
<220> FEATURE:
<223> OTHER INFORMATION: synthetic sequence

<400> SEQUENCE: 23
ctcattgtaa acgaaacagt tccaa                                         25

<210> SEQ ID NO 24
<211> LENGTH: 22
<212> TYPE: DNA
<213> ORGANISM: Artificial sequence
<220> FEATURE:
<223> OTHER INFORMATION: synthetic sequence

<400> SEQUENCE: 24

-continued cgaaatgaga cggtgcccag tc                                                          22

<210> SEQ ID NO 25
<211> LENGTH: 23
<212> TYPE: DNA
<213> ORGANISM: Artificial sequence
<220> FEATURE:
<223> OTHER INFORMATION: synthetic sequence

<400> SEQUENCE: 25
cccagcagat tctcagtcca aca                                                         23

<210> SEQ ID NO 26
<211> LENGTH: 23
<212> TYPE: DNA
<213> ORGANISM: Artificial sequence
<220> FEATURE:
<223> OTHER INFORMATION: synthetic sequence

<400> SEQUENCE: 26
ggagatgtcc ctgatgggta caa                                                        23

<210> SEQ ID NO 27
<211> LENGTH: 25
<212> TYPE: DNA
<213> ORGANISM: Artificial sequence
<220> FEATURE:
<223> OTHER INFORMATION: synthetic sequence

<400> SEQUENCE: 27
agatatccct gatggrtaca aggcc                                                      25

<210> SEQ ID NO 28
<211> LENGTH: 24
<212> TYPE: DNA
<213> ORGANISM: Artificial sequence
<220> FEATURE:
<223> OTHER INFORMATION: synthetic sequence

<400> SEQUENCE: 28
ggcctaaagg aactaactcc actc                                                       24

<210> SEQ ID NO 29
<211> LENGTH: 23
<212> TYPE: DNA
<213> ORGANISM: Artificial sequence
<220> FEATURE:
<223> OTHER INFORMATION: synthetic sequence

<400> SEQUENCE: 29
ggtggggctt tcaaggatcg att                                                        23

<210> SEQ ID NO 30
<211> LENGTH: 24
<212> TYPE: DNA
<213> ORGANISM: Artificial sequence
<220> FEATURE:
<223> OTHER INFORMATION: synthetic sequence

<400> SEQUENCE: 30
gatgattcag ggatgcccaa ggaa                                                       24

<210> SEQ ID NO 31
<211> LENGTH: 24
<212> TYPE: DNA

```
<213> ORGANISM: Artificial sequence
<220> FEATURE:
<223> OTHER INFORMATION: synthetic sequence

<400> SEQUENCE: 31
gggaagctga cacttttgag aagt                                             24

<210> SEQ ID NO 32
<211> LENGTH: 25
<212> TYPE: DNA
<213> ORGANISM: Artificial sequence
<220> FEATURE:
<223> OTHER INFORMATION: synthetic sequence

<400> SEQUENCE: 32
gatctatctg aaggctatga tgcgt                                            25

<210> SEQ ID NO 33
<211> LENGTH: 26
<212> TYPE: DNA
<213> ORGANISM: Artificial sequence
<220> FEATURE:
<223> OTHER INFORMATION: synthetic sequence

<400> SEQUENCE: 33
ctgtgaactc agcaatcaaa tatgaa                                           26

<210> SEQ ID NO 34
<211> LENGTH: 24
<212> TYPE: DNA
<213> ORGANISM: Artificial sequence
<220> FEATURE:
<223> OTHER INFORMATION: synthetic sequence

<400> SEQUENCE: 34
ggtcaaggag agattctcag ctgt                                             24

<210> SEQ ID NO 35
<211> LENGTH: 26
<212> TYPE: DNA
<213> ORGANISM: Artificial sequence
<220> FEATURE:
<223> OTHER INFORMATION: synthetic sequence

<400> SEQUENCE: 35
cagacttggt caagaagaga ttctca                                           26

<210> SEQ ID NO 36
<211> LENGTH: 26
<212> TYPE: DNA
<213> ORGANISM: Artificial sequence
<220> FEATURE:
<223> OTHER INFORMATION: synthetic sequence

<400> SEQUENCE: 36
gttcttcagc aaatagacat gactga                                           26

<210> SEQ ID NO 37
<211> LENGTH: 25
<212> TYPE: DNA
<213> ORGANISM: Artificial sequence
<220> FEATURE:
<223> OTHER INFORMATION: synthetic sequence

<400> SEQUENCE: 37
cgatgttgat agtaacagcg aagga                                            25
```

-continued

```
<210> SEQ ID NO 38
<211> LENGTH: 23
<212> TYPE: DNA
<213> ORGANISM: Artificial sequence
<220> FEATURE:
<223> OTHER INFORMATION: synthetic sequence

<400> SEQUENCE: 38
gccacatacg agagtggatt cac                                        23

<210> SEQ ID NO 39
<211> LENGTH: 23
<212> TYPE: DNA
<213> ORGANISM: Artificial sequence
<220> FEATURE:
<223> OTHER INFORMATION: synthetic sequence

<400> SEQUENCE: 39
ggtagagtcg gtggtgcaac tga                                        23

<210> SEQ ID NO 40
<211> LENGTH: 26
<212> TYPE: DNA
<213> ORGANISM: Artificial sequence
<220> FEATURE:
<223> OTHER INFORMATION: synthetic sequence

<400> SEQUENCE: 40
gactcacggt ctacaacaaa atacaa                                     26

<210> SEQ ID NO 41
<211> LENGTH: 24
<212> TYPE: DNA
<213> ORGANISM: Artificial sequence
<220> FEATURE:
<223> OTHER INFORMATION: synthetic sequence

<400> SEQUENCE: 41
ccgtacgctc aaatgtggat aaga                                       24

<210> SEQ ID NO 42
<211> LENGTH: 24
<212> TYPE: DNA
<213> ORGANISM: Artificial sequence
<220> FEATURE:
<223> OTHER INFORMATION: synthetic sequence

<400> SEQUENCE: 42
cgttgttaaa ggcaccaagg gctt                                       24

<210> SEQ ID NO 43
<211> LENGTH: 28
<212> TYPE: DNA
<213> ORGANISM: Artificial sequence
<220> FEATURE:
<223> OTHER INFORMATION: synthetic sequence

<400> SEQUENCE: 43
ggtcattaty ctctgaactt tcagaagc                                   28

<210> SEQ ID NO 44
<211> LENGTH: 27
<212> TYPE: DNA
<213> ORGANISM: Artificial sequence
<220> FEATURE:
```

-continued

```
<223> OTHER INFORMATION: synthetic sequence

<400> SEQUENCE: 44
cgctaytctg tagtcttcca gaaatca                                        27

<210> SEQ ID NO 45
<211> LENGTH: 24
<212> TYPE: DNA
<213> ORGANISM: Artificial sequence
<220> FEATURE:
<223> OTHER INFORMATION: synthetic sequence

<400> SEQUENCE: 45
gtgtccrata aaaggaaga tgga                                            24

<210> SEQ ID NO 46
<211> LENGTH: 27
<212> TYPE: DNA
<213> ORGANISM: Artificial sequence
<220> FEATURE:
<223> OTHER INFORMATION: synthetic sequence

<400> SEQUENCE: 46
gttstacaat ccttctggga caaagca                                        27

<210> SEQ ID NO 47
<211> LENGTH: 24
<212> TYPE: DNA
<213> ORGANISM: Artificial sequence
<220> FEATURE:
<223> OTHER INFORMATION: synthetic sequence

<400> SEQUENCE: 47
caatccttct gggacaaagc acac                                           24

<210> SEQ ID NO 48
<211> LENGTH: 23
<212> TYPE: DNA
<213> ORGANISM: Artificial sequence
<220> FEATURE:
<223> OTHER INFORMATION: synthetic sequence

<400> SEQUENCE: 48
gcagagcaga gaggtggaag act                                            23

<210> SEQ ID NO 49
<211> LENGTH: 24
<212> TYPE: DNA
<213> ORGANISM: Artificial sequence
<220> FEATURE:
<223> OTHER INFORMATION: synthetic sequence

<400> SEQUENCE: 49
gcctgtccta cattcctgga atga                                           24

<210> SEQ ID NO 50
<211> LENGTH: 23
<212> TYPE: DNA
<213> ORGANISM: Artificial sequence
<220> FEATURE:
<223> OTHER INFORMATION: synthetic sequence

<400> SEQUENCE: 50
cgccactctc cataagagca gca                                            23
```

-continued

```
<210> SEQ ID NO 51
<211> LENGTH: 26
<212> TYPE: DNA
<213> ORGANISM: Artificial sequence
<220> FEATURE:
<223> OTHER INFORMATION: synthetic sequence

<400> SEQUENCE: 51
gacaaaacgt caaatgggag atactc                                      26

<210> SEQ ID NO 52
<211> LENGTH: 25
<212> TYPE: DNA
<213> ORGANISM: Artificial sequence
<220> FEATURE:
<223> OTHER INFORMATION: synthetic sequence

<400> SEQUENCE: 52
ggacagaaaa cagagccaaa gactt                                       25

<210> SEQ ID NO 53
<211> LENGTH: 26
<212> TYPE: DNA
<213> ORGANISM: Artificial sequence
<220> FEATURE:
<223> OTHER INFORMATION: synthetic sequence

<400> SEQUENCE: 53
ggaracccag tggttcaagg agtgaa                                      26

<210> SEQ ID NO 54
<211> LENGTH: 25
<212> TYPE: DNA
<213> ORGANISM: Artificial sequence
<220> FEATURE:
<223> OTHER INFORMATION: synthetic sequence

<400> SEQUENCE: 54
cgttcaaatg agmgagagaa gcgca                                       25

<210> SEQ ID NO 55
<211> LENGTH: 26
<212> TYPE: DNA
<213> ORGANISM: Artificial sequence
<220> FEATURE:
<223> OTHER INFORMATION: synthetic sequence

<400> SEQUENCE: 55
ctctgatggt gaaaaggaag aaggca                                      26

<210> SEQ ID NO 56
<211> LENGTH: 23
<212> TYPE: DNA
<213> ORGANISM: Artificial sequence
<220> FEATURE:
<223> OTHER INFORMATION: synthetic sequence

<400> SEQUENCE: 56
gaaggcagat tcacagctca cct                                         23

<210> SEQ ID NO 57
<211> LENGTH: 25
<212> TYPE: DNA
<213> ORGANISM: Artificial sequence
<220> FEATURE:
<223> OTHER INFORMATION: synthetic sequence
```

-continued

<400> SEQUENCE: 57
ggcagattga cagtttacct caata                                                    25

<210> SEQ ID NO 58
<211> LENGTH: 26
<212> TYPE: DNA
<213> ORGANISM: Artificial sequence
<220> FEATURE:
<223> OTHER INFORMATION: synthetic sequence

<400> SEQUENCE: 58
agattcacaa ttcacctcaa taaagc                                                   26

<210> SEQ ID NO 59
<211> LENGTH: 25
<212> TYPE: DNA
<213> ORGANISM: Artificial sequence
<220> FEATURE:
<223> OTHER INFORMATION: synthetic sequence

<400> SEQUENCE: 59
ggtgaaaagg aagaaggcag attca                                                    25

<210> SEQ ID NO 60
<211> LENGTH: 24
<212> TYPE: DNA
<213> ORGANISM: Artificial sequence
<220> FEATURE:
<223> OTHER INFORMATION: synthetic sequence

<400> SEQUENCE: 60
gcagacccaa ggactcatcg tttt                                                     24

<210> SEQ ID NO 61
<211> LENGTH: 26
<212> TYPE: DNA
<213> ORGANISM: Artificial sequence
<220> FEATURE:
<223> OTHER INFORMATION: synthetic sequence

<400> SEQUENCE: 61
gaaaacagaa tcaaagactc accctt                                                   26

<210> SEQ ID NO 62
<211> LENGTH: 24
<212> TYPE: DNA
<213> ORGANISM: Artificial sequence
<220> FEATURE:
<223> OTHER INFORMATION: synthetic sequence

<400> SEQUENCE: 62
caggaacaaa ggagaatggg aggt                                                     24

<210> SEQ ID NO 63
<211> LENGTH: 25
<212> TYPE: DNA
<213> ORGANISM: Artificial sequence
<220> FEATURE:
<223> OTHER INFORMATION: synthetic sequence

<400> SEQUENCE: 63
gctcaaggaa caaaggagaa tggaa                                                    25

<210> SEQ ID NO 64
<211> LENGTH: 25

```
<212> TYPE: DNA
<213> ORGANISM: Artificial sequence
<220> FEATURE:
<223> OTHER INFORMATION: synthetic sequence

<400> SEQUENCE: 64
gcttcaggaa caaaggagaa tggga                                                    25

<210> SEQ ID NO 65
<211> LENGTH: 25
<212> TYPE: DNA
<213> ORGANISM: Artificial sequence
<220> FEATURE:
<223> OTHER INFORMATION: synthetic sequence

<400> SEQUENCE: 65
cggaaataaa cgaaggacaa ggatt                                                    25

<210> SEQ ID NO 66
<211> LENGTH: 25
<212> TYPE: DNA
<213> ORGANISM: Artificial sequence
<220> FEATURE:
<223> OTHER INFORMATION: synthetic sequence

<400> SEQUENCE: 66
gtggacagaa aagaagaaca aggac                                                    25

<210> SEQ ID NO 67
<211> LENGTH: 25
<212> TYPE: DNA
<213> ORGANISM: Artificial sequence
<220> FEATURE:
<223> OTHER INFORMATION: synthetic sequence

<400> SEQUENCE: 67
ggactatgtg gtaaatgaag tggca                                                    25

<210> SEQ ID NO 68
<211> LENGTH: 23
<212> TYPE: DNA
<213> ORGANISM: Artificial sequence
<220> FEATURE:
<223> OTHER INFORMATION: synthetic sequence

<400> SEQUENCE: 68
gaaggacagt gggcatttct cca                                                      23

<210> SEQ ID NO 69
<211> LENGTH: 24
<212> TYPE: DNA
<213> ORGANISM: Artificial sequence
<220> FEATURE:
<223> OTHER INFORMATION: synthetic sequence

<400> SEQUENCE: 69
gcacacgagg gtagcctttt gttt                                                     24

<210> SEQ ID NO 70
<211> LENGTH: 23
<212> TYPE: DNA
<213> ORGANISM: Artificial sequence
<220> FEATURE:
<223> OTHER INFORMATION: synthetic sequence

<400> SEQUENCE: 70
```

-continued gtcaaagtcg gtgaacaggc aga                                                                          23

<210> SEQ ID NO 71
<211> LENGTH: 40
<212> TYPE: DNA
<213> ORGANISM: Artificial sequence
<220> FEATURE:
<223> OTHER INFORMATION: synthetic sequence

<400> SEQUENCE: 71
ccagggtttt cccagtcacg ggtcactgat acggagctga                                            40

<210> SEQ ID NO 72
<211> LENGTH: 44
<212> TYPE: DNA
<213> ORGANISM: Artificial sequence
<220> FEATURE:
<223> OTHER INFORMATION: synthetic sequence

<400> SEQUENCE: 72
ccagggtttt cccagtcacc catttagacc ttcagatcac agct                            44

<210> SEQ ID NO 73
<211> LENGTH: 44
<212> TYPE: DNA
<213> ORGANISM: Artificial sequence
<220> FEATURE:
<223> OTHER INFORMATION: synthetic sequence

<400> SEQUENCE: 73
ccagggtttt cccagtcacg gatcagtttt cagttgaaag acca                            44

<210> SEQ ID NO 74
<211> LENGTH: 45
<212> TYPE: DNA
<213> ORGANISM: Artificial sequence
<220> FEATURE:
<223> OTHER INFORMATION: synthetic sequence

<400> SEQUENCE: 74
ccagggtttt cccagtcacc ctcagtcttc agataaagct cattt                          45

<210> SEQ ID NO 75
<211> LENGTH: 42
<212> TYPE: DNA
<213> ORGANISM: Artificial sequence
<220> FEATURE:
<223> OTHER INFORMATION: synthetic sequence

<400> SEQUENCE: 75
ccagggtttt cccagtcacg cccagacagc tccaagctac tt                                42

<210> SEQ ID NO 76
<211> LENGTH: 44
<212> TYPE: DNA
<213> ORGANISM: Artificial sequence
<220> FEATURE:
<223> OTHER INFORMATION: synthetic sequence

<400> SEQUENCE: 76
ccagggtttt cccagtcacc caacagtttg atgactatca ctct                            44

<210> SEQ ID NO 77
<211> LENGTH: 42
<212> TYPE: DNA
<213> ORGANISM: Artificial sequence

```
<220> FEATURE:
<223> OTHER INFORMATION: synthetic sequence

<400> SEQUENCE: 77
ccagggtttt cccagtcacg ccaccagaac aacgcaagaa ga                          42

<210> SEQ ID NO 78
<211> LENGTH: 41
<212> TYPE: DNA
<213> ORGANISM: Artificial sequence
<220> FEATURE:
<223> OTHER INFORMATION: synthetic sequence

<400> SEQUENCE: 78
ccagggtttt cccagtcacc aaggcctcca gaccaagcca a                           41

<210> SEQ ID NO 79
<211> LENGTH: 43
<212> TYPE: DNA
<213> ORGANISM: Artificial sequence
<220> FEATURE:
<223> OTHER INFORMATION: synthetic sequence

<400> SEQUENCE: 79
ccagggtttt cccagtcacg gcctaaagga actaactcca ctc                         43

<210> SEQ ID NO 80
<211> LENGTH: 44
<212> TYPE: DNA
<213> ORGANISM: Artificial sequence
<220> FEATURE:
<223> OTHER INFORMATION: synthetic sequence

<400> SEQUENCE: 80
ccagggtttt cccagtcacg ctgagatgct aaattcatcc ttct                        44

<210> SEQ ID NO 81
<211> LENGTH: 42
<212> TYPE: DNA
<213> ORGANISM: Artificial sequence
<220> FEATURE:
<223> OTHER INFORMATION: synthetic sequence

<400> SEQUENCE: 81
ccagggtttt cccagtcacg ctcagatgcc caatcagtcg ca                          42

<210> SEQ ID NO 82
<211> LENGTH: 42
<212> TYPE: DNA
<213> ORGANISM: Artificial sequence
<220> FEATURE:
<223> OTHER INFORMATION: synthetic sequence

<400> SEQUENCE: 82
ccagggtttt cccagtcacc agtcggccta acaattcttt ct                          42

<210> SEQ ID NO 83
<211> LENGTH: 45
<212> TYPE: DNA
<213> ORGANISM: Artificial sequence
<220> FEATURE:
<223> OTHER INFORMATION: synthetic sequence

<400> SEQUENCE: 83
ccagggtttt cccagtcacc gagagaagaa gtcatctttt tctct                       45
```

-continued

<210> SEQ ID NO 84
<211> LENGTH: 43
<212> TYPE: DNA
<213> ORGANISM: Artificial sequence
<220> FEATURE:
<223> OTHER INFORMATION: synthetic sequence

<400> SEQUENCE: 84
ccagggtttt cccagtcacc catcagtcat cccaacttat cct                          43

<210> SEQ ID NO 85
<211> LENGTH: 41
<212> TYPE: DNA
<213> ORGANISM: Artificial sequence
<220> FEATURE:
<223> OTHER INFORMATION: synthetic sequence

<400> SEQUENCE: 85
ccagggtttt cccagtcacc ctccagctca ctctgcagcc t                            41

<210> SEQ ID NO 86
<211> LENGTH: 43
<212> TYPE: DNA
<213> ORGANISM: Artificial sequence
<220> FEATURE:
<223> OTHER INFORMATION: synthetic sequence

<400> SEQUENCE: 86
ccagggtttt cccagtcacc agctaagtgt tcctcgaact cac                          43

<210> SEQ ID NO 87
<211> LENGTH: 43
<212> TYPE: DNA
<213> ORGANISM: Artificial sequence
<220> FEATURE:
<223> OTHER INFORMATION: synthetic sequence

<400> SEQUENCE: 87
ccagggtttt cccagtcacg ctgagtgtcc ttcaaactca cct                          43

<210> SEQ ID NO 88
<211> LENGTH: 42
<212> TYPE: DNA
<213> ORGANISM: Artificial sequence
<220> FEATURE:
<223> OTHER INFORMATION: synthetic sequence

<400> SEQUENCE: 88
ccagggtttt cccagtcacg gatacagggt ctcacggaag aa                           42

<210> SEQ ID NO 89
<211> LENGTH: 43
<212> TYPE: DNA
<213> ORGANISM: Artificial sequence
<220> FEATURE:
<223> OTHER INFORMATION: synthetic sequence

<400> SEQUENCE: 89
ccagggtttt cccagtcacc aagtttccaa tcagccggcc aaa                          43

<210> SEQ ID NO 90
<211> LENGTH: 40
<212> TYPE: DNA
<213> ORGANISM: Artificial sequence
<220> FEATURE:
<223> OTHER INFORMATION: synthetic sequence -continued

<400> SEQUENCE: 90
ccagggtttt cccagtcacg cttccaggcc gaaggacgac                                    40

<210> SEQ ID NO 91
<211> LENGTH: 43
<212> TYPE: DNA
<213> ORGANISM: Artificial sequence
<220> FEATURE:
<223> OTHER INFORMATION: synthetic sequence

<400> SEQUENCE: 91
ccagggtttt cccagtcacc ctggctattg cctctgacag aaa                               43

<210> SEQ ID NO 92
<211> LENGTH: 45
<212> TYPE: DNA
<213> ORGANISM: Artificial sequence
<220> FEATURE:
<223> OTHER INFORMATION: synthetic sequence

<400> SEQUENCE: 92
ccagggtttt cccagtcacc agttttcttg aacaaaagcg gcaaa                             45

<210> SEQ ID NO 93
<211> LENGTH: 46
<212> TYPE: DNA
<213> ORGANISM: Artificial sequence
<220> FEATURE:
<223> OTHER INFORMATION: synthetic sequence

<400> SEQUENCE: 93
ccagggtttt cccagtcacg ccgagtttag gaagagtaac tcctct                           46

<210> SEQ ID NO 94
<211> LENGTH: 43
<212> TYPE: DNA
<213> ORGANISM: Artificial sequence
<220> FEATURE:
<223> OTHER INFORMATION: synthetic sequence

<400> SEQUENCE: 94
ccagggtttt cccagtcacc agaagccaaa aagttccatc gga                              43

<210> SEQ ID NO 95
<211> LENGTH: 45
<212> TYPE: DNA
<213> ORGANISM: Artificial sequence
<220> FEATURE:
<223> OTHER INFORMATION: synthetic sequence

<400> SEQUENCE: 95
ccagggtttt cccagtcact caaatccatc agccttatca tttca                            45

<210> SEQ ID NO 96
<211> LENGTH: 44
<212> TYPE: DNA
<213> ORGANISM: Artificial sequence
<220> FEATURE:
<223> OTHER INFORMATION: synthetic sequence

<400> SEQUENCE: 96
ccagggtttt cccagtcacc aartccatca gccttgtcat ttca                             44

<210> SEQ ID NO 97

<211> LENGTH: 48
<212> TYPE: DNA
<213> ORGANISM: Artificial sequence
<220> FEATURE:
<223> OTHER INFORMATION: synthetic sequence

<400> SEQUENCE: 97
ccagggtttt cccagtcacg attcacaatc ttcttcaata aaagggag                48

<210> SEQ ID NO 98
<211> LENGTH: 44
<212> TYPE: DNA
<213> ORGANISM: Artificial sequence
<220> FEATURE:
<223> OTHER INFORMATION: synthetic sequence

<400> SEQUENCE: 98
ccagggtttt cccagtcacc gcrgctcttt gcacatttcc tcct                    44

<210> SEQ ID NO 99
<211> LENGTH: 42
<212> TYPE: DNA
<213> ORGANISM: Artificial sequence
<220> FEATURE:
<223> OTHER INFORMATION: synthetic sequence

<400> SEQUENCE: 99
ccagggtttt cccagtcacc ctcaacagtc actaagggac gt                      42

<210> SEQ ID NO 100
<211> LENGTH: 42
<212> TYPE: DNA
<213> ORGANISM: Artificial sequence
<220> FEATURE:
<223> OTHER INFORMATION: synthetic sequence

<400> SEQUENCE: 100
ccagggtttt cccagtcacc agctccttcc atctgcagaa gt                      42

<210> SEQ ID NO 101
<211> LENGTH: 45
<212> TYPE: DNA
<213> ORGANISM: Artificial sequence
<220> FEATURE:
<223> OTHER INFORMATION: synthetic sequence

<400> SEQUENCE: 101
ccagggtttt cccagtcacc tcagcaactc tggataaaga tgcta                   45

<210> SEQ ID NO 102
<211> LENGTH: 44
<212> TYPE: DNA
<213> ORGANISM: Artificial sequence
<220> FEATURE:
<223> OTHER INFORMATION: synthetic sequence

<400> SEQUENCE: 102
ccagggtttt cccagtcact ggataagaaa gccaaacgat tctc                    44

<210> SEQ ID NO 103
<211> LENGTH: 44
<212> TYPE: DNA
<213> ORGANISM: Artificial sequence
<220> FEATURE:
<223> OTHER INFORMATION: synthetic sequence

<400> SEQUENCE: 103

-continued

```
ccagggtttt cccagtcacg cttygaggct gagttcagca agag                    44

<210> SEQ ID NO 104
<211> LENGTH: 42
<212> TYPE: DNA
<213> ORGANISM: Artificial sequence
<220> FEATURE:
<223> OTHER INFORMATION: synthetic sequence

<400> SEQUENCE: 104
ccagggtttt cccagtcacg agccaccctt gacacytcca gc                      42

<210> SEQ ID NO 105
<211> LENGTH: 44
<212> TYPE: DNA
<213> ORGANISM: Artificial sequence
<220> FEATURE:
<223> OTHER INFORMATION: synthetic sequence

<400> SEQUENCE: 105
ccagggtttt cccagtcact ttacagctca cctcaataga gcca                    44

<210> SEQ ID NO 106
<211> LENGTH: 44
<212> TYPE: DNA
<213> ORGANISM: Artificial sequence
<220> FEATURE:
<223> OTHER INFORMATION: synthetic sequence

<400> SEQUENCE: 106
ccagggtttt cccagtcacc agctcaggtc aatagagcca gcct                    44

<210> SEQ ID NO 107
<211> LENGTH: 42
<212> TYPE: DNA
<213> ORGANISM: Artificial sequence
<220> FEATURE:
<223> OTHER INFORMATION: synthetic sequence

<400> SEQUENCE: 107
ccagggtttt cccagtcacc tcacctcaat aaggccagcc tg                      42

<210> SEQ ID NO 108
<211> LENGTH: 43
<212> TYPE: DNA
<213> ORGANISM: Artificial sequence
<220> FEATURE:
<223> OTHER INFORMATION: synthetic sequence

<400> SEQUENCE: 108
ccagggtttt cccagtcacc tcaatagagc cagcctgcat gtt                     43

<210> SEQ ID NO 109
<211> LENGTH: 45
<212> TYPE: DNA
<213> ORGANISM: Artificial sequence
<220> FEATURE:
<223> OTHER INFORMATION: synthetic sequence

<400> SEQUENCE: 109
ccagggtttt cccagtcacc tcaataaagc cagtctgcat ttctc                   45

<210> SEQ ID NO 110
<211> LENGTH: 41
<212> TYPE: DNA
```

<213> ORGANISM: Artificial sequence
<220> FEATURE:
<223> OTHER INFORMATION: synthetic sequence

<400> SEQUENCE: 110
ccagggtttt cccagtcacc cagcctgcat acttccctgc a 41

<210> SEQ ID NO 111
<211> LENGTH: 43
<212> TYPE: DNA
<213> ORGANISM: Artificial sequence
<220> FEATURE:
<223> OTHER INFORMATION: synthetic sequence

<400> SEQUENCE: 111
ccagggtttt cccagtcacg gataagaaag ccaaacgctt ctc 43

<210> SEQ ID NO 112
<211> LENGTH: 44
<212> TYPE: DNA
<213> ORGANISM: Artificial sequence
<220> FEATURE:
<223> OTHER INFORMATION: synthetic sequence

<400> SEQUENCE: 112
ccagggtttt cccagtcaca gaaaaccaaa cacctttccc tgca 44

<210> SEQ ID NO 113
<211> LENGTH: 47
<212> TYPE: DNA
<213> ORGANISM: Artificial sequence
<220> FEATURE:
<223> OTHER INFORMATION: synthetic sequence

<400> SEQUENCE: 113
ccagggtttt cccagtcacg gttaaagtca acattcaatt ctaagga 47

<210> SEQ ID NO 114
<211> LENGTH: 45
<212> TYPE: DNA
<213> ORGANISM: Artificial sequence
<220> FEATURE:
<223> OTHER INFORMATION: synthetic sequence

<400> SEQUENCE: 114
ccagggtttt cccagtcacc taaagtcagc atttgattct aagga 45

<210> SEQ ID NO 115
<211> LENGTH: 46
<212> TYPE: DNA
<213> ORGANISM: Artificial sequence
<220> FEATURE:
<223> OTHER INFORMATION: synthetic sequence

<400> SEQUENCE: 115
ccagggtttt cccagtcacc actgtcytac tgaacaagaa agacaa 46

<210> SEQ ID NO 116
<211> LENGTH: 46
<212> TYPE: DNA
<213> ORGANISM: Artificial sequence
<220> FEATURE:
<223> OTHER INFORMATION: synthetic sequence

<400> SEQUENCE: 116
ccagggtttt cccagtcacc atctctgttt atctctgctg accgga 46

```
<210> SEQ ID NO 117
<211> LENGTH: 42
<212> TYPE: DNA
<213> ORGANISM: Artificial sequence
<220> FEATURE:
<223> OTHER INFORMATION: synthetic sequence

<400> SEQUENCE: 117
ccagggtttt cccagtcacg ccgctcgaat gggtacagtt ac                          42

<210> SEQ ID NO 118
<211> LENGTH: 25
<212> TYPE: DNA
<213> ORGANISM: Artificial sequence
<220> FEATURE:
<223> OTHER INFORMATION: synthetic sequence

<400> SEQUENCE: 118
ctgcttttga tggctcaaac aagga                                             25

<210> SEQ ID NO 119
<211> LENGTH: 25
<212> TYPE: DNA
<213> ORGANISM: Artificial sequence
<220> FEATURE:
<223> OTHER INFORMATION: synthetic sequence

<400> SEQUENCE: 119
cctgagaccg aggatctttt aactg                                             25

<210> SEQ ID NO 120
<211> LENGTH: 54
<212> TYPE: DNA
<213> ORGANISM: Artificial sequence
<220> FEATURE:
<223> OTHER INFORMATION: synthetic sequence

<400> SEQUENCE: 120
ctgctgaacc gctcttccga tctatgttca ccttgggtgg agtcacattt ctca            54

<210> SEQ ID NO 121
<211> LENGTH: 54
<212> TYPE: DNA
<213> ORGANISM: Artificial sequence
<220> FEATURE:
<223> OTHER INFORMATION: synthetic sequence

<400> SEQUENCE: 121
ctgctgaacc gctcttccga tcttacagga ccttgggtgg agtcacattt ctca            54

<210> SEQ ID NO 122
<211> LENGTH: 54
<212> TYPE: DNA
<213> ORGANISM: Artificial sequence
<220> FEATURE:
<223> OTHER INFORMATION: synthetic sequence

<400> SEQUENCE: 122
ctgctgaacc gctcttccga tctgattata ccttgggtgg agtcacattt ctca            54

<210> SEQ ID NO 123
<211> LENGTH: 54
<212> TYPE: DNA
<213> ORGANISM: Artificial sequence
<220> FEATURE:
```

-continued

```
<223> OTHER INFORMATION: synthetic sequence

<400> SEQUENCE: 123
ctgctgaacc gctcttccga tctcacctgt ccttgggtgg agtcacattt ctca                54

<210> SEQ ID NO 124
<211> LENGTH: 54
<212> TYPE: DNA
<213> ORGANISM: Artificial sequence
<220> FEATURE:
<223> OTHER INFORMATION: synthetic sequence

<400> SEQUENCE: 124
ctgctgaacc gctcttccga tctagaccgc ccttgggtgg agtcacattt ctca                54

<210> SEQ ID NO 125
<211> LENGTH: 54
<212> TYPE: DNA
<213> ORGANISM: Artificial sequence
<220> FEATURE:
<223> OTHER INFORMATION: synthetic sequence

<400> SEQUENCE: 125
ctgctgaacc gctcttccga tcttgactta ccttgggtgg agtcacattt ctca                54

<210> SEQ ID NO 126
<211> LENGTH: 54
<212> TYPE: DNA
<213> ORGANISM: Artificial sequence
<220> FEATURE:
<223> OTHER INFORMATION: synthetic sequence

<400> SEQUENCE: 126
ctgctgaacc gctcttccga tctgtgctag ccttgggtgg agtcacattt ctca                54

<210> SEQ ID NO 127
<211> LENGTH: 54
<212> TYPE: DNA
<213> ORGANISM: Artificial sequence
<220> FEATURE:
<223> OTHER INFORMATION: synthetic sequence

<400> SEQUENCE: 127
ctgctgaacc gctcttccga tctctgacgt ccttgggtgg agtcacattt ctca                54

<210> SEQ ID NO 128
<211> LENGTH: 54
<212> TYPE: DNA
<213> ORGANISM: Artificial sequence
<220> FEATURE:
<223> OTHER INFORMATION: synthetic sequence

<400> SEQUENCE: 128
ctgctgaacc gctcttccga tctacggcta ccttgggtgg agtcacattt ctca                54

<210> SEQ ID NO 129
<211> LENGTH: 54
<212> TYPE: DNA
<213> ORGANISM: Artificial sequence
<220> FEATURE:
<223> OTHER INFORMATION: synthetic sequence

<400> SEQUENCE: 129
ctgctgaacc gctcttccga tcttcgaatg ccttgggtgg agtcacattt ctca                54
```

```
<210> SEQ ID NO 130
<211> LENGTH: 54
<212> TYPE: DNA
<213> ORGANISM: Artificial sequence
<220> FEATURE:
<223> OTHER INFORMATION: synthetic sequence

<400> SEQUENCE: 130
ctgctgaacc gctcttccga tctgcccaac ccttgggtgg agtcacattt ctca            54

<210> SEQ ID NO 131
<211> LENGTH: 54
<212> TYPE: DNA
<213> ORGANISM: Artificial sequence
<220> FEATURE:
<223> OTHER INFORMATION: synthetic sequence

<400> SEQUENCE: 131
ctgctgaacc gctcttccga tctcggagac ccttgggtgg agtcacattt ctca            54

<210> SEQ ID NO 132
<211> LENGTH: 53
<212> TYPE: DNA
<213> ORGANISM: Artificial sequence
<220> FEATURE:
<223> OTHER INFORMATION: synthetic sequence

<400> SEQUENCE: 132
ctgctgaacc gctcttccga tctatgttca gtacacagca ggttctgggt tct             53

<210> SEQ ID NO 133
<211> LENGTH: 53
<212> TYPE: DNA
<213> ORGANISM: Artificial sequence
<220> FEATURE:
<223> OTHER INFORMATION: synthetic sequence

<400> SEQUENCE: 133
ctgctgaacc gctcttccga tcttacagga gtacacagca ggttctgggt tct             53

<210> SEQ ID NO 134
<211> LENGTH: 53
<212> TYPE: DNA
<213> ORGANISM: Artificial sequence
<220> FEATURE:
<223> OTHER INFORMATION: synthetic sequence

<400> SEQUENCE: 134
ctgctgaacc gctcttccga tctgattata gtacacagca ggttctgggt tct             53

<210> SEQ ID NO 135
<211> LENGTH: 53
<212> TYPE: DNA
<213> ORGANISM: Artificial sequence
<220> FEATURE:
<223> OTHER INFORMATION: synthetic sequence

<400> SEQUENCE: 135
ctgctgaacc gctcttccga tctcacctgt gtacacagca ggttctgggt tct             53

<210> SEQ ID NO 136
<211> LENGTH: 53
<212> TYPE: DNA
<213> ORGANISM: Artificial sequence
<220> FEATURE:
<223> OTHER INFORMATION: synthetic sequence
```

-continued

<400> SEQUENCE: 136
ctgctgaacc gctcttccga tctagaccgc gtacacagca ggttctgggt tct          53

<210> SEQ ID NO 137
<211> LENGTH: 53
<212> TYPE: DNA
<213> ORGANISM: Artificial sequence
<220> FEATURE:
<223> OTHER INFORMATION: synthetic sequence

<400> SEQUENCE: 137
ctgctgaacc gctcttccga tcttgactta gtacacagca ggttctgggt tct          53

<210> SEQ ID NO 138
<211> LENGTH: 53
<212> TYPE: DNA
<213> ORGANISM: Artificial sequence
<220> FEATURE:
<223> OTHER INFORMATION: synthetic sequence

<400> SEQUENCE: 138
ctgctgaacc gctcttccga tctgtgctag gtacacagca ggttctgggt tct          53

<210> SEQ ID NO 139
<211> LENGTH: 53
<212> TYPE: DNA
<213> ORGANISM: Artificial sequence
<220> FEATURE:
<223> OTHER INFORMATION: synthetic sequence

<400> SEQUENCE: 139
ctgctgaacc gctcttccga tctctgacgt gtacacagca ggttctgggt tct          53

<210> SEQ ID NO 140
<211> LENGTH: 53
<212> TYPE: DNA
<213> ORGANISM: Artificial sequence
<220> FEATURE:
<223> OTHER INFORMATION: synthetic sequence

<400> SEQUENCE: 140
ctgctgaacc gctcttccga tctacggcta gtacacagca ggttctgggt tct          53

<210> SEQ ID NO 141
<211> LENGTH: 53
<212> TYPE: DNA
<213> ORGANISM: Artificial sequence
<220> FEATURE:
<223> OTHER INFORMATION: synthetic sequence

<400> SEQUENCE: 141
ctgctgaacc gctcttccga tcttcgaatg gtacacagca ggttctgggt tct          53

<210> SEQ ID NO 142
<211> LENGTH: 53
<212> TYPE: DNA
<213> ORGANISM: Artificial sequence
<220> FEATURE:
<223> OTHER INFORMATION: synthetic sequence

<400> SEQUENCE: 142
ctgctgaacc gctcttccga tctgcccaac gtacacagca ggttctgggt tct          53

<210> SEQ ID NO 143
<211> LENGTH: 53

```
<212> TYPE: DNA
<213> ORGANISM: Artificial sequence
<220> FEATURE:
<223> OTHER INFORMATION: synthetic sequence

<400> SEQUENCE: 143
ctgctgaacc gctcttccga tctcggagac gtacacagca ggttctgggt tct              53

<210> SEQ ID NO 144
<211> LENGTH: 15
<212> TYPE: PRT
<213> ORGANISM: Artificial sequence
<220> FEATURE:
<223> OTHER INFORMATION: synthetic sequence

<400> SEQUENCE: 144

Cys Ala Ser Gly Asp Ala Gly Gly Gly Gln Asn Thr Leu Tyr Phe
1               5                  10                  15

<210> SEQ ID NO 145
<211> LENGTH: 15
<212> TYPE: PRT
<213> ORGANISM: Artificial sequence
<220> FEATURE:
<223> OTHER INFORMATION: synthetic sequence

<400> SEQUENCE: 145

Cys Ala Ser Ser Leu Asp Gln Gly Trp Asp Glu Arg Leu Phe Phe
1               5                  10                  15

<210> SEQ ID NO 146
<211> LENGTH: 14
<212> TYPE: PRT
<213> ORGANISM: Artificial sequence
<220> FEATURE:
<223> OTHER INFORMATION: synthetic sequence

<400> SEQUENCE: 146

Cys Ala Ser Ser Leu Glu Gly His Gln Asp Thr Gln Tyr Phe
1               5                  10

<210> SEQ ID NO 147
<211> LENGTH: 14
<212> TYPE: PRT
<213> ORGANISM: Artificial sequence
<220> FEATURE:
<223> OTHER INFORMATION: synthetic sequence

<400> SEQUENCE: 147

Cys Ala Ser Ser Leu Glu Thr Ala Asn Thr Glu Val Phe Phe
1               5                  10

<210> SEQ ID NO 148
<211> LENGTH: 14
<212> TYPE: PRT
<213> ORGANISM: Artificial sequence
<220> FEATURE:
<223> OTHER INFORMATION: synthetic sequence

<400> SEQUENCE: 148

Cys Ala Ala Ser Glu Gly Gln Gly Gly Arg Ala Leu Ile Phe
1               5                  10

<210> SEQ ID NO 149
<211> LENGTH: 13
<212> TYPE: PRT
<213> ORGANISM: Artificial sequence
```

```
<220> FEATURE:
<223> OTHER INFORMATION: synthetic sequence

<400> SEQUENCE: 149

Cys Ala Leu Arg Asn Tyr Asn Gln Gly Lys Leu Ile Phe
1               5                   10

<210> SEQ ID NO 150
<211> LENGTH: 14
<212> TYPE: PRT
<213> ORGANISM: Artificial sequence
<220> FEATURE:
<223> OTHER INFORMATION: synthetic sequence

<400> SEQUENCE: 150

Cys Ala Ala Ser Gly Ala Asn Asn Asn Ala Pro Arg Phe
1               5                   10

<210> SEQ ID NO 151
<211> LENGTH: 14
<212> TYPE: PRT
<213> ORGANISM: Artificial sequence
<220> FEATURE:
<223> OTHER INFORMATION: synthetic sequence

<400> SEQUENCE: 151

Cys Ala Val Ser Ala Gly Thr Asn Ala Tyr Lys Val Ile Phe
1               5                   10

<210> SEQ ID NO 152
<211> LENGTH: 13
<212> TYPE: PRT
<213> ORGANISM: Artificial sequence
<220> FEATURE:
<223> OTHER INFORMATION: synthetic sequence

<400> SEQUENCE: 152

Cys Ala Ser Ser Gln Lys Asn Thr Gly Gln Leu Tyr Phe
1               5                   10

<210> SEQ ID NO 153
<211> LENGTH: 15
<212> TYPE: PRT
<213> ORGANISM: Artificial sequence
<220> FEATURE:
<223> OTHER INFORMATION: synthetic sequence

<400> SEQUENCE: 153

Cys Ala Ser Ser Pro Gly Gln Val Ser Asn Glu Arg Leu Phe Phe
1               5                   10                  15

<210> SEQ ID NO 154
<211> LENGTH: 14
<212> TYPE: PRT
<213> ORGANISM: Artificial sequence
<220> FEATURE:
<223> OTHER INFORMATION: synthetic sequence

<400> SEQUENCE: 154

Cys Ala Ser Ser Pro Thr Asp Ala Asn Thr Glu Val Phe Phe
1               5                   10

<210> SEQ ID NO 155
<211> LENGTH: 15
<212> TYPE: PRT
<213> ORGANISM: Artificial sequence
<220> FEATURE:
```

-continued

```
<223> OTHER INFORMATION: synthetic sequence

<400> SEQUENCE: 155

Cys Ala Ser Ser Leu Asn Pro Gly Ala Asn Thr Glu Val Phe Phe
1               5                   10                  15

<210> SEQ ID NO 156
<211> LENGTH: 14
<212> TYPE: PRT
<213> ORGANISM: Artificial sequence
<220> FEATURE:
<223> OTHER INFORMATION: synthetic sequence

<400> SEQUENCE: 156

Cys Ala Ser Ser Tyr Trp Gly Gly Ser Tyr Glu Gln Tyr Phe
1               5                   10

<210> SEQ ID NO 157
<211> LENGTH: 16
<212> TYPE: PRT
<213> ORGANISM: Artificial sequence
<220> FEATURE:
<223> OTHER INFORMATION: synthetic sequence

<400> SEQUENCE: 157

Cys Ala Ser Ser Ile Thr Pro Leu Gly Gly Leu Glu Thr Leu Tyr Phe
1               5                   10                  15

<210> SEQ ID NO 158
<211> LENGTH: 11
<212> TYPE: PRT
<213> ORGANISM: Artificial sequence
<220> FEATURE:
<223> OTHER INFORMATION: synthetic sequence

<400> SEQUENCE: 158

Cys Ala Ser Thr Asn Arg Gly Glu Val Phe Phe
1               5                   10

<210> SEQ ID NO 159
<211> LENGTH: 14
<212> TYPE: PRT
<213> ORGANISM: Artificial sequence
<220> FEATURE:
<223> OTHER INFORMATION: synthetic sequence

<400> SEQUENCE: 159

Cys Ala Ser Arg Ala Gly Gln Gly Ala Asp Thr Gln Tyr Phe
1               5                   10

<210> SEQ ID NO 160
<211> LENGTH: 15
<212> TYPE: PRT
<213> ORGANISM: Artificial sequence
<220> FEATURE:
<223> OTHER INFORMATION: synthetic sequence

<400> SEQUENCE: 160

Cys Ala Ser Ser Asp Arg Gly Leu Gly Gly Tyr Glu Gln Tyr Phe
1               5                   10                  15

<210> SEQ ID NO 161
<211> LENGTH: 13
<212> TYPE: PRT
<213> ORGANISM: Artificial sequence
<220> FEATURE:
<223> OTHER INFORMATION: synthetic sequence
```

-continued

<400> SEQUENCE: 161

Cys Ala Leu Glu His Asn Tyr Ala Gln Gly Leu Thr Phe
1               5                   10

<210> SEQ ID NO 162
<211> LENGTH: 15
<212> TYPE: PRT
<213> ORGANISM: Artificial sequence
<220> FEATURE:
<223> OTHER INFORMATION: synthetic sequence

<400> SEQUENCE: 162

Cys Ala Leu Arg Pro Pro Gly Ala Gly Asn Tyr Lys Tyr Val Phe
1               5                   10                  15

<210> SEQ ID NO 163
<211> LENGTH: 11
<212> TYPE: PRT
<213> ORGANISM: Artificial sequence
<220> FEATURE:
<223> OTHER INFORMATION: synthetic sequence

<400> SEQUENCE: 163

Cys Ala Thr Asp Pro Thr Asn Lys Val Val Phe
1               5                   10

<210> SEQ ID NO 164
<211> LENGTH: 14
<212> TYPE: PRT
<213> ORGANISM: Artificial sequence
<220> FEATURE:
<223> OTHER INFORMATION: synthetic sequence

<400> SEQUENCE: 164

Cys Ala Thr Asp Met Asn Tyr Asn Gln Gly Lys Leu Ile Phe
1               5                   10

<210> SEQ ID NO 165
<211> LENGTH: 12
<212> TYPE: PRT
<213> ORGANISM: Artificial sequence
<220> FEATURE:
<223> OTHER INFORMATION: synthetic sequence

<400> SEQUENCE: 165

Cys Ala Pro Gly Tyr Ser Asn Asn Arg Leu Thr Leu
1               5                   10

<210> SEQ ID NO 166
<211> LENGTH: 12
<212> TYPE: PRT
<213> ORGANISM: Artificial sequence
<220> FEATURE:
<223> OTHER INFORMATION: synthetic sequence

<400> SEQUENCE: 166

Cys Ala Leu Gly Gly Ser Asn Ala Lys Leu Thr Phe
1               5                   10

<210> SEQ ID NO 167
<211> LENGTH: 14
<212> TYPE: PRT
<213> ORGANISM: Artificial sequence
<220> FEATURE:
<223> OTHER INFORMATION: synthetic sequence

```
<400> SEQUENCE: 167

Cys Ala Leu Ser Asp Pro Gly Asn Asn Asn Ala Pro Arg Phe
1               5                   10

<210> SEQ ID NO 168
<211> LENGTH: 14
<212> TYPE: PRT
<213> ORGANISM: Artificial sequence
<220> FEATURE:
<223> OTHER INFORMATION: synthetic sequence

<400> SEQUENCE: 168

Cys Ala Leu Ser Glu Ser Ser Gly Ser Trp Gln Leu Ile Phe
1               5                   10

<210> SEQ ID NO 169
<211> LENGTH: 14
<212> TYPE: PRT
<213> ORGANISM: Artificial sequence
<220> FEATURE:
<223> OTHER INFORMATION: synthetic sequence

<400> SEQUENCE: 169

Cys Ala Val Asn Ser Ser Asn Met Gly Tyr Lys Leu Thr Phe
1               5                   10

<210> SEQ ID NO 170
<211> LENGTH: 11
<212> TYPE: PRT
<213> ORGANISM: Artificial sequence
<220> FEATURE:
<223> OTHER INFORMATION: synthetic sequence

<400> SEQUENCE: 170

Cys Ala Val Asp Ser Asn Tyr Gln Leu Ile Trp
1               5                   10

<210> SEQ ID NO 171
<211> LENGTH: 11
<212> TYPE: PRT
<213> ORGANISM: Artificial sequence
<220> FEATURE:
<223> OTHER INFORMATION: synthetic sequence

<400> SEQUENCE: 171

Cys Ala Leu Ser Asp Tyr Asn Arg Ile Phe Phe
1               5                   10

<210> SEQ ID NO 172
<211> LENGTH: 15
<212> TYPE: PRT
<213> ORGANISM: Artificial sequence
<220> FEATURE:
<223> OTHER INFORMATION: synthetic sequence

<400> SEQUENCE: 172

Cys Ala Ala Ser Val Asn Thr Glu Gly Ala Asp Arg Leu Thr Phe
1               5                   10                  15

<210> SEQ ID NO 173
<211> LENGTH: 12
<212> TYPE: PRT
<213> ORGANISM: Artificial sequence
<220> FEATURE:
<223> OTHER INFORMATION: synthetic sequence

<400> SEQUENCE: 173
```

```
Cys Ala Ala Ser Ser Gly Ser Trp Gln Leu Ile Phe
1               5               10
```

<210> SEQ ID NO 174
<211> LENGTH: 9
<212> TYPE: PRT
<213> ORGANISM: Artificial sequence
<220> FEATURE:
<223> OTHER INFORMATION: synthetic sequence

<400> SEQUENCE: 174

```
Cys Ala Met Ala Gly Lys Leu Ile Phe
1               5
```

<210> SEQ ID NO 175
<211> LENGTH: 8
<212> TYPE: PRT
<213> ORGANISM: Artificial sequence
<220> FEATURE:
<223> OTHER INFORMATION: synthetic sequence

<400> SEQUENCE: 175

```
Ala Ala Ala Thr Leu Val Ser Leu
1               5
```

<210> SEQ ID NO 176
<211> LENGTH: 8
<212> TYPE: PRT
<213> ORGANISM: Artificial sequence
<220> FEATURE:
<223> OTHER INFORMATION: synthetic sequence

<400> SEQUENCE: 176

```
Ala Ala Phe Val Gly Ala Ala Ala
1               5
```

<210> SEQ ID NO 177
<211> LENGTH: 8
<212> TYPE: PRT
<213> ORGANISM: Artificial sequence
<220> FEATURE:
<223> OTHER INFORMATION: synthetic sequence

<400> SEQUENCE: 177

```
Ala Ala Thr Leu Val Ser Leu Leu
1               5
```

<210> SEQ ID NO 178
<211> LENGTH: 8
<212> TYPE: PRT
<213> ORGANISM: Artificial sequence
<220> FEATURE:
<223> OTHER INFORMATION: synthetic sequence

<400> SEQUENCE: 178

```
Ala Ala Thr Tyr Asn Phe Ala Val
1               5
```

<210> SEQ ID NO 179
<211> LENGTH: 8
<212> TYPE: PRT
<213> ORGANISM: Artificial sequence
<220> FEATURE:
<223> OTHER INFORMATION: synthetic sequence

<400> SEQUENCE: 179

-continued

Ala Cys Ser Ala Val Pro Val Tyr
1               5

<210> SEQ ID NO 180
<211> LENGTH: 8
<212> TYPE: PRT
<213> ORGANISM: Artificial sequence
<220> FEATURE:
<223> OTHER INFORMATION: synthetic sequence

<400> SEQUENCE: 180

Ala Asp Ala Arg Met Tyr Gly Val
1               5

<210> SEQ ID NO 181
<211> LENGTH: 8
<212> TYPE: PRT
<213> ORGANISM: Artificial sequence
<220> FEATURE:
<223> OTHER INFORMATION: synthetic sequence

<400> SEQUENCE: 181

Ala Glu Phe Gln Met Thr Phe His
1               5

<210> SEQ ID NO 182
<211> LENGTH: 8
<212> TYPE: PRT
<213> ORGANISM: Artificial sequence
<220> FEATURE:
<223> OTHER INFORMATION: synthetic sequence

<400> SEQUENCE: 182

Ala Glu Gly Phe Tyr Thr Thr Gly
1               5

<210> SEQ ID NO 183
<211> LENGTH: 8
<212> TYPE: PRT
<213> ORGANISM: Artificial sequence
<220> FEATURE:
<223> OTHER INFORMATION: synthetic sequence

<400> SEQUENCE: 183

Ala Phe Pro Gly Lys Val Cys Gly
1               5

<210> SEQ ID NO 184
<211> LENGTH: 8
<212> TYPE: PRT
<213> ORGANISM: Artificial sequence
<220> FEATURE:
<223> OTHER INFORMATION: synthetic sequence

<400> SEQUENCE: 184

Ala Phe Pro Ser Lys Thr Ser Ala
1               5

<210> SEQ ID NO 185
<211> LENGTH: 8
<212> TYPE: PRT
<213> ORGANISM: Artificial sequence
<220> FEATURE:
<223> OTHER INFORMATION: synthetic sequence

<400> SEQUENCE: 185

Ala Phe Gln Tyr Val Ile Tyr Gly

```
1               5

<210> SEQ ID NO 186
<211> LENGTH: 8
<212> TYPE: PRT
<213> ORGANISM: Artificial sequence
<220> FEATURE:
<223> OTHER INFORMATION: synthetic sequence

<400> SEQUENCE: 186

Ala Phe Val Gly Ala Ala Ala Thr
1               5

<210> SEQ ID NO 187
<211> LENGTH: 8
<212> TYPE: PRT
<213> ORGANISM: Artificial sequence
<220> FEATURE:
<223> OTHER INFORMATION: synthetic sequence

<400> SEQUENCE: 187

Ala His Ser Leu Glu Arg Val Cys
1               5

<210> SEQ ID NO 188
<211> LENGTH: 8
<212> TYPE: PRT
<213> ORGANISM: Artificial sequence
<220> FEATURE:
<223> OTHER INFORMATION: synthetic sequence

<400> SEQUENCE: 188

Ala Leu Phe Cys Gly Cys Gly His
1               5

<210> SEQ ID NO 189
<211> LENGTH: 8
<212> TYPE: PRT
<213> ORGANISM: Artificial sequence
<220> FEATURE:
<223> OTHER INFORMATION: synthetic sequence

<400> SEQUENCE: 189

Ala Leu Leu Leu Ala Glu Gly Phe
1               5

<210> SEQ ID NO 190
<211> LENGTH: 8
<212> TYPE: PRT
<213> ORGANISM: Artificial sequence
<220> FEATURE:
<223> OTHER INFORMATION: synthetic sequence

<400> SEQUENCE: 190

Ala Leu Thr Gly Thr Glu Lys Leu
1               5

<210> SEQ ID NO 191
<211> LENGTH: 8
<212> TYPE: PRT
<213> ORGANISM: Artificial sequence
<220> FEATURE:
<223> OTHER INFORMATION: synthetic sequence

<400> SEQUENCE: 191

Ala Leu Thr Val Val Trp Leu Leu
1               5
```

```
<210> SEQ ID NO 192
<211> LENGTH: 8
<212> TYPE: PRT
<213> ORGANISM: Artificial sequence
<220> FEATURE:
<223> OTHER INFORMATION: synthetic sequence

<400> SEQUENCE: 192

Ala Pro Phe Ala Ser Leu Val Ala
1               5

<210> SEQ ID NO 193
<211> LENGTH: 8
<212> TYPE: PRT
<213> ORGANISM: Artificial sequence
<220> FEATURE:
<223> OTHER INFORMATION: synthetic sequence

<400> SEQUENCE: 193

Ala Arg Cys Leu Val Gly Ala Pro
1               5

<210> SEQ ID NO 194
<211> LENGTH: 8
<212> TYPE: PRT
<213> ORGANISM: Artificial sequence
<220> FEATURE:
<223> OTHER INFORMATION: synthetic sequence

<400> SEQUENCE: 194

Ala Arg Met Tyr Gly Val Leu Pro
1               5

<210> SEQ ID NO 195
<211> LENGTH: 9
<212> TYPE: PRT
<213> ORGANISM: Artificial sequence
<220> FEATURE:
<223> OTHER INFORMATION: synthetic sequence

<400> SEQUENCE: 195

Ala Ala Ala Thr Leu Val Ser Leu Leu
1               5

<210> SEQ ID NO 196
<211> LENGTH: 9
<212> TYPE: PRT
<213> ORGANISM: Artificial sequence
<220> FEATURE:
<223> OTHER INFORMATION: synthetic sequence

<400> SEQUENCE: 196

Ala Ala Phe Val Gly Ala Ala Ala Thr
1               5

<210> SEQ ID NO 197
<211> LENGTH: 9
<212> TYPE: PRT
<213> ORGANISM: Artificial sequence
<220> FEATURE:
<223> OTHER INFORMATION: synthetic sequence

<400> SEQUENCE: 197

Ala Ala Thr Leu Val Ser Leu Leu Thr
1               5
```

-continued

```
<210> SEQ ID NO 198
<211> LENGTH: 9
<212> TYPE: PRT
<213> ORGANISM: Artificial sequence
<220> FEATURE:
<223> OTHER INFORMATION: synthetic sequence

<400> SEQUENCE: 198

Ala Ala Thr Tyr Asn Phe Ala Val Leu
1               5

<210> SEQ ID NO 199
<211> LENGTH: 9
<212> TYPE: PRT
<213> ORGANISM: Artificial sequence
<220> FEATURE:
<223> OTHER INFORMATION: synthetic sequence

<400> SEQUENCE: 199

Ala Cys Ser Ala Val Pro Val Tyr Ile
1               5

<210> SEQ ID NO 200
<211> LENGTH: 9
<212> TYPE: PRT
<213> ORGANISM: Artificial sequence
<220> FEATURE:
<223> OTHER INFORMATION: synthetic sequence

<400> SEQUENCE: 200

Ala Asp Ala Arg Met Tyr Gly Val Leu
1               5

<210> SEQ ID NO 201
<211> LENGTH: 9
<212> TYPE: PRT
<213> ORGANISM: Artificial sequence
<220> FEATURE:
<223> OTHER INFORMATION: synthetic sequence

<400> SEQUENCE: 201

Ala Glu Phe Gln Met Thr Phe His Leu
1               5

<210> SEQ ID NO 202
<211> LENGTH: 9
<212> TYPE: PRT
<213> ORGANISM: Artificial sequence
<220> FEATURE:
<223> OTHER INFORMATION: synthetic sequence

<400> SEQUENCE: 202

Ala Glu Gly Phe Tyr Thr Thr Gly Ala
1               5

<210> SEQ ID NO 203
<211> LENGTH: 9
<212> TYPE: PRT
<213> ORGANISM: Artificial sequence
<220> FEATURE:
<223> OTHER INFORMATION: synthetic sequence

<400> SEQUENCE: 203

Ala Phe Pro Gly Lys Val Cys Gly Ser
1               5
```

-continued

```
<210> SEQ ID NO 204
<211> LENGTH: 9
<212> TYPE: PRT
<213> ORGANISM: Artificial sequence
<220> FEATURE:
<223> OTHER INFORMATION: synthetic sequence

<400> SEQUENCE: 204

Ala Phe Pro Ser Lys Thr Ser Ala Ser
1               5

<210> SEQ ID NO 205
<211> LENGTH: 9
<212> TYPE: PRT
<213> ORGANISM: Artificial sequence
<220> FEATURE:
<223> OTHER INFORMATION: synthetic sequence

<400> SEQUENCE: 205

Ala Phe Val Gly Ala Ala Ala Thr Leu
1               5

<210> SEQ ID NO 206
<211> LENGTH: 9
<212> TYPE: PRT
<213> ORGANISM: Artificial sequence
<220> FEATURE:
<223> OTHER INFORMATION: synthetic sequence

<400> SEQUENCE: 206

Ala His Ser Leu Glu Arg Val Cys His
1               5

<210> SEQ ID NO 207
<211> LENGTH: 9
<212> TYPE: PRT
<213> ORGANISM: Artificial sequence
<220> FEATURE:
<223> OTHER INFORMATION: synthetic sequence

<400> SEQUENCE: 207

Ala Leu Phe Cys Gly Cys Gly His Glu
1               5

<210> SEQ ID NO 208
<211> LENGTH: 9
<212> TYPE: PRT
<213> ORGANISM: Artificial sequence
<220> FEATURE:
<223> OTHER INFORMATION: synthetic sequence

<400> SEQUENCE: 208

Ala Leu Leu Leu Ala Glu Gly Phe Tyr
1               5

<210> SEQ ID NO 209
<211> LENGTH: 9
<212> TYPE: PRT
<213> ORGANISM: Artificial sequence
<220> FEATURE:
<223> OTHER INFORMATION: synthetic sequence

<400> SEQUENCE: 209

Ala Leu Thr Gly Thr Glu Lys Leu Ile
1               5

<210> SEQ ID NO 210
```

-continued

```
<211> LENGTH: 9
<212> TYPE: PRT
<213> ORGANISM: Artificial sequence
<220> FEATURE:
<223> OTHER INFORMATION: synthetic sequence

<400> SEQUENCE: 210

Ala Leu Thr Val Val Trp Leu Leu Val
1               5

<210> SEQ ID NO 211
<211> LENGTH: 9
<212> TYPE: PRT
<213> ORGANISM: Artificial sequence
<220> FEATURE:
<223> OTHER INFORMATION: synthetic sequence

<400> SEQUENCE: 211

Ala Pro Phe Ala Ser Leu Val Ala Thr
1               5

<210> SEQ ID NO 212
<211> LENGTH: 9
<212> TYPE: PRT
<213> ORGANISM: Artificial sequence
<220> FEATURE:
<223> OTHER INFORMATION: synthetic sequence

<400> SEQUENCE: 212

Ala Arg Cys Leu Val Gly Ala Pro Phe
1               5

<210> SEQ ID NO 213
<211> LENGTH: 9
<212> TYPE: PRT
<213> ORGANISM: Artificial sequence
<220> FEATURE:
<223> OTHER INFORMATION: synthetic sequence

<400> SEQUENCE: 213

Ala Arg Met Tyr Gly Val Leu Pro Trp
1               5

<210> SEQ ID NO 214
<211> LENGTH: 9
<212> TYPE: PRT
<213> ORGANISM: Artificial sequence
<220> FEATURE:
<223> OTHER INFORMATION: synthetic sequence

<400> SEQUENCE: 214

Ala Ser Phe Phe Phe Leu Tyr Gly Ala
1               5

<210> SEQ ID NO 215
<211> LENGTH: 9
<212> TYPE: PRT
<213> ORGANISM: Artificial sequence
<220> FEATURE:
<223> OTHER INFORMATION: synthetic sequence

<400> SEQUENCE: 215

Ala Ser Ile Gly Ser Leu Cys Ala Asp
1               5

<210> SEQ ID NO 216
<211> LENGTH: 10
```

-continued

```
<212> TYPE: PRT
<213> ORGANISM: Artificial sequence
<220> FEATURE:
<223> OTHER INFORMATION: synthetic sequence

<400> SEQUENCE: 216

Ala Ala Ala Thr Leu Val Ser Leu Leu Thr
1               5                   10

<210> SEQ ID NO 217
<211> LENGTH: 10
<212> TYPE: PRT
<213> ORGANISM: Artificial sequence
<220> FEATURE:
<223> OTHER INFORMATION: synthetic sequence

<400> SEQUENCE: 217

Ala Ala Phe Val Gly Ala Ala Ala Thr Leu
1               5                   10

<210> SEQ ID NO 218
<211> LENGTH: 10
<212> TYPE: PRT
<213> ORGANISM: Artificial sequence
<220> FEATURE:
<223> OTHER INFORMATION: synthetic sequence

<400> SEQUENCE: 218

Ala Ala Thr Leu Val Ser Leu Leu Thr Phe
1               5                   10

<210> SEQ ID NO 219
<211> LENGTH: 10
<212> TYPE: PRT
<213> ORGANISM: Artificial sequence
<220> FEATURE:
<223> OTHER INFORMATION: synthetic sequence

<400> SEQUENCE: 219

Ala Ala Thr Tyr Asn Phe Ala Val Leu Lys
1               5                   10

<210> SEQ ID NO 220
<211> LENGTH: 10
<212> TYPE: PRT
<213> ORGANISM: Artificial sequence
<220> FEATURE:
<223> OTHER INFORMATION: synthetic sequence

<400> SEQUENCE: 220

Ala Cys Ser Ala Val Pro Val Tyr Ile Tyr
1               5                   10

<210> SEQ ID NO 221
<211> LENGTH: 10
<212> TYPE: PRT
<213> ORGANISM: Artificial sequence
<220> FEATURE:
<223> OTHER INFORMATION: synthetic sequence

<400> SEQUENCE: 221

Ala Asp Ala Arg Met Tyr Gly Val Leu Pro
1               5                   10

<210> SEQ ID NO 222
<211> LENGTH: 10
<212> TYPE: PRT
```

-continued

```
<213> ORGANISM: Artificial sequence
<220> FEATURE:
<223> OTHER INFORMATION: synthetic sequence

<400> SEQUENCE: 222

Ala Glu Phe Gln Met Thr Phe His Leu Phe
1               5                   10

<210> SEQ ID NO 223
<211> LENGTH: 10
<212> TYPE: PRT
<213> ORGANISM: Artificial sequence
<220> FEATURE:
<223> OTHER INFORMATION: synthetic sequence

<400> SEQUENCE: 223

Ala Glu Gly Phe Tyr Thr Thr Gly Ala Val
1               5                   10

<210> SEQ ID NO 224
<211> LENGTH: 10
<212> TYPE: PRT
<213> ORGANISM: Artificial sequence
<220> FEATURE:
<223> OTHER INFORMATION: synthetic sequence

<400> SEQUENCE: 224

Ala Phe Pro Gly Lys Val Cys Gly Ser Asn
1               5                   10

<210> SEQ ID NO 225
<211> LENGTH: 10
<212> TYPE: PRT
<213> ORGANISM: Artificial sequence
<220> FEATURE:
<223> OTHER INFORMATION: synthetic sequence

<400> SEQUENCE: 225

Ala Phe Pro Ser Lys Thr Ser Ala Ser Ile
1               5                   10

<210> SEQ ID NO 226
<211> LENGTH: 10
<212> TYPE: PRT
<213> ORGANISM: Artificial sequence
<220> FEATURE:
<223> OTHER INFORMATION: synthetic sequence

<400> SEQUENCE: 226

Ala Phe Gln Tyr Val Ile Tyr Gly Thr Ala
1               5                   10

<210> SEQ ID NO 227
<211> LENGTH: 10
<212> TYPE: PRT
<213> ORGANISM: Artificial sequence
<220> FEATURE:
<223> OTHER INFORMATION: synthetic sequence

<400> SEQUENCE: 227

Ala Phe Val Gly Ala Ala Ala Thr Leu Val
1               5                   10

<210> SEQ ID NO 228
<211> LENGTH: 10
<212> TYPE: PRT
<213> ORGANISM: Artificial sequence
```

-continued

```
<220> FEATURE:
<223> OTHER INFORMATION: synthetic sequence

<400> SEQUENCE: 228

Ala His Ser Leu Glu Arg Val Cys His Cys
1               5                   10

<210> SEQ ID NO 229
<211> LENGTH: 10
<212> TYPE: PRT
<213> ORGANISM: Artificial sequence
<220> FEATURE:
<223> OTHER INFORMATION: synthetic sequence

<400> SEQUENCE: 229

Ala Leu Phe Cys Gly Cys Gly His Glu Ala
1               5                   10

<210> SEQ ID NO 230
<211> LENGTH: 10
<212> TYPE: PRT
<213> ORGANISM: Artificial sequence
<220> FEATURE:
<223> OTHER INFORMATION: synthetic sequence

<400> SEQUENCE: 230

Ala Leu Leu Leu Ala Glu Gly Phe Tyr Thr
1               5                   10

<210> SEQ ID NO 231
<211> LENGTH: 10
<212> TYPE: PRT
<213> ORGANISM: Artificial sequence
<220> FEATURE:
<223> OTHER INFORMATION: synthetic sequence

<400> SEQUENCE: 231

Ala Leu Thr Gly Thr Glu Lys Leu Ile Glu
1               5                   10

<210> SEQ ID NO 232
<211> LENGTH: 10
<212> TYPE: PRT
<213> ORGANISM: Artificial sequence
<220> FEATURE:
<223> OTHER INFORMATION: synthetic sequence

<400> SEQUENCE: 232

Ala Leu Thr Val Val Trp Leu Leu Val Phe
1               5                   10

<210> SEQ ID NO 233
<211> LENGTH: 10
<212> TYPE: PRT
<213> ORGANISM: Artificial sequence
<220> FEATURE:
<223> OTHER INFORMATION: synthetic sequence

<400> SEQUENCE: 233

Ala Pro Phe Ala Ser Leu Val Ala Thr Gly
1               5                   10

<210> SEQ ID NO 234
<211> LENGTH: 10
<212> TYPE: PRT
<213> ORGANISM: Artificial sequence
<220> FEATURE:
```

<223> OTHER INFORMATION: synthetic sequence

<400> SEQUENCE: 234

Ala Arg Cys Leu Val Gly Ala Pro Phe Ala
1               5                   10

<210> SEQ ID NO 235
<211> LENGTH: 10
<212> TYPE: PRT
<213> ORGANISM: Artificial sequence
<220> FEATURE:
<223> OTHER INFORMATION: synthetic sequence

<400> SEQUENCE: 235

Ala Arg Met Tyr Gly Val Leu Pro Trp Asn
1               5                   10

<210> SEQ ID NO 236
<211> LENGTH: 11
<212> TYPE: PRT
<213> ORGANISM: Artificial sequence
<220> FEATURE:
<223> OTHER INFORMATION: synthetic sequence

<400> SEQUENCE: 236

Ala Ala Ala Thr Leu Val Ser Leu Leu Thr Phe
1               5                   10

<210> SEQ ID NO 237
<211> LENGTH: 11
<212> TYPE: PRT
<213> ORGANISM: Artificial sequence
<220> FEATURE:
<223> OTHER INFORMATION: synthetic sequence

<400> SEQUENCE: 237

Ala Ala Phe Val Gly Ala Ala Ala Thr Leu Val
1               5                   10

<210> SEQ ID NO 238
<211> LENGTH: 11
<212> TYPE: PRT
<213> ORGANISM: Artificial sequence
<220> FEATURE:
<223> OTHER INFORMATION: synthetic sequence

<400> SEQUENCE: 238

Ala Ala Thr Leu Val Ser Leu Leu Thr Phe Met
1               5                   10

<210> SEQ ID NO 239
<211> LENGTH: 11
<212> TYPE: PRT
<213> ORGANISM: Artificial sequence
<220> FEATURE:
<223> OTHER INFORMATION: synthetic sequence

<400> SEQUENCE: 239

Ala Ala Thr Tyr Asn Phe Ala Val Leu Lys Leu
1               5                   10

<210> SEQ ID NO 240
<211> LENGTH: 11
<212> TYPE: PRT
<213> ORGANISM: Artificial sequence
<220> FEATURE:
<223> OTHER INFORMATION: synthetic sequence

<400> SEQUENCE: 240

Ala Cys Ser Ala Val Pro Val Tyr Ile Tyr Phe
1               5                   10

<210> SEQ ID NO 241
<211> LENGTH: 11
<212> TYPE: PRT
<213> ORGANISM: Artificial sequence
<220> FEATURE:
<223> OTHER INFORMATION: synthetic sequence

<400> SEQUENCE: 241

Ala Asp Ala Arg Met Tyr Gly Val Leu Pro Trp
1               5                   10

<210> SEQ ID NO 242
<211> LENGTH: 11
<212> TYPE: PRT
<213> ORGANISM: Artificial sequence
<220> FEATURE:
<223> OTHER INFORMATION: synthetic sequence

<400> SEQUENCE: 242

Ala Glu Phe Gln Met Thr Phe His Leu Phe Ile
1               5                   10

<210> SEQ ID NO 243
<211> LENGTH: 11
<212> TYPE: PRT
<213> ORGANISM: Artificial sequence
<220> FEATURE:
<223> OTHER INFORMATION: synthetic sequence

<400> SEQUENCE: 243

Ala Glu Gly Phe Tyr Thr Thr Gly Ala Val Arg
1               5                   10

<210> SEQ ID NO 244
<211> LENGTH: 11
<212> TYPE: PRT
<213> ORGANISM: Artificial sequence
<220> FEATURE:
<223> OTHER INFORMATION: synthetic sequence

<400> SEQUENCE: 244

Ala Phe Pro Gly Lys Val Cys Gly Ser Asn Leu
1               5                   10

<210> SEQ ID NO 245
<211> LENGTH: 11
<212> TYPE: PRT
<213> ORGANISM: Artificial sequence
<220> FEATURE:
<223> OTHER INFORMATION: synthetic sequence

<400> SEQUENCE: 245

Ala Phe Pro Ser Lys Thr Ser Ala Ser Ile Gly
1               5                   10

<210> SEQ ID NO 246
<211> LENGTH: 11
<212> TYPE: PRT
<213> ORGANISM: Artificial sequence
<220> FEATURE:
<223> OTHER INFORMATION: synthetic sequence

```
<400> SEQUENCE: 246

Ala Phe Gln Tyr Val Ile Tyr Gly Thr Ala Ser
1               5                   10

<210> SEQ ID NO 247
<211> LENGTH: 11
<212> TYPE: PRT
<213> ORGANISM: Artificial sequence
<220> FEATURE:
<223> OTHER INFORMATION: synthetic sequence

<400> SEQUENCE: 247

Ala Phe Val Gly Ala Ala Ala Thr Leu Val Ser
1               5                   10

<210> SEQ ID NO 248
<211> LENGTH: 11
<212> TYPE: PRT
<213> ORGANISM: Artificial sequence
<220> FEATURE:
<223> OTHER INFORMATION: synthetic sequence

<400> SEQUENCE: 248

Ala His Ser Leu Glu Arg Val Cys His Cys Leu
1               5                   10

<210> SEQ ID NO 249
<211> LENGTH: 11
<212> TYPE: PRT
<213> ORGANISM: Artificial sequence
<220> FEATURE:
<223> OTHER INFORMATION: synthetic sequence

<400> SEQUENCE: 249

Ala Leu Phe Cys Gly Cys Gly His Glu Ala Leu
1               5                   10

<210> SEQ ID NO 250
<211> LENGTH: 11
<212> TYPE: PRT
<213> ORGANISM: Artificial sequence
<220> FEATURE:
<223> OTHER INFORMATION: synthetic sequence

<400> SEQUENCE: 250

Ala Leu Leu Leu Ala Glu Gly Phe Tyr Thr Thr
1               5                   10

<210> SEQ ID NO 251
<211> LENGTH: 11
<212> TYPE: PRT
<213> ORGANISM: Artificial sequence
<220> FEATURE:
<223> OTHER INFORMATION: synthetic sequence

<400> SEQUENCE: 251

Ala Leu Thr Gly Thr Glu Lys Leu Ile Glu Thr
1               5                   10

<210> SEQ ID NO 252
<211> LENGTH: 11
<212> TYPE: PRT
<213> ORGANISM: Artificial sequence
<220> FEATURE:
<223> OTHER INFORMATION: synthetic sequence

<400> SEQUENCE: 252
```

```
Ala Pro Phe Ala Ser Leu Val Ala Thr Gly Leu
1               5                   10

<210> SEQ ID NO 253
<211> LENGTH: 11
<212> TYPE: PRT
<213> ORGANISM: Artificial sequence
<220> FEATURE:
<223> OTHER INFORMATION: synthetic sequence

<400> SEQUENCE: 253

Ala Arg Cys Leu Val Gly Ala Pro Phe Ala Ser
1               5                   10

<210> SEQ ID NO 254
<211> LENGTH: 11
<212> TYPE: PRT
<213> ORGANISM: Artificial sequence
<220> FEATURE:
<223> OTHER INFORMATION: synthetic sequence

<400> SEQUENCE: 254

Ala Arg Met Tyr Gly Val Leu Pro Trp Asn Ala
1               5                   10

<210> SEQ ID NO 255
<211> LENGTH: 11
<212> TYPE: PRT
<213> ORGANISM: Artificial sequence
<220> FEATURE:
<223> OTHER INFORMATION: synthetic sequence

<400> SEQUENCE: 255

Ala Ser Phe Phe Phe Leu Tyr Gly Ala Leu Leu
1               5                   10

<210> SEQ ID NO 256
<211> LENGTH: 11
<212> TYPE: PRT
<213> ORGANISM: Artificial sequence
<220> FEATURE:
<223> OTHER INFORMATION: synthetic sequence

<400> SEQUENCE: 256

Ala Ser Ile Gly Ser Leu Cys Ala Asp Ala Arg
1               5                   10

<210> SEQ ID NO 257
<211> LENGTH: 11
<212> TYPE: PRT
<213> ORGANISM: Artificial sequence
<220> FEATURE:
<223> OTHER INFORMATION: synthetic sequence

<400> SEQUENCE: 257

Ala Ser Leu Val Ala Thr Gly Leu Cys Phe Phe
1               5                   10

<210> SEQ ID NO 258
<211> LENGTH: 21
<212> TYPE: PRT
<213> ORGANISM: Artificial sequence
<220> FEATURE:
<223> OTHER INFORMATION: synthetic sequence

<400> SEQUENCE: 258
```

```
Met Glu Val Gly Trp Tyr Arg Ser Pro Phe Ser Arg Val Val His Leu
1               5                   10                  15

Tyr Arg Asn Gly Lys
            20
```

<210> SEQ ID NO 259
<211> LENGTH: 10
<212> TYPE: PRT
<213> ORGANISM: Artificial sequence
<220> FEATURE:
<223> OTHER INFORMATION: synthetic sequence

<400> SEQUENCE: 259

```
Val Gly Trp Tyr Arg Ser Pro Phe Ser Arg
1               5                   10
```

<210> SEQ ID NO 260
<211> LENGTH: 11
<212> TYPE: PRT
<213> ORGANISM: Artificial sequence
<220> FEATURE:
<223> OTHER INFORMATION: synthetic sequence

<400> SEQUENCE: 260

```
Phe Ser Arg Val Val His Leu Tyr Arg Asn Gly
1               5                   10
```

<210> SEQ ID NO 261
<211> LENGTH: 12
<212> TYPE: PRT
<213> ORGANISM: Artificial sequence
<220> FEATURE:
<223> OTHER INFORMATION: synthetic sequence

<400> SEQUENCE: 261

```
Ala Ala Thr Tyr Asn Phe Ala Val Leu Lys Leu Met
1               5                   10
```

<210> SEQ ID NO 262
<211> LENGTH: 12
<212> TYPE: PRT
<213> ORGANISM: Artificial sequence
<220> FEATURE:
<223> OTHER INFORMATION: synthetic sequence

<400> SEQUENCE: 262

```
Ala Glu Phe Gln Met Thr Phe His Leu Phe Ile Ala
1               5                   10
```

<210> SEQ ID NO 263
<211> LENGTH: 8
<212> TYPE: PRT
<213> ORGANISM: Artificial sequence
<220> FEATURE:
<223> OTHER INFORMATION: synthetic sequence

<400> SEQUENCE: 263

```
Cys Phe Leu Ser Leu Leu Leu Leu
1               5
```

<210> SEQ ID NO 264
<211> LENGTH: 8
<212> TYPE: PRT
<213> ORGANISM: Artificial sequence
<220> FEATURE:
<223> OTHER INFORMATION: synthetic sequence -continued

<400> SEQUENCE: 264

Phe Leu Phe Leu Gln His Arg Leu
1               5

<210> SEQ ID NO 265
<211> LENGTH: 8
<212> TYPE: PRT
<213> ORGANISM: Artificial sequence
<220> FEATURE:
<223> OTHER INFORMATION: synthetic sequence

<400> SEQUENCE: 265

Phe Ser Trp Pro Ser Cys Phe Leu
1               5

<210> SEQ ID NO 266
<211> LENGTH: 8
<212> TYPE: PRT
<213> ORGANISM: Artificial sequence
<220> FEATURE:
<223> OTHER INFORMATION: synthetic sequence

<400> SEQUENCE: 266

Phe Tyr Trp Val Asn Pro Gly Val
1               5

<210> SEQ ID NO 267
<211> LENGTH: 8
<212> TYPE: PRT
<213> ORGANISM: Artificial sequence
<220> FEATURE:
<223> OTHER INFORMATION: synthetic sequence

<400> SEQUENCE: 267

Gly Val Leu Thr Leu Ile Ala Leu
1               5

<210> SEQ ID NO 268
<211> LENGTH: 8
<212> TYPE: PRT
<213> ORGANISM: Artificial sequence
<220> FEATURE:
<223> OTHER INFORMATION: synthetic sequence

<400> SEQUENCE: 268

Ile Ala Leu Val Pro Thr Ile Leu
1               5

<210> SEQ ID NO 269
<211> LENGTH: 8
<212> TYPE: PRT
<213> ORGANISM: Artificial sequence
<220> FEATURE:
<223> OTHER INFORMATION: synthetic sequence

<400> SEQUENCE: 269

Ile Cys Tyr Asn Trp Leu His Arg
1               5

<210> SEQ ID NO 270
<211> LENGTH: 8
<212> TYPE: PRT
<213> ORGANISM: Artificial sequence
<220> FEATURE:
<223> OTHER INFORMATION: synthetic sequence

<400> SEQUENCE: 270

```
Ile Ser Glu Gly Lys Val Thr Leu
1               5

<210> SEQ ID NO 271
<211> LENGTH: 8
<212> TYPE: PRT
<213> ORGANISM: Artificial sequence
<220> FEATURE:
<223> OTHER INFORMATION: synthetic sequence

<400> SEQUENCE: 271

Ile Val Pro Val Leu Gly Pro Leu
1               5

<210> SEQ ID NO 272
<211> LENGTH: 8
<212> TYPE: PRT
<213> ORGANISM: Artificial sequence
<220> FEATURE:
<223> OTHER INFORMATION: synthetic sequence

<400> SEQUENCE: 272

Lys Ile Thr Leu Phe Val Ile Val
1               5

<210> SEQ ID NO 273
<211> LENGTH: 9
<212> TYPE: PRT
<213> ORGANISM: Artificial sequence
<220> FEATURE:
<223> OTHER INFORMATION: synthetic sequence

<400> SEQUENCE: 273

Ala Leu Ile Ile Cys Tyr Asn Trp Leu
1               5

<210> SEQ ID NO 274
<211> LENGTH: 9
<212> TYPE: PRT
<213> ORGANISM: Artificial sequence
<220> FEATURE:
<223> OTHER INFORMATION: synthetic sequence

<400> SEQUENCE: 274

Cys Phe Leu Ser Leu Leu Leu Leu Leu
1               5

<210> SEQ ID NO 275
<211> LENGTH: 9
<212> TYPE: PRT
<213> ORGANISM: Artificial sequence
<220> FEATURE:
<223> OTHER INFORMATION: synthetic sequence

<400> SEQUENCE: 275

Cys Ser Tyr Ala Gly Gln Phe Arg Val
1               5

<210> SEQ ID NO 276
<211> LENGTH: 9
<212> TYPE: PRT
<213> ORGANISM: Artificial sequence
<220> FEATURE:
<223> OTHER INFORMATION: synthetic sequence

<400> SEQUENCE: 276
```

-continued

```
Cys Tyr Asn Trp Leu His Arg Arg Leu
1               5

<210> SEQ ID NO 277
<211> LENGTH: 9
<212> TYPE: PRT
<213> ORGANISM: Artificial sequence
<220> FEATURE:
<223> OTHER INFORMATION: synthetic sequence

<400> SEQUENCE: 277

Glu Val Gly Trp Tyr Arg Ser Pro Phe
1               5

<210> SEQ ID NO 278
<211> LENGTH: 9
<212> TYPE: PRT
<213> ORGANISM: Artificial sequence
<220> FEATURE:
<223> OTHER INFORMATION: synthetic sequence

<400> SEQUENCE: 278

Phe Leu Ser Leu Leu Leu Leu Leu Leu
1               5

<210> SEQ ID NO 279
<211> LENGTH: 9
<212> TYPE: PRT
<213> ORGANISM: Artificial sequence
<220> FEATURE:
<223> OTHER INFORMATION: synthetic sequence

<400> SEQUENCE: 279

Phe Ser Trp Pro Ser Cys Phe Leu Ser
1               5

<210> SEQ ID NO 280
<211> LENGTH: 9
<212> TYPE: PRT
<213> ORGANISM: Artificial sequence
<220> FEATURE:
<223> OTHER INFORMATION: synthetic sequence

<400> SEQUENCE: 280

Phe Tyr Trp Val Asn Pro Gly Val Leu
1               5

<210> SEQ ID NO 281
<211> LENGTH: 9
<212> TYPE: PRT
<213> ORGANISM: Artificial sequence
<220> FEATURE:
<223> OTHER INFORMATION: synthetic sequence

<400> SEQUENCE: 281

Gly Val Leu Thr Leu Ile Ala Leu Val
1               5

<210> SEQ ID NO 282
<211> LENGTH: 9
<212> TYPE: PRT
<213> ORGANISM: Artificial sequence
<220> FEATURE:
<223> OTHER INFORMATION: synthetic sequence

<400> SEQUENCE: 282

His Ser Tyr Gln Glu Glu Ala Ala Met
```

1               5

<210> SEQ ID NO 283
<211> LENGTH: 9
<212> TYPE: PRT
<213> ORGANISM: Artificial sequence
<220> FEATURE:
<223> OTHER INFORMATION: synthetic sequence

<400> SEQUENCE: 283

Ile Ala Leu Val Pro Thr Ile Leu Leu
1               5

<210> SEQ ID NO 284
<211> LENGTH: 9
<212> TYPE: PRT
<213> ORGANISM: Artificial sequence
<220> FEATURE:
<223> OTHER INFORMATION: synthetic sequence

<400> SEQUENCE: 284

Ile Thr Leu Phe Val Ile Val Pro Val
1               5

<210> SEQ ID NO 285
<211> LENGTH: 9
<212> TYPE: PRT
<213> ORGANISM: Artificial sequence
<220> FEATURE:
<223> OTHER INFORMATION: synthetic sequence

<400> SEQUENCE: 285

Ile Val Pro Val Leu Gly Pro Leu Val
1               5

<210> SEQ ID NO 286
<211> LENGTH: 9
<212> TYPE: PRT
<213> ORGANISM: Artificial sequence
<220> FEATURE:
<223> OTHER INFORMATION: synthetic sequence

<400> SEQUENCE: 286

Leu Ala Gly Gln Phe Leu Glu Glu Leu
1               5

<210> SEQ ID NO 287
<211> LENGTH: 9
<212> TYPE: PRT
<213> ORGANISM: Artificial sequence
<220> FEATURE:
<223> OTHER INFORMATION: synthetic sequence

<400> SEQUENCE: 287

Leu Gln His Arg Leu Arg Gly Lys Leu
1               5

<210> SEQ ID NO 288
<211> LENGTH: 9
<212> TYPE: PRT
<213> ORGANISM: Artificial sequence
<220> FEATURE:
<223> OTHER INFORMATION: synthetic sequence

<400> SEQUENCE: 288

Pro Thr Ile Leu Leu Gln Val Pro Val
1               5

-continued

```
<210> SEQ ID NO 289
<211> LENGTH: 9
<212> TYPE: PRT
<213> ORGANISM: Artificial sequence
<220> FEATURE:
<223> OTHER INFORMATION: synthetic sequence

<400> SEQUENCE: 289

Gln Val Pro Val Gly Leu Val Phe Leu
1               5

<210> SEQ ID NO 290
<211> LENGTH: 9
<212> TYPE: PRT
<213> ORGANISM: Artificial sequence
<220> FEATURE:
<223> OTHER INFORMATION: synthetic sequence

<400> SEQUENCE: 290

Arg Val Ile Gly Pro Gly Tyr Pro Ile
1               5

<210> SEQ ID NO 291
<211> LENGTH: 9
<212> TYPE: PRT
<213> ORGANISM: Artificial sequence
<220> FEATURE:
<223> OTHER INFORMATION: synthetic sequence

<400> SEQUENCE: 291

Arg Val Pro Cys Trp Lys Ile Thr Leu
1               5

<210> SEQ ID NO 292
<211> LENGTH: 9
<212> TYPE: PRT
<213> ORGANISM: Artificial sequence
<220> FEATURE:
<223> OTHER INFORMATION: synthetic sequence

<400> SEQUENCE: 292

Ser Cys Phe Leu Ser Leu Leu Leu Leu
1               5

<210> SEQ ID NO 293
<211> LENGTH: 9
<212> TYPE: PRT
<213> ORGANISM: Artificial sequence
<220> FEATURE:
<223> OTHER INFORMATION: synthetic sequence

<400> SEQUENCE: 293

Ser Leu Leu Leu Leu Leu Leu Gln Leu
1               5

<210> SEQ ID NO 294
<211> LENGTH: 10
<212> TYPE: PRT
<213> ORGANISM: Artificial sequence
<220> FEATURE:
<223> OTHER INFORMATION: synthetic sequence

<400> SEQUENCE: 294

Cys Phe Leu Ser Leu Leu Leu Leu Leu Leu
1               5                   10
```

-continued

```
<210> SEQ ID NO 295
<211> LENGTH: 10
<212> TYPE: PRT
<213> ORGANISM: Artificial sequence
<220> FEATURE:
<223> OTHER INFORMATION: synthetic sequence

<400> SEQUENCE: 295

Cys Ser Tyr Ala Gly Gln Phe Arg Val Ile
1               5                   10

<210> SEQ ID NO 296
<211> LENGTH: 10
<212> TYPE: PRT
<213> ORGANISM: Artificial sequence
<220> FEATURE:
<223> OTHER INFORMATION: synthetic sequence

<400> SEQUENCE: 296

Cys Tyr Asn Trp Leu His Arg Arg Leu Ala
1               5                   10

<210> SEQ ID NO 297
<211> LENGTH: 10
<212> TYPE: PRT
<213> ORGANISM: Artificial sequence
<220> FEATURE:
<223> OTHER INFORMATION: synthetic sequence

<400> SEQUENCE: 297

Phe Arg Val Ile Gly Pro Gly Tyr Pro Ile
1               5                   10

<210> SEQ ID NO 298
<211> LENGTH: 10
<212> TYPE: PRT
<213> ORGANISM: Artificial sequence
<220> FEATURE:
<223> OTHER INFORMATION: synthetic sequence

<400> SEQUENCE: 298

Phe Ser Trp Pro Ser Cys Phe Leu Ser Leu
1               5                   10

<210> SEQ ID NO 299
<211> LENGTH: 10
<212> TYPE: PRT
<213> ORGANISM: Artificial sequence
<220> FEATURE:
<223> OTHER INFORMATION: synthetic sequence

<400> SEQUENCE: 299

Phe Val Ile Val Pro Val Leu Gly Pro Leu
1               5                   10

<210> SEQ ID NO 300
<211> LENGTH: 10
<212> TYPE: PRT
<213> ORGANISM: Artificial sequence
<220> FEATURE:
<223> OTHER INFORMATION: synthetic sequence

<400> SEQUENCE: 300

Gly Leu Val Phe Leu Phe Leu Gln His Arg
1               5                   10
```

```
<210> SEQ ID NO 301
<211> LENGTH: 10
<212> TYPE: PRT
<213> ORGANISM: Artificial sequence
<220> FEATURE:
<223> OTHER INFORMATION: synthetic sequence

<400> SEQUENCE: 301

Ile Ala Leu Val Pro Thr Ile Leu Leu Gln
1               5                   10

<210> SEQ ID NO 302
<211> LENGTH: 10
<212> TYPE: PRT
<213> ORGANISM: Artificial sequence
<220> FEATURE:
<223> OTHER INFORMATION: synthetic sequence

<400> SEQUENCE: 302

Ile Cys Tyr Asn Trp Leu His Arg Arg Leu
1               5                   10

<210> SEQ ID NO 303
<211> LENGTH: 10
<212> TYPE: PRT
<213> ORGANISM: Artificial sequence
<220> FEATURE:
<223> OTHER INFORMATION: synthetic sequence

<400> SEQUENCE: 303

Ile Gly Pro Gly Tyr Pro Ile Arg Ala Leu
1               5                   10

<210> SEQ ID NO 304
<211> LENGTH: 10
<212> TYPE: PRT
<213> ORGANISM: Artificial sequence
<220> FEATURE:
<223> OTHER INFORMATION: synthetic sequence

<400> SEQUENCE: 304

Ile Ser Pro Gly Lys Asn Ala Thr Gly Met
1               5                   10

<210> SEQ ID NO 305
<211> LENGTH: 10
<212> TYPE: PRT
<213> ORGANISM: Artificial sequence
<220> FEATURE:
<223> OTHER INFORMATION: synthetic sequence

<400> SEQUENCE: 305

Ile Thr Leu Phe Val Ile Val Pro Val Leu
1               5                   10

<210> SEQ ID NO 306
<211> LENGTH: 10
<212> TYPE: PRT
<213> ORGANISM: Artificial sequence
<220> FEATURE:
<223> OTHER INFORMATION: synthetic sequence

<400> SEQUENCE: 306

Leu Ala Gly Gln Phe Leu Glu Glu Leu Arg
1               5                   10

<210> SEQ ID NO 307
```

-continued

```
<211> LENGTH: 10
<212> TYPE: PRT
<213> ORGANISM: Artificial sequence
<220> FEATURE:
<223> OTHER INFORMATION: synthetic sequence

<400> SEQUENCE: 307

Leu Gln Val Pro Val Gly Leu Val Phe Leu
1               5                   10

<210> SEQ ID NO 308
<211> LENGTH: 10
<212> TYPE: PRT
<213> ORGANISM: Artificial sequence
<220> FEATURE:
<223> OTHER INFORMATION: synthetic sequence

<400> SEQUENCE: 308

Leu Ser Leu Leu Leu Leu Leu Leu Gln Leu
1               5                   10

<210> SEQ ID NO 309
<211> LENGTH: 10
<212> TYPE: PRT
<213> ORGANISM: Artificial sequence
<220> FEATURE:
<223> OTHER INFORMATION: synthetic sequence

<400> SEQUENCE: 309

Leu Thr Leu Ile Ala Leu Val Pro Thr Ile
1               5                   10

<210> SEQ ID NO 310
<211> LENGTH: 10
<212> TYPE: PRT
<213> ORGANISM: Artificial sequence
<220> FEATURE:
<223> OTHER INFORMATION: synthetic sequence

<400> SEQUENCE: 310

Leu Val Phe Leu Phe Leu Gln His Arg Leu
1               5                   10

<210> SEQ ID NO 311
<211> LENGTH: 10
<212> TYPE: PRT
<213> ORGANISM: Artificial sequence
<220> FEATURE:
<223> OTHER INFORMATION: synthetic sequence

<400> SEQUENCE: 311

Pro Phe Tyr Trp Val Asn Pro Gly Val Leu
1               5                   10

<210> SEQ ID NO 312
<211> LENGTH: 10
<212> TYPE: PRT
<213> ORGANISM: Artificial sequence
<220> FEATURE:
<223> OTHER INFORMATION: synthetic sequence

<400> SEQUENCE: 312

Pro Ser Cys Phe Leu Ser Leu Leu Leu Leu
1               5                   10

<210> SEQ ID NO 313
<211> LENGTH: 10
```

-continued

```
<212> TYPE: PRT
<213> ORGANISM: Artificial sequence
<220> FEATURE:
<223> OTHER INFORMATION: synthetic sequence

<400> SEQUENCE: 313

Arg Ala Glu Val Glu Asn Leu His Arg Thr
1               5                   10

<210> SEQ ID NO 314
<211> LENGTH: 11
<212> TYPE: PRT
<213> ORGANISM: Artificial sequence
<220> FEATURE:
<223> OTHER INFORMATION: synthetic sequence

<400> SEQUENCE: 314

Phe Ser Trp Pro Ser Cys Phe Leu Ser Leu Leu
1               5                   10

<210> SEQ ID NO 315
<211> LENGTH: 11
<212> TYPE: PRT
<213> ORGANISM: Artificial sequence
<220> FEATURE:
<223> OTHER INFORMATION: synthetic sequence

<400> SEQUENCE: 315

Gly Leu Val Phe Leu Phe Leu Gln His Arg Leu
1               5                   10

<210> SEQ ID NO 316
<211> LENGTH: 11
<212> TYPE: PRT
<213> ORGANISM: Artificial sequence
<220> FEATURE:
<223> OTHER INFORMATION: synthetic sequence

<400> SEQUENCE: 316

Ile Cys Tyr Asn Trp Leu His Arg Arg Leu Ala
1               5                   10

<210> SEQ ID NO 317
<211> LENGTH: 11
<212> TYPE: PRT
<213> ORGANISM: Artificial sequence
<220> FEATURE:
<223> OTHER INFORMATION: synthetic sequence

<400> SEQUENCE: 317

Ile Ile Cys Tyr Asn Trp Leu His Arg Arg Leu
1               5                   10

<210> SEQ ID NO 318
<211> LENGTH: 11
<212> TYPE: PRT
<213> ORGANISM: Artificial sequence
<220> FEATURE:
<223> OTHER INFORMATION: synthetic sequence

<400> SEQUENCE: 318

Leu Val Phe Leu Phe Leu Gln His Arg Leu Arg
1               5                   10

<210> SEQ ID NO 319
<211> LENGTH: 11
<212> TYPE: PRT
```

-continued

```
<213> ORGANISM: Artificial sequence
<220> FEATURE:
<223> OTHER INFORMATION: synthetic sequence

<400> SEQUENCE: 319

Ser Trp Pro Ser Cys Phe Leu Ser Leu Leu Leu
1               5                   10

<210> SEQ ID NO 320
<211> LENGTH: 11
<212> TYPE: PRT
<213> ORGANISM: Artificial sequence
<220> FEATURE:
<223> OTHER INFORMATION: synthetic sequence

<400> SEQUENCE: 320

Val Gly Trp Tyr Arg Ser Pro Phe Ser Arg Val
1               5                   10

<210> SEQ ID NO 321
<211> LENGTH: 12
<212> TYPE: PRT
<213> ORGANISM: Artificial sequence
<220> FEATURE:
<223> OTHER INFORMATION: synthetic sequence

<400> SEQUENCE: 321

Glu Val Gly Trp Tyr Arg Ser Pro Phe Ser Arg Val
1               5                   10

<210> SEQ ID NO 322
<211> LENGTH: 12
<212> TYPE: PRT
<213> ORGANISM: Artificial sequence
<220> FEATURE:
<223> OTHER INFORMATION: synthetic sequence

<400> SEQUENCE: 322

Phe Ser Trp Pro Ser Cys Phe Leu Ser Leu Leu Leu
1               5                   10

<210> SEQ ID NO 323
<211> LENGTH: 12
<212> TYPE: PRT
<213> ORGANISM: Artificial sequence
<220> FEATURE:
<223> OTHER INFORMATION: synthetic sequence

<400> SEQUENCE: 323

Gly Leu Val Phe Leu Phe Leu Gln His Arg Leu Arg
1               5                   10

<210> SEQ ID NO 324
<211> LENGTH: 11
<212> TYPE: PRT
<213> ORGANISM: Artificial sequence
<220> FEATURE:
<223> OTHER INFORMATION: synthetic sequence

<400> SEQUENCE: 324

Ala Ala Met Glu Leu Lys Val Glu Asp Pro Phe
1               5                   10

<210> SEQ ID NO 325
<211> LENGTH: 11
<212> TYPE: PRT
<213> ORGANISM: Artificial sequence
```

<220> FEATURE:
<223> OTHER INFORMATION: synthetic sequence

<400> SEQUENCE: 325

Asp Pro Phe Tyr Trp Val Asn Pro Gly Val Leu
1               5                   10

<210> SEQ ID NO 326
<211> LENGTH: 11
<212> TYPE: PRT
<213> ORGANISM: Artificial sequence
<220> FEATURE:
<223> OTHER INFORMATION: synthetic sequence

<400> SEQUENCE: 326

Phe Leu Ser Leu Leu Leu Leu Leu Leu Gln Leu
1               5                   10

<210> SEQ ID NO 327
<211> LENGTH: 11
<212> TYPE: PRT
<213> ORGANISM: Artificial sequence
<220> FEATURE:
<223> OTHER INFORMATION: synthetic sequence

<400> SEQUENCE: 327

Phe Val Ile Val Pro Val Leu Gly Pro Leu Val
1               5                   10

<210> SEQ ID NO 328
<211> LENGTH: 11
<212> TYPE: PRT
<213> ORGANISM: Artificial sequence
<220> FEATURE:
<223> OTHER INFORMATION: synthetic sequence

<400> SEQUENCE: 328

Phe Tyr Trp Val Asn Pro Gly Val Leu Thr Leu
1               5                   10

<210> SEQ ID NO 329
<211> LENGTH: 11
<212> TYPE: PRT
<213> ORGANISM: Artificial sequence
<220> FEATURE:
<223> OTHER INFORMATION: synthetic sequence

<400> SEQUENCE: 329

Ile Arg Ala Leu Val Gly Asp Glu Ala Glu Leu
1               5                   10

<210> SEQ ID NO 330
<211> LENGTH: 12
<212> TYPE: PRT
<213> ORGANISM: Artificial sequence
<220> FEATURE:
<223> OTHER INFORMATION: synthetic sequence

<400> SEQUENCE: 330

Ile Ile Cys Tyr Asn Trp Leu His Arg Arg Leu Ala
1               5                   10

<210> SEQ ID NO 331
<211> LENGTH: 12
<212> TYPE: PRT
<213> ORGANISM: Artificial sequence
<220> FEATURE:

-continued

```
<223> OTHER INFORMATION: synthetic sequence

<400> SEQUENCE: 331

Leu Ile Ile Cys Tyr Asn Trp Leu His Arg Arg Leu
1               5                   10

<210> SEQ ID NO 332
<211> LENGTH: 12
<212> TYPE: PRT
<213> ORGANISM: Artificial sequence
<220> FEATURE:
<223> OTHER INFORMATION: synthetic sequence

<400> SEQUENCE: 332

Leu Val Phe Leu Phe Leu Gln His Arg Leu Arg Gly
1               5                   10

<210> SEQ ID NO 333
<211> LENGTH: 12
<212> TYPE: PRT
<213> ORGANISM: Artificial sequence
<220> FEATURE:
<223> OTHER INFORMATION: synthetic sequence

<400> SEQUENCE: 333

Ser Phe Ser Trp Pro Ser Cys Phe Leu Ser Leu Leu
1               5                   10

<210> SEQ ID NO 334
<211> LENGTH: 12
<212> TYPE: PRT
<213> ORGANISM: Artificial sequence
<220> FEATURE:
<223> OTHER INFORMATION: synthetic sequence

<400> SEQUENCE: 334

Ser Trp Pro Ser Cys Phe Leu Ser Leu Leu Leu Leu
1               5                   10

<210> SEQ ID NO 335
<211> LENGTH: 12
<212> TYPE: PRT
<213> ORGANISM: Artificial sequence
<220> FEATURE:
<223> OTHER INFORMATION: synthetic sequence

<400> SEQUENCE: 335

Val Gly Leu Val Phe Leu Phe Leu Gln His Arg Leu
1               5                   10

<210> SEQ ID NO 336
<211> LENGTH: 12
<212> TYPE: PRT
<213> ORGANISM: Artificial sequence
<220> FEATURE:
<223> OTHER INFORMATION: synthetic sequence

<400> SEQUENCE: 336

Trp Ser Phe Ser Trp Pro Ser Cys Phe Leu Ser Leu
1               5                   10

<210> SEQ ID NO 337
<211> LENGTH: 12
<212> TYPE: PRT
<213> ORGANISM: Artificial sequence
<220> FEATURE:
<223> OTHER INFORMATION: synthetic sequence
```

-continued

<400> SEQUENCE: 337

Gly Gln Phe Arg Val Ile Gly Pro Gly Tyr Pro Ile
1               5                   10

<210> SEQ ID NO 338
<211> LENGTH: 12
<212> TYPE: PRT
<213> ORGANISM: Artificial sequence
<220> FEATURE:
<223> OTHER INFORMATION: synthetic sequence

<400> SEQUENCE: 338

His Arg Arg Leu Ala Gly Gln Phe Leu Glu Glu Leu
1               5                   10

<210> SEQ ID NO 339
<211> LENGTH: 12
<212> TYPE: PRT
<213> ORGANISM: Artificial sequence
<220> FEATURE:
<223> OTHER INFORMATION: synthetic sequence

<400> SEQUENCE: 339

Ile Leu Leu Gln Val Pro Val Gly Leu Val Phe Leu
1               5                   10

<210> SEQ ID NO 340
<211> LENGTH: 12
<212> TYPE: PRT
<213> ORGANISM: Artificial sequence
<220> FEATURE:
<223> OTHER INFORMATION: synthetic sequence

<400> SEQUENCE: 340

Leu Val Ala Leu Ile Ile Cys Tyr Asn Trp Leu His
1               5                   10

<210> SEQ ID NO 341
<211> LENGTH: 12
<212> TYPE: PRT
<213> ORGANISM: Artificial sequence
<220> FEATURE:
<223> OTHER INFORMATION: synthetic sequence

<400> SEQUENCE: 341

Pro Phe Tyr Trp Val Asn Pro Gly Val Leu Thr Leu
1               5                   10

<210> SEQ ID NO 342
<211> LENGTH: 12
<212> TYPE: PRT
<213> ORGANISM: Artificial sequence
<220> FEATURE:
<223> OTHER INFORMATION: synthetic sequence

<400> SEQUENCE: 342

Pro Leu Val Ala Leu Ile Ile Cys Tyr Asn Trp Leu
1               5                   10

<210> SEQ ID NO 343
<211> LENGTH: 12
<212> TYPE: PRT
<213> ORGANISM: Artificial sequence
<220> FEATURE:
<223> OTHER INFORMATION: synthetic sequence -continued

```
<400> SEQUENCE: 343

Thr Leu Phe Val Ile Val Pro Val Leu Gly Pro Leu
1               5                   10

<210> SEQ ID NO 344
<211> LENGTH: 12
<212> TYPE: PRT
<213> ORGANISM: Artificial sequence
<220> FEATURE:
<223> OTHER INFORMATION: synthetic sequence

<400> SEQUENCE: 344

Val Ala Leu Ile Ile Cys Tyr Asn Trp Leu His Arg
1               5                   10

<210> SEQ ID NO 345
<211> LENGTH: 12
<212> TYPE: PRT
<213> ORGANISM: Artificial sequence
<220> FEATURE:
<223> OTHER INFORMATION: synthetic sequence

<400> SEQUENCE: 345

Phe Arg Asp His Ser Tyr Gln Glu Glu Ala Ala Met
1               5                   10

<210> SEQ ID NO 346
<211> LENGTH: 8
<212> TYPE: PRT
<213> ORGANISM: Artificial sequence
<220> FEATURE:
<223> OTHER INFORMATION: synthetic sequence

<400> SEQUENCE: 346

Val Val His Phe Phe Lys Asn Ile
1               5

<210> SEQ ID NO 347
<211> LENGTH: 8
<212> TYPE: PRT
<213> ORGANISM: Artificial sequence
<220> FEATURE:
<223> OTHER INFORMATION: synthetic sequence

<400> SEQUENCE: 347

Arg Thr Thr His Tyr Gly Ser Leu
1               5

<210> SEQ ID NO 348
<211> LENGTH: 8
<212> TYPE: PRT
<213> ORGANISM: Artificial sequence
<220> FEATURE:
<223> OTHER INFORMATION: synthetic sequence

<400> SEQUENCE: 348

Ile Gly Arg Phe Phe Ser Gly Asp
1               5

<210> SEQ ID NO 349
<211> LENGTH: 8
<212> TYPE: PRT
<213> ORGANISM: Artificial sequence
<220> FEATURE:
<223> OTHER INFORMATION: synthetic sequence

<400> SEQUENCE: 349
```

-continued

```
Ser Ile Gly Arg Phe Phe Ser Gly
1               5

<210> SEQ ID NO 350
<211> LENGTH: 8
<212> TYPE: PRT
<213> ORGANISM: Artificial sequence
<220> FEATURE:
<223> OTHER INFORMATION: synthetic sequence

<400> SEQUENCE: 350

Leu Ile Arg Leu Phe Ser Arg Asp
1               5

<210> SEQ ID NO 351
<211> LENGTH: 8
<212> TYPE: PRT
<213> ORGANISM: Artificial sequence
<220> FEATURE:
<223> OTHER INFORMATION: synthetic sequence

<400> SEQUENCE: 351

Val His Phe Phe Lys Asn Ile Val
1               5

<210> SEQ ID NO 352
<211> LENGTH: 8
<212> TYPE: PRT
<213> ORGANISM: Artificial sequence
<220> FEATURE:
<223> OTHER INFORMATION: synthetic sequence

<400> SEQUENCE: 352

Thr Ser Ala Glu Asp Thr Ala Val
1               5

<210> SEQ ID NO 353
<211> LENGTH: 8
<212> TYPE: PRT
<213> ORGANISM: Artificial sequence
<220> FEATURE:
<223> OTHER INFORMATION: synthetic sequence

<400> SEQUENCE: 353

Ser Lys Tyr Leu Ala Thr Ala Ser
1               5

<210> SEQ ID NO 354
<211> LENGTH: 8
<212> TYPE: PRT
<213> ORGANISM: Artificial sequence
<220> FEATURE:
<223> OTHER INFORMATION: synthetic sequence

<400> SEQUENCE: 354

Arg Ser Lys Tyr Leu Ala Thr Ala
1               5

<210> SEQ ID NO 355
<211> LENGTH: 8
<212> TYPE: PRT
<213> ORGANISM: Artificial sequence
<220> FEATURE:
<223> OTHER INFORMATION: synthetic sequence

<400> SEQUENCE: 355
```

```
Val Phe Gly Glu Ala Asp Ala Ile
1               5

<210> SEQ ID NO 356
<211> LENGTH: 8
<212> TYPE: PRT
<213> ORGANISM: Artificial sequence
<220> FEATURE:
<223> OTHER INFORMATION: synthetic sequence

<400> SEQUENCE: 356

Tyr Leu Ala Thr Ala Ser Thr Met
1               5

<210> SEQ ID NO 357
<211> LENGTH: 8
<212> TYPE: PRT
<213> ORGANISM: Artificial sequence
<220> FEATURE:
<223> OTHER INFORMATION: synthetic sequence

<400> SEQUENCE: 357

Phe Phe Lys Asn Ile Val Thr Pro
1               5

<210> SEQ ID NO 358
<211> LENGTH: 8
<212> TYPE: PRT
<213> ORGANISM: Artificial sequence
<220> FEATURE:
<223> OTHER INFORMATION: synthetic sequence

<400> SEQUENCE: 358

Ala Ser Gly Gly Leu Asp Val Met
1               5

<210> SEQ ID NO 359
<211> LENGTH: 8
<212> TYPE: PRT
<213> ORGANISM: Artificial sequence
<220> FEATURE:
<223> OTHER INFORMATION: synthetic sequence

<400> SEQUENCE: 359

Ile Gln Asn Asn Gly Thr Ser Ala
1               5

<210> SEQ ID NO 360
<211> LENGTH: 8
<212> TYPE: PRT
<213> ORGANISM: Artificial sequence
<220> FEATURE:
<223> OTHER INFORMATION: synthetic sequence

<400> SEQUENCE: 360

Ala Ile Gln Asn Asn Gly Thr Ser
1               5

<210> SEQ ID NO 361
<211> LENGTH: 8
<212> TYPE: PRT
<213> ORGANISM: Artificial sequence
<220> FEATURE:
<223> OTHER INFORMATION: synthetic sequence

<400> SEQUENCE: 361

Asp Ser Arg Ser Gly Ser Pro Met
```

-continued

```
1               5

<210> SEQ ID NO 362
<211> LENGTH: 8
<212> TYPE: PRT
<213> ORGANISM: Artificial sequence
<220> FEATURE:
<223> OTHER INFORMATION: synthetic sequence

<400> SEQUENCE: 362

Asp Ala Ile Gln Asn Asn Gly Thr
1               5

<210> SEQ ID NO 363
<211> LENGTH: 8
<212> TYPE: PRT
<213> ORGANISM: Artificial sequence
<220> FEATURE:
<223> OTHER INFORMATION: synthetic sequence

<400> SEQUENCE: 363

Thr Gln Asp Glu Asn Pro Val Val
1               5

<210> SEQ ID NO 364
<211> LENGTH: 8
<212> TYPE: PRT
<213> ORGANISM: Artificial sequence
<220> FEATURE:
<223> OTHER INFORMATION: synthetic sequence

<400> SEQUENCE: 364

Asn Trp Gln Gly Ala His Pro Ala
1               5

<210> SEQ ID NO 365
<211> LENGTH: 9
<212> TYPE: PRT
<213> ORGANISM: Artificial sequence
<220> FEATURE:
<223> OTHER INFORMATION: synthetic sequence

<400> SEQUENCE: 365

Val Val His Phe Phe Lys Asn Ile Val
1               5

<210> SEQ ID NO 366
<211> LENGTH: 9
<212> TYPE: PRT
<213> ORGANISM: Artificial sequence
<220> FEATURE:
<223> OTHER INFORMATION: synthetic sequence

<400> SEQUENCE: 366

Pro Val Val His Phe Phe Lys Asn Ile
1               5

<210> SEQ ID NO 367
<211> LENGTH: 9
<212> TYPE: PRT
<213> ORGANISM: Artificial sequence
<220> FEATURE:
<223> OTHER INFORMATION: synthetic sequence

<400> SEQUENCE: 367

Gly Asn Arg Pro His Leu Ile Arg Leu
1               5
```

```
<210> SEQ ID NO 368
<211> LENGTH: 9
<212> TYPE: PRT
<213> ORGANISM: Artificial sequence
<220> FEATURE:
<223> OTHER INFORMATION: synthetic sequence

<400> SEQUENCE: 368

Ser Ile Gly Arg Phe Phe Ser Gly Asp
1               5

<210> SEQ ID NO 369
<211> LENGTH: 9
<212> TYPE: PRT
<213> ORGANISM: Artificial sequence
<220> FEATURE:
<223> OTHER INFORMATION: synthetic sequence

<400> SEQUENCE: 369

Thr Arg Thr Thr His Tyr Gly Ser Leu
1               5

<210> SEQ ID NO 370
<211> LENGTH: 9
<212> TYPE: PRT
<213> ORGANISM: Artificial sequence
<220> FEATURE:
<223> OTHER INFORMATION: synthetic sequence

<400> SEQUENCE: 370

Ser Gln Arg Ser Lys Tyr Leu Ala Thr
1               5

<210> SEQ ID NO 371
<211> LENGTH: 9
<212> TYPE: PRT
<213> ORGANISM: Artificial sequence
<220> FEATURE:
<223> OTHER INFORMATION: synthetic sequence

<400> SEQUENCE: 371

Val Met Ala Ser Gln Lys Arg Pro Ser
1               5

<210> SEQ ID NO 372
<211> LENGTH: 9
<212> TYPE: PRT
<213> ORGANISM: Artificial sequence
<220> FEATURE:
<223> OTHER INFORMATION: synthetic sequence

<400> SEQUENCE: 372

Val His Phe Phe Lys Asn Ile Val Thr
1               5

<210> SEQ ID NO 373
<211> LENGTH: 9
<212> TYPE: PRT
<213> ORGANISM: Artificial sequence
<220> FEATURE:
<223> OTHER INFORMATION: synthetic sequence

<400> SEQUENCE: 373

Ser Lys Tyr Leu Ala Thr Ala Ser Thr
1               5
```

-continued

```
<210> SEQ ID NO 374
<211> LENGTH: 9
<212> TYPE: PRT
<213> ORGANISM: Artificial sequence
<220> FEATURE:
<223> OTHER INFORMATION: synthetic sequence

<400> SEQUENCE: 374

Met Asp His Ala Arg His Gly Phe Leu
1               5

<210> SEQ ID NO 375
<211> LENGTH: 9
<212> TYPE: PRT
<213> ORGANISM: Artificial sequence
<220> FEATURE:
<223> OTHER INFORMATION: synthetic sequence

<400> SEQUENCE: 375

Ala Ala Ser Gly Gly Leu Asp Val Met
1               5

<210> SEQ ID NO 376
<211> LENGTH: 9
<212> TYPE: PRT
<213> ORGANISM: Artificial sequence
<220> FEATURE:
<223> OTHER INFORMATION: synthetic sequence

<400> SEQUENCE: 376

Asp Ala Ile Gln Asn Asn Gly Thr Ser
1               5

<210> SEQ ID NO 377
<211> LENGTH: 9
<212> TYPE: PRT
<213> ORGANISM: Artificial sequence
<220> FEATURE:
<223> OTHER INFORMATION: synthetic sequence

<400> SEQUENCE: 377

Lys Tyr Leu Ala Thr Ala Ser Thr Met
1               5

<210> SEQ ID NO 378
<211> LENGTH: 9
<212> TYPE: PRT
<213> ORGANISM: Artificial sequence
<220> FEATURE:
<223> OTHER INFORMATION: synthetic sequence

<400> SEQUENCE: 378

Ala Asp Pro Gly Asn Arg Pro His Leu
1               5

<210> SEQ ID NO 379
<211> LENGTH: 9
<212> TYPE: PRT
<213> ORGANISM: Artificial sequence
<220> FEATURE:
<223> OTHER INFORMATION: synthetic sequence

<400> SEQUENCE: 379

Asn Asn Trp Gln Gly Ala His Pro Ala
1               5
```

```
<210> SEQ ID NO 380
<211> LENGTH: 9
<212> TYPE: PRT
<213> ORGANISM: Artificial sequence
<220> FEATURE:
<223> OTHER INFORMATION: synthetic sequence

<400> SEQUENCE: 380

Ala Ile Gln Asn Asn Gly Thr Ser Ala
1               5

<210> SEQ ID NO 381
<211> LENGTH: 9
<212> TYPE: PRT
<213> ORGANISM: Artificial sequence
<220> FEATURE:
<223> OTHER INFORMATION: synthetic sequence

<400> SEQUENCE: 381

Phe Leu Pro Arg His Arg Asp Thr Gly
1               5

<210> SEQ ID NO 382
<211> LENGTH: 9
<212> TYPE: PRT
<213> ORGANISM: Artificial sequence
<220> FEATURE:
<223> OTHER INFORMATION: synthetic sequence

<400> SEQUENCE: 382

His Phe Phe Lys Asn Ile Val Thr Pro
1               5

<210> SEQ ID NO 383
<211> LENGTH: 9
<212> TYPE: PRT
<213> ORGANISM: Artificial sequence
<220> FEATURE:
<223> OTHER INFORMATION: synthetic sequence

<400> SEQUENCE: 383

Thr Ala Ser Glu Asp Ser Asp Val Phe
1               5

<210> SEQ ID NO 384
<211> LENGTH: 10
<212> TYPE: PRT
<213> ORGANISM: Artificial sequence
<220> FEATURE:
<223> OTHER INFORMATION: synthetic sequence

<400> SEQUENCE: 384

Ser Lys Tyr Leu Ala Thr Ala Ser Thr Met
1               5                   10

<210> SEQ ID NO 385
<211> LENGTH: 10
<212> TYPE: PRT
<213> ORGANISM: Artificial sequence
<220> FEATURE:
<223> OTHER INFORMATION: synthetic sequence

<400> SEQUENCE: 385

Thr Met Asp His Ala Arg His Gly Phe Leu
1               5                   10

<210> SEQ ID NO 386
```

```
<211> LENGTH: 10
<212> TYPE: PRT
<213> ORGANISM: Artificial sequence
<220> FEATURE:
<223> OTHER INFORMATION: synthetic sequence

<400> SEQUENCE: 386

Ser Thr Met Asp His Ala Arg His Gly Phe
1               5               10

<210> SEQ ID NO 387
<211> LENGTH: 10
<212> TYPE: PRT
<213> ORGANISM: Artificial sequence
<220> FEATURE:
<223> OTHER INFORMATION: synthetic sequence

<400> SEQUENCE: 387

Pro Val Val His Phe Phe Lys Asn Ile Val
1               5               10

<210> SEQ ID NO 388
<211> LENGTH: 10
<212> TYPE: PRT
<213> ORGANISM: Artificial sequence
<220> FEATURE:
<223> OTHER INFORMATION: synthetic sequence

<400> SEQUENCE: 388

Val His Phe Phe Lys Asn Ile Val Thr Pro
1               5               10

<210> SEQ ID NO 389
<211> LENGTH: 10
<212> TYPE: PRT
<213> ORGANISM: Artificial sequence
<220> FEATURE:
<223> OTHER INFORMATION: synthetic sequence

<400> SEQUENCE: 389

Ser Asp Val Phe Gly Glu Ala Asp Ala Ile
1               5               10

<210> SEQ ID NO 390
<211> LENGTH: 10
<212> TYPE: PRT
<213> ORGANISM: Artificial sequence
<220> FEATURE:
<223> OTHER INFORMATION: synthetic sequence

<400> SEQUENCE: 390

His Thr Arg Thr Thr His Tyr Gly Ser Leu
1               5               10

<210> SEQ ID NO 391
<211> LENGTH: 10
<212> TYPE: PRT
<213> ORGANISM: Artificial sequence
<220> FEATURE:
<223> OTHER INFORMATION: synthetic sequence

<400> SEQUENCE: 391

Val Val His Phe Phe Lys Asn Ile Val Thr
1               5               10

<210> SEQ ID NO 392
<211> LENGTH: 10
```

-continued

```
<212> TYPE: PRT
<213> ORGANISM: Artificial sequence
<220> FEATURE:
<223> OTHER INFORMATION: synthetic sequence

<400> SEQUENCE: 392

Gly Asn Arg Pro His Leu Ile Arg Leu Phe
1               5                   10

<210> SEQ ID NO 393
<211> LENGTH: 10
<212> TYPE: PRT
<213> ORGANISM: Artificial sequence
<220> FEATURE:
<223> OTHER INFORMATION: synthetic sequence

<400> SEQUENCE: 393

Ser Ile Gly Arg Phe Phe Ser Gly Asp Arg
1               5                   10

<210> SEQ ID NO 394
<211> LENGTH: 10
<212> TYPE: PRT
<213> ORGANISM: Artificial sequence
<220> FEATURE:
<223> OTHER INFORMATION: synthetic sequence

<400> SEQUENCE: 394

Asp Ala Ile Gln Asn Asn Gly Thr Ser Ala
1               5                   10

<210> SEQ ID NO 395
<211> LENGTH: 10
<212> TYPE: PRT
<213> ORGANISM: Artificial sequence
<220> FEATURE:
<223> OTHER INFORMATION: synthetic sequence

<400> SEQUENCE: 395

Phe Leu Pro Arg His Arg Asp Thr Gly Ile
1               5                   10

<210> SEQ ID NO 396
<211> LENGTH: 10
<212> TYPE: PRT
<213> ORGANISM: Artificial sequence
<220> FEATURE:
<223> OTHER INFORMATION: synthetic sequence

<400> SEQUENCE: 396

Ala Asp Ala Ile Gln Asn Asn Gly Thr Ser
1               5                   10

<210> SEQ ID NO 397
<211> LENGTH: 10
<212> TYPE: PRT
<213> ORGANISM: Artificial sequence
<220> FEATURE:
<223> OTHER INFORMATION: synthetic sequence

<400> SEQUENCE: 397

Thr Ala Ala Ser Gly Gly Leu Asp Val Met
1               5                   10

<210> SEQ ID NO 398
<211> LENGTH: 10
<212> TYPE: PRT
```

-continued

<213> ORGANISM: Artificial sequence
<220> FEATURE:
<223> OTHER INFORMATION: synthetic sequence

<400> SEQUENCE: 398

Thr Ala Val Thr Asp Ser Lys His Thr Ala
1               5                   10

<210> SEQ ID NO 399
<211> LENGTH: 10
<212> TYPE: PRT
<213> ORGANISM: Artificial sequence
<220> FEATURE:
<223> OTHER INFORMATION: synthetic sequence

<400> SEQUENCE: 399

Pro Ala Asp Pro Gly Asn Arg Pro His Leu
1               5                   10

<210> SEQ ID NO 400
<211> LENGTH: 10
<212> TYPE: PRT
<213> ORGANISM: Artificial sequence
<220> FEATURE:
<223> OTHER INFORMATION: synthetic sequence

<400> SEQUENCE: 400

Ala Asp Pro Gly Asn Arg Pro His Leu Ile
1               5                   10

<210> SEQ ID NO 401
<211> LENGTH: 11
<212> TYPE: PRT
<213> ORGANISM: Artificial sequence
<220> FEATURE:
<223> OTHER INFORMATION: synthetic sequence

<400> SEQUENCE: 401

Asn Pro Val Val His Phe Phe Lys Asn Ile Val
1               5                   10

<210> SEQ ID NO 402
<211> LENGTH: 11
<212> TYPE: PRT
<213> ORGANISM: Artificial sequence
<220> FEATURE:
<223> OTHER INFORMATION: synthetic sequence

<400> SEQUENCE: 402

Pro Val Val His Phe Phe Lys Asn Ile Val Thr
1               5                   10

<210> SEQ ID NO 403
<211> LENGTH: 11
<212> TYPE: PRT
<213> ORGANISM: Artificial sequence
<220> FEATURE:
<223> OTHER INFORMATION: synthetic sequence

<400> SEQUENCE: 403

Ser Ile Gly Arg Phe Phe Ser Gly Asp Arg Gly
1               5                   10

<210> SEQ ID NO 404
<211> LENGTH: 11
<212> TYPE: PRT
<213> ORGANISM: Artificial sequence

```
<220> FEATURE:
<223> OTHER INFORMATION: synthetic sequence

<400> SEQUENCE: 404

Val His Phe Phe Lys Asn Ile Val Thr Pro Arg
1               5                   10

<210> SEQ ID NO 405
<211> LENGTH: 11
<212> TYPE: PRT
<213> ORGANISM: Artificial sequence
<220> FEATURE:
<223> OTHER INFORMATION: synthetic sequence

<400> SEQUENCE: 405

Ser Thr Met Asp His Ala Arg His Gly Phe Leu
1               5                   10

<210> SEQ ID NO 406
<211> LENGTH: 11
<212> TYPE: PRT
<213> ORGANISM: Artificial sequence
<220> FEATURE:
<223> OTHER INFORMATION: synthetic sequence

<400> SEQUENCE: 406

Ser His Thr Arg Thr Thr His Tyr Gly Ser Leu
1               5                   10

<210> SEQ ID NO 407
<211> LENGTH: 11
<212> TYPE: PRT
<213> ORGANISM: Artificial sequence
<220> FEATURE:
<223> OTHER INFORMATION: synthetic sequence

<400> SEQUENCE: 407

Asp Ser Ile Gly Arg Phe Phe Ser Gly Asp Arg
1               5                   10

<210> SEQ ID NO 408
<211> LENGTH: 11
<212> TYPE: PRT
<213> ORGANISM: Artificial sequence
<220> FEATURE:
<223> OTHER INFORMATION: synthetic sequence

<400> SEQUENCE: 408

Ser Lys Tyr Leu Ala Thr Ala Ser Thr Met Asp
1               5                   10

<210> SEQ ID NO 409
<211> LENGTH: 11
<212> TYPE: PRT
<213> ORGANISM: Artificial sequence
<220> FEATURE:
<223> OTHER INFORMATION: synthetic sequence

<400> SEQUENCE: 409

Thr Met Asp His Ala Arg His Gly Phe Leu Pro
1               5                   10

<210> SEQ ID NO 410
<211> LENGTH: 11
<212> TYPE: PRT
<213> ORGANISM: Artificial sequence
<220> FEATURE:
```

<223> OTHER INFORMATION: synthetic sequence

<400> SEQUENCE: 410

Val Val His Phe Phe Lys Asn Ile Val Thr Pro
1               5                   10

<210> SEQ ID NO 411
<211> LENGTH: 11
<212> TYPE: PRT
<213> ORGANISM: Artificial sequence
<220> FEATURE:
<223> OTHER INFORMATION: synthetic sequence

<400> SEQUENCE: 411

Arg Ser Lys Tyr Leu Ala Thr Ala Ser Thr Met
1               5                   10

<210> SEQ ID NO 412
<211> LENGTH: 11
<212> TYPE: PRT
<213> ORGANISM: Artificial sequence
<220> FEATURE:
<223> OTHER INFORMATION: synthetic sequence

<400> SEQUENCE: 412

Phe Leu Pro Arg His Arg Asp Thr Gly Ile Leu
1               5                   10

<210> SEQ ID NO 413
<211> LENGTH: 11
<212> TYPE: PRT
<213> ORGANISM: Artificial sequence
<220> FEATURE:
<223> OTHER INFORMATION: synthetic sequence

<400> SEQUENCE: 413

Ala Asp Ala Ile Gln Asn Asn Gly Thr Ser Ala
1               5                   10

<210> SEQ ID NO 414
<211> LENGTH: 11
<212> TYPE: PRT
<213> ORGANISM: Artificial sequence
<220> FEATURE:
<223> OTHER INFORMATION: synthetic sequence

<400> SEQUENCE: 414

Gly Phe Leu Pro Arg His Arg Asp Thr Gly Ile
1               5                   10

<210> SEQ ID NO 415
<211> LENGTH: 11
<212> TYPE: PRT
<213> ORGANISM: Artificial sequence
<220> FEATURE:
<223> OTHER INFORMATION: synthetic sequence

<400> SEQUENCE: 415

Glu Ala Asp Ala Ile Gln Asn Asn Gly Thr Ser
1               5                   10

<210> SEQ ID NO 416
<211> LENGTH: 11
<212> TYPE: PRT
<213> ORGANISM: Artificial sequence
<220> FEATURE:
<223> OTHER INFORMATION: synthetic sequence

<400> SEQUENCE: 416

Pro Thr Ala Ala Ser Gly Gly Leu Asp Val Met
1               5                   10

<210> SEQ ID NO 417
<211> LENGTH: 11
<212> TYPE: PRT
<213> ORGANISM: Artificial sequence
<220> FEATURE:
<223> OTHER INFORMATION: synthetic sequence

<400> SEQUENCE: 417

Thr Gln Asp Glu Asn Pro Val Val His Phe Phe
1               5                   10

<210> SEQ ID NO 418
<211> LENGTH: 11
<212> TYPE: PRT
<213> ORGANISM: Artificial sequence
<220> FEATURE:
<223> OTHER INFORMATION: synthetic sequence

<400> SEQUENCE: 418

Asp Ala Ile Gln Asn Asn Gly Thr Ser Ala Glu
1               5                   10

<210> SEQ ID NO 419
<211> LENGTH: 12
<212> TYPE: PRT
<213> ORGANISM: Artificial sequence
<220> FEATURE:
<223> OTHER INFORMATION: synthetic sequence

<400> SEQUENCE: 419

Glu Asn Pro Val Val His Phe Phe Lys Asn Ile Val
1               5                   10

<210> SEQ ID NO 420
<211> LENGTH: 12
<212> TYPE: PRT
<213> ORGANISM: Artificial sequence
<220> FEATURE:
<223> OTHER INFORMATION: synthetic sequence

<400> SEQUENCE: 420

Ala Ser Thr Met Asp His Ala Arg His Gly Phe Leu
1               5                   10

<210> SEQ ID NO 421
<211> LENGTH: 12
<212> TYPE: PRT
<213> ORGANISM: Artificial sequence
<220> FEATURE:
<223> OTHER INFORMATION: synthetic sequence

<400> SEQUENCE: 421

Ala Asp Pro Gly Asn Arg Pro His Leu Ile Arg Leu
1               5                   10

<210> SEQ ID NO 422
<211> LENGTH: 12
<212> TYPE: PRT
<213> ORGANISM: Artificial sequence
<220> FEATURE:
<223> OTHER INFORMATION: synthetic sequence

<400> SEQUENCE: 422

Ser Ile Gly Arg Phe Phe Ser Gly Asp Arg Gly Ala
1               5                   10

<210> SEQ ID NO 423
<211> LENGTH: 12
<212> TYPE: PRT
<213> ORGANISM: Artificial sequence
<220> FEATURE:
<223> OTHER INFORMATION: synthetic sequence

<400> SEQUENCE: 423

Asp Ser His Thr Arg Thr Thr His Tyr Gly Ser Leu
1               5                   10

<210> SEQ ID NO 424
<211> LENGTH: 12
<212> TYPE: PRT
<213> ORGANISM: Artificial sequence
<220> FEATURE:
<223> OTHER INFORMATION: synthetic sequence

<400> SEQUENCE: 424

Ser Gln His Gly Arg Thr Gln Asp Glu Asn Pro Val
1               5                   10

<210> SEQ ID NO 425
<211> LENGTH: 12
<212> TYPE: PRT
<213> ORGANISM: Artificial sequence
<220> FEATURE:
<223> OTHER INFORMATION: synthetic sequence

<400> SEQUENCE: 425

Ala His Pro Ala Asp Pro Gly Asn Arg Pro His Leu
1               5                   10

<210> SEQ ID NO 426
<211> LENGTH: 8
<212> TYPE: PRT
<213> ORGANISM: Artificial sequence
<220> FEATURE:
<223> OTHER INFORMATION: synthetic sequence

<400> SEQUENCE: 426

Ala Ala Ala Arg Asp Thr Val Gln
1               5

<210> SEQ ID NO 427
<211> LENGTH: 8
<212> TYPE: PRT
<213> ORGANISM: Artificial sequence
<220> FEATURE:
<223> OTHER INFORMATION: synthetic sequence

<400> SEQUENCE: 427

Ala Ala Phe Pro Asn Thr Thr Leu
1               5

<210> SEQ ID NO 428
<211> LENGTH: 8
<212> TYPE: PRT
<213> ORGANISM: Artificial sequence
<220> FEATURE:
<223> OTHER INFORMATION: synthetic sequence

<400> SEQUENCE: 428

```
Ala Ala Arg Asp Thr Val Gln Cys
1               5

<210> SEQ ID NO 429
<211> LENGTH: 8
<212> TYPE: PRT
<213> ORGANISM: Artificial sequence
<220> FEATURE:
<223> OTHER INFORMATION: synthetic sequence

<400> SEQUENCE: 429

Ala Cys Leu Ala Glu Asn Ala Tyr
1               5

<210> SEQ ID NO 430
<211> LENGTH: 8
<212> TYPE: PRT
<213> ORGANISM: Artificial sequence
<220> FEATURE:
<223> OTHER INFORMATION: synthetic sequence

<400> SEQUENCE: 430

Ala Asp Ser Asn Pro Pro Pro Leu
1               5

<210> SEQ ID NO 431
<211> LENGTH: 8
<212> TYPE: PRT
<213> ORGANISM: Artificial sequence
<220> FEATURE:
<223> OTHER INFORMATION: synthetic sequence

<400> SEQUENCE: 431

Ala Glu Asn Ala Tyr Gly Gln Asp
1               5

<210> SEQ ID NO 432
<211> LENGTH: 8
<212> TYPE: PRT
<213> ORGANISM: Artificial sequence
<220> FEATURE:
<223> OTHER INFORMATION: synthetic sequence

<400> SEQUENCE: 432

Ala Glu Asn Gln Tyr Gly Gln Arg
1               5

<210> SEQ ID NO 433
<211> LENGTH: 8
<212> TYPE: PRT
<213> ORGANISM: Artificial sequence
<220> FEATURE:
<223> OTHER INFORMATION: synthetic sequence

<400> SEQUENCE: 433

Ala Glu Tyr Ala Glu Ile Arg Val
1               5

<210> SEQ ID NO 434
<211> LENGTH: 8
<212> TYPE: PRT
<213> ORGANISM: Artificial sequence
<220> FEATURE:
<223> OTHER INFORMATION: synthetic sequence

<400> SEQUENCE: 434
```

```
Ala Phe Ala Ile Leu Ile Ala Ile
1               5

<210> SEQ ID NO 435
<211> LENGTH: 8
<212> TYPE: PRT
<213> ORGANISM: Artificial sequence
<220> FEATURE:
<223> OTHER INFORMATION: synthetic sequence

<400> SEQUENCE: 435

Ala Phe Glu Gly Thr Cys Val Ser
1               5

<210> SEQ ID NO 436
<211> LENGTH: 8
<212> TYPE: PRT
<213> ORGANISM: Artificial sequence
<220> FEATURE:
<223> OTHER INFORMATION: synthetic sequence

<400> SEQUENCE: 436

Ala Phe Glu Leu Pro Ser Arg Asn
1               5

<210> SEQ ID NO 437
<211> LENGTH: 8
<212> TYPE: PRT
<213> ORGANISM: Artificial sequence
<220> FEATURE:
<223> OTHER INFORMATION: synthetic sequence

<400> SEQUENCE: 437

Ala Phe Asn Leu Ser Val Glu Phe
1               5

<210> SEQ ID NO 438
<211> LENGTH: 8
<212> TYPE: PRT
<213> ORGANISM: Artificial sequence
<220> FEATURE:
<223> OTHER INFORMATION: synthetic sequence

<400> SEQUENCE: 438

Ala Phe Pro Asn Thr Thr Leu Gln
1               5

<210> SEQ ID NO 439
<211> LENGTH: 8
<212> TYPE: PRT
<213> ORGANISM: Artificial sequence
<220> FEATURE:
<223> OTHER INFORMATION: synthetic sequence

<400> SEQUENCE: 439

Ala Gly Thr Glu Val Glu Val Ser
1               5

<210> SEQ ID NO 440
<211> LENGTH: 8
<212> TYPE: PRT
<213> ORGANISM: Artificial sequence
<220> FEATURE:
<223> OTHER INFORMATION: synthetic sequence

<400> SEQUENCE: 440

Ala His Arg Leu Met Trp Ala Lys
```

-continued

```
1               5

<210> SEQ ID NO 441
<211> LENGTH: 8
<212> TYPE: PRT
<213> ORGANISM: Artificial sequence
<220> FEATURE:
<223> OTHER INFORMATION: synthetic sequence

<400> SEQUENCE: 441

Ala Ile Glu Gly Ser His Val Ser
1               5

<210> SEQ ID NO 442
<211> LENGTH: 8
<212> TYPE: PRT
<213> ORGANISM: Artificial sequence
<220> FEATURE:
<223> OTHER INFORMATION: synthetic sequence

<400> SEQUENCE: 442

Ala Ile Leu Ile Ala Ile Val Cys
1               5

<210> SEQ ID NO 443
<211> LENGTH: 8
<212> TYPE: PRT
<213> ORGANISM: Artificial sequence
<220> FEATURE:
<223> OTHER INFORMATION: synthetic sequence

<400> SEQUENCE: 443

Ala Ile Val Cys Tyr Ile Thr Gln
1               5

<210> SEQ ID NO 444
<211> LENGTH: 8
<212> TYPE: PRT
<213> ORGANISM: Artificial sequence
<220> FEATURE:
<223> OTHER INFORMATION: synthetic sequence

<400> SEQUENCE: 444

Ala Lys Ile Gly Pro Val Gly Ala
1               5

<210> SEQ ID NO 445
<211> LENGTH: 8
<212> TYPE: PRT
<213> ORGANISM: Artificial sequence
<220> FEATURE:
<223> OTHER INFORMATION: synthetic sequence

<400> SEQUENCE: 445

Ala Lys Ser Leu Tyr Leu Asp Leu
1               5

<210> SEQ ID NO 446
<211> LENGTH: 9
<212> TYPE: PRT
<213> ORGANISM: Artificial sequence
<220> FEATURE:
<223> OTHER INFORMATION: synthetic sequence

<400> SEQUENCE: 446

Ala Ala Ala Arg Asp Thr Val Gln Cys
1               5
```

```
<210> SEQ ID NO 447
<211> LENGTH: 9
<212> TYPE: PRT
<213> ORGANISM: Artificial sequence
<220> FEATURE:
<223> OTHER INFORMATION: synthetic sequence

<400> SEQUENCE: 447

Ala Ala Phe Pro Asn Thr Thr Leu Gln
1               5

<210> SEQ ID NO 448
<211> LENGTH: 9
<212> TYPE: PRT
<213> ORGANISM: Artificial sequence
<220> FEATURE:
<223> OTHER INFORMATION: synthetic sequence

<400> SEQUENCE: 448

Ala Ala Arg Asp Thr Val Gln Cys Leu
1               5

<210> SEQ ID NO 449
<211> LENGTH: 9
<212> TYPE: PRT
<213> ORGANISM: Artificial sequence
<220> FEATURE:
<223> OTHER INFORMATION: synthetic sequence

<400> SEQUENCE: 449

Ala Cys Leu Ala Glu Asn Ala Tyr Gly
1               5

<210> SEQ ID NO 450
<211> LENGTH: 9
<212> TYPE: PRT
<213> ORGANISM: Artificial sequence
<220> FEATURE:
<223> OTHER INFORMATION: synthetic sequence

<400> SEQUENCE: 450

Ala Asp Ser Asn Pro Pro Pro Leu Leu
1               5

<210> SEQ ID NO 451
<211> LENGTH: 9
<212> TYPE: PRT
<213> ORGANISM: Artificial sequence
<220> FEATURE:
<223> OTHER INFORMATION: synthetic sequence

<400> SEQUENCE: 451

Ala Glu Asn Ala Tyr Gly Gln Asp Asn
1               5

<210> SEQ ID NO 452
<211> LENGTH: 9
<212> TYPE: PRT
<213> ORGANISM: Artificial sequence
<220> FEATURE:
<223> OTHER INFORMATION: synthetic sequence

<400> SEQUENCE: 452

Ala Glu Asn Gln Tyr Gly Gln Arg Ala
1               5
```

-continued

```
<210> SEQ ID NO 453
<211> LENGTH: 9
<212> TYPE: PRT
<213> ORGANISM: Artificial sequence
<220> FEATURE:
<223> OTHER INFORMATION: synthetic sequence

<400> SEQUENCE: 453

Ala Glu Tyr Ala Glu Ile Arg Val Lys
1               5

<210> SEQ ID NO 454
<211> LENGTH: 9
<212> TYPE: PRT
<213> ORGANISM: Artificial sequence
<220> FEATURE:
<223> OTHER INFORMATION: synthetic sequence

<400> SEQUENCE: 454

Ala Phe Ala Ile Leu Ile Ala Ile Val
1               5

<210> SEQ ID NO 455
<211> LENGTH: 9
<212> TYPE: PRT
<213> ORGANISM: Artificial sequence
<220> FEATURE:
<223> OTHER INFORMATION: synthetic sequence

<400> SEQUENCE: 455

Ala Phe Glu Gly Thr Cys Val Ser Ile
1               5

<210> SEQ ID NO 456
<211> LENGTH: 9
<212> TYPE: PRT
<213> ORGANISM: Artificial sequence
<220> FEATURE:
<223> OTHER INFORMATION: synthetic sequence

<400> SEQUENCE: 456

Ala Phe Glu Leu Pro Ser Arg Asn Val
1               5

<210> SEQ ID NO 457
<211> LENGTH: 9
<212> TYPE: PRT
<213> ORGANISM: Artificial sequence
<220> FEATURE:
<223> OTHER INFORMATION: synthetic sequence

<400> SEQUENCE: 457

Ala Phe Asn Leu Ser Val Glu Phe Ala
1               5

<210> SEQ ID NO 458
<211> LENGTH: 9
<212> TYPE: PRT
<213> ORGANISM: Artificial sequence
<220> FEATURE:
<223> OTHER INFORMATION: synthetic sequence

<400> SEQUENCE: 458

Ala Phe Pro Asn Thr Thr Leu Gln Phe
1               5
```

<210> SEQ ID NO 459
<211> LENGTH: 9
<212> TYPE: PRT
<213> ORGANISM: Artificial sequence
<220> FEATURE:
<223> OTHER INFORMATION: synthetic sequence

<400> SEQUENCE: 459

Ala Gly Thr Glu Val Glu Val Ser Cys
1               5

<210> SEQ ID NO 460
<211> LENGTH: 9
<212> TYPE: PRT
<213> ORGANISM: Artificial sequence
<220> FEATURE:
<223> OTHER INFORMATION: synthetic sequence

<400> SEQUENCE: 460

Ala His Arg Leu Met Trp Ala Lys Ile
1               5

<210> SEQ ID NO 461
<211> LENGTH: 9
<212> TYPE: PRT
<213> ORGANISM: Artificial sequence
<220> FEATURE:
<223> OTHER INFORMATION: synthetic sequence

<400> SEQUENCE: 461

Ala Ile Glu Gly Ser His Val Ser Leu
1               5

<210> SEQ ID NO 462
<211> LENGTH: 9
<212> TYPE: PRT
<213> ORGANISM: Artificial sequence
<220> FEATURE:
<223> OTHER INFORMATION: synthetic sequence

<400> SEQUENCE: 462

Ala Ile Leu Ile Ala Ile Val Cys Tyr
1               5

<210> SEQ ID NO 463
<211> LENGTH: 9
<212> TYPE: PRT
<213> ORGANISM: Artificial sequence
<220> FEATURE:
<223> OTHER INFORMATION: synthetic sequence

<400> SEQUENCE: 463

Ala Ile Val Cys Tyr Ile Thr Gln Thr
1               5

<210> SEQ ID NO 464
<211> LENGTH: 9
<212> TYPE: PRT
<213> ORGANISM: Artificial sequence
<220> FEATURE:
<223> OTHER INFORMATION: synthetic sequence

<400> SEQUENCE: 464

Ala Lys Ile Gly Pro Val Gly Ala Val
1               5

<210> SEQ ID NO 465

<211> LENGTH: 9
<212> TYPE: PRT
<213> ORGANISM: Artificial sequence
<220> FEATURE:
<223> OTHER INFORMATION: synthetic sequence

<400> SEQUENCE: 465

Ala Lys Ser Leu Tyr Leu Asp Leu Glu
1               5

<210> SEQ ID NO 466
<211> LENGTH: 10
<212> TYPE: PRT
<213> ORGANISM: Artificial sequence
<220> FEATURE:
<223> OTHER INFORMATION: synthetic sequence

<400> SEQUENCE: 466

Ala Ala Ala Arg Asp Thr Val Gln Cys Leu
1               5                   10

<210> SEQ ID NO 467
<211> LENGTH: 10
<212> TYPE: PRT
<213> ORGANISM: Artificial sequence
<220> FEATURE:
<223> OTHER INFORMATION: synthetic sequence

<400> SEQUENCE: 467

Ala Ala Phe Pro Asn Thr Thr Leu Gln Phe
1               5                   10

<210> SEQ ID NO 468
<211> LENGTH: 10
<212> TYPE: PRT
<213> ORGANISM: Artificial sequence
<220> FEATURE:
<223> OTHER INFORMATION: synthetic sequence

<400> SEQUENCE: 468

Ala Ala Arg Asp Thr Val Gln Cys Leu Cys
1               5                   10

<210> SEQ ID NO 469
<211> LENGTH: 10
<212> TYPE: PRT
<213> ORGANISM: Artificial sequence
<220> FEATURE:
<223> OTHER INFORMATION: synthetic sequence

<400> SEQUENCE: 469

Ala Cys Leu Ala Glu Asn Ala Tyr Gly Gln
1               5                   10

<210> SEQ ID NO 470
<211> LENGTH: 10
<212> TYPE: PRT
<213> ORGANISM: Artificial sequence
<220> FEATURE:
<223> OTHER INFORMATION: synthetic sequence

<400> SEQUENCE: 470

Ala Asp Ser Asn Pro Pro Leu Leu Thr
1               5                   10

<210> SEQ ID NO 471
<211> LENGTH: 10

-continued

```
<212> TYPE: PRT
<213> ORGANISM: Artificial sequence
<220> FEATURE:
<223> OTHER INFORMATION: synthetic sequence

<400> SEQUENCE: 471

Ala Glu Asn Ala Tyr Gly Gln Asp Asn Arg
1               5                   10

<210> SEQ ID NO 472
<211> LENGTH: 10
<212> TYPE: PRT
<213> ORGANISM: Artificial sequence
<220> FEATURE:
<223> OTHER INFORMATION: synthetic sequence

<400> SEQUENCE: 472

Ala Glu Asn Gln Tyr Gly Gln Arg Ala Thr
1               5                   10

<210> SEQ ID NO 473
<211> LENGTH: 10
<212> TYPE: PRT
<213> ORGANISM: Artificial sequence
<220> FEATURE:
<223> OTHER INFORMATION: synthetic sequence

<400> SEQUENCE: 473

Ala Phe Ala Ile Leu Ile Ala Ile Val Cys
1               5                   10

<210> SEQ ID NO 474
<211> LENGTH: 10
<212> TYPE: PRT
<213> ORGANISM: Artificial sequence
<220> FEATURE:
<223> OTHER INFORMATION: synthetic sequence

<400> SEQUENCE: 474

Ala Phe Glu Gly Thr Cys Val Ser Ile Pro
1               5                   10

<210> SEQ ID NO 475
<211> LENGTH: 10
<212> TYPE: PRT
<213> ORGANISM: Artificial sequence
<220> FEATURE:
<223> OTHER INFORMATION: synthetic sequence

<400> SEQUENCE: 475

Ala Phe Glu Leu Pro Ser Arg Asn Val Thr
1               5                   10

<210> SEQ ID NO 476
<211> LENGTH: 10
<212> TYPE: PRT
<213> ORGANISM: Artificial sequence
<220> FEATURE:
<223> OTHER INFORMATION: synthetic sequence

<400> SEQUENCE: 476

Ala Phe Asn Leu Ser Val Glu Phe Ala Pro
1               5                   10

<210> SEQ ID NO 477
<211> LENGTH: 10
<212> TYPE: PRT
```

<213> ORGANISM: Artificial sequence
<220> FEATURE:
<223> OTHER INFORMATION: synthetic sequence

<400> SEQUENCE: 477

Ala Phe Pro Asn Thr Thr Leu Gln Phe Glu
1               5                   10

<210> SEQ ID NO 478
<211> LENGTH: 10
<212> TYPE: PRT
<213> ORGANISM: Artificial sequence
<220> FEATURE:
<223> OTHER INFORMATION: synthetic sequence

<400> SEQUENCE: 478

Ala Gly Thr Glu Val Glu Val Ser Cys Met
1               5                   10

<210> SEQ ID NO 479
<211> LENGTH: 10
<212> TYPE: PRT
<213> ORGANISM: Artificial sequence
<220> FEATURE:
<223> OTHER INFORMATION: synthetic sequence

<400> SEQUENCE: 479

Ala His Arg Leu Met Trp Ala Lys Ile Gly
1               5                   10

<210> SEQ ID NO 480
<211> LENGTH: 10
<212> TYPE: PRT
<213> ORGANISM: Artificial sequence
<220> FEATURE:
<223> OTHER INFORMATION: synthetic sequence

<400> SEQUENCE: 480

Ala Ile Glu Gly Ser His Val Ser Leu Leu
1               5                   10

<210> SEQ ID NO 481
<211> LENGTH: 10
<212> TYPE: PRT
<213> ORGANISM: Artificial sequence
<220> FEATURE:
<223> OTHER INFORMATION: synthetic sequence

<400> SEQUENCE: 481

Ala Ile Leu Ile Ala Ile Val Cys Tyr Ile
1               5                   10

<210> SEQ ID NO 482
<211> LENGTH: 10
<212> TYPE: PRT
<213> ORGANISM: Artificial sequence
<220> FEATURE:
<223> OTHER INFORMATION: synthetic sequence

<400> SEQUENCE: 482

Ala Ile Val Cys Tyr Ile Thr Gln Thr Arg
1               5                   10

<210> SEQ ID NO 483
<211> LENGTH: 10
<212> TYPE: PRT
<213> ORGANISM: Artificial sequence
<220> FEATURE:
<223> OTHER INFORMATION: synthetic sequence

<400> SEQUENCE: 483

Ala Lys Ile Gly Pro Val Gly Ala Val Val
1               5                   10

<210> SEQ ID NO 484
<211> LENGTH: 10
<212> TYPE: PRT
<213> ORGANISM: Artificial sequence
<220> FEATURE:
<223> OTHER INFORMATION: synthetic sequence

<400> SEQUENCE: 484

Ala Lys Ser Leu Tyr Leu Asp Leu Glu Glu
1               5                   10

<210> SEQ ID NO 485
<211> LENGTH: 10
<212> TYPE: PRT
<213> ORGANISM: Artificial sequence
<220> FEATURE:
<223> OTHER INFORMATION: synthetic sequence

<400> SEQUENCE: 485

Ala Asn Gly His Arg Leu Gly Cys Gln Ala
1               5                   10

<210> SEQ ID NO 486
<211> LENGTH: 11
<212> TYPE: PRT
<213> ORGANISM: Artificial sequence
<220> FEATURE:
<223> OTHER INFORMATION: synthetic sequence

<400> SEQUENCE: 486

Ala Ala Ala Arg Asp Thr Val Gln Cys Leu Cys
1               5                   10

<210> SEQ ID NO 487
<211> LENGTH: 11
<212> TYPE: PRT
<213> ORGANISM: Artificial sequence
<220> FEATURE:
<223> OTHER INFORMATION: synthetic sequence

<400> SEQUENCE: 487

Ala Ala Phe Pro Asn Thr Thr Leu Gln Phe Glu
1               5                   10

<210> SEQ ID NO 488
<211> LENGTH: 11
<212> TYPE: PRT
<213> ORGANISM: Artificial sequence
<220> FEATURE:
<223> OTHER INFORMATION: synthetic sequence

<400> SEQUENCE: 488

Ala Ala Arg Asp Thr Val Gln Cys Leu Cys Val
1               5                   10

<210> SEQ ID NO 489
<211> LENGTH: 11
<212> TYPE: PRT
<213> ORGANISM: Artificial sequence
<220> FEATURE:

<223> OTHER INFORMATION: synthetic sequence

<400> SEQUENCE: 489

Ala Cys Leu Ala Glu Asn Ala Tyr Gly Gln Asp
1               5                   10

<210> SEQ ID NO 490
<211> LENGTH: 11
<212> TYPE: PRT
<213> ORGANISM: Artificial sequence
<220> FEATURE:
<223> OTHER INFORMATION: synthetic sequence

<400> SEQUENCE: 490

Ala Asp Ser Asn Pro Pro Pro Leu Leu Thr Trp
1               5                   10

<210> SEQ ID NO 491
<211> LENGTH: 11
<212> TYPE: PRT
<213> ORGANISM: Artificial sequence
<220> FEATURE:
<223> OTHER INFORMATION: synthetic sequence

<400> SEQUENCE: 491

Ala Glu Asn Ala Tyr Gly Gln Asp Asn Arg Thr
1               5                   10

<210> SEQ ID NO 492
<211> LENGTH: 11
<212> TYPE: PRT
<213> ORGANISM: Artificial sequence
<220> FEATURE:
<223> OTHER INFORMATION: synthetic sequence

<400> SEQUENCE: 492

Ala Glu Asn Gln Tyr Gly Gln Arg Ala Thr Ala
1               5                   10

<210> SEQ ID NO 493
<211> LENGTH: 11
<212> TYPE: PRT
<213> ORGANISM: Artificial sequence
<220> FEATURE:
<223> OTHER INFORMATION: synthetic sequence

<400> SEQUENCE: 493

Ala Phe Ala Ile Leu Ile Ala Ile Val Cys Tyr
1               5                   10

<210> SEQ ID NO 494
<211> LENGTH: 11
<212> TYPE: PRT
<213> ORGANISM: Artificial sequence
<220> FEATURE:
<223> OTHER INFORMATION: synthetic sequence

<400> SEQUENCE: 494

Ala Phe Glu Gly Thr Cys Val Ser Ile Pro Cys
1               5                   10

<210> SEQ ID NO 495
<211> LENGTH: 11
<212> TYPE: PRT
<213> ORGANISM: Artificial sequence
<220> FEATURE:
<223> OTHER INFORMATION: synthetic sequence

<400> SEQUENCE: 495

Ala Phe Glu Leu Pro Ser Arg Asn Val Thr Val
1               5                   10

<210> SEQ ID NO 496
<211> LENGTH: 11
<212> TYPE: PRT
<213> ORGANISM: Artificial sequence
<220> FEATURE:
<223> OTHER INFORMATION: synthetic sequence

<400> SEQUENCE: 496

Ala Phe Asn Leu Ser Val Glu Phe Ala Pro Ile
1               5                   10

<210> SEQ ID NO 497
<211> LENGTH: 11
<212> TYPE: PRT
<213> ORGANISM: Artificial sequence
<220> FEATURE:
<223> OTHER INFORMATION: synthetic sequence

<400> SEQUENCE: 497

Ala Phe Pro Asn Thr Thr Leu Gln Phe Glu Gly
1               5                   10

<210> SEQ ID NO 498
<211> LENGTH: 11
<212> TYPE: PRT
<213> ORGANISM: Artificial sequence
<220> FEATURE:
<223> OTHER INFORMATION: synthetic sequence

<400> SEQUENCE: 498

Ala Gly Thr Glu Val Glu Val Ser Cys Met Val
1               5                   10

<210> SEQ ID NO 499
<211> LENGTH: 11
<212> TYPE: PRT
<213> ORGANISM: Artificial sequence
<220> FEATURE:
<223> OTHER INFORMATION: synthetic sequence

<400> SEQUENCE: 499

Ala His Arg Leu Met Trp Ala Lys Ile Gly Pro
1               5                   10

<210> SEQ ID NO 500
<211> LENGTH: 11
<212> TYPE: PRT
<213> ORGANISM: Artificial sequence
<220> FEATURE:
<223> OTHER INFORMATION: synthetic sequence

<400> SEQUENCE: 500

Ala Ile Glu Gly Ser His Val Ser Leu Leu Cys
1               5                   10

<210> SEQ ID NO 501
<211> LENGTH: 11
<212> TYPE: PRT
<213> ORGANISM: Artificial sequence
<220> FEATURE:
<223> OTHER INFORMATION: synthetic sequence

```
<400> SEQUENCE: 501

Ala Ile Leu Ile Ala Ile Val Cys Tyr Ile Thr
1               5                   10

<210> SEQ ID NO 502
<211> LENGTH: 11
<212> TYPE: PRT
<213> ORGANISM: Artificial sequence
<220> FEATURE:
<223> OTHER INFORMATION: synthetic sequence

<400> SEQUENCE: 502

Ala Ile Val Cys Tyr Ile Thr Gln Thr Arg Arg
1               5                   10

<210> SEQ ID NO 503
<211> LENGTH: 11
<212> TYPE: PRT
<213> ORGANISM: Artificial sequence
<220> FEATURE:
<223> OTHER INFORMATION: synthetic sequence

<400> SEQUENCE: 503

Ala Lys Ile Gly Pro Val Gly Ala Val Val Ala
1               5                   10

<210> SEQ ID NO 504
<211> LENGTH: 11
<212> TYPE: PRT
<213> ORGANISM: Artificial sequence
<220> FEATURE:
<223> OTHER INFORMATION: synthetic sequence

<400> SEQUENCE: 504

Ala Lys Ser Leu Tyr Leu Asp Leu Glu Glu Val
1               5                   10

<210> SEQ ID NO 505
<211> LENGTH: 11
<212> TYPE: PRT
<213> ORGANISM: Artificial sequence
<220> FEATURE:
<223> OTHER INFORMATION: synthetic sequence

<400> SEQUENCE: 505

Ala Asn Gly His Arg Leu Gly Cys Gln Ala Ala
1               5                   10

<210> SEQ ID NO 506
<211> LENGTH: 12
<212> TYPE: PRT
<213> ORGANISM: Artificial sequence
<220> FEATURE:
<223> OTHER INFORMATION: synthetic sequence

<400> SEQUENCE: 506

Glu Asp Gly Val Tyr Ala Cys Leu Ala Glu Asn Ala
1               5                   10

<210> SEQ ID NO 507
<211> LENGTH: 12
<212> TYPE: PRT
<213> ORGANISM: Artificial sequence
<220> FEATURE:
<223> OTHER INFORMATION: synthetic sequence

<400> SEQUENCE: 507
```

-continued

```
Glu Glu Leu Ala Glu Tyr Ala Glu Ile Arg Val Lys
1               5                   10

<210> SEQ ID NO 508
<211> LENGTH: 12
<212> TYPE: PRT
<213> ORGANISM: Artificial sequence
<220> FEATURE:
<223> OTHER INFORMATION: synthetic sequence

<400> SEQUENCE: 508

Glu Glu Val Thr Pro Gly Glu Asp Gly Val Tyr Ala
1               5                   10

<210> SEQ ID NO 509
<211> LENGTH: 12
<212> TYPE: PRT
<213> ORGANISM: Artificial sequence
<220> FEATURE:
<223> OTHER INFORMATION: synthetic sequence

<400> SEQUENCE: 509

Glu Phe Ala Pro Ile Ile Leu Leu Glu Ser His Cys
1               5                   10

<210> SEQ ID NO 510
<211> LENGTH: 12
<212> TYPE: PRT
<213> ORGANISM: Artificial sequence
<220> FEATURE:
<223> OTHER INFORMATION: synthetic sequence

<400> SEQUENCE: 510

Glu Phe Arg Ile Ser Gly Ala Pro Asp Lys Tyr Glu
1               5                   10

<210> SEQ ID NO 511
<211> LENGTH: 12
<212> TYPE: PRT
<213> ORGANISM: Artificial sequence
<220> FEATURE:
<223> OTHER INFORMATION: synthetic sequence

<400> SEQUENCE: 511

Glu Phe Val Tyr Ser Glu Arg Ser Gly Leu Leu Leu
1               5                   10

<210> SEQ ID NO 512
<211> LENGTH: 12
<212> TYPE: PRT
<213> ORGANISM: Artificial sequence
<220> FEATURE:
<223> OTHER INFORMATION: synthetic sequence

<400> SEQUENCE: 512

Glu Gly Glu Thr Val Ser Ile Leu Cys Ser Thr Gln
1               5                   10

<210> SEQ ID NO 513
<211> LENGTH: 12
<212> TYPE: PRT
<213> ORGANISM: Artificial sequence
<220> FEATURE:
<223> OTHER INFORMATION: synthetic sequence

<400> SEQUENCE: 513
```

-continued

```
Gln Leu Gln Pro Phe Pro Gln Pro Glu Leu Pro Tyr
1               5                   10

<210> SEQ ID NO 514
<211> LENGTH: 11
<212> TYPE: PRT
<213> ORGANISM: Artificial sequence
<220> FEATURE:
<223> OTHER INFORMATION: synthetic sequence

<400> SEQUENCE: 514

Pro Gln Pro Glu Leu Pro Tyr Pro Gln Pro Glu
1               5                   10

<210> SEQ ID NO 515
<211> LENGTH: 12
<212> TYPE: PRT
<213> ORGANISM: Artificial sequence
<220> FEATURE:
<223> OTHER INFORMATION: synthetic sequence

<400> SEQUENCE: 515

Gln Gln Pro Phe Pro Gln Pro Glu Gln Pro Phe Pro
1               5                   10

<210> SEQ ID NO 516
<211> LENGTH: 12
<212> TYPE: PRT
<213> ORGANISM: Artificial sequence
<220> FEATURE:
<223> OTHER INFORMATION: synthetic sequence

<400> SEQUENCE: 516

Phe Pro Gln Pro Glu Gln Pro Phe Pro Trp Gln Pro
1               5                   10

<210> SEQ ID NO 517
<211> LENGTH: 26
<212> TYPE: DNA
<213> ORGANISM: Artificial sequence
<220> FEATURE:
<223> OTHER INFORMATION: synthetic sequence

<400> SEQUENCE: 517
aagcagtggt atcaacgcag agtact                                          26

<210> SEQ ID NO 518
<211> LENGTH: 30
<212> TYPE: DNA
<213> ORGANISM: Artificial sequence
<220> FEATURE:
<223> OTHER INFORMATION: synthetic sequence
<220> FEATURE:
<221> NAME/KEY: misc_RNA
<222> LOCATION: (28)..(30)

<400> SEQUENCE: 518
aagcagtggt atcaacgcag agtgaatggg                                      30

<210> SEQ ID NO 519
<211> LENGTH: 23
<212> TYPE: DNA
<213> ORGANISM: Artificial sequence
<220> FEATURE:
<223> OTHER INFORMATION: synthetic sequence

<400> SEQUENCE: 519
```
aagcagtggt atcaacgcag agt                                                                    23

```
<210> SEQ ID NO 520
<211> LENGTH: 10
<212> TYPE: PRT
<213> ORGANISM: Artificial sequence
<220> FEATURE:
<223> OTHER INFORMATION: synthetic sequence

<400> SEQUENCE: 520

Ala Thr His Gly Asn Phe Arg Ala Tyr Met
1               5                   10

<210> SEQ ID NO 521
<211> LENGTH: 10
<212> TYPE: PRT
<213> ORGANISM: Artificial sequence
<220> FEATURE:
<223> OTHER INFORMATION: synthetic sequence

<400> SEQUENCE: 521

Ile Ser Ile Glu Asn Met Arg Thr Arg Leu
1               5                   10

<210> SEQ ID NO 522
<211> LENGTH: 10
<212> TYPE: PRT
<213> ORGANISM: Artificial sequence
<220> FEATURE:
<223> OTHER INFORMATION: synthetic sequence

<400> SEQUENCE: 522

Val Ser Val Ala Asn Met Arg Val Arg Leu
1               5                   10

<210> SEQ ID NO 523
<211> LENGTH: 10
<212> TYPE: PRT
<213> ORGANISM: Artificial sequence
<220> FEATURE:
<223> OTHER INFORMATION: synthetic sequence

<400> SEQUENCE: 523

Ala Ser Asp Gly Asn Phe Arg Ser Tyr Met
1               5                   10

<210> SEQ ID NO 524
<211> LENGTH: 10
<212> TYPE: PRT
<213> ORGANISM: Artificial sequence
<220> FEATURE:
<223> OTHER INFORMATION: synthetic sequence

<400> SEQUENCE: 524

Asn His Arg Thr Asn Arg Tyr Phe Phe Leu
1               5                   10

<210> SEQ ID NO 525
<211> LENGTH: 10
<212> TYPE: PRT
<213> ORGANISM: Artificial sequence
<220> FEATURE:
<223> OTHER INFORMATION: synthetic sequence

<400> SEQUENCE: 525

Ala Ser Ile Ala Asn Trp Pro Leu Ala Ile
1               5                   10
```

```
<210> SEQ ID NO 526
<211> LENGTH: 10
<212> TYPE: PRT
<213> ORGANISM: Artificial sequence
<220> FEATURE:
<223> OTHER INFORMATION: synthetic sequence

<400> SEQUENCE: 526

Asn His Arg Asn Asn Arg Tyr Phe Phe Leu
1               5                   10

<210> SEQ ID NO 527
<211> LENGTH: 10
<212> TYPE: PRT
<213> ORGANISM: Artificial sequence
<220> FEATURE:
<223> OTHER INFORMATION: synthetic sequence

<400> SEQUENCE: 527

Gly Thr Glu Phe Asn His Trp Ala Ala Ile
1               5                   10

<210> SEQ ID NO 528
<211> LENGTH: 10
<212> TYPE: PRT
<213> ORGANISM: Artificial sequence
<220> FEATURE:
<223> OTHER INFORMATION: synthetic sequence

<400> SEQUENCE: 528

Phe Gln Arg Gly Asn Arg Leu Met Trp Leu
1               5                   10

<210> SEQ ID NO 529
<211> LENGTH: 9
<212> TYPE: PRT
<213> ORGANISM: Artificial sequence
<220> FEATURE:
<223> OTHER INFORMATION: synthetic sequence

<400> SEQUENCE: 529

Trp Ser Leu Arg Asn Leu Val Met Leu
1               5

<210> SEQ ID NO 530
<211> LENGTH: 9
<212> TYPE: PRT
<213> ORGANISM: Artificial sequence
<220> FEATURE:
<223> OTHER INFORMATION: synthetic sequence

<400> SEQUENCE: 530

Thr Arg Leu Val Asn Asp Val Asp Leu
1               5

<210> SEQ ID NO 531
<211> LENGTH: 9
<212> TYPE: PRT
<213> ORGANISM: Artificial sequence
<220> FEATURE:
<223> OTHER INFORMATION: synthetic sequence

<400> SEQUENCE: 531

Gln Arg His Glu Asn Leu His Arg Met
1               5
```

-continued

```
<210> SEQ ID NO 532
<211> LENGTH: 9
<212> TYPE: PRT
<213> ORGANISM: Artificial sequence
<220> FEATURE:
<223> OTHER INFORMATION: synthetic sequence

<400> SEQUENCE: 532

Arg Asp Val His Asn Pro Asp Val Ile
1               5

<210> SEQ ID NO 533
<211> LENGTH: 9
<212> TYPE: PRT
<213> ORGANISM: Artificial sequence
<220> FEATURE:
<223> OTHER INFORMATION: synthetic sequence

<400> SEQUENCE: 533

Arg Arg Ile Leu Asn Leu Gly Gly Met
1               5

<210> SEQ ID NO 534
<211> LENGTH: 9
<212> TYPE: PRT
<213> ORGANISM: Artificial sequence
<220> FEATURE:
<223> OTHER INFORMATION: synthetic sequence

<400> SEQUENCE: 534

Thr Cys Ala Tyr Asn Pro Arg Gly Met
1               5

<210> SEQ ID NO 535
<211> LENGTH: 10
<212> TYPE: PRT
<213> ORGANISM: Artificial sequence
<220> FEATURE:
<223> OTHER INFORMATION: synthetic sequence

<400> SEQUENCE: 535

Cys Ala Cys Trp Asp Ser Ser Gly Phe His
1               5                   10

<210> SEQ ID NO 536
<211> LENGTH: 11
<212> TYPE: PRT
<213> ORGANISM: Artificial sequence
<220> FEATURE:
<223> OTHER INFORMATION: synthetic sequence

<400> SEQUENCE: 536

Cys Ser Tyr Gly Leu Tyr Ser Ser Phe Gly His
1               5                   10

<210> SEQ ID NO 537
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 537
```

```
Cys Ser Tyr Gly Xaa Tyr Ser Ser Phe Gly His
1               5                   10
```

<210> SEQ ID NO 538
<211> LENGTH: 13
<212> TYPE: PRT
<213> ORGANISM: Artificial sequence
<220> FEATURE:
<223> OTHER INFORMATION: synthetic sequence

<400> SEQUENCE: 538

```
Cys Gly Ser Asp Ile Gly Gly Ser Ser Trp Asp Thr Arg
1               5                   10
```

<210> SEQ ID NO 539
<211> LENGTH: 17
<212> TYPE: PRT
<213> ORGANISM: Artificial sequence
<220> FEATURE:
<223> OTHER INFORMATION: synthetic sequence

<400> SEQUENCE: 539

```
Cys Ala Ser Ser Gly Tyr Ile Gly Gly Ile Arg Ala Thr Asp Lys Leu
1               5                   10                  15

Val
```

<210> SEQ ID NO 540
<211> LENGTH: 18
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 540

```
Cys Ala Ser Gly Tyr Xaa Ile Gly Gly Ile Arg Ala Xaa Thr Asp Lys
1               5                   10                  15

Leu Val
```

<210> SEQ ID NO 541
<211> LENGTH: 19
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 541

```
Cys Ala Leu Met Glu Arg Xaa Ile Gly Gly Ile Arg Ala Xaa Thr Asp
1               5                   10                  15

Lys Leu Val
```

MANIPULATION AND USE OF ANTIGEN-SPECIFIC REGULATORY T CELLS

CROSS REFERENCE

This application is a 371 and claims the benefit of PCT Application No. PCT/US2020/045006, filed Aug. 5, 2020, which claims benefit of U.S. Provisional Patent Application No. 62/882,810 filed Aug. 5, 2019, which applications are incorporated herein by reference in their entirety.

INCORPORATION BY REFERENCE OF SEQUENCE LISTING

A Sequence Listing is provided herewith as a Sequence Listing text, STAN-1630_SEQ_LIST_ST25" created on Jan. 4, 2022 and having a size of 163,262,696 bytes. The contents of the Sequence Listing text are incorporated herein by reference in their entirety.

BACKGROUND

There is a long-standing interest in manipulating cells of the immune system to achieve control of autoimmune and other inflammatory diseases. Conventional methods of treatment have generally been non-antigen-specific. For example, general immunosuppression utilizes agents such as methylprednisolone, other steroids, methotrexate, cladribine, cyclophosphamide. However the overall immunosuppression that these therapies provide has considerable undesirable side effects.

More selective modification of the immune system utilizes agents such as cytokine blocking agents, e.g. anti-TNFα antibodies, soluble TNFα receptor, soluble IL-1 receptor (Anakinra), and anti-IL-6R antibodies (Tocilizumab); T cell targeted therapies (CTLA4-Ig [Abatacept]), B cell targeted therapies (anti-CD20 [Rituximab]), and the like. Alternatively, anti-inflammatory cytokines also find use, such as interferon beta (IFNβ)-1b (Betaferon/Betaseron). But although these therapies are more targeted, there is still immune suppression of a whole class of responses, not specifically the undesirable response.

The promise of highly selective, antigen-specific therapies thus remains alluring, although elusive. Such specificity could potentially provide for effective treatment of undesirable immune responses without comprising whole immune system populations or responses. But in spite of known autoantigen targets; a strong correlation of many autoimmune diseases with specific major histocompatibility complex (MHC) class II alleles; and well-established T cell involvement, antigen-targeted therapies has not been readily translated to clinical use.

Development of therapies for this purpose are provided herein.

SUMMARY

Compositions and methods are provided for isolating, manipulating and using for therapeutic and other purposes, mammalian, MHC Class I restricted, antigen-specific regulatory T cells. The regulatory T cells can be characterized as CD8+ cells that specifically suppress the responses of self-reactive and/or pathogenic CD4+ T cells by cytotoxic mechanisms including, without limitation, perforin, other components of the perforin/granzyme apoptosis pathway, etc. The regulatory T cells are antigen-specific, but are not activated by the same antigen as the self-reactive and/or pathogenic CD4+ T cells. This novel regulatory CD8+ T cell subset is demonstrated to be present in humans, with the activity of suppressing pathogenic CD4+ T cells arising from self-reactivity in autoimmune disorders or cross-reactivity to autoantigens in infectious diseases via cytotoxicity. The regulatory T cells express cytotoxic molecules and have shown to cause programmed cell death of self-reactive CD4+ T cells. The ability of the antigen-specific regulatory cells to selectively target specific, activated CD4+ cells provides a means for highly selective treatment of inflammatory diseases, e.g. autoimmune diseases, such as multiple sclerosis, rheumatoid arthritis, type I diabetes; systemic lupus erythematosus, transplant rejection; atopic conditions, and the like, and is thus a highly desirable method of treatment.

It is shown herein that during the development of a T cell response to an initiating antigen there is an expansion of CD4$^+$ T cells that are specific for the initiating antigen over a period of from about 1 to about 3 weeks; with a concomitant expansion of regulatory CD8$^+$ cells that can specifically suppress those CD4$^+$ cells. Expansion of the relevant T cell populations is seen in peripheral blood, and in relevant tissues for disease, such as synovial tissue, CNS, sites of autoimmune lesions, and the like.

Initiating antigens can include, without limitation, autoantigens involved in disease development, including known autoantigens such as myelin oligodendrocyte glycoprotein (MOG), myelin basic protein (MBP), aquaporin, glutamic acid decarboxylase (GAD), insulin and pro-insulin, matrix metalloprotease-1 (MMP-1), type II collagen (COLII), thyroglobulin, proteolipid protein (PLP), myelin associated glycoprotein (MAG), chondrocyte glycoprotein, heat shock proteins (HSPs), citrullinated proteins such as filaggrin, etc. Initiating antigens may also include non-autoantigens, including, for example non-autoantigens that trigger autoimmune responses; antigens present on transplanted tissues, pathogen antigens including, for example, viral antigens such as SARS-CoV-2 proteins, bacterial antigens including *Borellia*, etc.

The regulatory T cells are characterized by the phenotype of being CD8$^+$ and MHC Class I restricted. In humans, the regulatory T cells express inhibitory KIR proteins, and in mouse express the murine counterpart, Ly49 proteins. Specific KIR proteins expressed by the cells can include one or more of the inhibitory KIR proteins, e.g. KIR2DL1, KIR2DL2, KIR2DL3, KIR2DL5, KIR3DL1, KIR3DL2; and may specifically include one or more of KIR2DL2, KIR2DL3, and KIR3DL1. The regulatory T cells can also be characterized as being CD44+, CD122+, and are not Qa-1b restricted. In multiple sclerosis, the regulatory cells can be brain homing, with the phenotype of CD8$^+$CD38$^+$HLA-DR$^+$KIR$^+$CD29$^+$. Affinity agents specific for one or more of the cell surface markers can be used for detecting and isolating the regulatory T cells.

In some embodiments, methods are provided to treating undesirable T cell-mediated inflammatory conditions, which may include without limitation, autoimmune diseases, transplant rejection, etc. The methods of treatment provide for antigen-specific suppression of specific pathogenic CD4+ T cells by cytotoxic mechanisms. In some embodiments an effective dose of regulatory T cells is provided to an individual. In some embodiments the regulatory T cells are autologous to the individual being treated. In some embodiments the regulatory T cells are allogeneic to the individual being treated. In other embodiments an effective dose of a regulatory peptide is administered to an individual, which regulatory peptide elicits an antigen-specific regulatory response. The peptide may be administered in a suitable format, e.g. complexed with antigen-presenting cells, as a multimer, as a free peptide, etc.

The treatment may be administered at the onset of disease symptoms. The treatment may be administered at the onset of a disease relapse, at the peak of a disease relapse, etc. The treatment may be administered in combination with an additional agent, e.g. a disease modifying therapy, e.g. interferon beta, glatiramer acetate, teriflunomide, dimethyl fumarate, fingolimod, natalizumab, ocrelizumab, alemtuzumab, cladribine, mitoxantrone, and the like. The additional agent(s) may be administered concomitantly, staggered, following the antigen-specific therapy, etc.

In certain embodiments the treatment is directed to an autoimmune disease. In some embodiments the autoimmune disease is a demyelinating disease, e.g. multiple sclerosis, neuromyelitis optica, etc. In some embodiments the inflammatory condition is initiated with autoantigen. In some embodiments the initiating autoantigen is a peptide of a myelin-related protein, e.g. MOG, MBP, MAG, etc. In other embodiments the inflammatory condition is initiated by an infection, e.g. a viral infection.

In COVID-19 patients, for example, who can suffer from serious clinical problems that are suggestive of autoimmunity, there are elevated levels of KIR$^+$CD8$^+$ T cells correlated with disease severity and onset of vasculitis, suggesting that many of the complications of COVID-19 are the results of various types of autoimmunity.

In some embodiments, methods are provided for determining the antigenic specificity of regulatory T cells, thereby providing identification of regulatory peptide sequences. In one such method, T cell receptors (TCR) of an antigen-specific regulatory T cell, e.g. an α/β TCR pair, are expressed as a soluble multimer, for example as a tetramer. The TCR multimer is utilized in a binding assay against a library of diverse peptides in an MHC context, for example in a yeast display system. The use of human MHC proteins associated with inflammatory disease is of particular interest. After one or more rounds of binding and selection, the enriched peptide sequence provides identification for the antigenic specificity of the regulatory T cell. The peptide antigen thus identified may be the native peptide; or may be a surrogate peptide that acts to specifically activate regulatory T cells of interest.

In a related embodiment, peptide antigens are provided that specifically bind to and activate regulatory T cells are provided, which peptides can be identified by the methods described herein. It is a feature of regulatory peptides that they activate regulatory T cells to an antigen and MHC class I restricted, anti-T cell response. In other words, the regulatory T cells are activated by a regulatory peptide to a state where the regulatory T cells will suppress the responses of self-reactive and/or pathogenic CD4+ T cells by cytotoxic mechanisms.

Compositions of regulatory peptides may be pharmaceutical compositions, comprising pharmaceutically acceptable excipients, where the peptides are in a form that is suitable for T cell activation. In certain of such embodiments, a package is provided comprising includes an anti-CD49e agent, and one or more second therapeutic compounds, and a package insert or label that indicates that the anti-CD49e agent is to be administered in combination with the second compound to a patient for the treatment of a neurological inflammatory disease.

In some embodiments an isolated population of antigen specific, MHC Class I restricted CD8+ regulatory T cells is provided. In some embodiments the regulatory T cells are activated in vivo following administration of an initiating antigen to an individual, and isolated from a sample from the individual, e.g. peripheral blood, lymph node, etc. In some embodiments the regulatory T cells are activated in an in vitro culture system following administration of an initiating antigen. In other embodiments the T cells are activated in vitro by contact with a regulatory peptide, for example in co-culture with suitable antigen-presenting cells. In some embodiments the regulatory T cells, whether initially activated in vivo or in vitro, are expanded in an in vitro culture system, for example in the medium comprising one or more suitable cytokines for expansion, including without limitation IL-15, IL-1, IL-18, IL-33, etc.

In some embodiments the regulatory T cells express an engineered T cell receptor with specificity for a regulatory peptide. In some embodiments the T cells are obtained from an individual to be treated, and are engineered in vitro to express a TCR specific for a regulatory peptide in an MHC class I context. In some embodiments the T cells are obtained from the individual in the expansion period following an immune challenge, e.g. following vaccination. In other embodiments the regulatory T cells are allogeneic with respect to an individual being treated.

In some embodiments, methods are provided for analysis of inflammatory, including infectious disease, including without limitation viral infection such as SARS-CoV-2, in an individual, the method comprising detecting the presence, or detecting changes in levels, of regulatory CD8+ T cells, particularly CD8+KIR+ T cells. The methods may comprise, for example, detecting by flow cytometry, mass cytometry, etc. the presence of CD8$^+$KIR$^+$ cells in a patient sample or in a time series of patient samples, e.g. following therapeutic treatment, during a disease flare, etc. The cells may be more specifically characterized by expression of specific KIR proteins, including without limitation one or more of KIR2DL1, KIR2DL2, KIR2DL3, KIR2DL5, KIR3DL1, KIR3DL2; and may specifically include one or more of KIR2DL2, KIR2DL3, and KIR3DL1. The cells may be further characterized by expression of markers including, without limitation, CD38, HLA-DR, CD29, CD44, CD122, etc. The cells may be also be characterized for expression of a TCR associated with regulatory T cells, e.g. by binding a multimeric peptide/MHC polypeptide. The presence of increased levels of regulatory T cells can be associated with an improved disease prognosis, although in viral disease can be indicative of the presence of autoimmune related complications. Patients may be treated in accordance of the prognosis, by treatment methods described herein, or by conventional methods of treatment. Analysis may also assess a patient sample for the presence, e.g. expansion, of pathogenic CD4+ T cells specific for an autoantigen, etc.; for expansion of γδ T cells, and the like.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Figure 1:
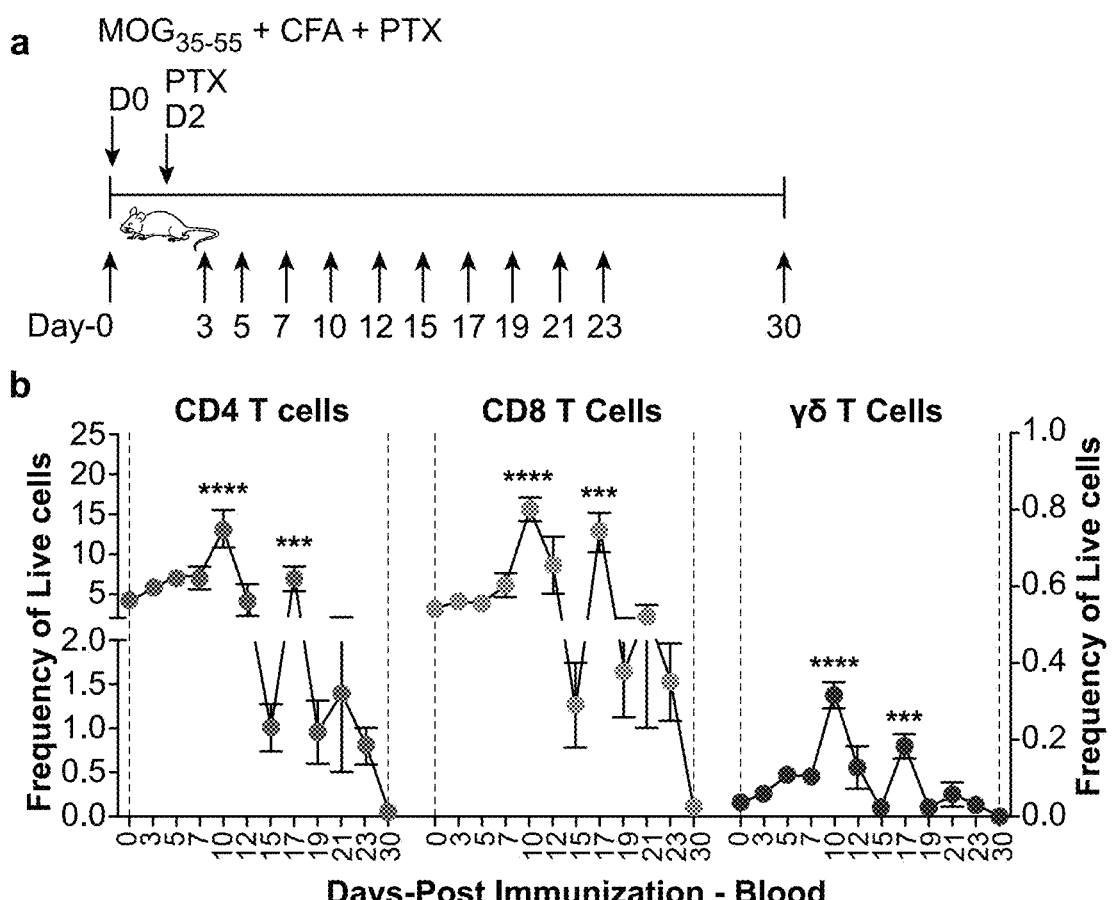
FIG. 1 Concomitant activation of all T cells after EAE immunization. a, C57BL/6J mice were immunized for EAE induction, and cells from blood, CNS, spleen and draining LNs were isolated and analysed for the total frequency of T cells at different days post-immunization (PI). b-e, The total frequency of $CD4^+$, $CD8^+$ and $\gamma\delta^+$ T cells in the blood (b), CNS (c), LNs (d) at spleen (e) at different days after immunization (D0 (unimmunized) (n=5), D3 (n=4), D5 (n=4), D7 (n=4), D10 (n=4), D12 (n=4), D15 (n=5), D17 (n=5), D19 (n=5), D21 (n=5), D23 (n=5), and D30 (n=3)). Data are mean±s.e.m. and representative of two independent experiments. *P=0.05; P=0.0097; *P=0.0008; ****P<0.0001; one-way analysis of variance (ANOVA) followed by Dunnets post hoc multiple comparison test.
Figure 1:
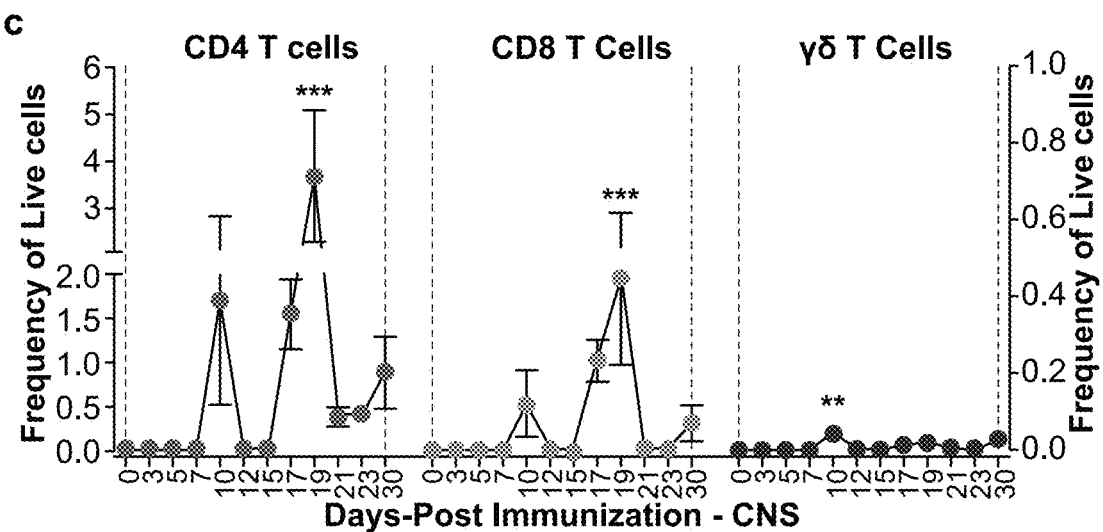
Figure 1:
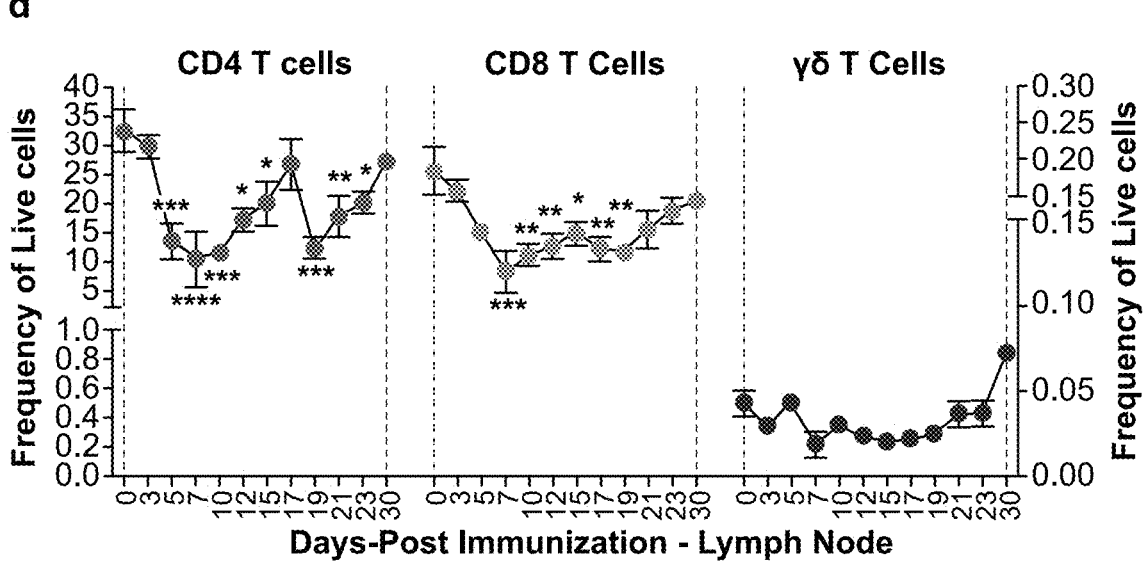
Figure 1:
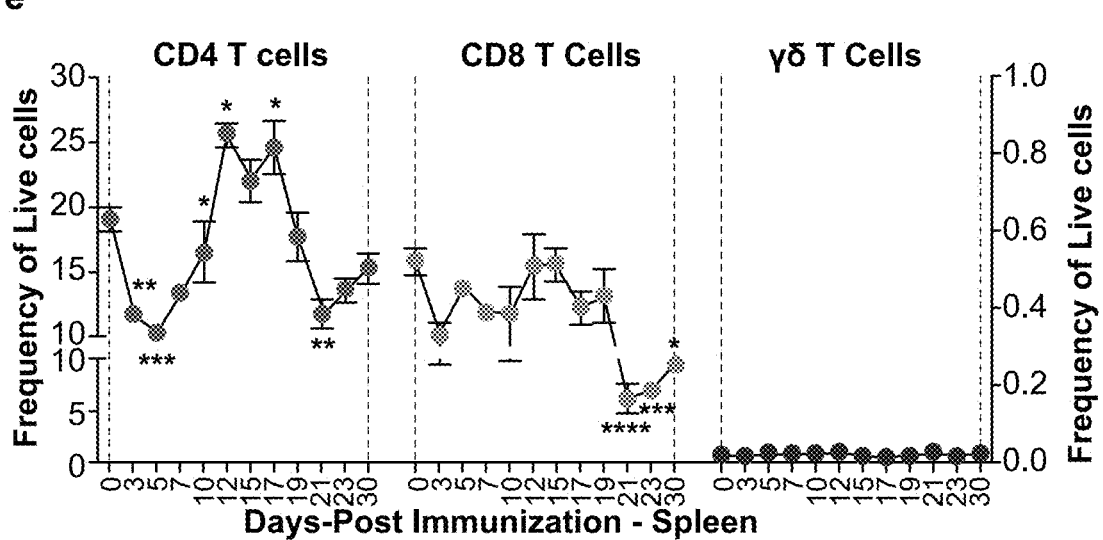

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

The present inventions have been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Compositions and methods are provided that relate to the characterization, use, and manipulation of antigen specific, class I MHC restricted, CD8+ regulatory T cells.

The subject methods may be used for prophylactic or therapeutic purposes. As used herein, the term "treating" is used to refer to both prevention of relapses, and treatment of pre-existing conditions. For example, the prevention of autoimmune disease may be accomplished by administration of the agent prior to development of a relapse. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom. The treatment of ongoing disease, where the treatment stabilizes or improves the clinical symptoms of the patient, is of particular interest.

"Inhibiting" the onset of a disorder shall mean either lessening the likelihood of the disorder's onset, or preventing the onset of the disorder entirely. Reducing the severity of a relapse shall mean that the clinical indicia associated with a relapse are less severe in the presence of the therapy than in an untreated disease. As used herein, onset may refer to a relapse in a patient that has ongoing relapsing remitting disease. The methods of the invention can be specifically applied to patients that have been diagnosed with inflammatory disease, including for example autoimmune disease.

Treatment may be aimed at the treatment or reducing severity of relapses, which are an exacerbation of a pre-existing condition.

"Diagnosis" as used herein generally includes determination of a subject's susceptibility to a disease or disorder, determination as to whether a subject is presently affected by a disease or disorder, prognosis of a subject affected by a disease or disorder (e.g., identification of disease states, stages of disease, or responsiveness of disease to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood, cerebral spinal fluid, and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "individual," "subject," "host," and "patient," used interchangeably herein and refer to any mammalian subject for whom diagnosis, treatment, or therapy is desired, for example humans, non-human primate, mouse, rat, guinea pig, rabbit, etc.

The term "agent" as used herein includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

"Suitable conditions" shall have a meaning dependent on the context in which this term is used. That is, when used in connection with an antibody, the term shall mean conditions that permit an antibody to bind to its corresponding antigen. When used in connection with contacting an agent to a cell, this term shall mean conditions that permit an agent capable of doing so to enter a cell and perform its intended function. In one embodiment, the term "suitable conditions" as used herein means physiological conditions.

A "subject" or "patient" in the context of the present teachings is generally a mammal. Mammals other than humans can be advantageously used as subjects that represent animal models of inflammation. A subject can be male or female.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). In particular the cell surface markers of the present teachings can be analyzed by any of various conventional methods known in the art. To "analyze" can include performing a statistical analysis to, e.g., determine whether a subject is a responder or a non-responder to a therapy (e.g., administration of a regulatory peptide treatment as described herein).

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that is generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

Disease Conditions

In some embodiments the methods of the invention comprise treating, isolating cell populations from, or diagnosing individuals "at-risk" for development of, or in the "early-stages" of, an inflammatory disease. "At risk" for development of an inflammatory disease includes: (1) individuals whom are at increased risk for development of an inflammatory disease, and (2) individuals exhibiting a "pre-clinical" disease state, but do not meet the diagnostic criteria for the inflammatory disease (and thus are not formally considered to have the inflammatory disease).

Individuals "at increased risk" for development (also termed "at-risk" for development) of an inflammatory disease are individuals with a higher likelihood of developing an inflammatory disease or disease associated with inflammation compared to the general population. Such individuals can be identified based on their exhibiting or possessing one or more of the following: a family history of inflammatory disease; the presence of certain genetic variants (genes) or combinations of genetic variants which predispose the individual to such an inflammatory disease; the presence of physical findings, laboratory test results, imaging findings, marker test results (also termed "biomarker" test results) associated with development of the inflammatory disease, or marker test results associated with development of a metabolic disease; the presence of clinical signs related to the inflammatory disease; the presence of certain symptoms related to the inflammatory disease (although the individual is frequently asymptomatic); the presence of markers (also termed "biomarkers") of inflammation; and other findings that indicate an individual has an increased likelihood over the course of their lifetime to develop an inflammatory disease or disease associated with inflammation. Most individuals at increased risk for development of an inflammatory disease or disease associated with inflammation are asymptomatic, and are not experiencing any symptoms related to the disease that they are at an increased risk for developing.

Included, without limitation, in the group of individuals at increased risk of developing an inflammatory disease or a disease associated with inflammation, are individuals exhibiting "a pre-clinical disease state". The pre-disease state may be diagnosed based on developing symptoms, physical findings, laboratory test results, imaging results, and other findings that result in the individual meeting the diagnostic criteria for the inflammatory disease, and thus being formally diagnosed. Individuals with "pre-clinical disease" exhibit findings that suggest that the individual is in the process of developing the inflammatory disease, but do not exhibit findings, including the symptoms, clinical findings, laboratory findings, and/or imaging findings, etc. that are necessary to meet the diagnostic criteria for a formal diagnosis of the inflammatory disease. In some embodiments, individuals exhibiting a pre-clinical disease state possess a genetic variant or a combination of genetic variants that place them at increased risk for development of disease as compared to individuals who do not possess that genetic variant or that combination of genetic variants. In some embodiments, these individuals have laboratory results, or physical findings, or symptoms, or imaging findings that place them at increased risk for development of an inflammatory disease. In some embodiments, individuals with preclinical disease states are asymptomatic. In some embodiments, individuals with pre-clinical disease states exhibit increased or decreased levels of the expression of certain genes, certain proteins, inflammatory markers, metabolic markers, and other markers.

In certain embodiments, this invention is directed to the treatment of individuals with established inflammatory disease or disease associated with inflammation. The inflammatory disease can be diagnosed based on an individual exhibiting symptoms, signs, clinical features, laboratory test results, imaging test results, biomarker results, and other findings that enable a physician to formally diagnose that individual with the inflammatory disease, which findings can include the specific expansion of disease causing $CD4^+$ T cells, the expansion of γδ T cells, and the concomitant expansion of regulatory $CD8^+$ T cells.

In some embodiments, established inflammatory disease is an inflammatory disease for which an individual has had a formal diagnosis of the disease made by a physician for longer than 6 months. In established inflammatory disease, the signs or symptoms of disease may be more severe as compared to, for example, the symptoms for an individual diagnosed with early-stage inflammatory disease. In established inflammatory disease, the disease process may cause tissue or organ damage. As described herein, in certain embodiments, determination of inflammation in an individual with established disease can comprise analyzing the individual for the presence of at least one marker indicative of the presence of inflammation.

An inflammatory disease is considered a disease which exhibits clinical manifestations (abnormal clinical markers) such as visible inflammation including pain, swelling, warmth, and redness, and with respect to the present invention, will involve as a causative agent antigen-specific pathologic CD4+ T cells. Inflammatory diseases include without limitation autoimmune diseases, and may further include diseases with a specific T cell mediated component. Autoimmune diseases include, for example, MS, SLE, RA, IDDM, NMO, etc.

Inflammatory demyelinating diseases of the central nervous system are of particular interest and include, without limitation, multiple sclerosis (MS), neuromyelitis optica (NO), and experimental acquired encephalitis (EAE). Demyelinating diseases may be initiated by peptides of myelin associated proteins, e.g. MOG, MBP, MAG, etc. Demyelinating inflammatory diseases of the peripheral nervous system include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy. Although not traditionally classified as an inflammatory disease, ALS has been found to have increased numbers of CD49e macrophages, and may be treated by the methods described herein.

Multiple sclerosis is characterized by various symptoms and signs of CNS dysfunction, with remissions and recurring exacerbations. Classifications of interest for analysis by the methods of the invention include relapsing remitting MS (RRMS), primary progressive MS (PPMS) and secondary progressive MS (SPMS). The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat can accentuate symptoms and signs.

Neuromyelitis optica (NMO), or Devic's disease, is an autoimmune, inflammatory disorder of the optic nerves and spinal cord. Although inflammation can affect the brain, the disorder is distinct from multiple sclerosis, having a different pattern of response to therapy, possibly a different pattern of autoantigens and involvement of different lymphocyte subsets.

The main symptoms of Devic's disease are loss of vision and spinal cord function. As for other etiologies of optic neuritis, the visual impairment usually manifests as decreased visual acuity, although visual field defects, or loss of color vision can occur in isolation or prior to formal loss of acuity. Spinal cord dysfunction can lead to muscle weakness, reduced sensation, or loss of bladder and bowel control. The damage in the spinal cord can range from inflammatory demyelination to necrotic damage of the white and grey matter. The inflammatory lesions in Devic's disease have been classified as type II lesions (complement mediated demyelinization), but they differ from MS pattern II lesions in their prominent perivascular distribution. Therefore, the pattern of inflammation is often quite distinct from that seen in MS.

Rheumatoid Arthritis (RA) is a chronic syndrome characterized usually by symmetric inflammation of the peripheral joints, potentially resulting in progressive destruction of articular and periarticular structures, with or without generalized manifestations (Firestein (2003) Nature 423(6937): 356-61; McInnes and Schett. (2011) N Engl J Med. 365(23): 2205-19). The cause is unknown. A genetic predisposition has been identified, and, in some populations, localized to a pentapeptide in the HLA-DR beta1 locus of class II histocompatibility genes. Environmental factors may also play a role.

Prominent immunologic abnormalities that may be important in pathogenesis include antibodies and immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

Systemic lupus erythematosus (SLE) is a systemic autoimmune disease characterized by malar rashes, oral ulcers, photosensitivity, serositis, seizures, low white blood cell counts, low platelet counts, seizures, a positive anti-nuclear antibody (ANA) test, and other positive autoantibodies. SLE is an autoimmune disease often characterized by polyclonal B cell activation, which results in a variety of anti-protein and non-protein autoantibodies that result in immune complexes and inflammation which contributes to tissue damage, however pathologic $CD4^+$ T cells can also be involved. SLE has a variable course characterized by exacerbations and remissions and can be difficult to study. For example, some patients may demonstrate predominantly skin rash and joint pain, show spontaneous remissions, and require little medication. The other end of the spectrum includes patients who demonstrate severe and progressive kidney involvement (glomerulonephritis and cerebritis) that requires therapy with high doses of steroids and cytotoxic drugs such as cyclophosphamide.

Inflammatory bowel diseases, include Crohn's disease and ulcerative colitis, involve autoimmune attack of the bowel. These diseases cause chronic diarrhea, frequently bloody, as well as symptoms of colonic dysfunction.

Systemic sclerosis (SSc, or scleroderma) is an autoimmune disease characterized by fibrosis of the skin and internal organs and widespread vasculopathy. Patients with SSc are classified according to the extent of cutaneous sclerosis: patients with limited SSc have skin thickening of the face, neck, and distal extremities, while those with diffuse SSc have involvement of the trunk, abdomen, and proximal extremities as well. Internal organ involvement tends to occur earlier in the course of disease in patients with diffuse compared with limited disease (Laing et al. (1997) Arthritis. Rheum. 40:734-42). The majority of patients with diffuse SSc who develop severe internal organ involvement will do so within the first three years after diagnosis at the same time the skin becomes progressively fibrotic (Steen and Medsger (2000) Arthritis Rheum. 43:2437-44.). Common manifestations of diffuse SSc that are responsible for substantial morbidity and mortality include interstitial lung disease (ILD), Raynaud's phenomenon and digital ulcerations, pulmonary arterial hypertension (PAH) (Trad et al. (2006) Arthritis. Rheum. 54:184-91.), musculoskeletal symptoms, and heart and kidney involvement (Ostojic and Damjanov (2006) Clin. Rheumatol. 25:453-7). Current therapies focus on treating specific symptoms, but disease-modifying agents targeting the underlying pathogenesis are lacking.

Autoimmune hepatitis is a disease in which the body's immune system attacks liver cells. This immune response causes inflammation of the liver, also called hepatitis. A genetic factor may make some people more susceptible to autoimmune diseases. Four subtypes of autoimmune hepatitis are recognized, but the clinical utility of distinguishing subtypes is limited. (1) positive ANA and SMA, elevated immunoglobulin G (classic form, responds well to low dose steroids); (2) positive LKM-1 (typically female children and teenagers; disease can be severe), LKM-2 or LKM-3; (3) positive antibodies against soluble liver antigen (this group behaves like group 1) (anti-SLA, anti-LP), and (4) no autoantibodies detected (~20%) (of debatable validity/importance) (Krawitt et al. Autoimmune hepatitis. New England Journal of Medicine, 1996 334 (14): 897-903).

Many degenerative diseases have an underlying inflammatory component, and examples of such degenerative diseases include osteoarthritis (OA), Alzheimer's disease (AD), and macular degeneration.

Osteoarthritis (OA) affects nearly 27 million people in the United States, accounting for 25% of visits to primary care physicians, and half of all NSAID prescriptions. OA is a chronic arthropathy characterized by disruption and potential loss of joint cartilage along with other joint changes, including bone remodeling that may include bone hypertrophy (osteophyte formation), subchondral sclerosis, and formation of subchondral cysts. OA is viewed as failure of the synovial joint. OA results in the degradation of joints, including articular cartilage and subchondral bone, resulting in mechanical abnormalities and impaired joint function. Symptoms may include joint pain, tenderness, stiffness, sometimes an effusion, and impaired joint function. A variety of causes can initiate processes leading to loss of cartilage.

Alzheimer's disease (AD) is the most common neurodegenerative disease in the population. AD affects approximately 10% of people over age 65 and almost 50% of people over age 85. It is estimated that by the year 2025, about 22 million individuals will be afflicted with AD. AD is characterized by a slowly progressive dementia. The definitive diagnosis of AD is made if the triad of dementia, neurofibrillary tangles, and senile plaques are found post-mortem. Senile plaques are invariably found in the brains of patients with Alzheimer disease. The principal constituent of senile plaques is amyloid beta protein ($A\beta$). $A\beta$ is a 42 amino acid peptide that is derived from the amyloid precursor protein (APP), which is a transmembrane glycoprotein with a variety of physiologic roles, including cell proliferation, adhesion, cell signaling, and neurite outgrowth. APP is normally cleaved within the $A\beta$ domain to generate a secreted fragment. However, alternative processing leads to the cleavage of APP to generate soluble $A\beta$ that can accumulate within senile plaques. Currently available drugs are central cholinesterase inhibitors aimed at increasing the concentration of postsynaptic acetylcholine in the brain. These drugs provide minimal clinical benefit in only a few cognitive parameters.

Macular degeneration can be of the wet type related to retinal neovascularization and vascular leak but is more commonly of the dry type also known as age-related macular degeneration (AMD). AMD is a chronic disease associated with loss of central vision, blurred vision, and ultimately blindness. Though the causes and risk factors for AMD are multifactorial, activation of innate immunity involving complement activation as well as cytokine production by macrophage and microglia has been implicated in development of AMD. Anti-inflammatory therapy including corticosteroids, non-steroidal anti-inflammatory agents, methotrexate, rapamycin, and biologic agents including TNF inhibitors and complement inhibitors have been suggested to slow progression of AMD (Wang et al, 2011. Eye (2011)25, 127-139). However, because these treatments are not curative and AMD is a chronic, non-fatal disease, their use is limited by risk of toxicity.

IDDM is a cell-mediated autoimmune disorder leading to destruction of insulin-secreting beta cells and overt hyperglycemia. T lymphocytes invade the islets of Langerhans, and specifically destroy insulin-producing β-cells. The depletion of β-cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic beta cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease.

Type II diabetes mellitus and metabolic syndrome. Type II diabetes mellitus is characterized by insulin resistance and hyperglycemia, which in turn can cause retinopathy, nephropathy, neuropathy, or other morbidities. Additionally, diabetes is a well-known risk factor for atherosclerotic cardiovascular disease. Metabolic syndrome refers to a group of factors, including hypertension, obesity, hyperlipidemia, and insulin resistance (manifesting as frank diabetes or high fasting blood glucose or impaired glucose tolerance), that raises the risk of developing heart disease, diabetes, or other health problems. There is a well-characterized progression from normal metabolic status to a state of impaired fasting glucose (IFG: fasting glucose levels greater than 100 mg/dL) or to a state of impaired glucose tolerance (IGT: two-hour glucose levels of 140 to 199 mg/dl after a 75 gram oral glucose challenge). Both IFG and IGT are considered prediabetic states, with over 50% of subjects with IFG progressing to frank type II diabetes within, on average, three years. The insulin resistance is caused, at least in part, by chronic low-grade inflammation. Macrophages accumulate in obese adipose tissue, where they produce TNF and other inflammatory cytokines in response to stimulation with saturated fatty acids and circulating lipopolysaccharide (LPS). Moreover, TNF inhibition can abrogate insulin resistance.

Atherosclerosis and atherosclerotic cardiovascular disease are diseases of the arterial wall. They are characterized by accumulation of fatty materials in the arterial wall, resulting in development of fatty plaques, which may rupture and cause vascular occlusion and ischemia. If such vascular occlusion and ischemia occur in a coronary artery, myocardial infarction may result. The atherosclerotic lesion comprises a highly inflammatory milieu characterized by the accumulation of inflammatory cells, including macrophages and to a lesser extent T and B cells, and the production of high levels of inflammatory cytokines, chemokines, and MMPs (Libby et al, Nature 2011. 473(7347):3170-25). Atherosclerosis may also be associated with low-grade systemic inflammation, as evidenced by high levels of high-sensitivity CRP (hsCRP) in the blood, an abnormality that can be partially countered by treatment with the drug rosuvastatin (Libby et al, Nature 2011. 473(7347):3170-25).

In addition to autoimmune diseases, inflammatory diseases and diseases associated with inflammation may include but are not limited to acne vulgaris, acne conglobata, acne fulminans, asthma, celiac disease, chronic prostatitis, ulcerative colitis, microscopic colitis, collagenous colitis, Crohn's disease, atopic dermatitis, diverticulitis, glomerulonephritis, interstitial cystitis, viral hepatitis including but not limited to hepatitis B and hepatitis C, interstitial cystitis, irritable bowel syndrome, reperfusion Injury, sarcoidosis, amyloidosis, and transplant rejection including but not limited to heart, lung, kidney, pancreas, bone marrow, stem cell, skin, corneal, and islet cell transplants. Additional inflammatory diseases and diseases associated with inflammation include infectious diseases associated with inflammation which include but are not limited to chronic infection with human immunodeficiency virus (HIV), hepatitis C virus (HCV), hepatitis B virus (HBV), syphilis, rickettsial diseases, lyme disease, bacterial cellulitis, chronic fungal infection, ehrlichiosis, HHV-6, Herpes simplex virus 1 and 2, stongyloidiasis, Epstein barr virus, cytomegalovirus, mycoplasma infection, Creutzfeldt-Jacob disease, oncocerciasis, nocardia, Whipples disease, mycobacterial disease, tinea infection, and alphaviruses including but not limited to chikungunya, ross river virus, or other alphaviruses. Additional inflammatory diseases and diseases associated with inflammation include but are not limited to anti-phosholipid syndrome, Hashimoto's thyroiditis, Dequervains thyroiditis, Graves thyroiditis, adrenalitis, type I diabetes mellitus, hypophysitis, pemphigus vulgaris, bullous pemphigoid, Eaton Lambert syndrome, myasthenia gravis, Addison's disease, ankylosing spondylitis, alopecia aureate, autoimmune hemolytic anemia, immune thrombocytopenia purpura, autoimmune hepatitis, Behcets disease, cardiomyopathy, chronic fatigue syndrome, chronic inflammatory demyelinating polyneuropathy, autoimmune inner ear disease, cicatricial pemphigoid, Dego's Disease, dermatomyositis/juvenile dermatomyositis, polymyositis, inclusion body myositis, Guillain-Barre syndrome, Meniere's Disease, mixed connective tissue disease, pernicious anemia vasculitis, polychondritis, polyglandular autoimmune syndrome, polymyalgia rheumatic, primary biliary cirrhosis, psoriasis, psoriatic arthritis, Raynaud's phenomenon, Reiter's syndrome, reactive arthritis, rheumatic fever, scleroderma, Sjogren's syndrome, stiff-man syndrome, Takayasu arteritis, temporal arteritis/giant cell arteritis, polyartereitis nodosa, uveitis, vitiligo, autoimmune Wilsons disease, bleeding disorders due to autoreactivity against clotting factors, chronic urticaria, vasculitis including but not limited to granulomatosus with polyangiitis, eosinophilic granulomatosis with polyangiits, microscopic polyangiits, henoch schonlien purpura, hypersensitivity vasculitis, hypocomplementemic urticarial vasculitis, polyarteritis nodosa.

Inflammatory conditions can also arise in the context of infection, including without limitation bacterial, viral, protozoan, and fungal infections, where cross-reactivity with a pathogen antigen and self-antigens leads to inflammation and undesirable CD4+ T cell activity against self-antigens. Viral pathogens of interest include without limitation, coronavirus infection, e,g, SARS-CoV-1, SARS-CoV-2, MERS-COV, and the like, and other viruses that cause an enhanced inflammatory response and self-reactive T cell responses. Other microbes of interest, but not limited to the following, include: *Yersinia* sp., e.g. *Y. pestis, Y. pseudotuberculosis, Y enterocolitica; Franciscella* sp.; *Pasteurella* sp.; *Vibrio* sp., e.g. *V. cholerae, V. parahemolyticus; Legionella* sp., e.g. *L. pneumophila; Listeria* sp., e.g. *L. monocytogenes; Mycoplasma* sp., e.g. *M. hominis, M. pneumoniae; Mycobacte-*

*rium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori,* etc. Also included are intracellular protozoan pathogens, e.g. *Plasmodium* sp, *Trypanosoma* sp., *Giardia* sp., *Toxoplasma* sp., *Leishmania* sp., etc.

Identification and Isolation of Regulatory T Cells

Antigen-specific, MHC Class I restricted T cells are shown herein to have a distinct timing for expansion after exposure to an antigen, and to have a distinct phenotype, which can be conveniently described as a cell-surface phenotype that allows for ease of identification and isolation.

As described in the Examples, upon contact (e.g. immunization) with an initiating antigen, there is an increase in the frequency of total CD4$^+$ T cells in the blood from up to about day 8-12 post-immunization, which declines over the next 7-10 days. There is a concomitant increase in the frequency of total CD8$^+$ and $\gamma\delta^+$ T cells in the blood, which matches the declines and increases of CD4$^+$ T cells. This pattern of synchronous behavior in these T cell populations was also observed in other tissues, for example in the CNS, etc. Tissues that are a source of T cells, such as spleen and lymph node, may have a different pattern of synchronous behavior, with a gradual decline in the frequency of total CD4$^+$, CD8$^+$, and $\gamma\delta^+$ T cells up to day 7, then a rise in frequency. All three types of T cells showed increased clonal expansion, starting at about day 7 after immunization. The clonally expanded CD4+ cells are activated, for example being CD44$^{high}$CD6L$^{low}$ and are specific for the initiating antigen. The clonally expanded CD8+ cells are not responsive to the initiating antigen.

Isolated populations of the regulatory (CD8+KIR+) T cells can be used as therapeutic agents, can be genetically engineered to express an exogenous TCR, can be screened to determine the antigen specificity of the TCR, and the like. Cells may be isolated from a cell-containing biologic sample from an individual of interest at any time, but conveniently may be obtained at the time of greatest expansion in the blood. Following immune stimulation, including, for example, immunization, the peak of regulatory cells in the blood may be at about day 7, about day 8, about day 9, about day 10, about day 11, about day 12, about day 13 following immunization. The number of regulatory T cells in the blood is typically low, for example less than about 2%, less than about 1.5%, less than about 1%, less than about 0.5%, of total PBMC.

Markers of the regulatory T cells include CD8, and typically one or more KIR proteins, including without limitation one or more of KIR2DL1, KIR2DL2, KIR2DL3, KIR2DL5, KIR3DL1, KIR3DL2; and may specifically include one or more of KIR2DL2, KIR2DL3, and KIR3DL1. The cells may be further characterized by expression of markers including, without limitation, CD38, HLA-DR, CD29, CD44, CD122, etc. The cells can be characterized as activated, e.g. CD44$^{high}$CD6L$^{low}$. The cells may be also be characterized for expression of a TCR associated with regulatory T cells, e.g. by binding a multimeric peptide/MHC polypeptide.

Markers can be detected, and/or used for selection or isolation of cells by binding to an affinity reagent, e.g. a specific binding member that, through chemical or physical means specifically binds to the marker on the cell (i.e., second specific binding member). Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; etc. The specific binding pairs may include analogs, derivatives and fragments of the original specific binding member. For example, a receptor and ligand pair may include peptide fragments, chemically synthesized peptidomimetics, labeled protein, derivatized protein, etc.

Especially useful reagents are antibodies specific for markers present on the desired cells (for positive selection) and undesired cells (for negative selection). Whole antibodies may be used, or fragments, e.g. Fab, F(ab)$_2$, light or heavy chain fragments, etc. Such selection antibodies may be polyclonal or monoclonal and are generally commercially available or alternatively, readily produced by techniques known to those skilled in the art. Antibodies selected for use will have a low level of non-specific staining and will usually have an affinity of at least about 100 µM for the antigen.

In one embodiment of the invention, antibodies for selection are coupled to a plate, bead, magnetic reagent, and the like; or are labeled with a label, such as a fluorescent label, a mass label, etc. that allows for selection. The exact method for coupling is not critical to the practice of the invention, and a number of alternatives are known in the art. Direct coupling attaches the antibodies to the plate, particles, magnetic reagent, etc. Indirect coupling can be accomplished by several methods. The antibodies may be coupled to one member of a high affinity binding system, e.g. biotin, and the particles attached to the other member, e.g. avidin. One may also use second stage antibodies that recognize species-specific epitopes of the antibodies, e.g. anti-mouse Ig, anti-rat Ig, etc.

Functionally relevant regulatory T cells can be purified from tissue samples or from cultures. The purified cell populations are useful in analysis of gene expression, drug screening assays, for therapeutic purposes, for in vitro cultures and co-cultures, and the like.

The cell compositions thus obtained are highly purified, where the desired cells, may be at least about 50% of the desired cell type, at least about, at least about 75%, at least about 80%, at least about 90%, at least about 95%, or more.

For positive or negative selection, separation of the subject cell population utilizes affinity separation to provide a substantially pure population. Techniques for affinity separation may include magnetic separation using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Any technique may be employed which is not unduly detrimental to the viability of the cells.

Positive immunoselection utilizes a reagent that selectively binds to, for example, CD8, inhibitory KIR proteins, etc. on the cells surface. Negative immunoselection is optionally performed to deplete cells of other lineages, for example CD4, B cell markers, monocyte markers, etc. Size, for example forward scatter, can be used to gate out blood cells other than lymphocytes. In some embodiments two, three, four, five or more negative immunoselection reagents are used, e.g. in a cocktail or in separate negative selections. In some embodiments, a lineage cocktail comprising reagents for negative selection of each of myeloid cells; B cells, CD4+ T cells, etc. Where negative separation is used, it is often performed prior to the positive selection, in order to deplete the cell population of undesirable cells. A positive selection is then performed.

Specific binding members, usually antibodies, are added to the suspension of cells, and incubated for a period of time sufficient to bind the available antigens. The incubation will usually be at least about 2 minutes and can be less than about 30 minutes. It is desirable to have a sufficient concentration of antibodies in the reaction mixture so that the efficiency of the separation is not limited by lack of reagent. The appropriate concentration is determined by titration.

The medium in which the cells are separated will be any medium which maintains the viability of the cells. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc. The cells may be placed in culture, formulated for therapy, frozen, etc.

The compositions thus obtained have a variety of uses in clinical therapy, research, development, and commercial purposes. For therapeutic purposes, for example, a therapeutically effective dose may be administered to selectively suppress undesirable pathogenic T cell responses, optionally after expansion in culture.

Expansion or activation in culture may utilize cytokines and/or antigen presenting cells (APC). The contacting may be performed in any suitable culture medium. Where present, APC can be loaded with a suitable peptide antigen or protein, which is then presented on the cell surface. The ratio of T cell to APC, if present, may be anywhere from about 1:20 to about 20:1, and is not critical so long as the number of APC is not limiting. A period of from up to 8 days, up to 10 days, up to 12 days, up to 14 days may be sufficient (see, for example, Dudley et al, JCO 2005; 23(10):2346-2357). The regulatory T cells thus primed may be used for any desired purpose, including experimental purposes relating to determination of antigen specificity, cytokine profiling, and the like, and for delivery in vivo.

Cytokines that are useful for expansion in vitro include, without limitation, one or more cytokines that enhance proliferation of CD8+ T cells, which may include, without limitation, Type I IFNs (IFNα and IFNβ), IL-1, IL-2, IL-6, IL-7, IL-12, IL-15, IL-18, IL-21, IL-25, IL-27, IL-33, etc. Cells may be cultured in conventional nutrient media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Ex vivo T-cell activation may be achieved by procedures established in the art including cell-based T-cell activation, antibody-based activation or activation using a variety of bead-based activation reagents. Cell-based T-cell activation may be achieved by exposure of the T-cells to antigen presenting cells, such as dendritic cells or artificial antigen presenting cells such as irradiated K562 cells. Antibody based activation of T-cell surface CD3 molecules with soluble anti-CD3 monoclonal antibodies also supports T-cell activation in the presence of IL-2.

T cells can be cultures in contact with a surface providing an agent that stimulates a CD3 TCR complex associated signal (e.g., an anti-CD3 antibody) and an agent that stimulates a co-stimulatory molecule on the surface of the T-cells (e.g an anti-CD28 antibody). Bead-based activation of T-cells may be achieved using commercially available T-cell activation reagents including but not limited to the Invitrogen® CTS Dynabeads® CD3/28 (Life Technologies, Inc. Carlsbad CA) or Miltenyi MACS® GMP ExpAct Treg beads or Miltenyi MACS GMP TransAct™ CD3/28 beads (Miltenyi Biotec, Inc.). Conditions appropriate for T-cell culture are well known in the art. Lin, et al. (2009) Cytotherapy 11(7):912-922; Smith, et al. (2015) Clinical & Translational Immunology 4:e31 published online 16 Jan. 2015. The target cells are maintained under conditions necessary to support growth, for example, an appropriate temperature (e.g., 37° C.) and atmosphere (e.g., air plus 5% $CO_2$).

The regulatory T cells thus isolated and optionally expanded are optionally genetically modified, for example to express a TCR other than the native TCR. A regulatory T cells expanded during an immune response to a vaccine, for example, may be modified to express a TCR specific for suppression of an autoimmune disease, a transplantation antigen, etc. Transduction of T-cells with an expression vector may be accomplished using techniques well known in the art including but not limited co-incubation with host T-cells with viral vectors, electroporation, and/or chemically enhanced delivery.

Alternatively an engineered TCR can be inserted by, for example, CRISPR/Cas9; meganuclease; engineered I-CreI homing endonuclease, etc. See, for example, Eyquem et al. (2017) Nature 543:113-117, and Georgiadis et al. (2018) Mol. Ther. 26:1215-1227.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether the administered cells or progeny thereof are still present.

For therapeutic purposes, cells may be autologous or allogeneic. The MHC restriction of the regulatory T cell will be matched to the MHC type of the recipient in such cases.

An effective dose of regulatory cells are infused to the recipient and allowed to contact CD4+ T cells in their native environment, e.g. in lymph nodes, etc. Dosage and frequency may vary depending on the agent; mode of administration; and the like. It will be understood by one of skill in the art that such guidelines will be adjusted for the individual circumstances. The dosage may also be varied for localized administration, e.g. intranasal, inhalation, etc., or for systemic administration, e.g. i.m., i.p., i.v., and the like. An enhanced immune response may be manifest as an increase in the cytolytic response of regulatory T cells towards the target cells present in the recipient, e.g. decrease in symptoms of autoimmune disease; and the like.

Regulatory T cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bolus or slow infusion), intraarterial, intraperitoneal, intrathecal or subcutaneous administration.

The regulatory T cells may be infused to the subject in any physiologically acceptable medium, normally intravascularly, although they may also be introduced into any other convenient site, where the cells may find an appropriate site for growth. Generally at least about $10^4$ cells/kg are administered, at least about $10^5$ cells/kg; at least about $10^6$ cells/kg, at least about $10^7$ cells/kg, or more, usually being limited by the number of T cells that are obtained during collection.

A course of therapy may be a single dose or in multiple doses over a period of time. In some embodiments, the cells are administered in a single dose. In some embodiments, the cells are administered in two or more split doses administered over a period of 1, 2, 3, 4, 5, 6, 7, 8, 9, 10, 11, 12, 13, 14, 21, 28, 30, 60, 90, 120 or 180 days. The quantity of cells administered in such split dosing protocols may be the same in each administration or may be provided at different levels. Multi-day dosing protocols over time periods may be provided by the skilled artisan (e.g. physician) monitoring the administration of the cells taking into account the response of the subject to the treatment including adverse effects of the treatment and their modulation as discussed above.
Screening for Antigenic Specificity The selected regulatory T cells can be used as a source of sequences encoding TCRs providing for antigen-specific suppression of undesirable CD4+ T cell mediated responses. The TCR encoding sequences can be isolated by any convenient method, for example as detailed in the Examples.

The TCR of interest can be expressed in soluble form, and multimerized for use as a selective binding agent. The soluble protein may be a single chain, or more usually a heterodimer. In some embodiments, a soluble TCR is modified by the addition of a biotin acceptor peptide sequence at the C terminus of one polypeptide. After biotinylation at the acceptor peptide, the TCR can be multimerized by binding to biotin binding partner, e.g. avidin, streptavidin, traptavidin, neutravidin, etc. The biotin binding partner can comprise a detectable label, e.g. a fluorophore, mass label, etc., or can be bound to a particle, e.g. a paramagnetic particle. Selection of ligands bound to the TCR can be performed by flow cytometry, magnetic selection, and the like as known in the art.

The TCR multimer is utilized in a binding assay to a library of diverse peptide antigens. The peptide ligand is from about 8 to about 20 amino acids in length, usually from about 8 to about 18 amino acids, from about 8 to about 16 amino acids, from about 8 to about 14 amino acids, from about 8 to about 12 amino acids, from about 10 to about 14 amino acids, from about 10 to about 12 amino acids. It will be appreciated that a fully random library would represent an extraordinary number of possible combinations. In some methods, the diversity is limited at the residues that anchor the peptide to the MHC binding domains, which are referred to herein as MHC anchor residues. The position of the anchor residues in the peptide are determined by the specific MHC binding domains. Diversity may also be limited at other positions as informed by binding studies, e.g. at TCR anchors. At least $10^6$, at least $10^7$, more usually at least $10^8$ different peptide ligands are present in the library.

The MHC proteins used in the libraries may be from any mammalian or avian species; of particular interest are the human HLA proteins. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and β₂-microglobulin.

The MHC binding domains are typically a soluble form of the normally membrane-bound protein. The soluble form is derived from the native form by deletion of the transmembrane domain. Conveniently, the protein is truncated, removing both the cytoplasmic and transmembrane domains. In some such embodiments the binding domains have been subjected to mutagenesis and selected for amino acid changes that enhance the solubility of the single chain polypeptide, without altering the peptide binding contacts. For class I proteins, the binding domains may include the α1, α2 and α3 domain of a Class I allele, including without limitation HLA-A, HLA-B, HLA-C, H-2K, H-2D, H-2L, which are combined with β₂-microglobulin. Not more than about 10, usually not more than about 5, preferably none of the amino acids of the transmembrane domain will be included. The deletion will be such that it does not interfere with the ability of the domains to bind peptide ligands.

The library of diverse sequences are generated and inserted into to a vector suitable for the host cell of interest, where the vector can be, without limitation, suitable for expression in yeast cells, and where the yeast cells may be induced to express the polypeptide library. Once introduced in the host cells, expression of the library is induced and the cells maintained for a period of time sufficient to provide cell surface display of the polypeptides of the library.

Selection for a peptide that binds to the regulatory TCR is performed by combining a multimerized TCR with the population of host cells expressing the library. Rounds of selection are performed until the selected population has a signal above background, usually at least three and more usually at least four rounds of selection are performed.

After a final round of selection, polynucleotides are isolated from the selected host cells, and the sequence of the selected peptide ligands are determined, usually by high throughput sequencing.

Sequencing platforms that can be used in the present disclosure include but are not limited to: pyrosequencing, sequencing-by-synthesis, single-molecule sequencing, second-generation sequencing, nanopore sequencing, sequencing by ligation, or sequencing by hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, MA) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLID sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503;

7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

As shown in the Examples, the peptide antigen thus identified may be a native peptide of the individual, or may be a surrogate peptide that specifically activates regulatory T cells of interest. The peptide, termed a regulatory peptide, is useful as a screening tool, and finds particular use as a therapeutic agent to activate regulatory T cells. Regulatory peptides can be used to activate T cells in vitro or in vivo.

Inflammatory diseases, including autoimmune diseases as discussed herein, can be treated by administering to the subject a therapeutically effective amount of an regulatory peptide, or active fragment or derivative thereof. The peptides may be administered as a single agent, as a cocktail of both peptides; or in combination with a second therapeutic agent.

Regulatory peptides usually comprise at least about 6 amino acids, at least about 7 amino acids, at least about 8 amino acids, at least about 9 amino acids, at least about 10 amino acids, at least about 11 amino acids, at least about 12 amino acids, or more, and may further include fusion polypeptides as known in the art in addition to the provided sequences. Regulatory peptides useful in this invention also include derivatives, variants, and biologically active fragments of naturally occurring regulatory peptides, and the like. The regulatory peptide sequence may be a designed sequenced derived from mutagenesis in the diverse peptide library. The specificity of the TCR may be conformational, and thus a peptide that activates a regulatory T cell of interest may have a sequence essentially unrelated to a native peptide.

Regulatory peptides can be modified, e.g., joined to a wide variety of other oligopeptides or proteins for a variety of purposes. For example, post-translationally modified, for example by prenylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, variants of the present invention include variants having phosphorylated amino acid residues, e.g. phosphotyrosine, phosphoserine, or phosphothreonine.

The ability of an regulatory peptide to modulate lymphocyte activity can be determined, for example, by the ability of the peptide to induce a cytotoxic effect on activated pathologic lymphocytes; and the like, as disclosed in the Examples provided herein.

In some embodiments, an regulatory peptide is provided as a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. These fusion proteins can facilitate purification and show an increased half-life in vivo. Fusion proteins having disulfide-linked dimeric structures (due to the IgG)

can also be more efficient in binding and neutralizing other molecules than the monomeric secreted protein or protein fragment alone.

In some other embodiments, regulatory peptide variants of the present invention include variants further modified to improve their resistance to proteolytic degradation or to optimize solubility properties or to render them more suitable as a therapeutic agent. For example, variants of the present invention further include analogs containing residues other than naturally occurring L-amino acids, e.g. D-amino acids or non-naturally occurring synthetic amino acids. D-amino acids may be substituted for some or all of the amino acid residues.

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

A regulatory peptide can be provided in pharmaceutical compositions suitable for therapeutic use, e.g. for human treatment. In some embodiments, pharmaceutical compositions include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent.

Therapeutic entities are often administered as pharmaceutical compositions comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Also provided are combination therapy methods, where the combination may provide for additive or synergistic benefits. Combinations of an regulatory peptide may be obtained with a second agent selected from one or more of the general classes of drugs commonly used in the non-antigen specific treatment of autoimmune disease, which include corticosteroids and disease modifying drugs; or from an antigen-specific agent. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Disease modifying drugs are also useful in combined therapy. These agents include methotrexate, leflunomiden etanercept, infliximab, adalimumab, anakinra, rituximab, CTLA4-Ig (abatacept), antimalarials, gold salts, sulfasalazine, d-penicillamine, cyclosporin A, cyclophosphamide azathioprine; and the like. Treatments for MS may include interferon β, Copaxone, and anti-VLA4, which reduce relapse rate. MS is also treated with immunosuppressive agents including methylprednisolone, other steroids, methotrexate, cladribine and cyclophosphamide.

Combination therapies may be sequentially staged, provided in a co-administration formulation, or concomitant administration during the same time period. "Concomitant administration" of a known therapeutic drug with a pharmaceutical composition of the present invention means administration of the drug and regulatory peptide at such time that both the known drug and the composition of the present invention will have a therapeutic effect. Such concomitant administration may involve concurrent (i.e. at the same time), prior, or subsequent administration of the drug with respect to the administration of a compound of the invention. A person of ordinary skill in the art would have no difficulty determining the appropriate timing, sequence and dosages of administration for particular drugs and compositions of the present invention.

Regulatory peptides can serve as the active ingredient in pharmaceutical compositions formulated for the treatment of various disorders as described above. The active ingredient is present in a therapeutically effective amount, i.e., an amount sufficient when administered to treat a disease or medical condition mediated thereby, in particular by reducing the activity of inflammatory lymphocytes. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The peptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal method.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

The regulatory peptide compositions may be administered in a single dose, or in multiple doses, usually multiple doses over a period of time, e.g. daily, every-other day, weekly, semi-weekly, monthly etc. for a period of time sufficient to reduce severity of the inflammatory disease, which may comprise 1, 2, 3, 4, 6, 10, or more doses.

Determining a therapeutically or prophylactically effective amount can be done based on animal data using routine computational methods. In one embodiment, the therapeutically or prophylactically effective amount contains between about 0.1 mg and about 1 g of protein. In another embodiment, the effective amount contains between about 1 mg and about 100 mg of protein. In a further embodiment, the effective amount contains between about 10 mg and about 50 mg of the protein. The effective dose will depend at least in part on the route of administration. The dose may be from about 0.1 μg/kg patient weight; about 1 μg/kg; about 10. μg/kg; to about 100 μg/kg.

In methods of use, an effective dose of an agent of the invention is administered alone, or combined with additional active agents for the treatment of a condition as listed above. The effective dose may be from about 1 ng/kg weight, 10 ng/kg weight, 100 ng/kg weight, 1 μg/kg weight, 10 μg/kg weight, 25 μg/kg weight, 50 μg/kg weight, 100 μg/kg weight, 250 g/kg weight, 500 μg/kg weight, 750 μg/kg weight, 1 mg/kg weight, 5 mg/kg weight, 10 mg/kg weight, 25 mg/kg weight, 50 mg/kg weight, 75 mg/kg weight, 100 mg/kg weight, 250 mg/kg weight, 500 mg/kg weight, 750 mg/kg weight, and the like. The dosage may be administered multiple times as needed, e.g. every 4 hours, every 6 hours, every 8 hours, every 12 hours, every 18 hours, daily, every 2 days, every 3 days, weekly, and the like. The dosage may be administered orally.

The compositions can be administered in a single dose, or in multiple doses, usually multiple doses over a period of time, e.g. daily, every-other day, weekly, semi-weekly, monthly etc. for a period of time sufficient to reduce severity of the inflammatory disease, which can comprise 1, 2, 3, 4, 6, 10, or more doses.

Determining a therapeutically or prophylactically effective amount of an agent according to the present methods can be done based on animal data using routine computational methods. The effective dose will depend at least in part on the route of administration.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

Example 1

Opposing T Cell Responses in Experimental Autoimmune Encephalomyelitis

In experimental autoimmune encephalomyelitis (EAE), a model for multiple sclerosis (MS), induction generates successive waves of clonally expanded CD4+, CD8+, and γδ+ T cells in the blood and central nervous system. In MS patients, we also observe major expansions of CD8+ T cells.

In EAE, we find that most expanded CD4+ T cells are specific for the inducing myelin peptide MOG35-55 but in contrast, peptide ligands derived from a yeast peptide-MHC display library for some of the clonally expanded CD8+ T cells inhibit disease by suppressing the proliferation of MOG-specific CD4+ T cells. These results demonstrate that the induction of autoreactive CD4+ T cells triggers an opposing mobilization of regulatory CD8+ T cells.

Here, we asked whether a coordinated T cell response occurs in EAE, and found that it does, both in the blood and in the central nervous system (CNS). While the expanded CD4+ T cells are largely specific for the MOG35-55 peptide as expected, clonally expanded CD8+ T cells were nonresponsive to myelin peptides or proteins.

To identify the target antigens, we screened six CD8+ TCRs on a class I MHC molecule H2-Db yeast p-MHC display library and obtained surrogate peptides for two of these TCRs. We found that instead of exacerbating EAE, they greatly reduced severity. Further analyses show that these T cells represent a unique subset of regulatory CD8+ T cells that suppress MOG35-55 specific CD4+ T cell proliferation. The induction of autoreactive CD4+ T cells in EAE triggers a counteracting wave of regulatory CD8+ T cells. In newly diagnosed MS patients, TCR analysis showed very pronounced CD8+ T cell clonal expansions in activated, brain homing T cells, and similar skewing towards an IL-17 phenotype in the γδ+ T cells. CD4+ clonal expansions were generally modest. Most importantly, it seems likely that pathogenic CD4+ and γδ+ T cell responses opposed by regulatory CD8+ T cell responses is a common phenomenon across autoimmune diseases.

Results

Figure 6:
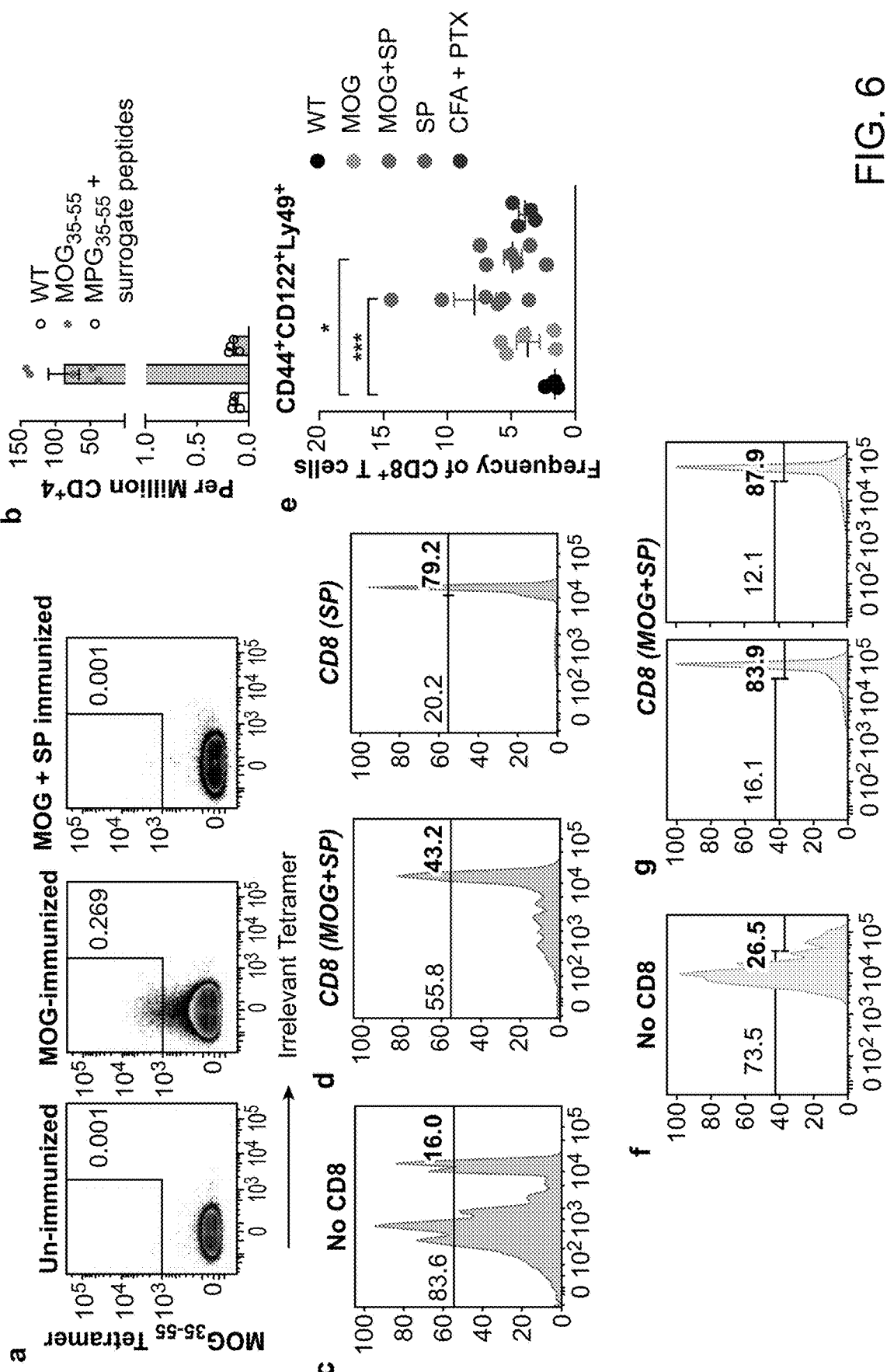
FIG. 6 $CD8^+$ T-cell-specific SP immunization suppresses $MOG_{35-55}$-specific $CD4^+$ T cells. a, b, C57BL/6J mice were immunized with an emulsion containing $MOG_{35-55}$, CFA and PTX, with (n=4) or without (n=5) SP. a, Spleen and LN cells were isolated from unimmunized (n=4) and D10 post-immunized (n=5 mice per group) mice, and enriched for $MOG_{35-55}$ $I\text{-}A^b$ pMHC-specific $CD4^+$ T cells. FACS dot plots from representative mice from different groups are shown. b, Frequency of $MOG_{35-55}$-specific $CD4^+$ T cells from each group. Data are mean±s.e.m. and representative of two independent experiments. c, d, C57BL/6J mice were immunized as in a and b with (n=2 mice) or without (n=2 mice) SP, and isolated spleen and LN cells from unimmu-nized (n=2) and D10 post-immunized mice were enriched for $CD4^+$, $CD8^+$ T cells, or antigen presenting cells (APCs). Dye-labelled $CD4^+$ T cells from MOG-immunized mice were co-cultured with APCs from MOG-immunized mice in the absence (c) or presence (d) of $CD8^+$ T cells from mice immunized with MOG, MOG and SP or SP alone. Cells were analysed for proliferation 7 days after co-culture. Representative data from two independent experiments. e, Frequency of $CD8^+$ T cells with a regulatory phenotype ($CD44^+CD122^+Ly49^+$) are shown among wild-type (n=4) and different immunization groups (n=5 mice per group). Data are mean±s.e.m. and representative of two independent experiments. *P=0.0382; ***P=0.001; one-way ANOVA followed by Tukey's post hoc multiple comparison test. f-h, CD4+ T cells from MOG-immunized mice were co-cultured without (f) or with total $CD8^+$ T cells (g), or with purified $CD8^+CD44^+CD122^+Ly49^+$ (Ly49$^+$) (h) or $CD8^+CD44^+$ $CD122^+Ly49^-$(Ly49$^-$) (i) T cells from mice immunized with MOG and SP (n=2 mice per group). Data are representative of two independent experiments. j, Heat map of gene expression in RNA-seq samples. Genes were selected on the basis that they are differentially expressed ($\log_2$-transformed fold change>0.75 and adjusted P<0.005; and two-tailed Benjamini-Hochberg adjusted P<0.005) as defined by DESeq2 in both Ly49$^+$ versus Ly49$^-$ and MOG versus MOG plus SP comparisons. Columns show samples; rows and columns are ordered based on hierarchical clustering. Nor-malized gene expression values are centred for each gene by subtracting the average value of all samples from each sample value. Data are representative of two independent experiments.
Figure 6:
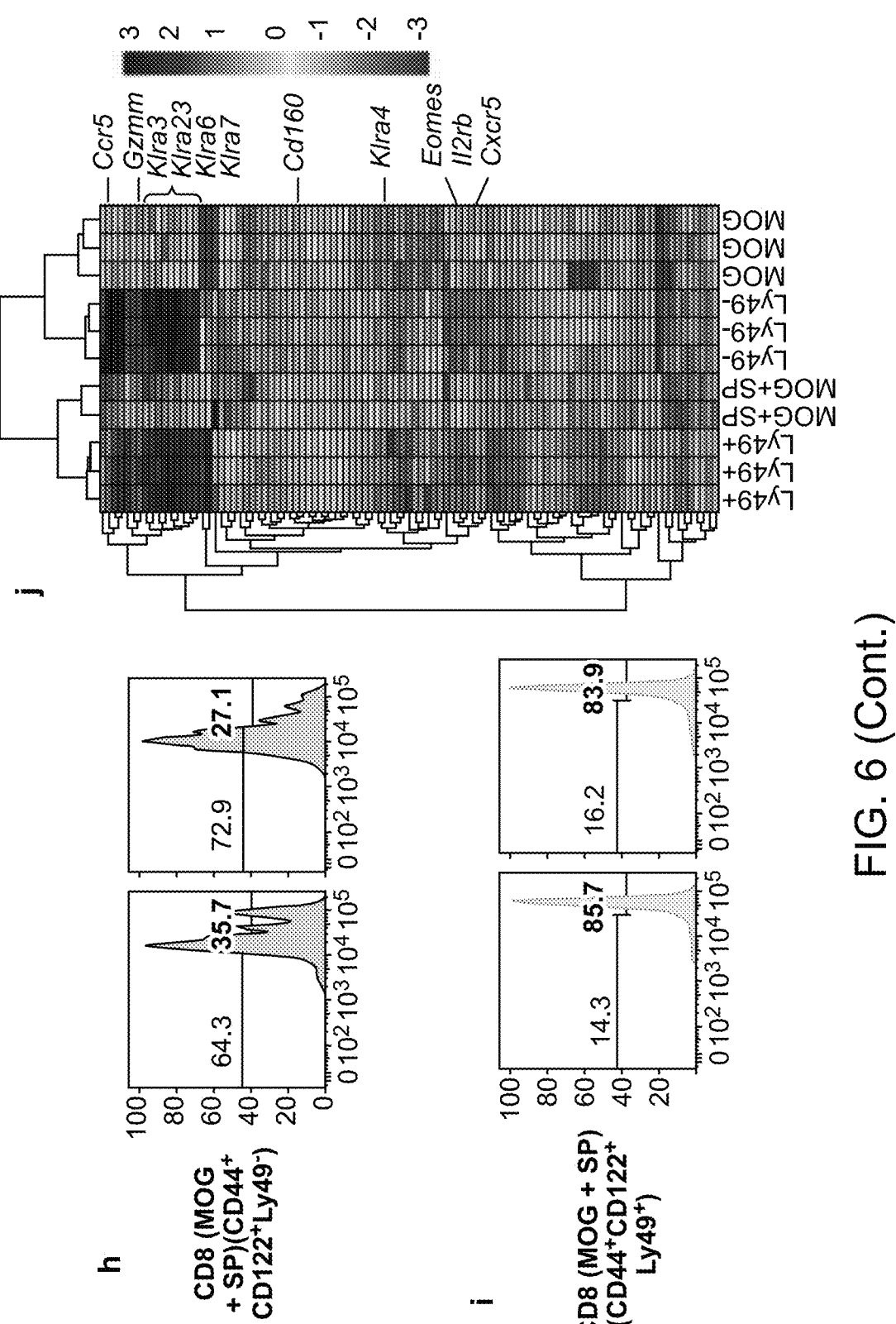
Figure 7:
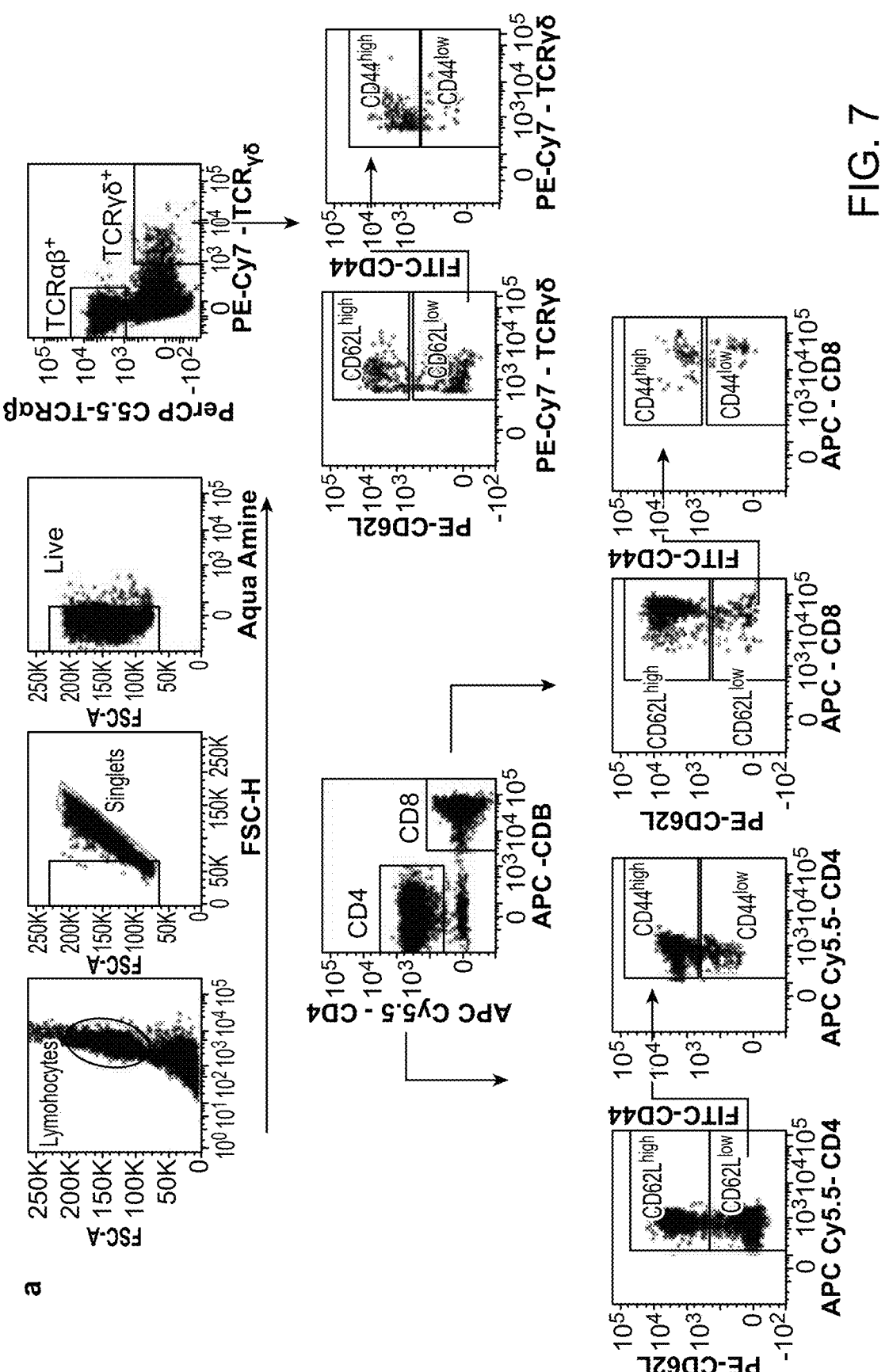
FIG. 7. Massive clonal expansion of all T cells after EAE immunization. a-e, C57BL/6J mice were immunized for EAE induction, and cells from blood, draining LN, spleen and the CNS were isolated and stained with a cocktail of cell-surface antibodies on different days after immunization (D0 (unimmunized), D3, D5, D7, D10, D12, D15, D17, D19, D21, D23 and D3) . . . a, Infiltrating $CD4^+$, $CD8^+$ and $\gamma\delta^+$ T cells were single-cell sorted on D0 (unimmunized), D7, D10, D15 and D19 after immunization. The cells underwent single-cell paired TCR sequencing. (n=3 mice per group/time point). In total, we sequenced 1,302 ($CD4^+$), 1,660 ($CD8^+$), and 1,451 ($\gamma\delta^+$) paired TCR sequences. b-d, Average percentage clonal expansion of $CD4^+$ (b) $CD8^+$ (c) and $\gamma\delta^+$ (d) T cells among unimmunized and immunized mice in all days and tissues combined together. Data are mean±s.e.m. e, Percentage of identical $CD4^+$, $CD8^+$ and $\gamma\delta^+$ TCR sequences shared between blood and the CNS within each day after immunization. f, Frequency of major groups (groups 1-4) of thymus-derived $\gamma\delta^+$ T17 (tT$\gamma\delta$17) cells in blood and CNS on different days after immunization. g, Corresponding paired TCR$\gamma$ (from top to bottom: SEQ ID NOs: 535-537, 537) and TCR$\delta$ (from top to bottom: SEQ ID NOs: 538-541) sequences that define each major group (groups 1-4) of tT$\gamma\delta$17 cells.
Figure 8:
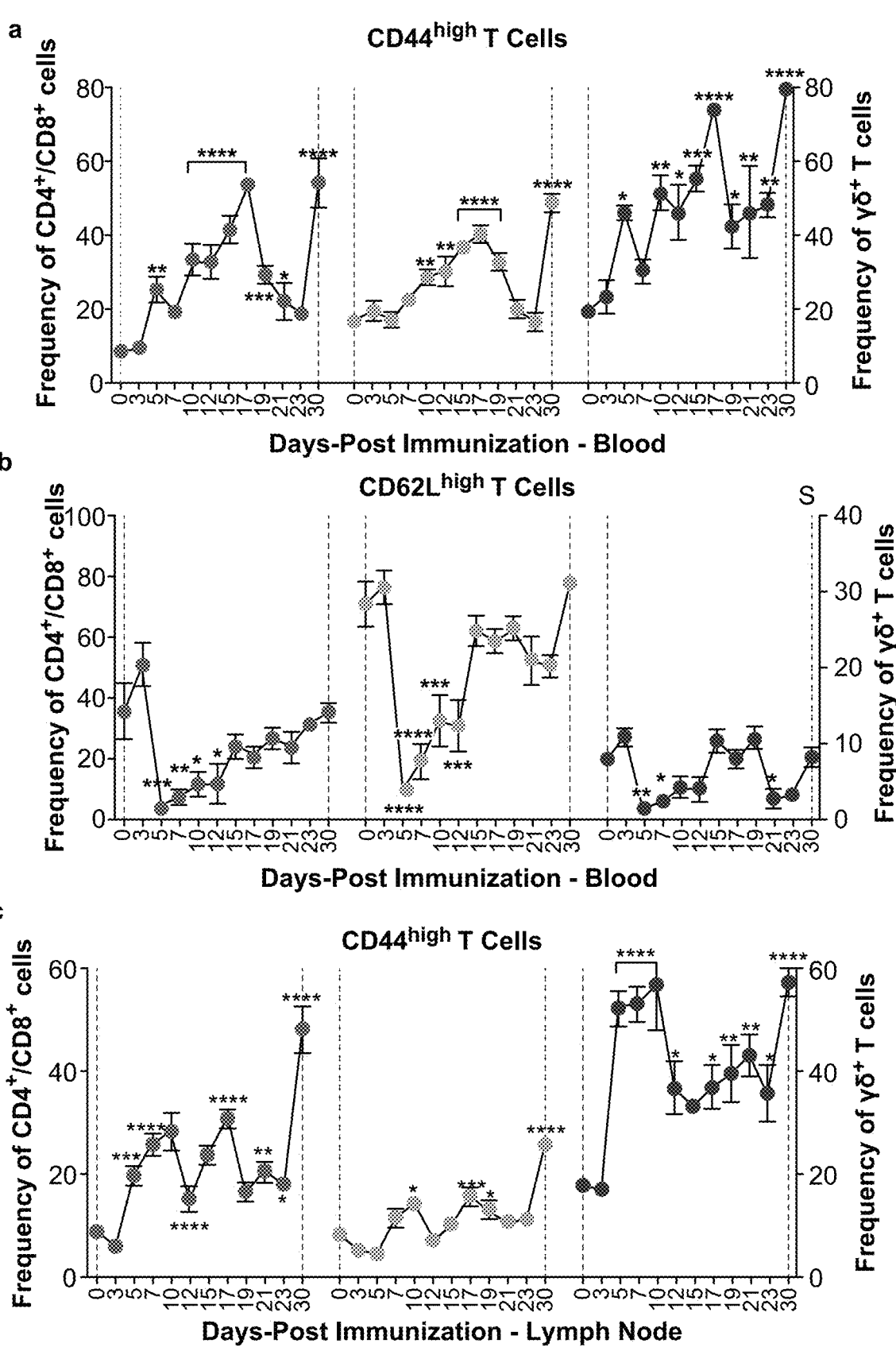
FIG. 8. Concomitant activation of all T cells after EAE immunization and clonally expanded CD8 TCRs are not specific to myelin peptides or proteins. a-f, C57BL/6J mice were immunized for EAE induction and cells from blood, draining LN and spleen were isolated and analysed for total frequency of activated ($CD44^{high}$) (a, c, e) and naive ($CD62L^{high}$) (b, d, f) $CD4^+$, $CD8^+$ cells. Data are mean±s.e.m. and representative of two independent experiments. *P=0.046; P=0.0023; *P=0.0002; ****P<0.0001, one-way ANOVA followed by Dunnets post hoc multiple comparison test. g, Nine clonally expanded CD8 TCRs (EAE1-CD8 to EAE9-CD8) were retrovirally transduced to express on 58 $\alpha\beta^{-/-}$ cells. Untransduced and transduced cell lines were stained with fluorochrome-labelled anti-TCR$\beta$ and anti-CD3 to determine the surface expression of TCRs. h, Untransduced and transduced EAE-CD8 TCR cell lines were stimulated with plate-bound anti-CD3 and soluble anti-CD28 for 12-16 h and surface-stained with activation marker CD69. i, Untransduced 58 $\alpha\beta^{-/-}$ or OT-1 TCR transduced cell lines were stimulated with BMDCs pulsed with SEQ ID NO:6 SIINFEKL peptide or whole OVA protein for 12-16 h, washed, and stained with CD69. j, Unstimulated 58 $\alpha\beta^{-/-}$ or EAE-CD8 TCR transduced cell lines were stimulated with pool of peptides (PP1-PP7) from MOG, MBP, PLP, MAG and SEQ ID NO:6 SIINFEKL peptides, and examined for expression of CD69 (CD69 expression shown in figure for EAE1-CD8 TCR). Peptides are of variable lengths (8-12 nucleotides). Each peptide pool contained 50 peptides. Data are representative of three independent experiments.

Mobilization of three distinct T cell types following EAE induction. Here, we performed a broad survey of T cell dynamics post EAE induction in the blood, spleen, lymph node (LN), and CNS infiltrating lymphocytes (FIG. 1a and FIG. 6). We observed a gradual and significant increase in the frequency of total CD4+ T cells in the blood from day (D)0-D10 post-immunization (PI), peaking around D10, declining to below baseline level at D15, with an eventual recovery on D17. A similar drop and recovery in the frequency of total CD4+ T cells was again observed on D19 and D21, respectively (FIG. 1b). In addition, we also observed a similar significant increase in the frequency of total CD8+ and γδ+ T cells in the blood at D10 PI, and the kinetics and the magnitude with which these cells decline and increase precisely matched that of CD4+ T cells (FIG. 1b). This pattern of synchronous behavior in these T cell populations was also observed in the CNS (FIG. 1c). Splenic and LN T cells exhibited a different pattern of synchronous behavior, with a gradual decline in the frequency of total CD4+, CD8+, and γδ+ T cells from D0-D7, a rise in frequency until D17, and another dip between D17 and D30 (FIGS. 1d and 1e). Parallel to this, there was also corresponding changes in the frequency of effector cells (CD44$^{hi}$CD6L$^{low}$) (FIGS. 8a, 8c, and 8e) and naïve cells (CD44$^{low}$CD62L$^{hi}$) PI (FIGS. 8b, 8d, and 8f).

Figure 2:
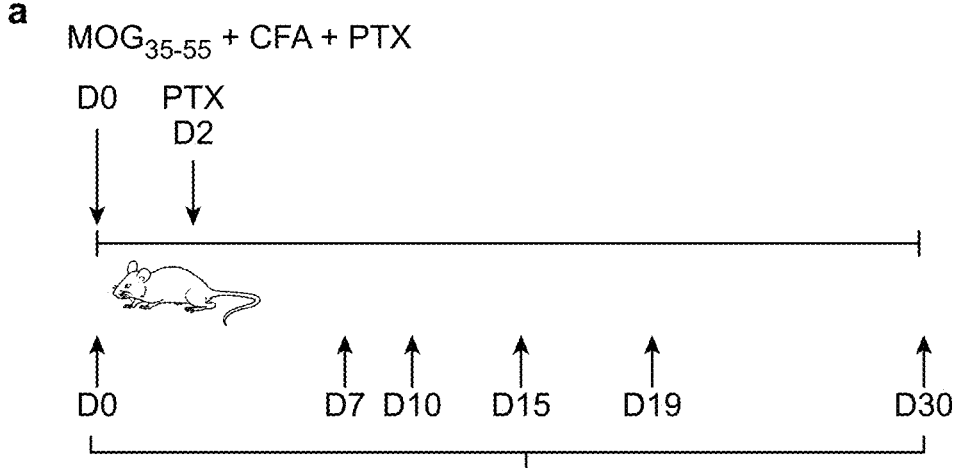
FIG. 2 $CD4^+$, $CD8^+$ and $\gamma\delta^+$ T cells are clonally expanded after EAE. a, b, C57BL/6J mice were immunized for EAE induction (a), and at different days after immunization (DO (unimmunized), D7, D10, D15 and D19) blood and CNS-infiltrating $CD4^+$, $CD8^+$ and $\gamma\delta^+$ T cells were single-cell FACS-sorted based on activation markers ($CD44^{hi}CD62L^{low}$) and their TCRs were sequenced (b). CFA, complete Freund's adjuvant; PTX, pertussis toxin. c, d, Pie chart depicting clonal expansion of $CD4^+$, $CD8^+$ and $\gamma\delta^+$ T cells at different days after immunization in blood (c) and the CNS (d). Each pie chart is an aggregate of the number of TCR sequences from three individual mice pooled together per time point per tissue. The number of cells with $\beta$ or both $\gamma$ and $\delta$ chains successfully identified is shown above each pie chart. For each TCR clone expressed by two or more cells (clonally expanded), the absolute number of cells expressing that clone is shown by a distinct coloured section. Sequencing data are from one experiment constituting three individual mice per time point.
Figure 2:
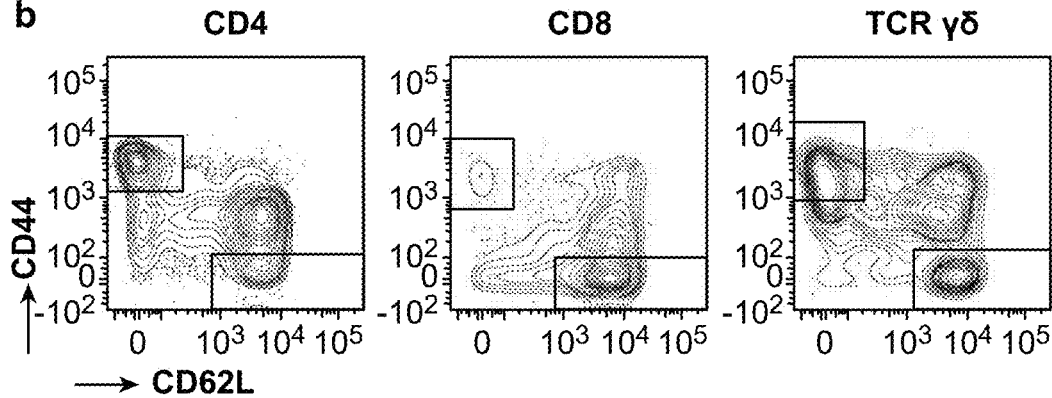
Figure 2:
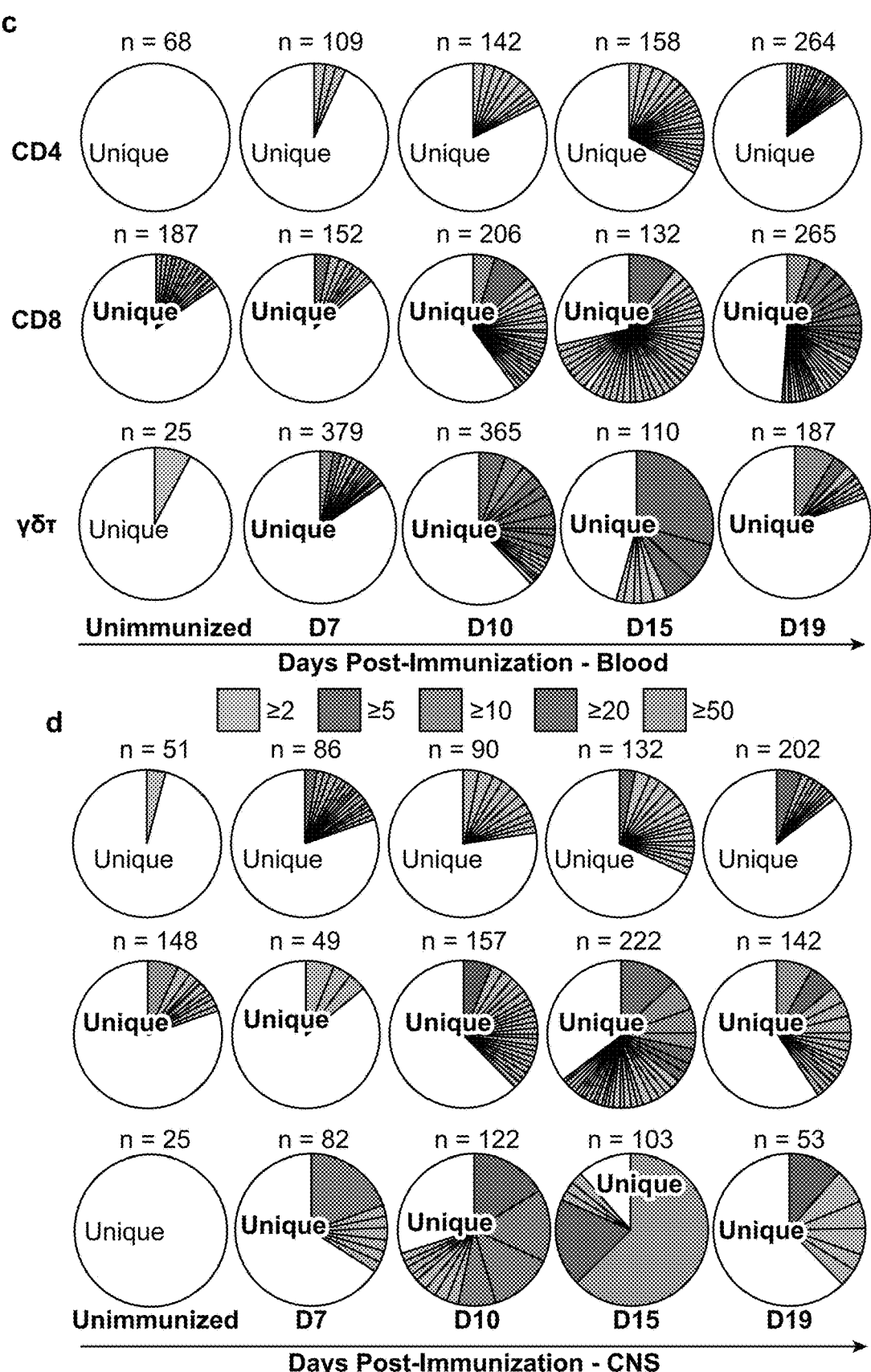

CD4+, CD8+, and γδ+ T cells clonally expand following EAE induction in both blood and CNS. To determine whether these waves of T cells constitute a focused immune response, we performed single-cell paired TCR sequencing (FIG. 2a) of effector (CD44$^{high}$CD6L$^{low}$) CD4+, CD8+, and γδ+ T cells at various timepoints (FIG. 2b and Table. 1). All three types of T cells showed increased clonal expansion as the disease progressed, starting at D7 (FIG. 2c and FIG.

Figure 9:
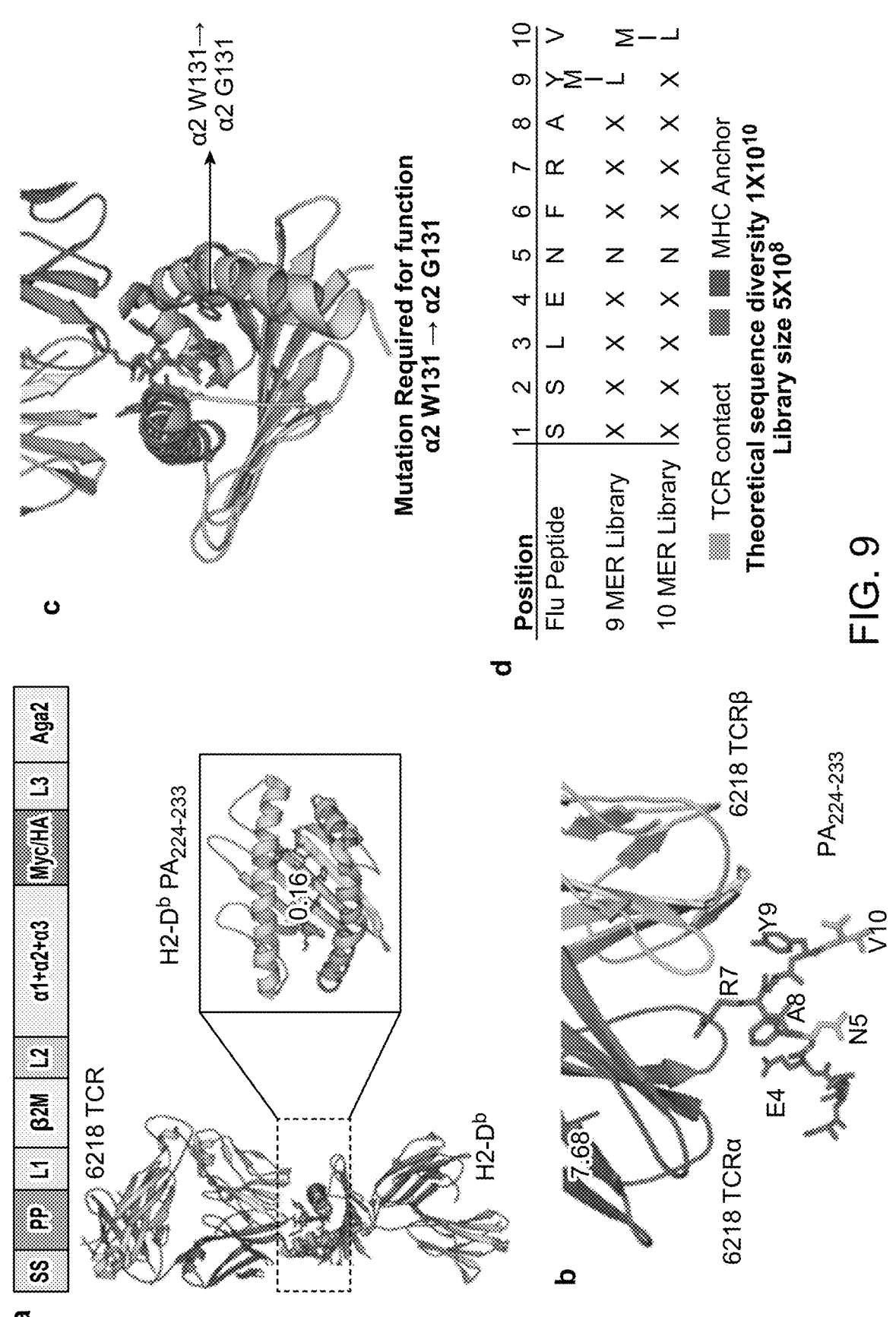
FIG. 9. Generation and functional validation of a $H2-D^b$ yeast peptide-MHC library. a, Schematic of the mouse class I MHC $H2-D^b$ displayed on yeast as $\beta2m$, $\alpha1$, $\alpha2$ and $\alpha3$ with peptide covalently linked to the MHC N terminus. b, Design of the peptide library displayed by $H2-D^b$. Design is based on the structure of the 6218 TCR bound to $H2-D^{b}$-restricted acid polymerase peptide 224-233 (SSLENFRAYV (SEQ ID NO: 5), $D^bPA_{224}$) (PDB accession 3PQY). c, Mutation required for proper folding of the $H2-D^b$ displayed on yeast ($\alpha2$-W131 to $\alpha2$-G131). Mutations were derived from error prone mutagenesis. d, Design for two different lengths of $H2-D^b$ libraries. For the nine-amino-acid (9 MER) library, residues from P1 to P9 were randomized, with limited diversity at MHC anchor positions P5 (Asn, N) and P9 (Met, Ile and Leu, M/I/L). For the ten-amino-acid (10 MER) library, residues from P1 to P10 were randomized, with limited diversity at MHC anchor positions P5 (Asn, N) and P10 (Met, Ile and Leu, M/I/L). TCR contact residues are coloured pink and MHC anchor residues are coloured red or blue. e-g, Selection of $PA_{224}-H2-D^b$ error-prone library with 6218 soluble TCR. Increased cMyc expression among induced yeast peptide-$H2-D^b$ error prone library at different rounds (RD1-RD4) of selection (e, g) and 6218 soluble TCR tetramer staining on the post-RD4 error prone $H2-D^b$ library (g). Each TCR was screened on the yeast library once.
Figure 9:
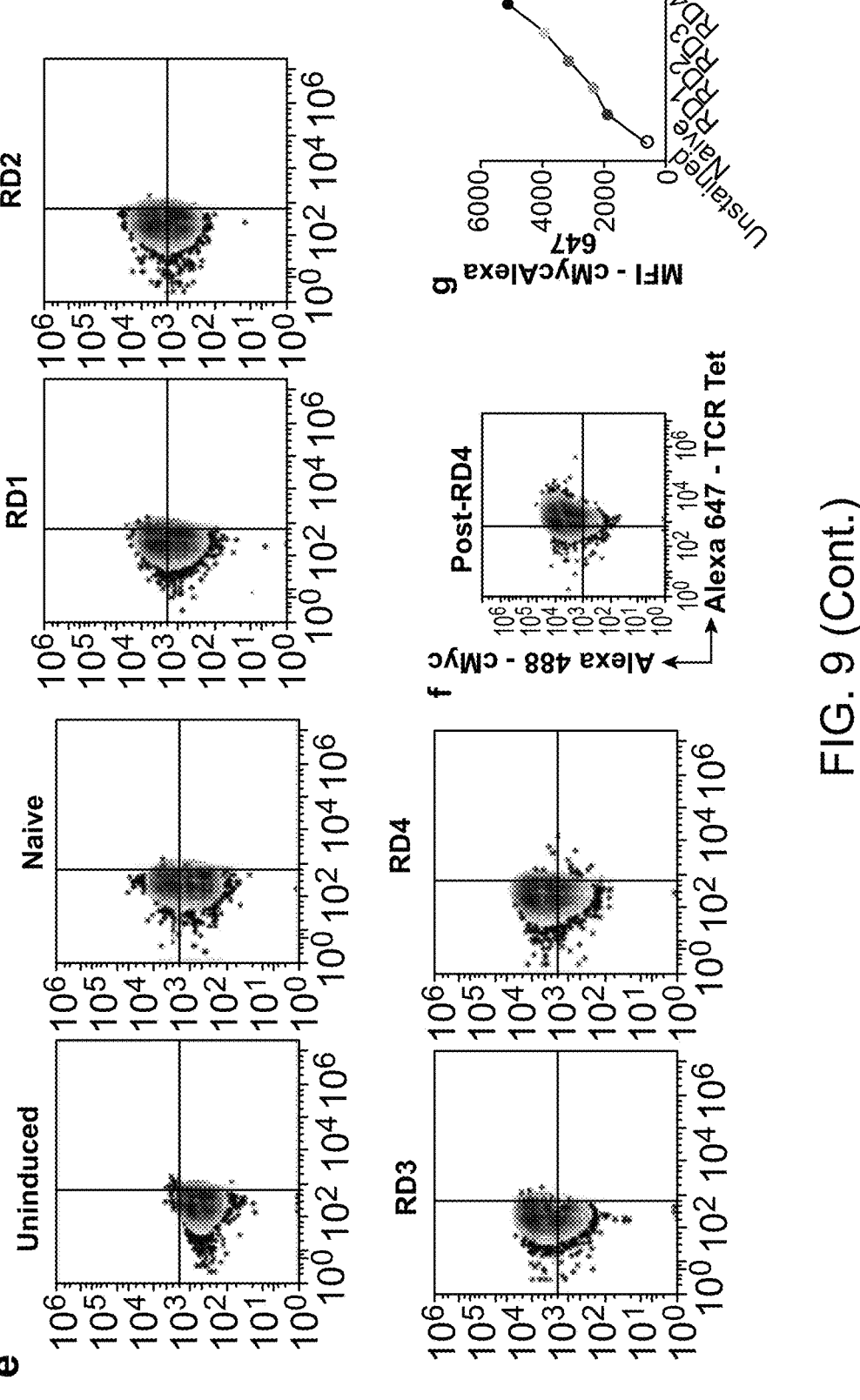

9a-c)). Identical TCRs were rare or absent between mice, as expected, but we did find identical TCR sequences being shared between blood and the CNS in each day within each mouse, with maximal sharing of sequences on D15 (FIG. 9d). Among γδ+ T cells, we found that nearly all the clonally expanded and some non-clonal γδ+ T cells in the blood and CNS are enriched for TCRs that are known to be expressed by natural γδ+ T cells (nTγδ17) 13 (FIG. 9e) with the levels peaking at D15 representing 96% of total γδ+ T cells in the CNS (FIGS. 9e and 9f).

Clonally expanded CD8+ T cells are not responsive to myelin antigens. To determine whether the expanded CD4+ T cell clones are responsive to the MOG35-55 peptide, we expressed four of the these CD4+ TCRs (Table 2) in SKWαβ$^{-/-}$ cells and stained them with a MOG35-55 I-Ab peptide-MHC tetramer. All four of these CD4+ TCRs bound to the tetramer (FIG. 3a-d), reinforcing the primacy of MOG specific CD4+ T cells in this disease and validating our strategy of sequencing activated/effector cells (CD44$^{high}$CD6L$^{low}$) as a way to enrich for clonally expanded T cells important in an immune response.

Figure 3:
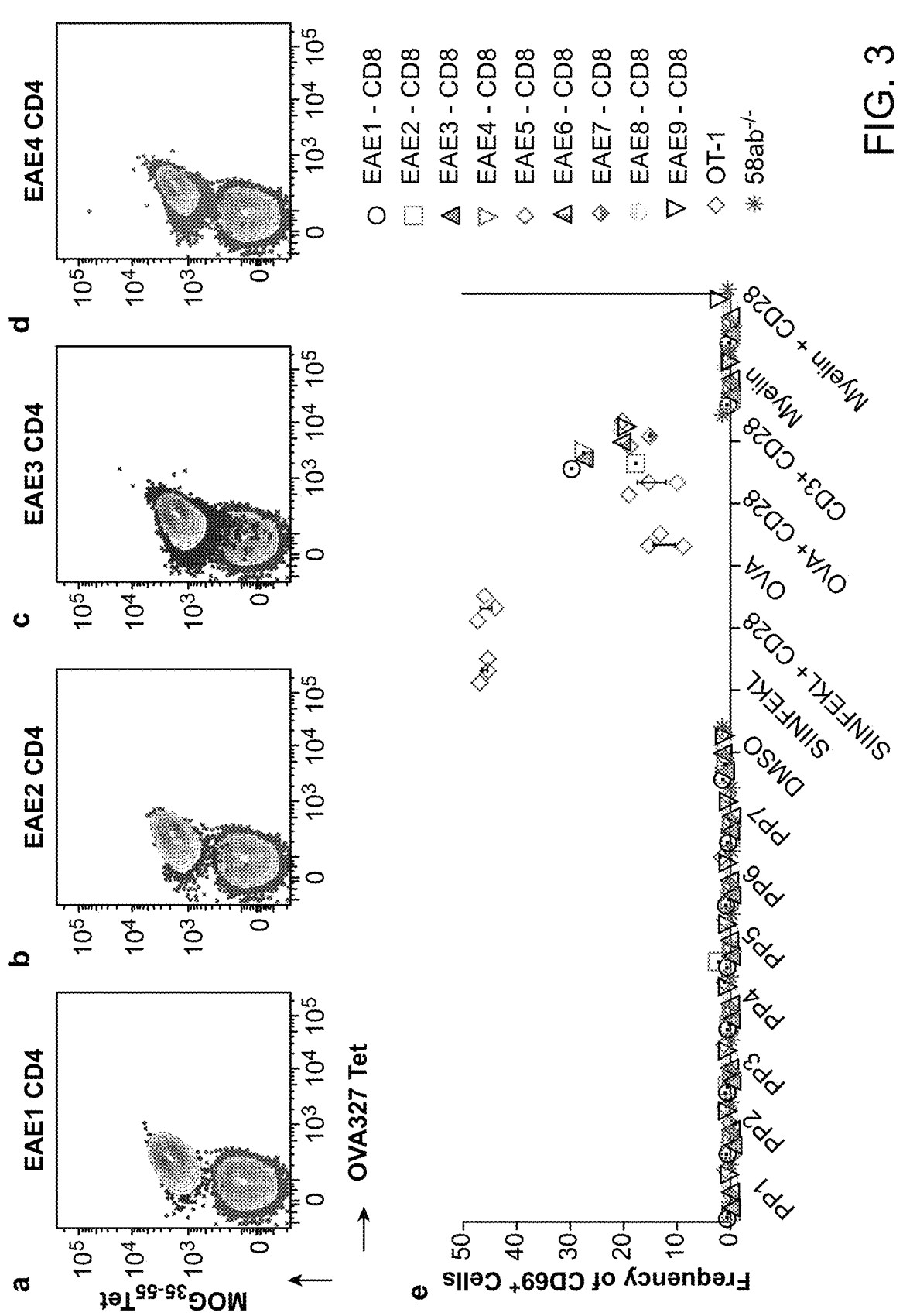
FIG. 3 Clonally expanded CD8 TCRs are not responsive to myelin. a-d, Four clonally expanded CD4 TCRs (EAE1-CD4 (a), EAE2-CD4 (b), EAE3-CD4 (c) and EAE4-CD4 (d)) were expressed on SKW $\alpha\beta^{-/-}$cells and stained with $MOG_{35-55}$ and ovalbumin 327-337 $(OVA_{327})/-A^b$ pMHC tetramer. e, Nine clonally expanded CD8 TCRs (EAE1-CD8 to EAE9-CD8) were expressed on 58 $\alpha\beta^{-/-}$ cells. Cells were stimulated with pools of myelin peptides from MOG, myelin basic protein (MBP), proteolipid protein (PLP), myelin associated glycoprotein (MAG), SEQ ID NO:6 SIINFEKL, myelin or ovalbumin protein, and with anti-CD3 and anti-CD28 for 12-16 h, and examined for expression of the activation marker CD69. Each peptide pool (PP1-PP7) consisted of variable-length peptides (8-12 nucleotides), and each peptide pool contained 50 peptides. 58 $\alpha\beta^{-/-}$ cells expressing OT-1 TCR were stimulated with either SEQ ID NO:6 SIINFEKL peptide or ovalbumin protein. Data are representative of three independent experiments.
Figure 10:
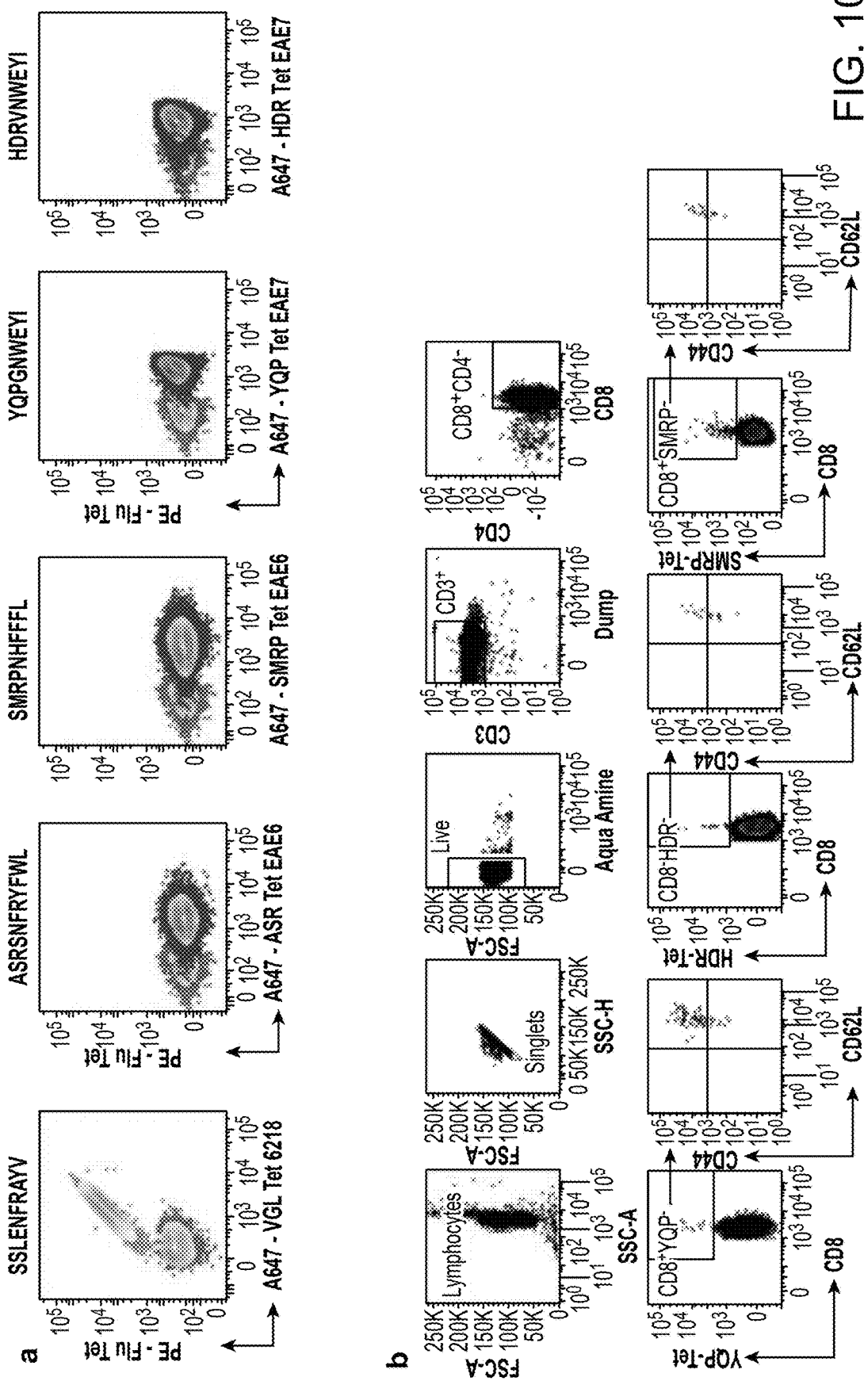
FIG. 10. In vitro and in vivo characterization of $CD8^+$ T cells specific for surrogate peptides after EAE. a, Jurkat $\alpha\beta^{-/-}$ T cells expressing 6218, EAE6 and EAE7-CD8 TCRs were stained with corresponding yeast library-enriched pMHC tetramers (SSLENFRAYV (SEQ ID NO: 5), ASRSNRYFWL (SEQ ID NO: 2), SMRPNHFFFL (SEQ ID NO: 1), YQPGNWEYI (SEQ ID NO: 4) and HDRVNWEYI (SEQ ID NO: 3)), respectively. b, From unimmunized mice (n=4), or mice immunized with MOG (n=5), MOG+SP (n=5), or SP (n=5), spleen and LN cells were isolated, and cells were enriched for SP-specific $CD8^+$ T cells with pMHC tetramers. Representative flow cytometry gating strategy is shown for different cell surface markers and tetramer-specific cells. c, Representative flow cytometry data are shown for activation status (defined as $CD44^+CD62L^-$) on $CD8^+$ T cells specific for SP (ASR, HDR, SMRP and YQP-tet+) from wild-type and different immunization groups (MOG, MOG+SP, and SP). d, Activated/effector phenotype of $CD8^+$ T cells specific for SP (ASR, HDR, SMRP and YQP-tet$^+$) from wild-type (n=5) and different immunization groups (MOG (n=3), MOG+SP (n=4), and SP (n=3)) is quantified (n=5 mice per group). *P=0.0169; P=0.0020; **P<0.0001, one-way ANOVA followed by Tukey's post hoc multiple comparison test. Data are mean±s.e.m. e, C57BL/6J mice were immunized for EAE with an emulsion containing $MOG_{35-55}$, CFA plus PTX with (n=10) or without (n=10) influenza peptide (SSLENFRAYV). The clinical scores after immunization were recorded. Data are mean±s.e.m. and representative of two independent experiments.

To investigate the antigen(s) specificity of the CD8+ T cells in EAE, we expressed nine of the clonally expanded and common CD8+ TCRs in 58αβ$^{-/-}$ cells (FIG. 10a and Table 3). These CD8+ TCRs (EAE1-CD8 to EAE9-CD8) were co-cultured with bone marrow derived dendritic cells (BMDCs) pulsed with myelin protein derived peptide pools (Table 4) and their activation was measured. Surprisingly, none of the 350-myelin peptides stimulated any of the CD8+ TCR cell lines (FIG. 3e). Cells expressing ovalbumin specific TCR (OT-1) co-cultured with BMDCs loaded with the ovalbumin derived SEQ ID NO:6 SIINFEKL peptide, gave a robust activation (FIG. 3e and FIG. 10c) as well as anti-CD3+anti-CD28 stimulation (FIG. 10b). The myelin proteins also did not stimulate any of the CD8+ TCR cell lines, whereas OT-1 T cells were robustly stimulated with ovalbumin protein (FIG. 3e and Extended Data FIGS. 4c and 4d), suggesting that that very few of the activated and clonally expanded CD8+ T cells induced during EAE are specific for myelin antigens.

Figure 11:
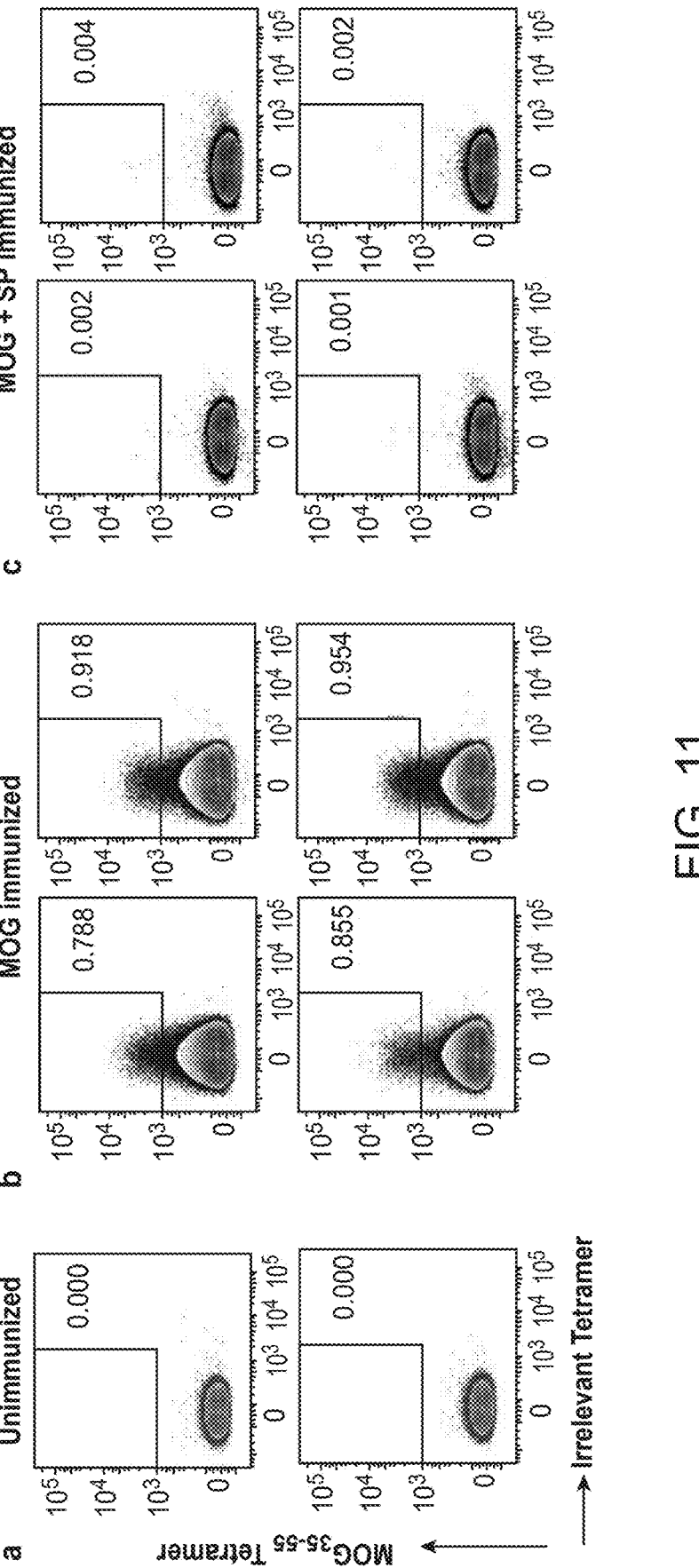
FIG. 11. $CD8^+$ T cell-specific SP immunization suppresses $MOG_{35-55}$-specific $CD4^+$ T cells and induces $CD8^+$ T cells with a regulatory phenotype. a-c, C57BL/6J mice were immunized with an emulsion containing $MOG_{35-55}$, CFA and PTX (n=5), or $MOG_{35-55}$, CFA, PTX and SP (n=5). From unimmunized mice (a) and mice 10 days after immunization (b, c) spleen and LN cells were isolated, stained and enriched for $MOG_{35-55}$ I-$A^b$ pMHC-specific $CD4^+$ T cells and an irrelevant tetramer. Representative FACS plots for different groups are shown. d-g, Spleen and LN cells were isolated from unimmunized mice (n=5) (d) and mice 10 days after immunization with MOG (n=5) (g), MOG plus SP (n=5) (f) or SP alone (n=4) (e), and then stained and enriched for SP-specific $CD8^+$ T cells using pMHC tetramer. Representative FACS dot plots for $CD8^+$ T cell with a regulatory phenotype ($CD44^+CD122^+Ly49^+$) from each group are shown. h, Tetramer-positive (that is, ASR, HDR, SMRP and YQP-tet$^+$) $CD8^+$ T cells were sub-gated for CD122, CD44 and Ly49, and the frequency of $CD122^+CD44^+Ly49^+$ cells among SP-specific cells are shown among different immunization groups. ***P=0.0002, one-way ANOVA followed by Tukey's post hoc multiple comparison test. Data are mean±s.e.m. and representative of two independent experiments.

Generation of a H2-D$^b$ yeast peptide-MHC library. Recently, Garcia and colleagues have developed yeast peptide-MHC library system for identification of αβ TCR ligands. To discover the peptide antigens for these EAE-CD8 TCRs, we designed H2-K$^b$ and H2-D$^b$ constructs as described previously with SIINFEKL (SEQ ID NO: 6) or SSLENFRAYV (SEQ ID NO: 5) peptides (FIGS. 11a and 11b). While the initial constructs were correctly routed to the yeast surface, they did not bind to their cognate TCRs, indicating incorrect folding. To rescue proper folding, we subjected both the H2-Kb and H2-Db full length construct to error-prone mutagenesis. While this was unsuccessful with H2-K$^b$, we found that a single H2-D$^b$ mutation restored TCR recognition (FIGS. 11c and 11e-g) and thus we generated two different peptide libraries with this mutation and mutagenized the 9 and 10 aa inserts with limited diversity at the two primary MHC-binding anchor residues (FIG. 11a-d). The estimated diversity for both peptide libraries were 5×10$^8$.

Figure 4:
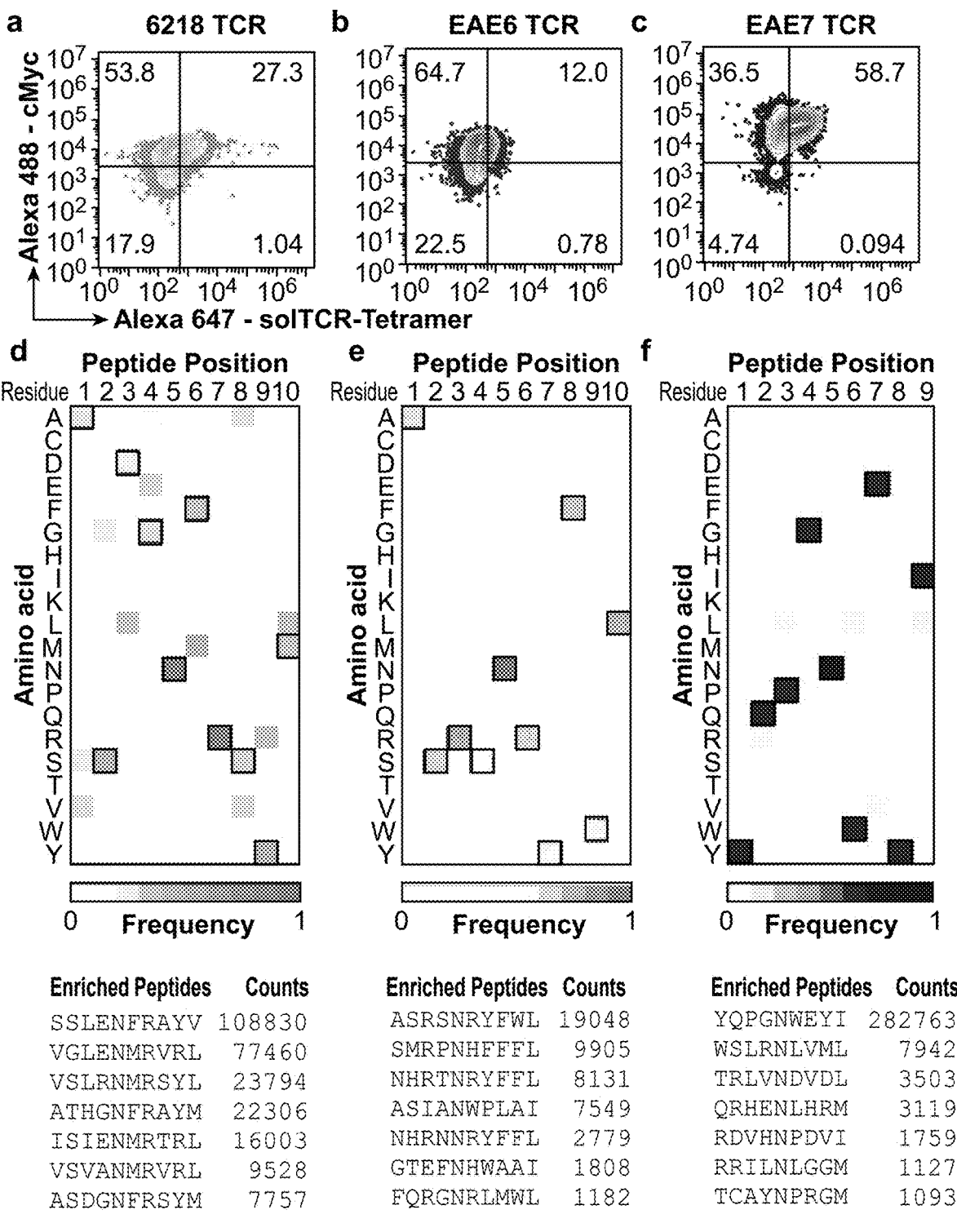
FIG. 4 Clonally expanded EAE CD8 TCRs bind to novel peptides. a-c, Tetramer staining of a 9-nucleotide and 10-nucleotide $H2\text{-}D^b$ yeast-pMHC library with 6218 TCR (a), EAE6-CD8 TCR (b) and EAE7-CD8 TCR (c) at the end of three rounds of selection. d-f, Heat maps of amino acid preference by position for 6218 (left) sequences below are SEQ ID NO:5; 17; 18; 520; 521; 522; 523 (d), EAE6-CD8 (centre) sequences below are SEQ ID NO:2; 1; 524; 525; 526; 527; 528 (e) and EAE7-CD8 (right) sequence below are SEQ ID NO:4; 529; 530; 531; 532; 533; 534 (f) TCRs after three rounds of selection. The sequences of the top-seven peptides after three rounds of selection for each TCR are shown below with its amino acid preference. MHC anchor residues are coloured red (P5, Asn; N) or blue (P9/10, Met, Ile and Let; M/I/L). Each TCR was screened on the yeast library once.

Class I peptides Immunization protects mice from EAE. Six of the clonally expanded EAE-CD8 TCRs (Table 3) were used to screen the H2-D$^b$ yeast-pMHC libraries. After four rounds of selection, the flu specific control (6218), EAE6, and EAE7 TCRs showed robust tetramer staining (FIG. 4a-c and Table 5). While we obtained a perfect match with the flu TCR and its known peptide (FIG. 4d), we did not find any matches in the mouse genome for the two EAE TCR peptides. Nevertheless, they can still serve as important surrogates when complexed with H2-D$^b$.

Figure 12:
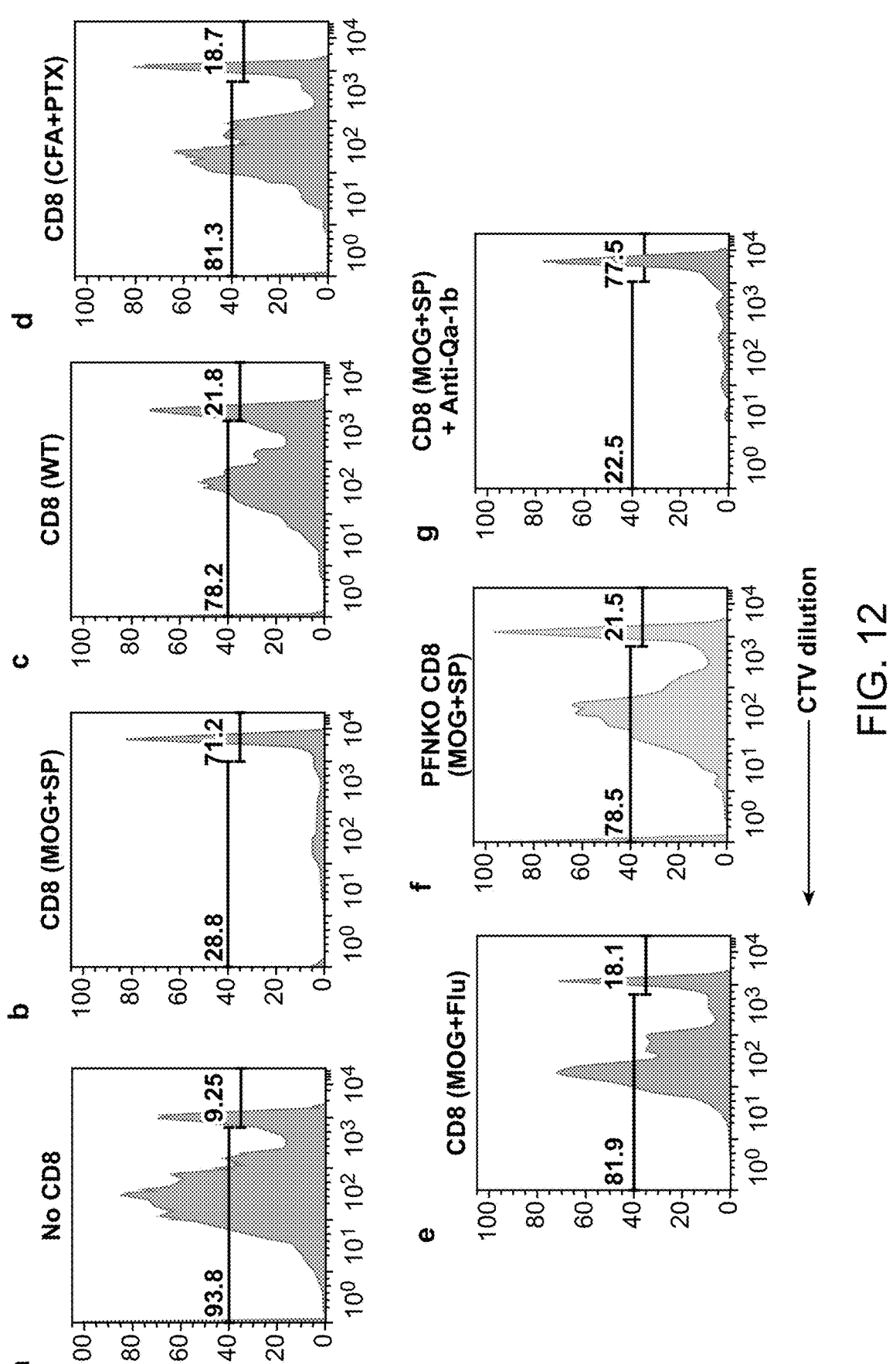
FIG. 12. CD8$^+$T cells elicited after MOG+SP immunization are specific, their suppression is mediated by perforin, adoptive transfer of CD122$^+$CD44$^+$Ly49$^+$ abrogates EAE, and SP triggers a more severe, inflammatory retinal uveitis than IRBP peptide alone. a-g, C57BL/6J mice were immunized with an emulsion containing MOG$_{35-55}$, CFA and PTX, MOG$_{35-55}$, CFA, PTX and SP (b), or MOG$_{35-55}$, CFA, PTX and influenza peptide (e). Spleen and LN cells were isolated from mice 10 days after immunization, and cells were enriched for CD4$^+$ or CD8$^+$ T cells or APCs by FACS. CD4$^+$ T cells from MOG-immunized mice were labelled with CTV and co-cultured with APCs from MOG-immunized mice in the absence (a) or presence of CD8$^+$ T cells from wild-type mice (c) or mice immunized with MOG plus SP (b), CFA plus PTX (d), MOG plus influenza peptide (e), or CD8$^+$ T cells from perforin-knockout (PENKO) mice immunized with MOG plus SP (f). g, CTV-labelled CD4$^+$ T cells from mice immunized with MOG$_{35-55}$, CFA plus PTX were co-cultured with CD8$^+$ T cells from mice immunized with MOG$_{35-55}$, CFA, PTX plus SP in the presence of anti-Qa-1b antibody (10 μg ml-1). h, CTV-labelled CD4$^+$ T cells from mice immunized with OVA$_{329-337}$, CFA plus PTX were co-cultured with CD8$^+$ T cells from mice immunized with MOG$_{35-55}$, CFA, PTX plus SP. Seven days after co-culture, cells were washed and stained with surface markers and analysed for CD4$^+$ T cell proliferation (CTV dilution). Representative data are from two independent experiments. i, C57BL/6J mice were immunized with MOG$_{35-55}$, CFA, PTX plus SP (n=10) and 10 days after immunization spleen and LN cells were isolated, stained and enriched for CD8$^+$T cells followed by FACS for Ly49$^+$ and Ly49$^-$ cells. Sorted Ly49$^+$ and Ly49$^-$ cells were adoptively transferred (8 million cells per mouse) to C57BL/6J mice (n=5 mice per group) at the time of immunization. The clinical scores after adoptive transfer and immunization are shown. ****P<0.0001, regression analysis with two-way ANOVA followed by Bonferroni post hoc multiple comparison test. Data are mean±s.e.m. and representative of two independent experiments. j, In the wild-type, untreated mouse eye, the retina shows a normal laminar pattern and there are no leukocytes in the vitreous. k, After subcutaneous injection of IRBP peptide antigen, there was only a mild inflammatory response in 40% of eyes with activated leukocyte invasion of the vitreous (red arrow) and mild disruption of the and retina outer nuclear layer photoreceptors (black arrow). I, After subcutaneous injection of both IRBP and SP there was a severe inflammatory response in 80% of eyes with activated leukocyte invasion of the vitreous (red arrows) and severe disruption of the retina photoreceptors (black arrows). INL, inner nuclear layer; IPL, inner plexiform layer; ONL, outer nuclear layer; OPL, outer plexiform layer; RGC, retinal ganglion cell layer; RPE, retinal plexiform layer. Five C57BL/6J mice were examined for each condition. EAU was induced, and mice were euthanized on day 21 after immunization. Mouse eyes were enucleated, fixed and pupil-optic nerve sections were examined by histology. m-o, C57BL/6J mice were immunized with IRBP, CFA and PTX with or without SP. Spleen and LN cells were isolated from mice 10 days after immunization, and cells were enriched for CD4$^+$ or CD8$^+$ T cells, or APCs by FACS. CTV-labelled CD4$^+$ T cells from IRBP-immunized mice were co-cultured with APCs from IRBP-immunized mice and purified CD8$^+$ Ly49$^+$ T cells (n), CD8$^+$Ly49$^-$ T cells (o) or without CD8$^+$ T cells (m) from mice immunized with IRBP and SP. Seven days after co-culture, cells were washed and stained with surface markers and analysed for CD4$^+$ T cell proliferation.

To characterize these CD8 surrogate peptides (SP), Jurkat αβ$^{-/-}$ cells expressing 6218, EAE6, and EAE7-CD8 TCRs were stained with corresponding yeast library enriched pMHC tetramers (SSLENFRAYV (SEQ ID NO: 5) for 6218, ASRSNRYFWL (SEQ ID NO: 2) and SMRPNHFFFL (SEQ ID NO: 1) for EAE6-CD8, and YQPGNWEYI (SEQ ID NO: 4) for EAE7-CD8), which showed robust staining (FIG. 12a). Moreover, upon analyzing the enriched peptide sequences for EAE7-CD8 TCR, we noticed that the 36th enriched peptide (HDRVNWEYI) (SEQ ID NO: 3) was very similar to the top enriched YQPGNWEYI (SEQ ID NO: 4) peptide. EAE7-CD8 TCR cell line was stained with YQPGNWEYI (SEQ ID NO: 4) and HDRVNWEYI (SEQ ID NO: 3) H2-D$^b$ pMHC tetramers which showed robust tetramer staining (FIG. 12a).

Figure 5:
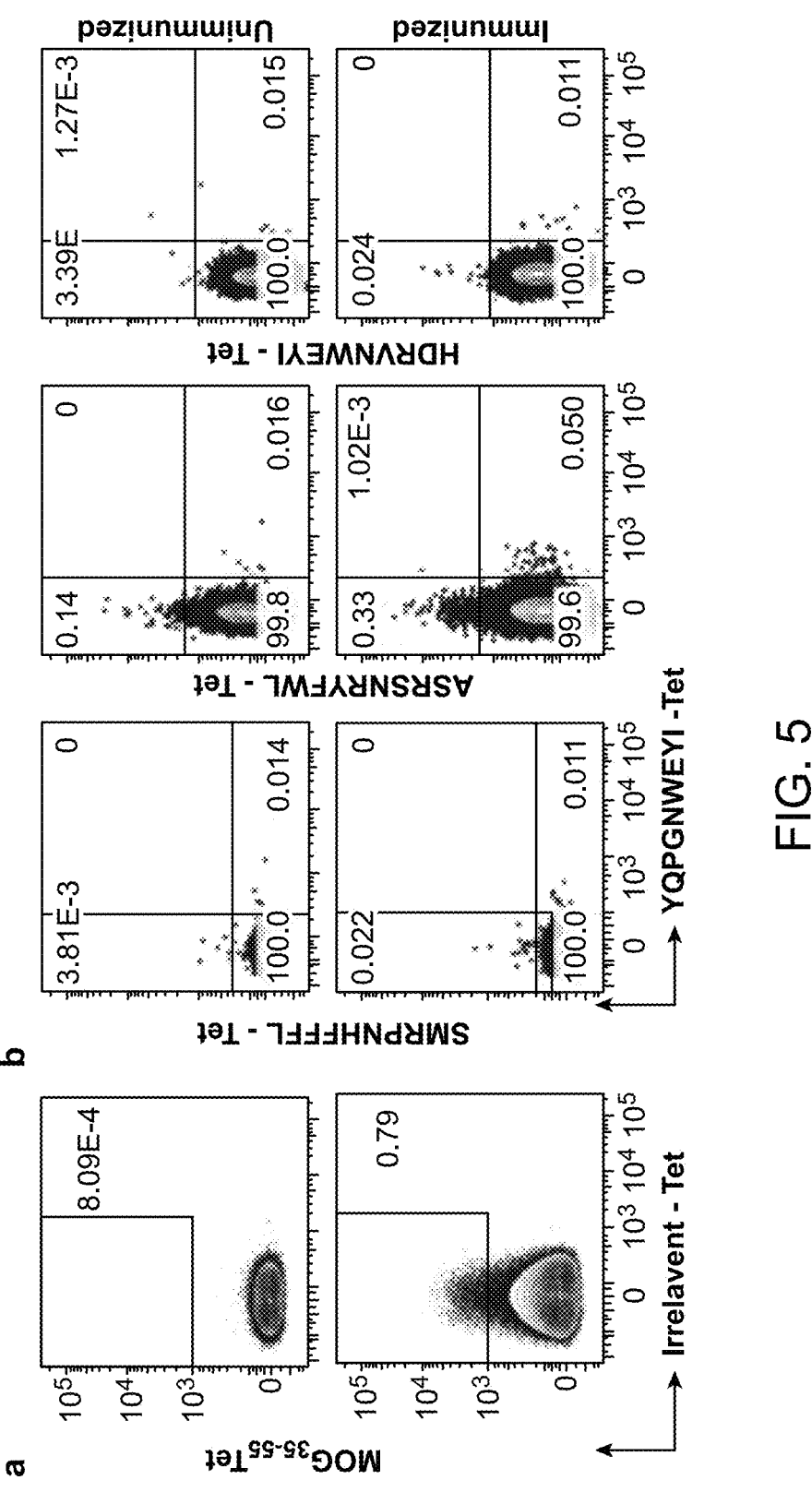
FIG. 5 $CD8^+$ T cell-specific SP immunization abrogates EAE. a, b, Spleen and LN cells were isolated from unim-munized mice and mice 10 days after immunization, and cells were enriched for $CD4^+$ T cells specific for $I\text{-}A^b$ $MOG_{35-55}$ (a) or for $CD8^+$ T cells specific for SP (SMRPNHFFFL (SEQ ID NO: 1), ASRSNRYFWL (SEQ ID NO: 2), HDRVNWEYI (SEQ ID NO: 3) and YQPGNWEYI (SEQ ID NO: 4)) (b). Representative dot plots are shown for unimmunized and immunized mice. Representative data are from two independent experiments. c, Frequency of $CD4^+$ T cells specific for $MOG_{35-55}$ among wild-type (n=4) and immunized (n=5 mice) mice are shown. Data are mean±s.e.m. d, Frequency of SP-specific $CD8^+$ T cells among wild-type (n=4) and different immunization groups (n=5 mice per group). Data are mean±s.e.m. e, EAE clinical scores among C57BL/6J mice immunized with an emulsion containing $MOG_{35-55}$ plus CFA and PTX (n=10), or $MOG_{35-55}$ plus CFA, PTX and SP (n=10), or just SP, CFA and PTX (n=10). f, EAE clinical scores among C57BL/6J mice immunized with $MOG_{35-55}$ plus CFA and PTX (n=10), and then challenged with SP, ICFA and PTX seven days after immunization (n=10). g, EAE clinical scores among C57BL/6J mice immunized with SP, CFA and PTX, and then challenged with $MOG_{35-55}$ plus ICFA and PTX seven days after immunization (n=10). Data are mean±s.e.m. and rep-resentative of two independent experiments. P=0.0040, **P<0.0001, regression analysis with two-way ANOVA followed by Bonferroni post hoc multiple comparison test.

To determine the immune response elicited by these SP, we immunized mice either with adjuvant (CFA+PTX), MOG35-55, all four peptides together [YQPGNWEYI (YQP; SEQ ID NO: 4), HDRVNWEYI (HDR; SEQ ID NO: 3), ASRSNRYFWL (ASR; SEQ ID NO: 2), and SMRPNHFFFL (SMRP; SEQ ID NO: 1) SP immunization], or MOG35-55 with all four peptides together (MOG+SP immunization). 10D PI, spleen and LN CD8+ T cells were enriched separately with SP-H2-D$^b$ tetramers (FIG. 12b). We also tetramer enriched MOG specific CD4+ T cells from mice immunized with MOG35-55. EAE immunization elicited MOG$_{35-55}$ specific CD4+ T cells (FIGS. 5a and 5c). We detected very few SP specific CD8+ T cells in WT, MOG$_{35-55}$, or adjuvant immunized mice. However, with MOG+SP immunization, the frequency of CD8+ T cells specific for ASR, HDR, and SMRP increased (FIGS. 5b and 5d). In comparison to WT mice, SP immunization, elicited a higher frequency of CD8+ T cells specific for HDR and SMRP, with no change in the number of ASR and YQP specific CD8+ T cells (FIGS. 5b and 5d). A higher proportion of SP specific CD8+ T cells exhibited activated and effecter phenotypes after immunization (FIG. 12b-d). Thus, these SP's identify a pre-existing pool of specific CD8+ T cells in mice that can be activated, and some proliferate upon immunization.

To test the effect of these peptides on EAE, we induced EAE with or without the SPs. While the MOG immunization induced severe disease in 100% of the mice, the addition of the SP with MOG resulted in much less severe or no disease, with only a 30% incidence of very mild disease, with most mice exhibiting no symptoms at all (FIG. 5e and Table 6). Immunization of another group of mice with MOG$_{35-55}$+a flu peptide resulted in no significant difference on EAE severity (FIG. 12e). We tested the prophylactic or therapeutic effect of these peptides in EAE by immunizing the mice with SP a week prior or after MOG immunization (MOG and SP Challenge, respectively) and with both of these challenges, mice had less severe disease (FIGS. 5f and 5g and Table 7). Overall, MOG+SP immunization significantly ameliorates EAE.

Figure 13:
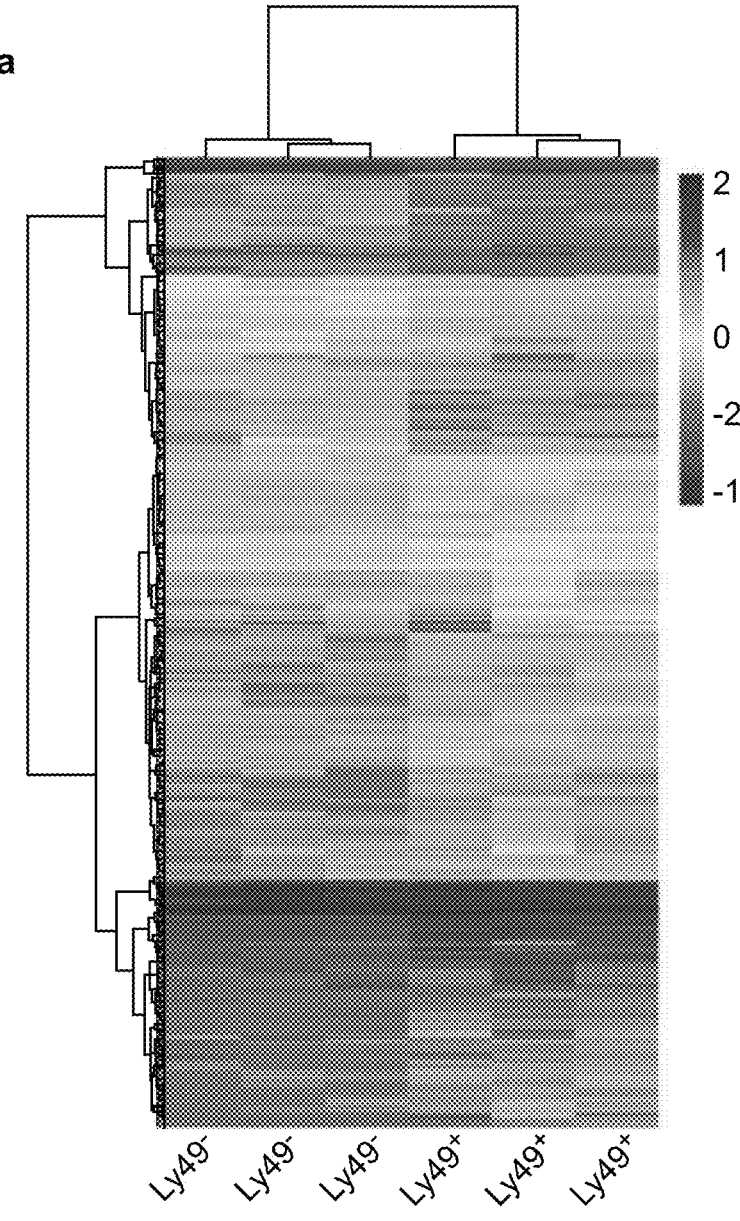
FIG. 13. Transcriptional profiling of Ly49$^+$ versus Ly49$^-$ cells. C57BL/6J mice were immunized with SP, CFA and PTX (n=3). Spleen and LN cells were isolated from D10 mice, and enriched for CD8$^+$ T cells by FACS and sorting for Ly49$^-$ and Ly49$^+$ cells, followed by bulk RNA-seq analysis. a, A heat map of differentially expressed genes (log$_2$-transformed fold change>2, and adjusted P<0.005) in Ly49$^+$/Ly49$^-$ RNA-seq samples. Columns show samples, and rows and columns are ordered based on hierarchical clustering. Normalized gene expression values are centred for each gene by subtracting the average value of all samples from each sample value (2-3 mice per group). b, Gene Ontology enrichment analysis of differentially expressed genes (log$_2$-transformed fold change>2, and two-tailed Benjamini-Hochberg adjusted P<0.005 from DESeq2) between Ly49$^+$ and Ly49$^-$ RNA-seq samples. The y axis represents the top-30 enriched Gene Ontologies (genes from Gene Ontologies highlighted in green are in Supplementary Table 6). The x-axis value is the fraction of genes in that ontology that are differentially expressed. The colour of the dot represents that significance of the Gene Ontology enrichment (one-tailed Fisher's exact test), and the size of the dot represents the number of genes differentially expressed. The plot was made with the R package 'clusterProfiler'. c, Volcano plot representing gene expression differences between the Ly49$^+$ and Ly49$^-$ samples (3 mice per group). Each point is a gene. List of genes specifically expressed in CD4$^+$ T regulatory cells[25] are coloured red if they are expressed in both MOG and SP RNA-seq samples, and green if not. The horizontal dotted line is made at −log$_{10}$(0.05), and the two vertical dotted lines represent a fold change of log$_2$(2). Genes with a negative fold change are highly expressed in Ly49$^+$ cells.

Class I peptides immunization suppresses MOG$_{35-55}$ specific CD4 T cells. To investigate whether this decreased severity with the SP addition was directly affecting MOG$_{35-55}$ specific CD4+ T cells, we analyzed the frequency of MOG$_{35-55}$ specific CD4+ T cells in spleen and LN with a MOG$_{35-55}$ I-Ab tetramer upon MOG or MOG+SP immunizations. As expected, MOG immunization resulted in an increase in the number of MOG$_{35-55}$ I-Ab tetramer+CD4+ T cells (FIGS. 6a and 6b and FIG. 13a). Interestingly, there was a significant reduction in the frequency of these T cells among MOG+SP immunized mice (FIG. 6*a* and FIGS. 13*b* and 13*c*).

Figure 14:
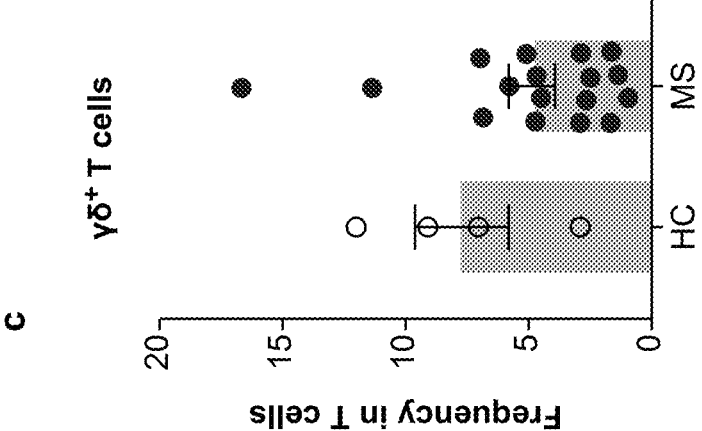
FIG. 14. Major clonal expansion of CD8+ T cells in patients with recent-onset MS. a-c, BMCs from healthy controls (HC) (n=4) and patients with MS (n=18) were stained and analysed by flow cytometry to determine the frequency of T cells. The frequency of CD4$^+$ (a), CD8$^+$ (b) and γδ$^+$ (c) T cells is shown. Data are mean±s.e.m. d, e, Brain homing and activated (CD49d$^+$CD29$^+$HLA-DR$^+$CD38$^+$) CD8$^+$ T cells were single-cell sorted from PBMCs of healthy controls (d) and newly diagnosed patients with MS (e). The cells underwent single-cell paired TCR sequencing. Pie charts depicting clonal expansion of CD8$^+$ T cells among healthy controls (n=10) and patients with MS (n=18). The number of cells with β chain successfully identified is shown above its pie chart. For each TCR clone expressed by two or more cells (clonally expanded), the absolute number of cells expressing that clone (≥2, ≥5, ≥10, ≥20 and ≥50) is shown by a distinct coloured section.
Figure 14:
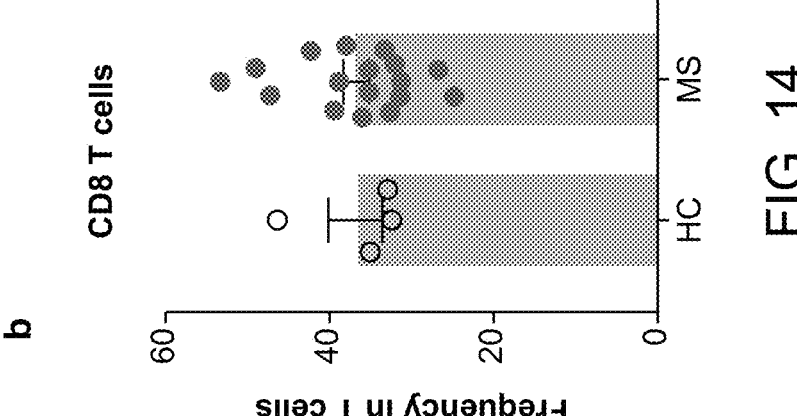
Figure 14:
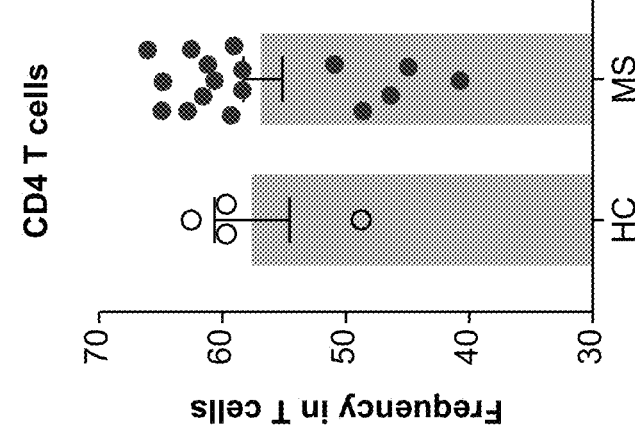
Figure 14:
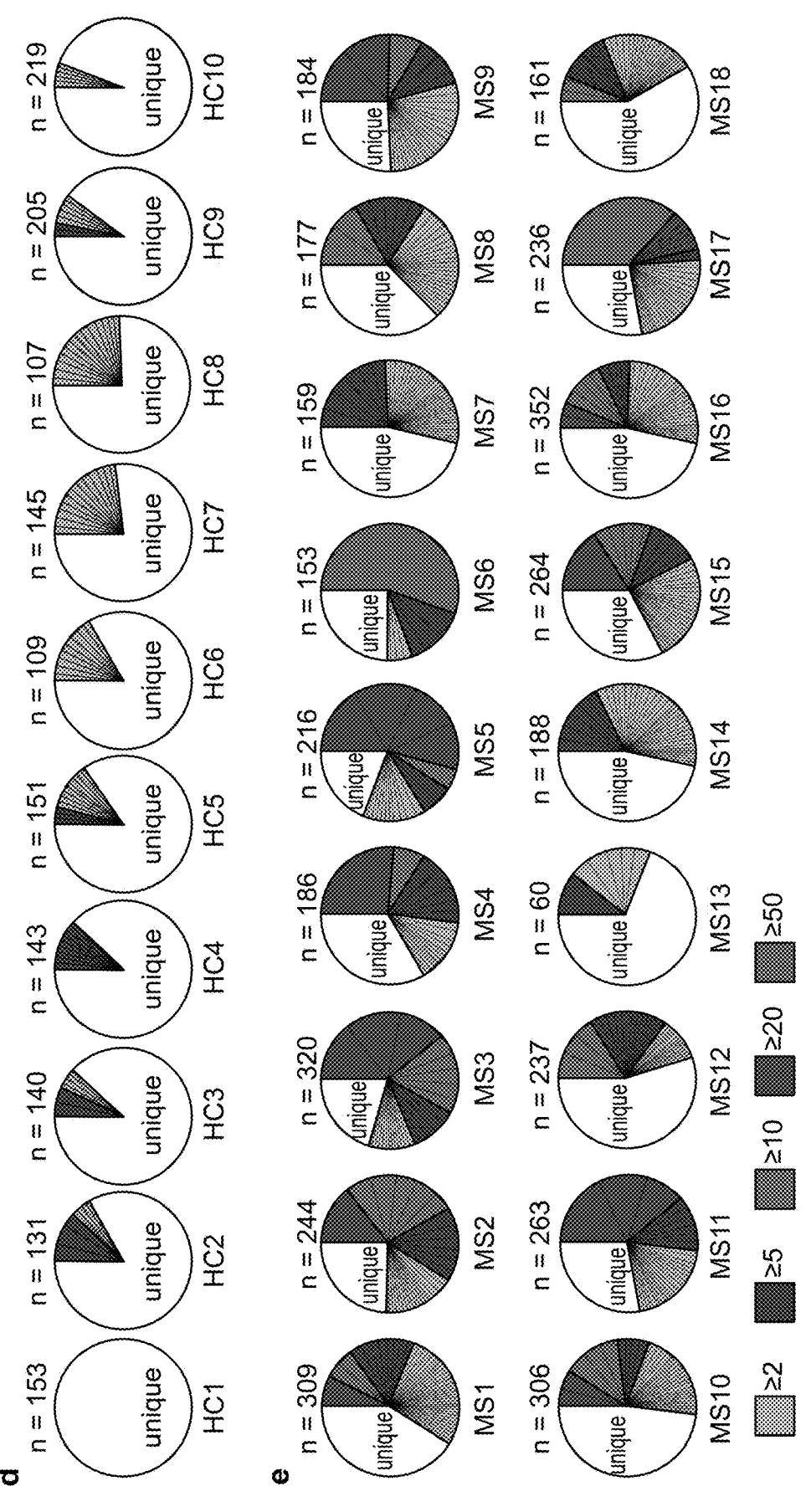

To examine this in vitro, we used CellTrace™ Violet Dye (CTV) to label CD4+ T cells from MOG immunized mice that were co-cultured and stimulated with MOG$_{35-55}$ in the presence or absence of CD8+ T cells derived from MOG+SP or SP immunized mice and the magnitude of CD4+ T cell proliferation was quantified. CD4+ T cells proliferated robustly to MOG$_{35-55}$ in the absence of CD8+ T cells (FIG. 6*c*). However, the addition of CD8+ T cells from either MOG+SP or SP immunized mice resulted in a significant decline in the proliferative capacity of CD4+ T cells (FIG. 6*d*) indicating that either condition elicits CD8+ T cells which actively suppresses MOG35-55 specific CD4+ T cells proliferation. However, CD8+ T cells from either the WT, MOG+flu peptide immunized or from the adjuvant immunized mice did not suppress MOG$_{35-55}$ stimulated CD4+ T cells (FIG. 14*a-d*). Furthermore, MOG+SP induced CD8+ T cells did not suppress the proliferative capacity of ovalbumin specific CD4+ T cells, suggesting that suppression is antigen specific (FIG. 14*h*).

Class I peptides immunization elicits a unique subset of regulatory CD8+ T cells. Interestingly, we find that MOG+ SP and SP immunization elicits a significantly higher frequency of CD8+ T cells expressing CD44, CD122, and Ly49, which are believed to be the markers for Qa-1b restricted regulatory CD8+ T cells (FIG. 6*e*). Moreover, among individual SP specific CD8+ T cells there was a significant increase in the frequency of CD8+ T cells with these markers (FIG. 13*d-h*). We find that the EAE CD8-TCRs described here are not Qa-1b restricted, as we did not see any effect of the anti-Qa-1b antibody on the CD8 suppression of MOG specific CD4+ T cells (FIG. 14*g*).

To determine whether CD8+ T cells with this phenotype can actively suppress MOG$_{35-55}$ specific CD4+ T cells in vitro, CD4+ T cells from MOG immunized were co-cultured either with total CD8+ T cells or purified CD8+CD44+ CD122+Ly49+(Ly49+) or CD8+CD44+CD122+Ly49– (Ly49–) T cells from MOG+SP immunized mice. We found that total CD8+ T cells as well as Ly49+CD8+ T cells from MOG+SP immunized mice suppressed MOG$_{35-55}$ specific CD4+ T cell proliferation. Additionally, we adoptively transferred Ly49+ and Ly49– cells into mice prior to EAE induction and found Ly49+ cells from MOG+SP immunized mice significantly reduced EAE with no effect upon transferring Ly49– cells (FIG. 14*i*). This shows that not only Ly49+ cells can suppress CD4+ T cells in vitro but that they also suppress EAE in vivo.

Figure 15:
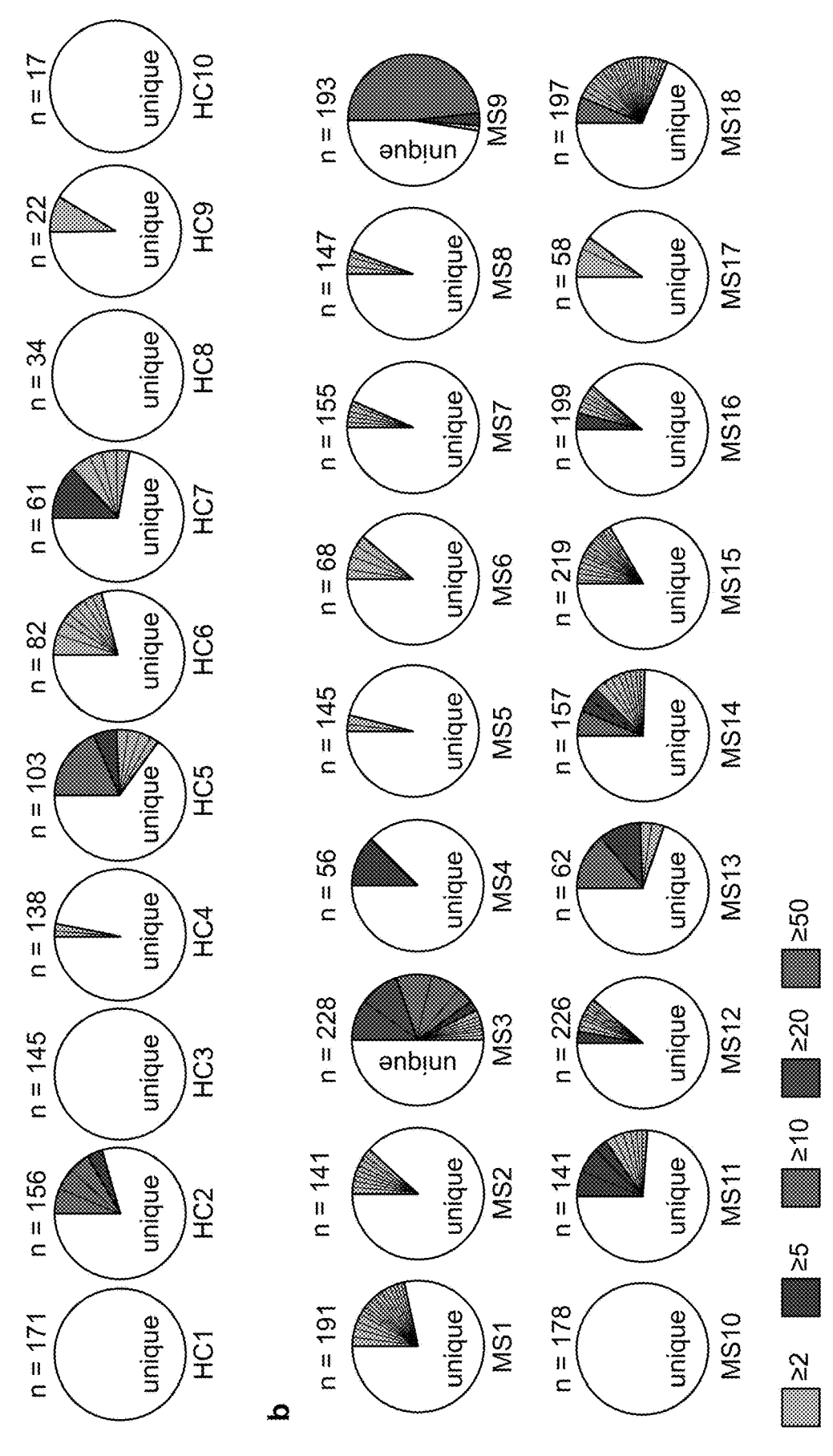
FIG. 15. TCR repertoire of brain homing activated CD4$^+$ T cells in patients with recent-onset MS. a, b, Brain homing and activated (CD49d$^+$CD29$^+$HLA-DR$^+$CD38$^+$) CD4$^+$ T cells were single-cell sorted from PBMCs of healthy controls (a) and patients with recent-onset MS (b). The cells underwent single-cell paired TCR sequencing. Pie charts depicting clonal expansion of CD4$^+$ T cells among healthy controls (n=10) and patients with MS (n=18). The number of cells with β chain successfully identified is shown above its pie chart. For each TCR clone expressed by two or more cells (clonally expanded), the absolute number of cells expressing that clone (≥2, ≥5, ≥10, ≥20 and ≥50) is shown by a distinct coloured section.

We also tested the effects of SP on another autoimmune disease model, Experimental autoimmune uveitis (EAU). We induced EAU in C57BL6/J mice using standard methods and compared EAU pathology to mice immunized with human interphotoreceptor binding protein (IRBP)+SP. IRBP immunization mice produced a mild inflammatory response in 40% of the mice (FIGS. 15*a* and 15*b*). Interestingly, IRBP+SP immunization resulted in a more severe inflammatory response in a much greater fraction of the mice (80%) (FIG. 15*c*). We also performed in vitro suppression assays in which we found that CD4+ T cells robustly proliferated in the absence of CD8+ T cells from IRBP+SP immunized mice (FIG. 15*d*) and neither Ly49+ or the Ly49– CD8+ T cells from IRBP+SP mice were able to suppress the proliferation of IRBP specific CD4+ T cells (FIGS. 15*e* and 15*f*). Thus, the EAE SPs seem specific to that disease.

Figure 16:
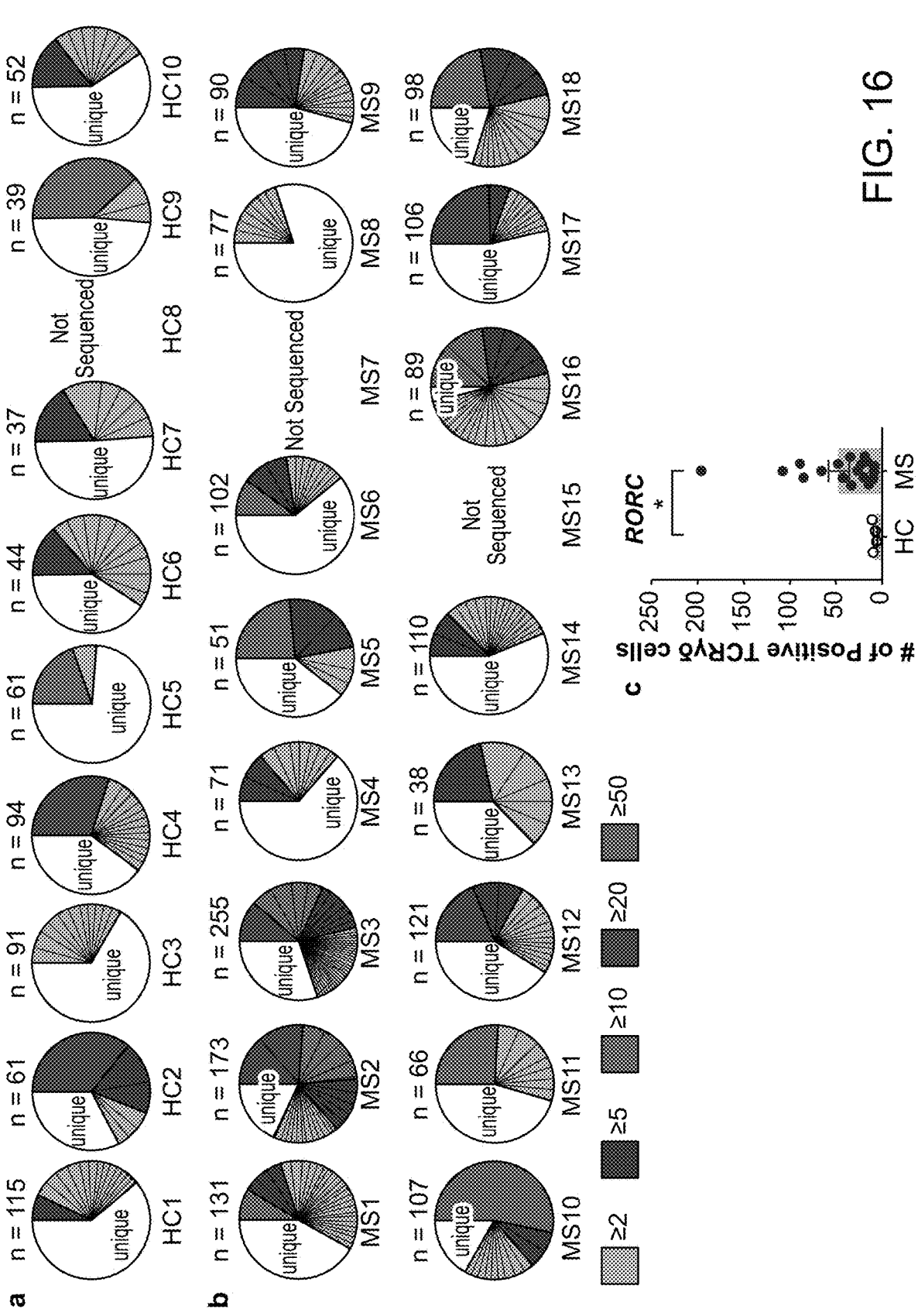
FIG. 16. TCR repertoire of brain-homing-activated γδ$^+$ T cells in patients with recent-onset MS. a, b, Brain homing and activated (CD49d$^+$CD29$^+$HLA-DR$^+$CD38$^+$) γδ$^+$ T cells were single-cell sorted from PBMCs of healthy controls (a) and patients with recent-onset MS (b). The cells underwent single-cell paired TCR sequencing. Pie charts depicting clonal expansion of $\gamma\delta^+$ T cells among healthy controls and patients with MS. The number of cells with $\delta$ chain successfully identified is shown above its pie chart. For each TCR clone expressed by two or more cells (clonally expanded), the absolute number of cells expressing that clone ($\geq 2$, $\geq 5$, $\geq 10$, $\geq 20$ and $\geq 50$) is shown by a distinct coloured section. From the single-cell sorted $\gamma\delta^+$ T cells, RAR-related orphan receptor (ROR) transcripts were amplified using gene-specific primers and sequenced simultaneously with $\gamma$ and $\delta$ chains. c, The number of $\gamma\delta^+$ T cells positive for the RORC transcript is shown among healthy controls (n=10) and patients with MS (n=18). *P=0.0301, paired t-test. Data are mean±s.e.m.

It has been shown that Qa-1b restricted regulatory cells mediate their effect through Perforin, which is important for cytotoxicity. To test this possible mechanism in our system, we co-cultured CD4+ T cells from MOG$_{35-55}$ immunized mice with CD8+ T cells derived from Perforin knockout mice immunized with MOG+SP and found that the this completely abolished their suppressive capacity (FIG. 14*f*). Additionally, we performed RNA-seq analysis of SP specific CD8+ T cells from MOG and MOG+SP immunized mice as well as CD8+ (Ly49+versus Ly49–) T cells from MOG+SP immunized mice. Gene ontology enrichment analysis of the differentially expressed genes between Ly49+ vs Ly49– showed genes involved in various T cell functions (FIGS. 16*a* and 16*b* and Table 8).

Interestingly, SP specific CD8+ T cells showed a marked upregulation of Ly49 genes, most of which are inhibitory, in addition to NK cell receptor genes, and genes associated with CD8+ T cell effector and memory functions (FIG. 6*j*). In addition, Ly49+ and SP specific CD8+ T cells also express many genes associated with regulatory CD4+ T cells (FIG. 16*c*). Overall, our results strongly suggest that the SP immunization elicits CD8+ T cells with a regulatory phenotype which suppresses pathogenic MOG35-55 specific CD4+ T cells through cytotoxicity, ultimately resulting in resistance to EAE.

Figure 18:
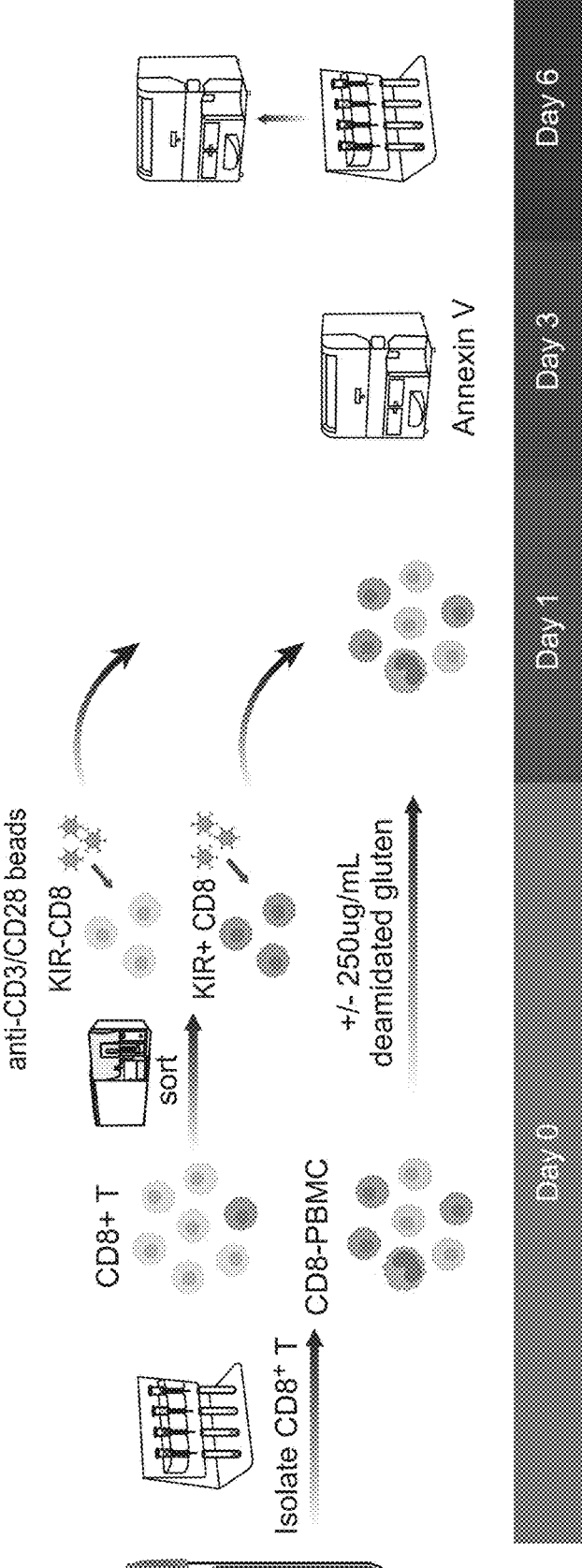
FIG. 18. Elimination of gliadin-specific CD4+ T cells by KIR+ CD8+ T cells. a, Experimental schematic. b, Representative contour plots showing the tetramer binding of 715 CD4+ T cells after enrichment by MACS columns and summary of number of gliadin-specific CD4+ T cells (binding to HLA-DQ2.5 tetramers complexed with gliadin peptides) per 1 million CD4+ T cells on Day 6 (N=5). *P<0.05, P<0.01, Friedman test corrected for multiple comparisons. c, Representative contour plots and summarized scatter plot displaying Annexin V binding of gliadins-specific (tetramer-positive) CD4+ T cells from the culture harvested on Day 3. P<0.01, one-way ANOVA corrected for multiple comparisons.
Figure 18:
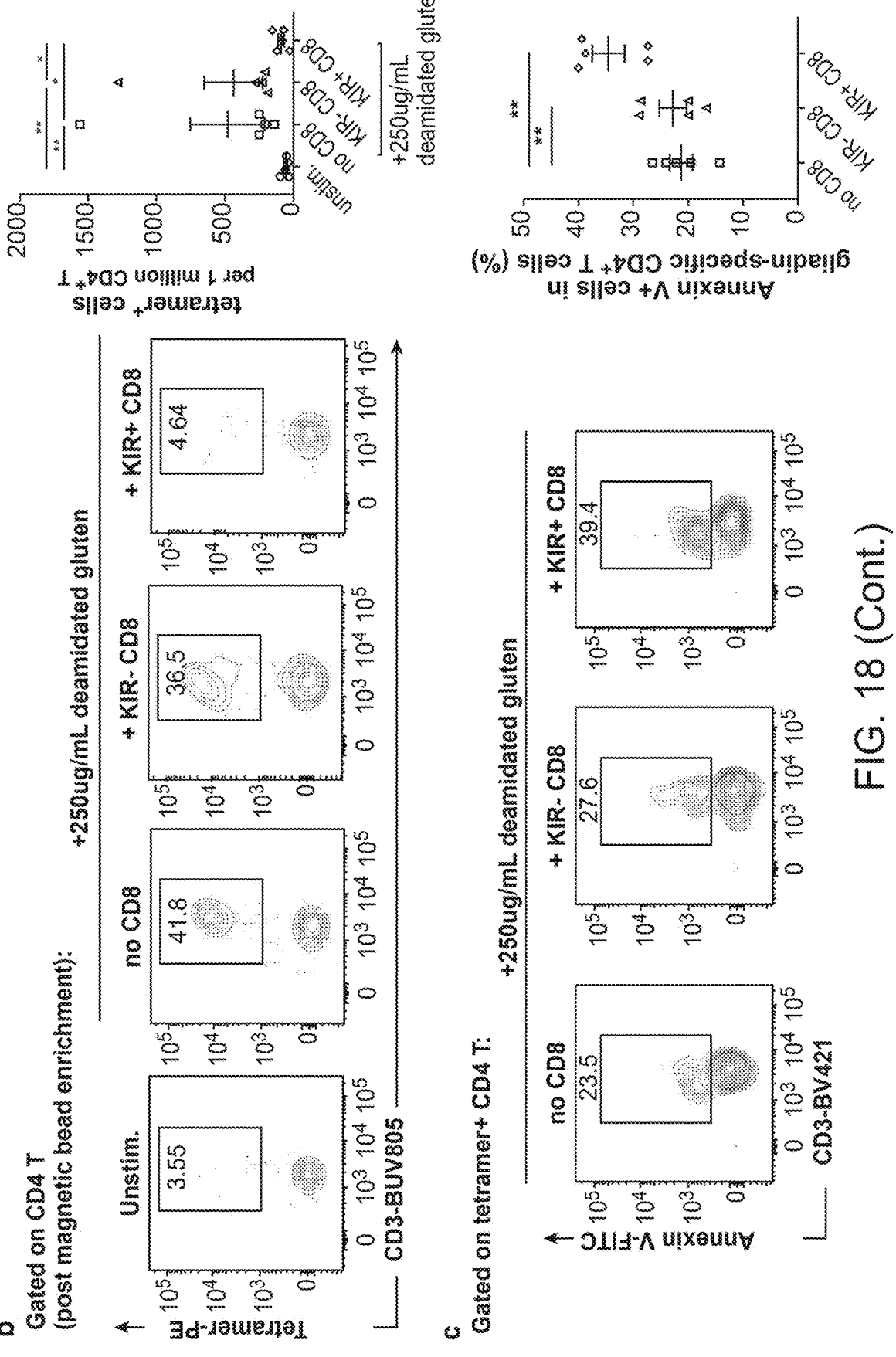
Figure 19:
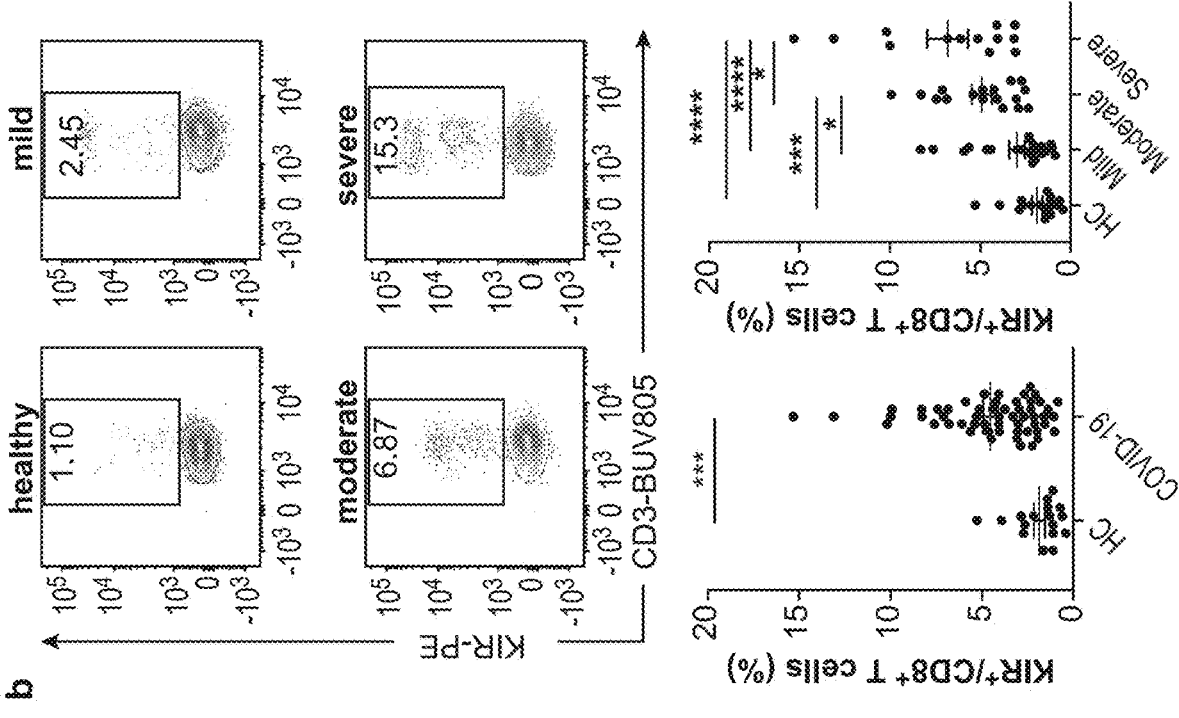
FIG. 19. Increased KIR+CD8+ T cells in COVID-19 patients. a, Frequency of autoimmune CD4+ T cells (CD45RA−, CD62L−, PD-1+, CXCR3+, CD39+, CD38+, CD127−, CD25low, CD161+ and ICOS+ CD4+ T cells) in healthy adults (N=18) versus COVID-19 patients (N=54) (left, *P<0.05, unpaired t test) and in healthy adults versus COVID-19 patients with mild (N=23), moderate (N=17) or severe (N=13) disease (right, *P<0.05, P<0.01, P<0.0001, one-way ANOVA corrected for multiple comparisons). b, Representative contour plots and summarized scatter plots showing percentage of KIR+ cells in CD8+ T cells from the blood of healthy controls and COVID-19 patients with varying disease severity. left: *P<0.001, unpaired t test; right: *P<0.05, *P<0.001, **P<0.0001, one-way ANOVA corrected for multiple comparisons. c, Correlation between frequency of KIR+ CD8+ T cells and autoimmune CD4+ T cells in the blood of COVID-19 patients (N=54). r=0.2811, P=0.0377*. d, Frequency of autoimmune CD4+ T cells, KIR+CD8+ T cells and CD4+ Treg (CD25hiCD127low) in the blood of COVID-19 patients with or without vasculitis. *P<0.05, ****P<0.0001, unpaired t test. e, Expression of KIR transcripts (KIR3DL1, KIR3DL2, KIR2DL3 and KIR2DL1) in CD8+ T cells from the bronchoalveolar lavage fluid of healthy controls and COVID-19 patients with moderate or severe disease.
Figure 19:
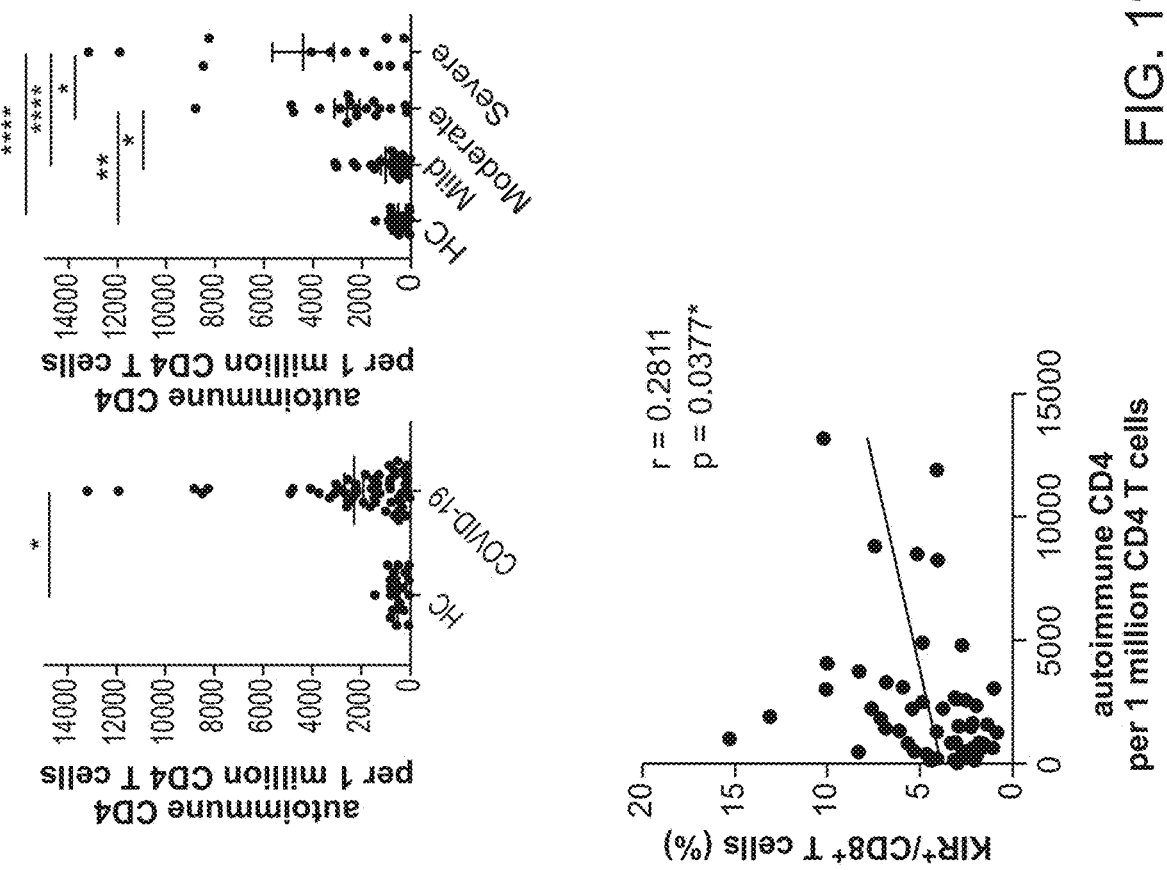
Figure 19:
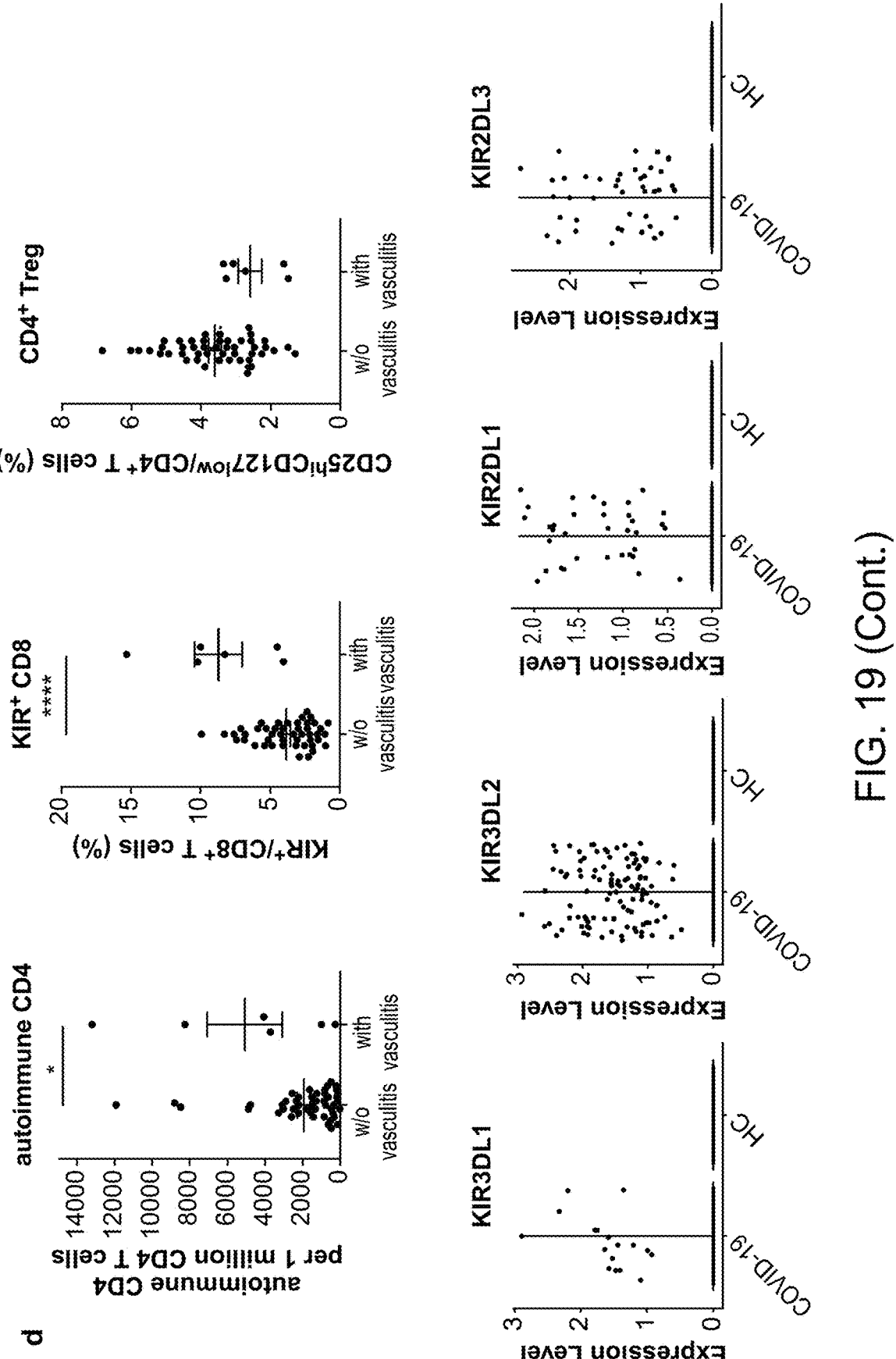
Figure 20:
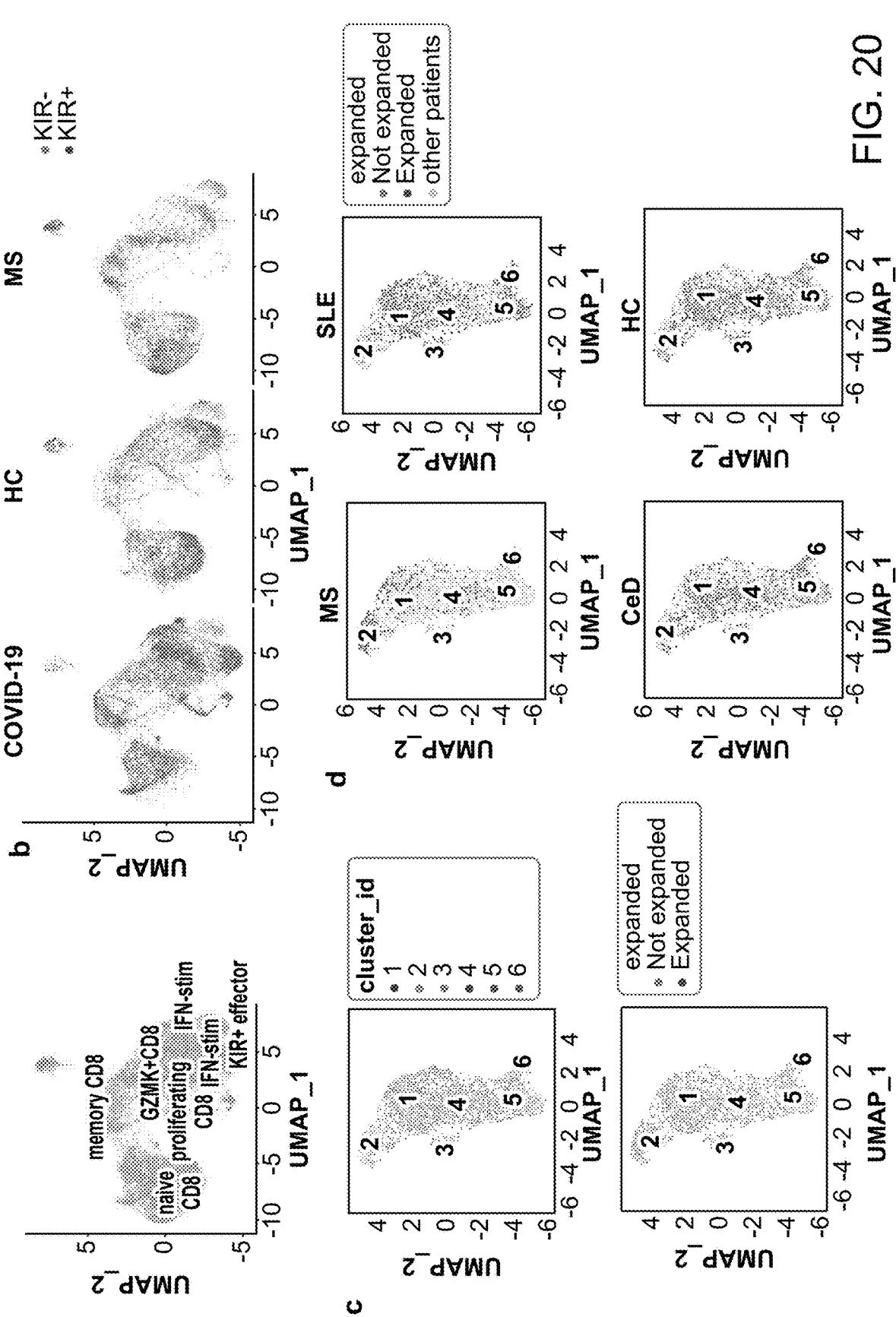
FIG. 20. Single cell RNA-seq analysis of KIR+ CD8+ T cells in the blood. a-b, Single cell RNA-seq analysis of total CD8+ T cells from the blood of healthy subjects (N=10), MS patients (N=6) and COVID-19 patients (N=25) by 10× Genomics. a, UMAP plot of the 8 subpopulations identified by unsupervised clustering based on expression of marker genes in each cluster. b, UMAP plots showing the distribution of KIR+CD8+ T cells (expressing KIR3DL1, KIR3DL2, KIR2DL1 or KIR2DL3 transcripts) and KIR-CD8+ T cells from healthy controls (HC), MS patients and COVID-19 patients. c-e, KIR+ CD8+ T cells in the blood of healthy controls (N=10) and patients with MS (N=2), SLE (N=6) and CeD (N=5) were sorted for single cell RNA-seq using the Smart-seq2 protocol and analyzed using the R package 'Seurat'. c, UMAP plots showing KIR+ CD8+ T cells segregated into 6 clusters (upper) and the distribution of expanded ($\geq 2$ cells expressing same TCR) and unexpanded (cell expressing unique TCR) cells (lower). d, UMAP plots of KIR+ CD8+ T cells from MS, SLE, CeD and HC are shown, with expanded and unexpanded cells annotated with different colors (expanded: red, unexpanded: blue, other diseases: grey). e, Heatmap showing expression of the top 10 genes differentially expressed in each cluster, with the categories of each group of genes annotated on the left. f, Representation of the role of KIR+CD8+ T cells in autoimmune disorders and infection: KIR+CD8+ T cells suppress pathogenic CD4+ T cells arising from self-reactivity in autoimmune disorders or cross-reactivity to autoantigens in infectious diseases via their cytolytic activity.

Parallels with Multiple Sclerosis. To determine if there are any similarities with MS, we first determined the frequency of CD4+, CD8+, and γδ+ T cells directly in recently diagnosed MS patients and found no differences in the frequency of total T cells in the peripheral blood compared to healthy controls (HC) (FIG. 117*a-c*). However, when we performed single cell TCR sequencing of activated brain homing (CD38+HLA-DR+CD49d+CD29+) CD4+, CD8+, and γδ+ T cells from PBMCs of newly diagnosed MS patients and HCs Table 9), similar to EAE and celiac disease, we observed a massive oligoclonal expansion of CD8+ T cells in MS patients compared to HCs (FIG. 18*a*). We also observed only a few oligoclonal expansions of CD4+ T cells in MS patients (FIG. 19*a*). Additionally, we find that γδ+ T cells are clonally expanded in MS patients and also in HCs (FIG. 20*a*).

The oligoclonal expansions of γδ+ T cells in MS has been noted before. Unlike mouse nTγδ17 cells which are largely "pre-programmed" in the thymus, the differentiation of human γδ17 T cells and their TCRs is poorly understood. It has been shown that, in vitro activation of Vγ9+δ2+ T cells with TCR specific agonists in the presence of cytokines, induces ROR-related orphan receptor gamma (RORγ) expression and IL-17 production. In fact, we detected a significant increase in the frequency of RORC transcript positive γδ+ T cells in MS patients (FIG. 20*b*). Therefore, in chronic autoinflammatory setting like MS some of these expanded γδ+ T cells may produce IL-17 and contribute to disease pathogenesis as like EAE.

In summary, we show here that the simultaneous mobilization of oligoclonal CD4+, CD8+, and γδ+ T cells has a parallel not only in EAE, but also in newly diagnosed MS patients. Furthermore, when we systematically characterized each of these cell types, we found two of the three are likely pathogenic: specifically, the γδ+ T cells that dominate the response are well known to be producers of IL-17, a pro-inflammatory cytokine known to be important in EAE pathology, while the CD4+ T cell response is predominantly MOG-specific, a key driver of EAE pathology.

In contrast to these two cell types, the clonally expanded CD8+ T cells exhibit a regulatory function. These T cells have a distinct phenotype, and extends observations centered on Qa-1b restricted regulatory CD8+ T cells to include peptides presented by the classical class I MHC molecule H2-D$^b$.

More importantly, our study shows the value of studying T cell specificity and activity from "the ground up", that is, identifying the T cells that are most active in a given response by single cell, paired TCR sequencing, using both activation markers and clonal expansion as key indicators, and then to ligand identification either with a yeast display library or candidate antigens and reporter cells transfected with the relevant TCR pairs. This is in contrast to traditional methods which typically involve knowing (or guessing) what the relevant antigens.

In summary, the work presented here indicates that there is a subset of CD8+ T cells that can suppress pathogenic CD4+ T cells in mice and in humans, and that this gives rise to the dynamic of co-mobilization upon disease induction. Determining the ligands for these regulatory CD8+ T cells in autoimmune diseases is of significant value therapeutically.

Methods

Laboratory animals. Female C57BL/6J mice (referred to as either B6 or WT) and female Perforin knockout mice (Stock No: 002407) were purchased from The Jackson Laboratory (Bar Harbor, ME, USA). The experimental procedures used in this study were approved by the Animal Care and Use Committee of the Stanford University.

Human Samples. Peripheral blood mononuclear cells (PBMCs) were obtained from healthy blood donations from Stanford Blood Center. Healthy human subjects were male and female, ages 22-47 yrs. PBMCs from Multiple sclerosis patients were obtained from the Multiple Sclerosis Center at the University of California, San Francisco (UCSF). The committee on Human Research at UCSF approved protocol, and informed consent was obtained from all participants. Detailed information on the patient population included in the study is provided as Table 9.

Generation of soluble TCRs. Soluble TCRs were generated as previously described. TCR variable mouse-constant human (VmCh) chimeras containing an engineered C domain disulfide were cloned into the pAcGP67a insect expression vector (BD Biosciences, 554756) encoding either a C-terminal acidic GCN4-zipper-Biotin acceptor peptide (BAP)-6×His tag (for α chain) or a C-terminal basic GCN4 zipper-6×His tag (for β chain). Each chain also encoded a 3 C protease site between the C terminus of the TCR ectodomains and the GCN4 zippers to allow for cleavage of zippers. Baculoviruses for each TCR construct were created in SF9 cells via co-transfection of BD baculogold linearized baculovirus DNA (BD Biosciences, 554739) with Cellfectin II (Life Technologies, 10362-100). TCRα and β chain viruses were coinfected in a small volume (2 ml) of High Five cells in various ratios to find a ratio to ensure 1:1 α:β stoichiometry.

To prepare soluble TCRs, 1 L of High Five cells were infected with the appropriate ratio of TCRα and TCRβ viruses for 48 hr at 28° C. Collected culture media was conditioned with 100 mM Tris-HCl (pH 8.0), 1 mM NiCl2, 5 mM CaCl2 and the subsequent precipitation was cleared via centrifugation. The media was then incubated with Ni-NTA resin (QIAGEN 30250) at room temperature for 3 hr and eluted in 1×HBS+200 mM imidazole (pH 7.2). TCRs were then site-specifically biotinylated by adding recombinant BirA ligase, 100 μM biotin, 50 mM Bicine pH 8.3, 10 mM ATP, and 10 mM Magnesium Acetate and incubating 4 C overnight. The reaction was then purified via size-exclusion chromatography using an AKTAPurifier (GE Healthcare) on a Superdex 200 column (GE Healthcare). Peak fractions were pooled and then tested for biotinylation using an SDS-PAGE gel shift assay. Proteins were typically 100% biotinylated.

Generation of a mouse yeast displayed H2-D$^b$ peptide library, Tag enrichment, Staining, and selection. The single chain trimer (SCT) H2-Db yeast constructs were synthesized as N-terminal fusions to the yeast surface protein Aga2p. Full length SCT H2-D$^b$ constructs were cloned into the vector pYAL. These constructs contained an Aga2p leader sequence followed by the 9-10MER peptide sequence, a Gly-Ser (GGGGS)3 (SEQ ID NO: 7) linker, the murine β2-microglobulin (B2M) sequence, a second glycine linker (GGGGS)4 (SEQ ID NO: 7), the mouse H2-D$^b$ heavy chain sequence, either a Myc or HA epitope tag, a third glycine linker (GGGGS)3 (SEQ ID NO: 7), and the Aga2 protein. SCT H2-Db MHC constructs were then electroporated into EBY-100 yeast as previously described and induced for expression in SGCAA pH 4.5 media at 20 C 24-72 hr until maximum epitope tag staining was observed (typically 40%-70% of total population). The full length H2-D$^b$ yeast construct was mutagenized as described previously. Briefly, the construct was mutagenized via error prone PCR (Genemorph II kit, Agilent 200550), with final error rate of ~4-5 nucleotide substitutions per kbp as judged by ligating error prone constructs into the pYAL vector and sequencing the clones. Yeast libraries were created by electroporation of competent EBY-100 cells via homologous recombination of linearized pYAL-cMyc/HA vector. Final libraries contained approximately 5×10⁸ yeast transformants.

Peptide libraries were created in the same manner as the error prone libraries, except pMHC constructs were instead randomized along the peptide by using mutagenic primers allowing all 20 amino acids via an NNK codon as previously described. The libraries allowed only limited diversity at the known MHC anchor residues to maximize the number of correctly folded and displayed pMHC clones in the library. For H2-D$^b$, P5 and P9 anchors were limited to Asn (N) and Met/Ile/Leu (M/I/L) using AAC and MTS codons, respectively. The resulting PCR product was used as template for a second PCR reaction in which 50 nucleotides of sequence homologous to the vector was added to both ends of the PCR product. Then, 50 μg of this second PCR product and ~10 μg of linearized vector were purified and used for electroporating yeast to create each library. Before selecting on the H2-Db 9MER and 10MER pMHC libraries, each was enriched for its respective epitope tag to maximize the percentage of yeast in the initial pool with correctly folded and displayed pMHC molecules presented on their surface. To achieve this, each of the libraries was induced separately in 500 mL SGCAA at 20 C for 24-72 hr with a starting density of 1×10⁷ cells/mL. When maximum epitope tag staining was observed, approximately 1.4×10⁹ induced yeast cells were washed once in PBS+0.5% BSA and 1 mM EDTA (PBE buffer) and resuspended in 5 mL PBE with 200 μL of Miltenyi streptavidin microbeads (Miltenyi, 130-048-101). The cell and bead mixture were incubated at 4 C with rotation for 1 hr, washed again in PBE, resuspended in 5 mL PBE, and passed through a cell strainer onto a prewet MACS LD column (Miltenyi 130-042-901). After allowing the column to fully empty, it was washed twice with 2 mL PBE and the flow-through was collected.

Cells were isolated from the flow-through by centrifugation and resuspended in 5 mL PBE with 80 μL of anti-cMyc AlexaFluor647 or anti-HA AlexFluor647 antibody (Cell signaling, 2233 and 3444), respectively incubated at 4 C with rotation for one hour. The cells were washed and resuspended in 5 ml PBE, 220 µL of Miltenyi anti-AlexaFluor647 microbeads were added (Miltenyi, 130-091-395), and this mixture was incubated at 4 C for 30 minutes with rotation and protected from light. The cells were then washed, resuspended in 6 mL PBE, and split evenly between two pre-wet MACS LS columns (Miltenyi, 130-042-401). After allowing the columns to fully empty, each column was washed two times with 3 mL of PBE and the flow-through was set aside. The cells were eluted from the columns with 5 mL PBE per column. A small fraction of the eluate (5-20 µL) was reserved to compare AlexaFluor647 staining to that of the flow through for a quantification of tag enrichment. The rest of the eluted cells were pooled, collected by centrifugation, resuspended in a total of 40 mL SDCAA media, and the cell density was measured by spectrophotometer at 600 nm. The cell density was then adjusted to an OD of or less with the addition of SDCAA, and the yeast were cultured at 30 C overnight. The cells were the passaged for another round of overnight growth in SDCAA.

For induction of the tag eluate were taken for culture at 20 C in 500 mL of SGCAA. To stain pMHC with TCR tetramers, biotinylated TCR was incubated with streptavidin coupled to AlexaFluor647, AlexaFluor488, or Phycoerythrin in a 5:1 ratio for 5 min on ice to ensure complete tetramer formation. Yeast cells were then stained with 250 nM tetramer+anti-Myc-AlexaFluor488 or anti-HA-AlexaFluor488 antibodies (Cell Signaling, 2279 or 2350, respectively) for 3 hr on ice and washed twice with ice cold PBE buffer before analysis via flow cytometry (Accuri C6 flow cytometer). All the yeast selections and sequencing of yeast libraries were done as previously described.

List of primers used for H2-D$^b$ Libraries. For generating H2-D$^b$ error-prone libraries: Forward primer: -5'TGCAGT-TACTTCGCTGTTTTTCAATATTTTCTGTTAT-TGCTAGCGT TTTAGCAAGCAGCCTG-GAGAACTTCAGAGCCTACGTGG-3' (SEQ ID NO: 8) Reverse: 5'-GAACAAAAGCTTATCTCCGAAGAA-GACTTG-3' (SEQ ID NO: 9). For the random H2-Db library: Forward primer for 9MER HA library (initial randomization PCR): 5'-TCAATATTTTCTGTT ATTGCTAGCGTTTTAGCANNKNNKNNKNN-KAACNNKNNKNNKMTSGGTGGAGGAG GTTCTG-3' (SEQ ID NO: 10). Reverse primer for 9MER HA library (initial randomization PCR): 5'-TCCACCACCACCAGC GTAGTCTGGAACGTCGTATGGGTAG-GATCCCTCCCA-3' (SEQ ID NO: 11). To add overlap for homologous recombination with linearized pYAL vector: Forward primer: 5'-ATTTTCAATTAAGATGCAGT-TACTTCGCTGTTTTTCAATATTTTCTG TTAT-TGCTAGCGTTTTAGCA-3' (SEQ ID NO: 12). Reverse primer: 5'-TCCACCACCACCAGCGTAGTCTG-GAACGTCGTATG GGTAGGATCC CTCCCA-3' (SEQ ID NO: 11).

Class I and Class II peptide monomer production, tetramerization, and tetramer enrichment. Peptide-I-Ab monomer production: The peptide-I-Ab monomer was generated as previously described. Briefly, the extracellular portion of I-A$^b$ α chain was linked to acidic zipper on the C-terminus, followed by AviTag (GLNDIFEAQKIEWHE; SEQ ID NO: 13) and 6× Histidine tag. The peptides-myelin oligodendrocyte glycoprotein (MOG) 38-48 (GWYR-SPFSRVV; SEQ ID NO: 14) or ovalbumin (OVA) 327-337 (VHAAHAEINEA; SEQ ID NO: 15) were tethered to the N-terminus of I-Ab β chain, followed by basic zipper and 6× Histidine tag. The "disulfide trap" is introduced through the oxidation of the cysteine at p+2 position and the cysteine at position 72 of I-Ab α chain mutated from valine to ensure the proper peptide binding register.

The α chain and the peptide-β chain were cloned separately into the pAcGP67A vectors by Gibson Assembly (New England Biosciences, E2611S). Baculoviruses for each construct were created in SF9 cells via co-transfection of BD baculogold linearized baculovirus DNA (BD Biosciences, 554739) with Cellfectin II (Life Technologies, 10362-100). The a and B chain viruses were coinfected in a small volume (2 ml) of High Five cells in various ratios to find a ratio to ensure 1:1 α:β stoichiometry.

To prepare soluble monomers, 1 L of High Five cells were infected with the appropriate ratio of α and β viruses for 48 hr at 28° C. Collected culture media was conditioned with 100 mM Tris-HCl (pH 8.0), 1 mM NiCl$_2$, 5 mM CaCl$_2$) and the subsequent precipitation was cleared via centrifugation. The media is then incubated with Ni-NTA resin (QIAGEN, 30250) at room temperature for 3 hr and eluted in 1×HBS+ 200 mM imidazole (pH 7.2). TCRs were then site-specifically biotinylated by adding recombinant BirA ligase, 100 µM biotin, 50 mM Bicine pH 8.3, 10 mM ATP, and 10 mM Magnesium Acetate and incubating 4 C overnight. The reaction was then purified via size-exclusion chromatography using an AKTAPurifier (GE Healthcare) on a Superdex 200 column (GE Healthcare). Peak fractions were pooled and then tested for biotinylation using an SDS-PAGE gel shift assay. Proteins were typically 100% biotinylated.

Peptide-H2-D$^b$ monomer production: The peptide-H2-D$^b$ monomers were refolded with the appropriate peptide and human β2-microglobulin as previously described. Briefly, H2-D$^b$ and human β2-microglobulin were separately expressed in BL21DE3 (ThermoFisher, C600003) in the form of inclusion bodies. In the H2-D$^b$ construct, H2-D$^b$ α chain was linked to AviTag and 6× Histidine tag. The refolding was carried out using rapid dilution. Following biotinylation by BirA, protein was purified by size-exclusion chromatography (Superdex 200 10/300 GL) and stored in −80 C. For YQPGNWEYI (YQP; SEQ ID NO: 4), HDRVNWEYI (HDR; SEQ ID NO: 3), ASRSNRYFWL (ASR; SEQ ID NO: 2) and SMRPNHFFFL (SMRP; SEQ ID NO: 1), we individually refolded the monomers and purified them. For peptide-H2-Db monomer of 6218 flu peptides (QGLSNMRVRL (SEQ ID NO: 16), VGLENMRVRL (SEQ ID NO: 17), VSLRNMRSYL (SEQ ID NO: 18) and SSLEN-FRAYV (SEQ ID NO: 5)), we refolded H2-Db with a photo-cleavable peptide (FAPGNY-Anp-AL; SEQ ID NO: 19) and exchanged the target peptides into H2-Db upon UV cleavage of FAPGNY-Anp-AL45 (SEQ ID NO: 19).

Peptide-MHC tetramer formation: All tetramers were freshly prepared as previously described. Briefly, for tetramerization, the amount of fluorophore-conjugated streptavidin and pMHC monomer were mixed with 4:1 molar ratio. One fifth amount of the fluorophore-conjugated streptavidin was added to the monomer solution every 10 minutes in room temperature.

Enrichment of tetramer-positive T cells in mice and cell lines: Single cell suspensions of spleen and LN cells were prepared from unimmunized or immunized mice, resuspended in 200 µL FACS buffer (Ca2+/Mg2+-free sterile PBS with 0.5% BSA, 0.5 mM EDTA) with Fc block (1:100) and 10 UM biotin. Following tetramer concentrations were used for staining cells: I-A$^b$-MOG$_{38-48}$ tetramer (15 nM), I-Ab-OVA$_{327-337}$ tetramer (15 nM), H2-D$^b$-ASR tetramer (25 nM), H2-D$^b$-SMRP tetramer (10 nM), H2-D$^b$-YQP tetramer (25 nM) and H2-D$^b$-HDR tetramer (25 nM). The cells were tetramer stained for an hour at room temperature and washed with FACS buffer. For I-Ab-MOG$_{38-48}$ and I-Ab-OVA$_{327-337}$ tetramers, the enrichment of tetramer-positive cells was done using the EasySep™ PE Positive Selection Kit (STEMCELL Technologies, 18557). If the cells were stained with both I-Ab tetramers and H2-Db tetramers, the enrichment of tetramer-positive cells were done using anti-PE MicroBeads (Miltenyi Biotec, 130-048-801) and anti-His MicroBeads (Miltenyi Biotec, 130-094-258) according to manufacturer instructions.

Following tetramer enrichment, cells were surface stained with an antibody cocktail for 20 minutes at 4 C. Stained cells were washed using FACS buffer and analyzed on LSR II (Becton Dickinson) or single cell sorted/bulk sorted on FACS Aria Fusion SORP (Becton Dickinson). Lentivirally TCR transduced Jurkat TCR$\alpha\beta^{-/-}$ cell lines were stained with tetramers at 20 nM concentration in FACS buffer with 10 μM biotin at room temperate for 1 hr and followed by surface staining with appropriate antibodies for 20 minutes 4 C. Following surface staining the cells were washed with FACS buffer and analyzed on LSR II (Becton Dickinson).

Single cell mouse and human TCR sequencing and data analysis. All human TCR primers used were previously published. All mouse TCR primer sequences are provided in Table 1. TCR sequencing was done according to previously established protocols.

Induction and evaluation of EAE. EAE was actively induced in C57BL/6J mice according to previously established protocol. Briefly, for the induction of EAE mice were injected subcutaneously in the posterior right and left flank with an emulsion containing 200 μg of MOG$_{35-55}$ or CD8 specific SP derived from yeast library ASRSNRYFWL (SEQ ID NO: 2), SMRPNHFFFL (SEQ ID NO: 1) YQPGNWEYI (SEQ ID NO: 4), and HDRVNWEYI (SEQ ID NO: 3), and an equal volume of complete Freund's adjuvant (CFA; Sigma-Aldrich, F5881) supplemented with 200 μg of *Mycobacterium tuberculosis* H37Ra (Difco Laboratories, 231141). On the day of immunization and 2 days post-immunization, each mouse received 200 ng of PTX (List Biological Laboratories, 180) by intraperitoneal injection. Mice were scored daily for clinical signs of EAE beginning on d5 after injection as follows: 0, no clinical expression of disease; 1, flaccid tail without hind-limb weakness; 2, hind limb weakness; 3, complete hind-limb paralysis and floppy tail; 4, hind-limb paralysis accompanied by a floppy tail and urinary or fecal incontinence; and 5, moribund. Clinical quantitative trait variables were assessed as described previously.

CNS-infiltrating mononuclear cell isolation. CNS infiltrating cells were isolated according to previously established protocol. Briefly, at different days post-immunization, animals were perfused with saline, and brains and spinal cords were removed. A single-cell suspension was obtained and passed through a 70-μm strainer. Mononuclear cells were obtained by Percoll gradient (37%/70%) centrifugation and collected from the interphase. Cells were washed, labeled with antibody conjugated to fluorochrome dyes, and analyzed by flow cytometry.

Expression of TCRs, H2-D$^b$, and Qa-1b by lentiviral transduction. TCRα, β, H2-D$^b$, and B2M constructs were cloned into a lentiviral construct. For TCR expression, alpha and beta TCR lentiviral constructs were transfected into 293X cells separately. The virus was harvested after 72 hr of transfection and transduced into Jurkat αβ$^{-/-}$ or SKW αβ$^{-/-}$ cells. SKW or Jurkat cells were enriched for highest expression of TCRαβ by using a Miltenyi anti-APC selection (Miltenyi 130-090-855). Similar strategy was used for the expression of H2-D$^b$ and B2M, except that T2 cells were used for transduction and expression.

T cell stimulation assays. T cell stimulation assays were performed as previously described. All the T cell peptide stimulation experiments were done in 96 well round bottom plates with a 200 μl total volume. T2, K562 cells or BMDCs were pulsed with 10-100 μg of the peptides for 45 minutes, washed once and plated (10,000 cells/well). Cell lines expressing TCRs (100,000 cells/well) were co-cultured with APCs for 18 hr. At the end of stimulation, cells were harvested, washed, and stained with TCRβ, human CD3, and CD69 and analyzed on LSR II (Becton Dickinson) for activation.

In vitro proliferation/suppression assay. Spleen and LN cells were harvested from WT or immunized mice. Single cell suspensions were prepared, and RBCs were lysed using Ack lysis buffer (ThermoFisher scientific A1049201). Total CD4+ (Miltenyi 130-049-201) and CD8+ (Miltenyi 130-049-401) T cells were positively purified using Miltenyi kits following established manufacturer protocol followed by FACS sorting. Similarly, antigen presenting cells were isolated using Miltenyi Pan Dendritic Cell (DC) Isolation Kit (Miltenyi 130-100-875). Post CD4+ T cell enrichment, cells were counted and labelled with CellTrace™ Violet Dye (ThermoFisher scientific C34557) according to manufacturer instructions.

In vitro proliferation/suppression assays were set up according to previously published protocol. Briefly, labelled CD4+ T cells were co-cultured either with CD8+ T cells (1:1 ratio, 0.25×106 cells/well) or without CD8+ T cells in the presence of pan DC's (0.75×10$^6$ cells/well). In some of the suppression experiments cells were pre-included with 10 μg/ml of anti-Qa-1b neutralizing antibody (6A8.6F10.1A16, BD Biosciences). Cells were cultured in a total volume of 200 μl in a 96-well round bottom plate. The CD4+ T cells were stimulated with either MOG$_{35-55}$ or not. On day 7, the cells were washed and stained with surface antibodies and analyzed on LSR II (Becton Dickinson).

Adoptive transfer. EAE was actively induced in C57BL/6J mice were actively immunized with an emulsion containing 200 μg of MOG$_{35-55}$+CD8 specific PPTs derived from yeast library (ASRSNRYFWL (SEQ ID NO: 2), SMRPNHFFFL (SEQ ID NO: 1), YQPGNWEYI (SEQ ID NO: 4), and HDRVNWEYI (SEQ ID NO: 3)), and an equal volume of complete Freund's adjuvant (CFA; Sigma-Aldrich, F5881) supplemented with 200 μg of *Mycobacterium tuberculosis* H37Ra (Difco Laboratories, 231141). On the day of immunization and 2 days post-immunization, each mouse received 200 ng of PTX (List Biological Laboratories, 180) by intraperitoneal injection. Day 10 post-immunization, spleen and lymph nodes were harvested, CD8+ cells were obtained using a CD8 enrichment kit and sorted for CD44+CD122+Ly49+ (Ly49+) and CD44+CD122+ Ly49- (Ly49-) cells.

FACS purified Ly49+ and Ly49- cells (8 million cells/mice) were adoptively transferred at the time of active MOG immunization and mice were scored daily for clinical signs of EAE beginning on Day 5 after as described previously.

Induction and evaluation of EAU. Experimental autoimmune uveitis (EAU) was induced in mice as described previously. Briefly, for the induction of EAE mice were injected subcutaneously in the posterior right and left flank with an emulsion containing 300 μg of human interphotoreceptor binding protein (IRBP) peptide 1-20 in CFA (1:1 v/v), 0.2 μg of PTX on day 0 and 0.2 μg again on day 2. Mice were euthanized on day 21 post-immunization. Mouse eyes were enucleated, fixed, and pupil-optic nerve sections were examined by histology as previously described.

Whole transcriptome sequencing and data analysis. Whole transcriptome sequencing was done as previously described, T cells were bulk sorted directly into Trizol (Qaigen). RNA was extracted with a RNeasy Plus Micro Kit (Qiagen). After analysis on the 2100 Bioanalyzer and the resulting library was sequenced on the HiSeq 4000 platform (Illumina). For each sample in the whole transcriptome sequencing library, 75-basepair paired-end reads were acquired from the sequencer. Each sample condition was completed in triplicate, except for the WT sample for which one sample was generated. Read quality was determined with FastQC 0.11.4. Using TopHat v2.0.13, we aligned the reads to the mouse reference genome (NCBI/assembly GRCm38). On average, 90% of reads were aligned to the reference genome. One MOG+SP sample was removed from downstream analysis as an identified outlier. Differential gene expression analysis and read count normalization used as input for heatmaps were determined via DESeq251. TPM values were calculated with RSEM v1.3.052. Heatmaps were generated with the R package "pheatmap" 53. Gene ontology analysis plots were generated with the R package "enrichplot". Data availability RNA-seq data and Yeast p-MHC selection data are deposited to the Gene Expression Omnibus (GEO) data repository with accession number GSE130975. Source Data for each figure are provided.

TABLE 1

| List of Mouse Phase 1 TCR Primers | |
| --- | --- |
| musTRBV1Ph1 | GGGACAAAGAGGTCAAATCTCTTC |
| musTRBV2Ph1 | CCTCAAGTCGCTTCCAACCTCAAA |
| musTRBV3Ph1 | GTCATGGAGAAGTCTAAACTGTTTAA |
| musTRBV4Ph1 | CTCATTGTAAACGAAACAGTTCCAA |
| musTRBV5Ph1 | CGAAATGAGACGGTGCCCAGTC |
| musTRBV12-1,2Ph1 | CCCAGCAGATTCTCAGTCCAACA |
| musTRBV13-1Ph1 | GGAGATGTCCCTGATGGGTACAA |
| musTRBV13-2,3Ph1 | AGATATCCCTGATGGRTACAAGGCC |
| musTRBV14Ph1 | GGCCTAAAGGAACTAACTCCACTC |
| musTRBV15Ph1 | GGTGGGGCTTTCAAGGATCGATT |
| musTRBV16Ph1 | GATGATTCAGGGATGCCCAAGGAA |
| musTRBV17Ph1 | GGGAAGCTGACACTTTTGAGAAGT |
| musTRBV19Ph1 | GATCTATCTGAAGGCTATGATGCGT |
| musTRBV20Ph1 | CTGTGAACTCAGCAATCAAATATGAA |
| musTRBV23Ph1 | GGTCAAGGAGAGATTCTCAGCTGT |
| musTRBV24Ph1 | CAGACTTGGTCAAGAAGAGATTCTCA |
| musTRBV26Ph1 | GTTCTTCAGCAAATAGACATGACTGA |
| musTRBV29Ph1 | CGATGTTGATAGTAACAGCGAAGGA |
| musTRBV30Ph1 | GCCACATACGAGAGTGGATTCAC |
| musTRBV31Ph1 | GGTAGAGTCGGTGGTGCAACTGA |
| musTRAV21Ph1 | GACTCACGGTCTACAACAAAATACAA |
| musTRAV19Ph1 | CCGTACGCTCAAATGTGGATAAGA |
| musTRAV17Ph1 | CGTTGTTAAAGGCACCAAGGGCTT |
| musTRAV16Ph1 | GGTCATTATYCTCTGAACTTTCAGAAGC |
| musTRAV15Ph1 | CGCTAYTCTGTAGTCTTCCAGAAATCA |
| musTRAV14Ph1 | GTGTCCRATAAAAAGGAAGATGGA |
| musTRAV13-1/4Ph1 | GTTSTACAATCCTTCTGGGACAAAGCA |
| musTRAV13-2/4Ph1 | CAATCCTTCTGGGACAAAGCACAC |
| musTRAV13-3/D3/N3Ph1 | GCAGAGCAGAGAGGTGGAAGACT |
| musTRAV13-5.01Ph1 | GCCTGTCCTACATTCCTGGAATGA |
| musTRAV12Ph1 | CGCCACTCTCCATAAGAGCAGCA |

TABLE 1-continued

| | |
|---|---|
| musTRAV11Ph1 | GACAAAACGTCAAATGGGAGATACTC |
| musTRAV10Ph1 | GGACAGAAAACAGAGCCAAAGACTT |
| musTRAV9Ph1 | GGARACCCAGTGGTTCAAGGAGTGAA |
| musTRAV8Ph1 | CGTTCAAATGAGMGAGAGAAGCGCA |
| musTRAV7-5Ph1 | CTCTGATGGTGAAAAGGAAGAAGGCA |
| musTRAV7-4Ph1 | GAAGGCAGATTCACAGCTCACCT |
| musTRAV7-6Ph1 | GGCAGATTGACAGTTTACCTCAATA |
| musTRAV7-3Ph1 | AGATTCACAATTCACCTCAATAAAGC |
| musTRAV7-2Ph1 | GGTGAAAAGGAAGAAGGCAGATTCA |
| musTRAV5-4Ph1 | GCAGACCCAAGGACTCATCGTTTT |
| musTRAV5-1.01Ph1 | GAAAACAGAATCAAAGACTCACCCTT |
| musTRAV4Ph1 | CAGGAACAAAGGAGAATGGGAGGT |
| musTRAV4-2Ph1 | GCTCAAGGAACAAAGGAGAATGGAA |
| musTRAV4-4Ph1 | GCTTCAGGAACAAAGGAGAATGGGA |
| musTRAV3-3Ph1 | CGGAAATAAACGAAGGACAAGGATT |
| musTRAV3-1,4Ph1 | GTGGACAGAAAAGAAGAACAAGGAC |
| musTRAV2Ph1 | GGACTATGTGGTAAATGAAGTGGCA |
| musTRAV1Ph1 | GAAGGACAGTGGGCATTTCTCCA |
| musTRBCPh1 | GCACACGAGGGTAGCCTTTTGTTT |
| musTRACPh1 | GTCAAAGTCGGTGAACAGGCAGA |
| List of Mouse Phase 2 TCR Primers | |
| musTRBV1Ph2 | CCAGGGTTTTCCCAGTCACGGGTCACTGATACGGAgctga |
| musTRBV2Ph2 | CCAGGGTTTTCCCAGTCACCCATTTAGACCTTCAGATCACAGCT |
| musTRBV3Ph2 | CCAGGGTTTTCCCAGTCACGGATCAGTTTTCAGTTGAAAGACCA |
| musTRBV4Ph2 | CCAGGGTTTTCCCAGTCACCCTCAGTCTTCAGATAAAGCTCATTT |
| musTRBV5Ph2 | CCAGGGTTTTCCCAGTCACGCCCAGACAGCTCCAAGCTACTT |
| musTRBV12-1,2Ph2 | AGGGTTTTCCCAGTCACCCAACAGTTTGATGACTATCACTCT |
| musTRBV13-1Ph2 | CCAGGGTTTTCCCAGTCACGCCACCAGAACAACGCAAGAAGA |
| musTRBV13-2,3Ph2 | CCAGGGTTTTCCCAGTCACCAAGGCCTCCAGACCAAGCCAA |
| musTRBV14Ph2 | CCAGGGTTTTCCCAGTCACGGCCTAAAGGAACTAACTCCACTC |
| musTRBV15Ph2 | CCAGGGTTTTCCCAGTCACGCTGAGATGCTAAATTCATCCTTCT |
| musTRBV16Ph2 | CCAGGGTTTTCCCAGTCACGCTCAGATGCCCAATCAGTCGCA |
| musTRBV17Ph2 | CCAGGGTTTTCCCAGTCACCAGTCGGCCTAACAATTCTTTCT |
| musTRBV19Ph2 | CCAGGGTTTTCCCAGTCACCGAGAGAAGAAGTCATCTTTTTCTCT |
| musTRBV20Ph2 | CCAGGGTTTTCCCAGTCACCCATCAGTCATCCCAACTTATCCT |
| musTRBV23Ph2 | CCAGGGTTTTCCCAGTCACCCTCCAGCTCACTCTGCAGCCT |
| musTRBV24Ph2 | CCAGGGTTTTCCCAGTCACCAGCTAAGTGTTCCTCGAACTCaC |
| musTRBV26Ph2 | CCAGGGTTTTCCCAGTCACGCTGAGTGTCCTTCAAACTCACCT |
| musTRBV29Ph2 | CCAGGGTTTTCCCAGTCACGGATACAGGGTCTCACGGAAGAA |

TABLE 1-continued

| | |
|---|---|
| musTRBV30Ph2 | CCAGGGTTTTCCCAGTCACCAAGTTTCCAATCAGCCGGCCAAA |
| musTRBV31Ph2 | CCAGGGTTTTCCCAGTCACGCTTCCAGGCCGAAGGACGAC |
| musTRAV21Ph2 | CCAGGGTTTTCCCAGTCACCCTGGCTATTGCCTCTGACAGAAA |
| musTRAV19Ph2 | CCAGGGTTTTCCCAGTCACCAGTTTTCTTGAACAAAAGCGGCAAA |
| musTRAV17Ph2 | CCAGGGTTTTCCCAGTCACGCCGAGTTTAGGAAGAGTAACTCCTCT |
| musTRAV16Ph2 | CCAGGGTTTTCCCAGTCACCAGAAGCCAAAAAGTTCCATCGGA |
| musTRAV15N1Ph2 | CCAGGGTTTTCCCAGTCACTCAAATCCATCAGCCTTATCATTTCA |
| musTRAV15Ph3 | CCAGGGTTTTCCCAGTCACCAARTCCATCAGCCTTgTCATTTCA |
| musTRAV14Ph2 | CCAGGGTTTTCCCAGTCACGATTCACAATCTTCTTCAATAAAAGGGAG |
| musTRAV13Ph2 | CCAGGGTTTTCCCAGTCACCGCRGCTCTTTGCACATTTCCTCCT |
| musTRAV13-<br>5.01Ph2 | CCAGGGTTTTCCCAGTCACCCTCAACAGTCACTAAGGGACGT |
| musTRAV12Ph2 | CCAGGGTTTTCCCAGTCACCAGCTCCTTCCATCTGCAGAAGT |
| musTRAV11Ph2 | CCAGGGTTTTCCCAGTCACCTCAGCAACTCTGGATAAAGATGCTA |
| musTRAV10Ph2 | CCAGGGTTTTCCCAGTCACTGGATAAGAAAGCCAAACGATTCTC |
| musTRAV9Ph2 | CCAGGGTTTTCCCAGTCACGCTTYGAGGCTGAGTTCAGCAAGAG |
| musTRAV8Ph2 | CCAGGGTTTTCCCAGTCACGAGCCACCCTTGACACYTCCAGC |
| musTRAV7-5Ph2 | CCAGGGTTTTCCCAGTCACTTTACAGCTCACCTCAATAGAGCCA |
| musTRAV7-5.02Ph2 | CCAGGGTTTTCCCAGTCACCAGCTCAGGTCAATAGAGCCAGCCT |
| musTRAV7-4Ph2 | CCAGGGTTTTCCCAGTCACCTCACCTCAATAAGGCCAGCCTG |
| musTRAV7-6Ph2 | CCAGGGTTTTCCCAGTCACCTCAATAGAGCCAGCCTGCATGTT |
| musTRAV7-3Ph2 | CCAGGGTTTTCCCAGTCACCTCAATAAAGCCAGTCTGCATTTCTC |
| musTRAV7-2Ph2 | CCAGGGTTTTCCCAGTCACCCAGCCTGCATACTTCCCTGCA |
| musTRAV5-4Ph2 | CCAGGGTTTTCCCAGTCACGGATAAGAAAGCCAAACGCTTCTC |
| musTRAV5-1.01Ph2 | CCAGGGTTTTCCCAGTCACAGAAAACCAAACACCTTTCCCTGCA |
| musTRAV4Ph2 | CCAGGGTTTTCCCAGTCACGGTTAAAGTCAACATTCAATTCTAAGGA |
| musTRAV4-4Ph2 | CCAGGGTTTTCCCAGTCACCTAAAGTCAGCATTTGATTCTAAGGA |
| musTRAV3Ph2 | CCAGGGTTTTCCCAGTCACCACTGTCYTACTGAACAAGAAAGACAA |
| musTRAV2Ph2 | CCAGGGTTTTCCCAGTCACCATCTCTGTTTATCTCTGCTGACCGGA |
| musTRAV1Ph2 | CCAGGGTTTTCCCAGTCACGCCGCTCGAATGGGTACAGTTAC |
| musTRBCPh2 | CTGCTTTTGATGGCTCAAACAAGGA |

List of Mouse Phase 3 TCRA and TCRB Barcode Primers

| | |
|---|---|
| musTRACPh2 | CCTGAGACCGAGGATCTTTTAACTG |
| musBetaBC1 | CTGCTGAACCGCTCTTCCGATCTatGTTCACCTTGGGTGGAGTCACATTTCT CA |
| musBetaBC2 | CTGCTGAACCGCTCTTCCGATCTtaCAGGACCTTGGGTGGAGTCACATTTCT CA |
| musBetaBC3 | CTGCTGAACCGCTCTTCCGATCTgaTTATACCTTGGGTGGAGTCACATTTCT CA |
| musBetaBC4 | CTGCTGAACCGCTCTTCCGATCTcaCCTGTCCTTGGGTGGAGTCACATTTCT CA |
| musBetaBC5 | CTGCTGAACCGCTCTTCCGATCTagACCGCCCTTGGGTGGAGTCACATTTC TCA |
| musBetaBC6 | CTGCTGAACCGCTCTTCCGATCTtgACTTACCTTGGGTGGAGTCACATTTCT CA |
| musBetaBC7 | CTGCTGAACCGCTCTTCCGATCTgtGCTAGCCTTGGGTGGAGTCACATTTCT CA |

TABLE 1-continued

| | |
|---|---|
| musBetaBC8 | CTGCTGAACCGCTCTTCCGATCTctGACGTCCTTGGGTGGAGTCACATTTCT CA |
| musBetaBC9 | CTGCTGAACCGCTCTTCCGATCTacGGCTACCTTGGGTGGAGTCACATTTC TCA |
| musBetaBC10 | CTGCTGAACCGCTCTTCCGATCTtcGAATGCCTTGGGTGGAGTCACATTTCT CA |
| musBetaBC11 | CTGCTGAACCGCTCTTCCGATCTgcCCAACCCTTGGGTGGAGTCACATTTCT CA |
| musBetaBC12 | CTGCTGAACCGCTCTTCCGATCTcgGAGACCCTTGGGTGGAGTCACATTTC TCA |
| musAlphaBC1 | CTGCTGAACCGCTCTTCCGATCTatGTTCAGTACACAGCAGGTTCTGGGTTC T |
| musAlphaBC2 | CTGCTGAACCGCTCTTCCGATCTtaCAGGAGTACACAGCAGGTTCTGGGTT CT |
| musAlphaBC3 | CTGCTGAACCGCTCTTCCGATCTgaTTATAGTACACAGCAGGTTCTGGGTTC T |
| musAlphaBC4 | CTGCTGAACCGCTCTTCCGATCTcaCCTGTGTACACAGCAGGTTCTGGGTT CT |
| musAlphaBC5 | CTGCTGAACCGCTCTTCCGATCTagACCGCGTACACAGCAGGTTCTGGGTT CT |
| musAlphaBC6 | CTGCTGAACCGCTCTTCCGATCTtgACTTAGTACACAGCAGGTTCTGGGTTC T |
| musAlphaBC7 | CTGCTGAACCGCTCTTCCGATCTgtGCTAGGTACACAGCAGGTTCTGGGTT CT |
| musAlphaBC8 | CTGCTGAACCGCTCTTCCGATCTctGACGTGTACACAGCAGGTTCTGGGTTC T |
| musAlphaBC9 | CTGCTGAACCGCTCTTCCGATCTacGGCTAGTACACAGCAGGTTCTGGGTT CT |
| musAlphaBC10 | CTGCTGAACCGCTCTTCCGATCTtcGAATGGTACACAGCAGGTTCTGGGTTC T |
| musAlphaBC11 | CTGCTGAACCGCTCTTCCGATCTgcCCAACGTACACAGCAGGTTCTGGGTT CT |
| musAlphaBC12 | CTGCTGAACCGCTCTTCCGATCTcgGAGACGTACACAGCAGGTTCTGGGTT CT |

TABLE 2

The sequences of EAE-CD4 TCRs used for T cell transductants and soluble TCRs

| Mouse/Tissue/Day | | Vbeta | beta-CDR3 | Jbeta | Valpha | Jalpha | alpha-CDR3 | freq |
|---|---|---|---|---|---|---|---|---|
| EAE1-CD4 | M2/CNS/D15 | mTRBV13-2 | CASGDAGGGQNTLYF (SEQ ID NO: 144) | mTRBJ2-4 | mTRAV7N-4 | mTRAJ15 | CAASEGQGGRAL IF (SEQ ID NO: 148) | 1 (96) |
| | M3/CNS/D15 | mTRBV13-2 | CASGDAGGGQNTLYF (SEQ ID NO: 144) | mTRBJ2-4 | mTRAV7N-4 | mTRAJ15 | CAASEVQGGRAL IF (SEQ ID NO: 148) | 2 (96) |
| | M1/BL/D7 | mTRBV13-2 | CASGDAGGGQNTLYF (SEQ ID NO: 144) | mTRBJ2-4 | mTRAV7N-4 | mTRAJ15 | CAASEGQGGRAL IF (SEQ ID NO: 148) | 1 (96) |
| | M3/BL/D7 | mTRBV13-2 | CASGDAGGGQNTLYF (SEQ ID NO: 144) | mTRBJ2-4 | mTRAV7N-4 | mTRAJ15 | CAASEGQGGRAL IF (SEQ ID NO: 148) | 1 (96) |
| | M3/BL/D15 | mTRBV13-2 | CASGDAGGGQNTLYF (SEQ ID NO: 144) | mTRBJ2-4 | mTRAV7N-4 | mTRAJ15 | CAASEGQGGRAL IF (SEQ ID NO: 148) | 4 (96) |
| EAE2-CD4 | M3/CNS/D15 | mTRBV16 | CASSLDQGWDERLFF (SEQ ID NO: 145) | mTRBJ1-4 | mTRAV12-1 | mTRAJ23 | CALRNYNQGKLI F (SEQ ID NO: 149) | 2 (96) |
| | M3/BL/D15 | mTRBV16 | CASSLDQGWDERLFF (SEQ ID NO: 145) | mTRBJ1-4 | mTRAV12-1 | mTRAJ23 | CALRNYNQGKLI F (SEQ ID NO: 149) | 4 (96) |
| EAE3-CD4 | M2/CNS/D15 | mTRBV3 | CASSLEGHQDTQYF (SEQ ID NO: 146) | mTRBJ2-5 | | | | 1 (96) |
| | M2/BL/D15 | mTRBV3 | CASSLEGHQDTQYF (SEQ ID NO: 146) | mTRBJ2-5 | mTRAV14D-1 | mTRAJ43 | CAASGANNNNAP RF (SEQ ID NO: 150) | 4 (96) |
| EAE4-CD4 | M3/CNS/D15 | mTRBV16 | CASSLETANTEVFF (SEQ ID NO: 147) | mTRBJ1-1 | mTRAV3N-3 | mTRAJ30 | CAVSAGTNAYKV IF (SEQ ID NO: 151) | 5 (96) |

List of CD4 TCR pairs used of generating reporter cell lines. Mouse (M1, M2, and M3), Blood (BL), and D, day.

TABLE 3

The sequences of EAE-CD8 TCRs used T cell transductants and soluble TCRs

| Mouse/Tissue/Day | | Vbeta | beta-CDR3 | Jbeta | Valpha | Jalpha | alpha-CDR3 | freq |
|---|---|---|---|---|---|---|---|---|
| EAE1 -CD8 | M2/CNS/D15 | mTRBV14 | CASSQKNTGQLYF (SEQ ID NO: 152) | mTRBJ2-2 | mTRAV13-2 | mTRAJ26 | CALEHNYAQGLTF (SEQ ID NO: 161) | 28 (96) |
| EAE2 -CD8 | M1/CNS/D15 | mTRBV19 | CASSPGQVSNERLFF (SEQ ID NO: 153) | mTRBJ1-4 | mTRAV12-2 | mTRAJ40 | CALRPPGAGNYKYVF (SEQ ID NO: 162) | 8 (96) |
| | M2/BL/D15 | mTRBV19 | CASSPGQVSNERLFF (SEQ ID NO: 153) | mTRBJ1-4 | mTRAV8D-2 | mTRAJ34 | CATDPTNKVVF (SEQ ID NO: 163) | 5 (96) |
| | M2/BL/D15 | mTRBV19 | CASSPGQVSNERLFF (SEQ ID NO: 153) | mTRBJ1-4 | mTRAV8-1 | mTRAJ23 | CATDMNYNQGKLIF (SEQ ID NO: 164) | 1 (96) |
| | M2/BL/D15 | mTRBV19 | CASSPGQVSNERLFF (SEQ ID NO: 153) | mTRBJ1-4 | mTRAV12-2 | mTRAJ7 | CAPGYSNNRLTL (SEQ ID NO: 165) | 1 (96) |
| | M2/BL/D15 | mTRBV19 | CASSPGQVSNERLFF (SEQ ID NO: 153) | mTRBJ1-4 | mTRAV12-2 | mTRAJ42 | CALGGSNAKLTF (SEQ ID NO: 166) | 1 (96) |
| EAE3 -CD8 | M1/CNS/D15 | mTRBV13-1 | CASSPTDANTEVFF (SEQ ID NO: 154) | mTRBJ1-1 | mTRAV12-2 | mTRAJ43 | CALSDPGNNNAPRF (SEQ ID NO: 167) | 12 (96) |
| | M2/BL/D15 | mTRBV13-1 | CASSPTDANTEVFF (SEQ ID NO: 154) | mTRBJ1-1 | mTRAV12-2 | mTRAJ22 | CALSESSGSWQLIF (SEQ ID NO: 168) | 1 (96) |
| | M2/BL/D15 | mTRBV13-1 | CASSPTDANTEVFF (SEQ ID NO: 154) | mTRBJ1-1 | mTRAV12-1 | mTRAJ23 | | 1 (96) |
| EAE4 -CD8 | M3/CNS/D10 | mTRBV16 | CASSLNPGANTEVFF (SEQ ID NO: 155) | mTRBJ1-1 | mTRAV7-3 | mTRAJ9 | CAVNSSNMGYKLTF (SEQ ID NO: 169) | 11 (43) |
| | M3/BL/D10 | mTRBV16 | CASSLNPGANTEVFF (SEQ ID NO: 155) | mTRBJ1-1 | mTRAV7-3 | mTRAJ9 | CAVNSSNMGYKLTF (SEQ ID NO: 169) | 6 (68) |
| EAE5 -CD8 | M1/CNS/D15 | mTRBV4 | CASSYWGGSYEQYF (SEQ ID NO: 156) | mTRBJ2-7 | mTRAV12-2 | mTRAJ31 | CAVDSNYQLIW (SEQ ID NO: 170) | 8 (96) |
| EAE6 -CD8 | M3/CNS/D10 | mTRBV19 | F CASSITPLGGLETLY (SEQ ID NO: 157) | mTRBJ2-3 | mTRAV12-1 | mTRAJ31 | CALSDYNRIFF (SEQ ID NO: 171) | 2 (43) |
| | M3/BL/D10 | mTRBV19 | CASSITPLGGLETLY F (SEQ ID NO: 157) | mTRBJ2-3 | mTRAV12-1 | mTRAJ31 | CALSDYNRIFF (SEQ ID NO: 171) | 4 (68) |
| EAE7 -CD8 | M1/CNS/D15 | mTRBV15 | CASTNRGEVFF (SEQ ID NO: 158) | mTRBJ1-1 | mTRAV5D-4 | mTRAJ45 | CAASVNTEGADRLTF (SEQ ID NO: 172) | 4 (96) |
| | M1/BL/D15 | mTRBV15 | CASTNRGEVFF (SEQ ID NO: 158) | mTRBJ1-1 | mTRAV5D-4 | mTRAJ45 | CAASVNTEGADRLTF (SEQ ID NO: 172) | 1 (95) |
| | M2/BL/D15 | mTRBV15 | CASTNRGEVFF (SEQ ID NO: 158) | mTRBJ1-1 | mTRAV13-2 | mTRAJ16 | | 1 (95) |
| EAE8 -CD8 | M1/BL/D7 | mTRBV29 | CASRAGQGADTQYF (SEQ ID NO: 159) | mTRBJ2-5 | mTRAV7-5 | mTRAJ22 | CAASSGSWQLIF (SEQ ID NO: 173) | 5 (96) |
| EAE9 -CD8 | M2/CNS/D15 | mTRBV13-3 | (SEQ ID NO: 160) CASSDRGLGGYEQYF | mTRBJ2-7 | mTRAV13-4/DV7 | mTRAJ37 | CAMAGKLIF (SEQ ID NO: 174) | 5 (96) |

List of CD8 TCRαβ pairs used for generating reporter cell lines and soluble TCRs. Mouse (M1, M2, and M3), Blood (BL), and day (D).

TABLE 4

Myelin peptides used for EAE-CD8 TCR cell line stimulation

Peptide Pool-1

| Prot | Len | Sequence | ID |
|---|---|---|---|
| PLP | 8 | AAATLVSL | 175 |
| PLP | 8 | AAFVGAAA | 176 |
| PLP | 8 | AATLVSLL | 177 |
| PLP | 8 | AATYNFAV | 178 |
| PLP | 8 | ACSAVPVY | 179 |
| PLP | 8 | ADARMYGV | 180 |
| PLP | 8 | AEFQMTFH | 181 |

TABLE 4-continued

Myelin peptides used for EAE-CD8 TCR cell line stimulation

| | | | |
|---|---|---|---|
| PLP | 8 | AEGFYTTG | 182 |
| PLE | 8 | AFPGKVCG | 183 |
| PLP | 8 | AFPSKTSA | 184 |
| PLP | 8 | AFQYVIYG | 185 |
| PLP | 8 | AFVGAAAT | 186 |
| PLP | 8 | AHSLERVC | 187 |
| PLP | 8 | ALFCGCGH | 188 |
| PLP | 8 | ALLLAEGF | 189 |
| PLP | 8 | ALTGTEKL | 190 |

TABLE 4-continued

Myelin peptides used for EAE-CD8
TCR cell line stimulation

| PLP | 8 | ALTVVWLL | 191 |
|-----|---|----------|-----|
| PLP | 8 | APFASLVA | 192 |
| PLP | 8 | ARCLVGAP | 193 |
| PLP | 8 | ARMYGVLP | 194 |
| PLP | 9 | AAATLVSLL | 195 |
| PLP | 9 | AAFVGAAAT | 196 |
| PLP | 9 | AATLVSLLT | 197 |
| PLP | 9 | AATYNFAVL | 198 |
| PLP | 9 | ACSAVPVYI | 199 |
| PLP | 9 | ADARMYGVL | 200 |
| PLP | 9 | AEFQMTFHL | 201 |
| PLP | 9 | AEGFYTTGA | 202 |
| PLP | 9 | AFPGKVCGS | 203 |
| PLP | 9 | AFPSKTSAS | 204 |
| PLP | 9 | AFVGAAATL | 205 |
| PLP | 9 | AHSLERVCH | 206 |
| PLP | 9 | ALFCGCGHE | 207 |
| PLP | 9 | ALLLAEGFY | 208 |
| PLP | 9 | ALTGTEKLI | 209 |
| PLP | 9 | ALTVVWLLV | 210 |
| PLP | 9 | APFASLVAT | 211 |
| PLP | 9 | ARCLVGAPF | 212 |
| PLP | 9 | ARMYGVLPW | 213 |
| PLP | 9 | ASFFFLYGA | 214 |
| PLP | 9 | ASIGSLCAD | 215 |
| PLP | 10 | AAATLVSLLI | 216 |
| PLP | 10 | AAFVGAAATL | 217 |
| PLP | 10 | AATLVSLLTE | 218 |
| PLP | 10 | AATYNFAVLK | 219 |
| PLP | 10 | ACSAVPVYIY | 220 |
| PLP | 10 | ADARMYGVLP | 221 |
| PLP | 10 | AEFQMTFHLE | 222 |
| PLP | 10 | AEGFYTTGAV | 223 |
| PLP | 10 | AFPGKVCGSN | 224 |

Peptide Pool-2

| Prot | Leng | Sequence | ID |
|------|------|----------|-----|
| PLP | 10 | AFPSKTSASI | 225 |
| PLP | 10 | AFQYVIYGTA | 226 |
| PLP | 10 | AFVGAAATLV | 227 |

TABLE 4-continued

Myelin peptides used for EAE-CD8
TCR cell line stimulation

| PLP | 10 | AHSLERVCHC | 228 |
|-----|----|-----------|-----|
| PLP | 10 | ALFCGCGHEA | 229 |
| PLP | 10 | ALLLAEGFYT | 230 |
| PLE | 10 | ALTGTEKLIE | 231 |
| PLP | 10 | ALTVVWLLVF | 232 |
| PLP | 10 | APFASLVATG | 233 |
| PLP | 10 | ARCLVGAPFA | 234 |
| PLE | 10 | ARMYGVLPWN | 235 |
| PLP | 11 | AAATLVSLLTF | 236 |
| PLE | 11 | AAFVGAAATLV | 237 |
| PLP | 11 | AATLVSLLTEM | 238 |
| PLE | 11 | AATYNFAVLKL | 239 |
| PLP | 11 | ACSAVPVYIYE | 240 |
| PLP | 11 | ADARMYGVLPW | 241 |
| PLE | 11 | AEFQMTFHLFI | 242 |
| PLP | 11 | AEGFYTTGAVR | 243 |
| PLP | 11 | AFPGKVCGSNL | 244 |
| PLP | 11 | AFPSKTSASIG | 245 |
| PLP | 11 | AFQYVIYGTAS | 246 |
| PLP | 11 | AFVGAAATLVS | 247 |
| PLP | 11 | AHSLERVCHCL | 248 |
| PLP | 11 | ALFCGCGHEAL | 249 |
| PLP | 11 | ALLLAEGFYTT | 250 |
| PLE | 11 | ALTGTEKLIET | 251 |
| PLE | 11 | APFASLVATGL | 252 |
| PLP | 11 | ARCLVGAPFAS | 253 |
| PLP | 11 | ARMYGVLPWNA | 254 |
| PLP | 11 | ASFFFLYGALL | 255 |
| PLP | 11 | ASIGSLCADAR | 256 |
| PLP | 11 | ASLVATGLCFF | 257 |
| MOG35 | | MEVGWYRSPFSRVV | 258 |
| MOG37 | | VGWYRSPFSR | 259 |
| MOG44 | | FSRVVHLYRNG | 260 |
| PLP | 12 | AATYNFAVLKLM | 261 |
| PLP | 12 | AATYNFAVLKLM | 261 |
| PLP | 12 | AEFQMTFHLFIA | 262 |
| MOG | 8 | CFLSLLLL | 263 |
| MOG | 8 | FLFLQHRL | 264 |

TABLE 4-continued

| Myelin peptides used for EAE-CD8 TCR cell line stimulation | | | |
|---|---|---|---|
| MOG | 8 | FSWPSCFL | 265 |
| MOG | 8 | FYWVNPGV | 266 |
| MOG | 8 | GVLTLIAL | 267 |
| MOG | 8 | IALVPTIL | 268 |
| MOG | 8 | ICYNWLHR | 269 |
| MOG | 8 | ISEGKVTL | 270 |
| MOG | 8 | IVPVLGPL | 271 |
| MOG | 8 | KITLFVIV | 272 |
| MOG | 9 | ALIICYNWL | 273 |

| Peptide Pool-3 | | | |
|---|---|---|---|
| Prote | Leng | Sequence | ID |
| MOG | 9 | CFLSLLLLL | 274 |
| MOG | 9 | CSYAGQFRV | 275 |
| MOG | 9 | CYNWLHRRL | 276 |
| MOG | 9 | EVGWYRSPF | 277 |
| MOG | 9 | FLSLLLLLL | 278 |
| MOG | 9 | FSWPSCELS | 279 |
| MOG | 9 | FYWVNPGVL | 280 |
| MOG | 9 | GVLTLIALV | 281 |
| MOG | 9 | HSYQEEAAM | 282 |
| MOG | 9 | IALVPTILL | 283 |
| MOG | 9 | ITLFVIVPV | 284 |
| MOG | 9 | IVPVLGPLV | 285 |
| MOG | 9 | LAGQFLEEL | 286 |
| MOG | 9 | LQHRLRGKL | 287 |
| MOG | 9 | PTILLQVPV | 288 |
| MOG | 9 | QVPVGLVEL | 289 |
| MOG | 9 | RVIGPGYPI | 290 |
| MOG | 9 | RVPCWKITL | 291 |
| MOG | 9 | SCFLSLLLL | 292 |
| MOG | 9 | SLLLLLLQL | 293 |
| MOG | 10 | CFLSLLLLLL | 294 |
| MOG | 10 | CSYAGQFRVI | 295 |
| MOG | 10 | CYNWLHRRLA | 296 |
| MOG | 10 | FRVIGPGYPI | 297 |
| MOG | 10 | FSWPSCFLSL | 298 |
| MOG | 10 | FVIVPVLGPL | 299 |
| MOG | 10 | GLVFLFLQHR | 300 |
| MOG | 10 | IALVPTILLQ | 301 |

TABLE 4-continued

| Myelin peptides used for EAE-CD8 TCR cell line stimulation | | | |
|---|---|---|---|
| MOG | 10 | ICYNWLHRRL | 302 |
| MOG | 10 | IGPGYPIRAL | 303 |
| MOG | 10 | ISPGKNATGM | 304 |
| MOG | 10 | ITLFVIVPVL | 305 |
| MOG | 10 | LAGQFLEELR | 306 |
| MOG | 10 | LQVPVGLVFL | 307 |
| MOG | 10 | LSLLLLLLQL | 308 |
| MOG | 10 | LTLIALVPTI | 309 |
| MOG | 10 | LVFLFLQHRL | 310 |
| MOG | 10 | PFYWVNPGVL | 311 |
| MOG | 10 | PSCFLSLLLL | 312 |
| MOG | 10 | RAEVENLHRT | 313 |
| MOG | 11 | FSWPSCFLSLL | 314 |
| MOG | 11 | GLVFLFLQHRL | 315 |
| MOG | 11 | ICYNWLHRRLA | 316 |
| MOG | 11 | IICYNWLHRRL | 317 |
| MOG | 11 | LVFLFLQHRLR | 318 |
| MOG | 11 | SWPSCFLSLLL | 319 |
| MOG | 11 | VGWYRSPFSRV | 320 |
| MOG | 12 | EVGWYRSPFSR | 321 |
| MOG | 12 | FSWPSCFLSLL | 322 |
| MOG | 12 | GLVFLFLQHRL | 323 |

| Peptide Pool-3 | | | |
|---|---|---|---|
| Prot | Leng | Sequence | ID |
| MOG | 11 | AAMELKVEDPF | 324 |
| MOG | 11 | DPFYWVNPGVL | 325 |
| MOG | 11 | FLSLLLLLLQL | 326 |
| MOG | 11 | FSWPSCFLSLL | 314 |
| MOG | 11 | FVIVPVLGPLV | 327 |
| MOG | 11 | FYWVNPGVLTL | 328 |
| MOG | 11 | IRALVGDEAEL | 329 |
| MOG | 12 | IICYNWLHRRLA | 330 |
| MOG | 12 | LIICYNWLHRRL | 331 |
| MOG | 12 | LVFLFLQHRLRG | 332 |
| MOG | 12 | SFSWPSCFLSLL | 333 |
| MOG | 12 | SWPSCFLSLLLL | 334 |
| MOG | 12 | VGLVFLFLQHRL | 335 |
| MOG | 12 | WSFSWPSCELSL | 336 |

TABLE 4-continued

Myelin peptides used for EAE-CD8
TCR cell line stimulation

| MOG | 12 | GQFRVIGPGYPI | 337 |
| MOG | 12 | HRRLAGQFLEEL | 338 |
| MOG | 12 | ILLQVPVGLVFL | 339 |
| MOG | 12 | LVALIICYNWLH | 340 |
| MOG | 12 | PFYWVNPGVLTL | 341 |
| MOG | 12 | PLVALIICYNWL | 342 |
| MOG | 12 | SFSWPSCFLSLL | 333 |
| MOG | 12 | TLFVIVPVLGPL | 343 |
| MOG | 12 | VALIICYNWLHR | 344 |
| MOG | 12 | VGLVFLFLQHRL | 335 |
| MOG | 12 | WSFSWPSCELSL | 336 |
| MOG | 12 | FRDHSYQEEAAM | 345 |
| MBF | 8 | VVHFFKNI | 346 |
| MBE | 8 | RTTHYGSL | 347 |
| MBP | 8 | IGRFFSGD | 348 |
| MBP | 8 | SIGRFFSG | 349 |
| MBP | 8 | LIRLFSRD | 350 |
| MBE | 8 | VHFFKNIV | 351 |
| MBP | 8 | TSAEDTAV | 352 |
| MBE | 8 | SKYLATAS | 353 |
| MBP | 8 | RSKYLATA | 354 |
| MBE | 8 | VFGEADAI | 355 |
| MBP | 8 | YLATASTM | 356 |
| MBP | 8 | FFKNIVTP | 357 |
| MBP | 8 | ASGGLDVM | 358 |
| MBP | 8 | IQNNGTSA | 359 |
| MBP | 8 | VVHFFKNI | 346 |
| MBP | 8 | AIQNNGTS | 360 |
| MBE | 8 | DSRSGSPM | 361 |
| MBE | 8 | DAIQNNGT | 362 |
| MBF | 8 | TQDENPVV | 363 |
| MBP | 8 | NWQGAHPA | 364 |
| MBP | 9 | VVHFFKNIV | 365 |
| MBP | 9 | PVVHFFKNI | 366 |
| MBP | 9 | GNRPHLIRL | 367 |
| MBP | 9 | SIGRFFSGD | 368 |

TABLE 4-continued

Myelin peptides used for EAE-CD8
TCR cell line stimulation

| Peptide Pool-5 | | | |
| --- | --- | --- | --- |
| Prot | Leng | Sequence | ID NO |
| MBP | 9 | TRTTHYGSL | 369 |
| MBP | 9 | SQRSKYLAT | 370 |
| MBP | 9 | VMASQKRPS | 371 |
| MBP | 9 | VHFFKNIVT | 372 |
| MBP | 9 | SKYLATAST | 373 |
| MBP | 9 | MDHARHGFL | 374 |
| MBP | 9 | AASGGLDVM | 375 |
| MBP | 9 | DAIQNNGTS | 376 |
| MBP | 9 | KYLATASTM | 377 |
| MBP | 9 | ADPGNRPHL | 378 |
| MBP | 9 | NNWQGAHPA | 379 |
| MBP | 9 | AIQNNGTSA | 380 |
| MBP | 9 | FLPRHRDTG | 381 |
| MBP | 9 | VVHFFKNIV | 365 |
| MBP | 9 | HFFKNIVTP | 382 |
| MBP | 9 | TASEDSDVF | 383 |
| MBP | 10 | SKYLATASTM | 384 |
| MBP | 10 | TMDHARHGFL | 385 |
| MBP | 10 | STMDHARHGF | 386 |
| MBP | 10 | PVVHFFKNIV | 387 |
| MBP | 10 | VHFFKNIVTP | 388 |
| MBP | 10 | SDVFGEADAI | 389 |
| MBP | 10 | HTRTTHYGSL | 390 |
| MBP | 10 | VVHFFKNIVT | 391 |
| MBP | 10 | GNRPHLIRLF | 392 |
| MBP | 10 | SIGRFFSGDR | 393 |
| MBP | 10 | DAIQNNGTSA | 394 |
| MBP | 10 | FLPRHRDTGI | 395 |
| MBP | 10 | ADAIQNNGTS | 396 |
| MBP | 10 | TAASGGLDVM | 397 |
| MBP | 10 | SKYLATASTM | 384 |
| MBP | 10 | TMDHARHGFL | 385 |
| MBP | 10 | TAVTDSKHTA | 398 |
| MBP | 10 | PADPGNRPHL | 399 |
| MBP | 10 | VHFFKNIVTP | 388 |
| MBP | 10 | ADPGNRPHLI | 400 |
| MBP | 11 | NPVVHFFKNIV | 401 |

TABLE 4-continued

Myelin peptides used for EAE-CD8
TCR cell line stimulation

| MBP | 11 | PVVHFFKNIVT | 402 |
|---|---|---|---|
| MBP | 11 | SIGRFFSGDRG | 403 |
| MBP | 11 | VHFFKNIVTPR | 404 |
| MBP | 11 | STMDHARHGFL | 405 |
| MBP | 11 | SHTRTTHYGSL | 406 |
| MBP | 11 | DSIGRFFSGDR | 407 |
| MBP | 11 | SKYLATASTMD | 408 |
| MBP | 11 | TMDHARHGFLP | 409 |
| MBP | 11 | VVHFFKNIVTP | 410 |
| MBP | 11 | RSKYLATASTM | 411 |
| MBP | 11 | FLPRHRDTGIL | 412 |
| MBP | 11 | ADAIQNNGTSA | 413 |
| MBP | 11 | GFLPRHRDTGI | 414 |

Peptide Pool-6

| Protein | Leng | Sequence | ID NO |
|---|---|---|---|
| MBP | 11 | EADAIQNNGTS | 415 |
| MBP | 11 | PTAASGGLDVM | 416 |
| MBP | 11 | TQDENPVVHFF | 417 |
| MBP | 11 | DAIQNNGTSAE | 418 |
| MBP | 11 | VVHFFKNIVTP | 410 |
| MBE | 11 | STMDHARHGFL | 405 |
| MBP | 12 | ENPVVHFFKNIV | 419 |
| MBP | 12 | ASTMDHARHGFL | 420 |
| MBP | 12 | ADPGNRPHLIRL | 421 |
| MBP | 12 | SIGRFFSGDRGA | 422 |
| MBP | 12 | DSHTRTTHYGSL | 423 |
| MBP | 12 | SQHGRTQDENPV | 424 |
| MBP | 12 | AHPADPGNRPHL | 425 |
| MAG | 8 | AAARDTVQ | 426 |
| MAG | 8 | AAFPNTTL | 427 |
| MAG | 8 | AARDTVQC | 428 |
| MAG | 8 | ACLAENAY | 429 |
| MAG | 8 | ADSNPPPL | 430 |
| MAG | 8 | AENAYGQD | 431 |
| MAG | 8 | AENQYGQR | 432 |
| MAG | 8 | AEYAEIRV | 433 |
| MAG | 8 | AFAILIAI | 434 |
| MAG | 8 | AFEGTCVS | 435 |

TABLE 4-continued

Myelin peptides used for EAE-CD8
TCR cell line stimulation

| MAG | 8 | AFELPSRN | 436 |
|---|---|---|---|
| MAG | 8 | AFNLSVEF | 437 |
| MAG | 8 | AFPNTTLQ | 438 |
| MAG | 8 | AGTEVEVS | 439 |
| MAG | 8 | AHRLMWAK | 440 |
| MAG | 8 | AIEGSHVS | 441 |
| MAG | 8 | AILIAIVC | 442 |
| MAG | 8 | AIVCYITQ | 443 |
| MAG | 8 | AKIGPVGA | 444 |
| MAG | 8 | AKSLYLDL | 445 |
| MAG | 9 | AAARDTVQC | 446 |
| MAG | 9 | AAFPNTTLQ | 447 |
| MAG | 9 | AARDTVQCL | 448 |
| MAG | 9 | ACLAENAYG | 449 |
| MAG | 9 | ADSNPPPLL | 450 |
| MAG | 9 | AENAYGQDN | 451 |
| MAG | 9 | AENQYGQRA | 452 |
| MAG | 9 | AEYAEIRVK | 453 |
| MAG | 9 | AFAILIAIV | 454 |
| MAG | 9 | AFEGTCVSI | 455 |
| MAG | 9 | AFELPSRNV | 456 |
| MAG | 9 | AFNLSVEFA | 457 |
| MAG | 9 | AFPNTTLQF | 458 |
| MAG | 9 | AGTEVEVSC | 459 |
| MAG | 9 | AHRLMWAKI | 460 |
| MAG | 9 | AIEGSHVSL | 461 |
| MAG | 9 | AILIAIVCY | 462 |

Peptide Pool-7

| Protein | Length | Sequence | ID NO |
|---|---|---|---|
| MAG | 9 | AIVCYITQT | 463 |
| MAG | 9 | AKIGPVGAV | 464 |
| MAG | 9 | AKSLYLDLE | 465 |
| MAG | 10 | AAARDTVQCL | 466 |
| MAG | 10 | AAFPNTTLQF | 467 |
| MAG | 10 | AARDTVQCLC | 468 |
| MAG | 10 | ACLAENAYGQ | 469 |
| MAG | 10 | ADSNPPPLLT | 470 |
| MAG | 10 | AENAYGQDNR | 471 |
| MAG | 10 | AENQYGQRAT | 472 |


TABLE 4-continued

| Myelin peptides used for EAE-CD8 TCR cell line stimulation | | | |
|---|---|---|---|
| MAG | 10 | AFAILIAIVC | 473 |
| MAG | 10 | AFEGTCVSIP | 474 |
| MAG | 10 | AFELPSRNVT | 475 |
| MAG | 10 | AFNLSVEFAP | 476 |
| MAG | 10 | AFPNTTLQFE | 477 |
| MAG | 10 | AGTEVEVSCM | 478 |
| MAG | 10 | AHRLMWAKIG | 479 |
| MAG | 10 | AIEGSHVSLL | 480 |
| MAG | 10 | AILIAIVCYI | 481 |
| MAG | 10 | AIVCYITQTR | 482 |
| MAG | 10 | AKIGPVGAVV | 483 |
| MAG | 10 | AKSLYLDLEE | 484 |
| MAG | 10 | ANGHRLGCQA | 485 |
| MAG | 11 | AAARDTVQCLC | 486 |
| MAG | 11 | AAFPNTTLQFE | 487 |
| MAG | 11 | AARDTVQCLCV | 488 |
| MAG | 11 | ACLAENAYGQD | 489 |
| MAG | 11 | ADSNPPPLLTW | 490 |
| MAG | 11 | AENAYGQDNRT | 491 |
| MAG | 11 | AENQYGQRATA | 492 |
| MAG | 11 | AFAILIAIVCY | 493 |

TABLE 4-continued

| Myelin peptides used for EAE-CD8 TCR cell line stimulation | | | |
|---|---|---|---|
| MAG | 11 | AFEGTCVSIPC | 494 |
| MAG | 11 | AFELPSRNVTV | 495 |
| MAG | 11 | AFNLSVEFAPI | 496 |
| MAG | 11 | AFPNTTLQFEG | 497 |
| MAG | 11 | AGTEVEVSCMV | 498 |
| MAG | 11 | AHRLMWAKIGP | 499 |
| MAG | 11 | AIEGSHVSLLC | 500 |
| MAG | 11 | AILIAIVCYIT | 501 |
| MAG | 11 | AIVCYITQTRR | 502 |
| MAG | 11 | AKIGPVGAVVA | 503 |
| MAG | 11 | AKSLYLDLEEV | 504 |
| MAG | 11 | ANGHRLGCQAA | 505 |
| MAG | 12 | EDGVYACLAENA | 506 |
| MAG | 12 | EELAEYAEIRVK | 507 |
| MAG | 12 | EEVTPGEDGVYA | 508 |
| MAG | 12 | EFAPIILLESHC | 509 |
| MAG | 12 | EFRISGAPDKYE | 510 |
| MAG | 12 | EFVYSERSGLLL | 511 |
| MAG | 12 | EGETVSILCSTQ | 512 |

List of 350 peptides derived from myelin oligodendrocyte glycoprotein (MOG), proteolipid protein (PLP), myelin basic protein (MBP), myelin associated glycoprotein (MAG). These peptides mixed into 7 peptide pools (PP1-7) and used for TCR cell line stimulation

TABLE 5

| Yeast H2-D$^b$ deep sequencing reads per round and enrichment | | | | |
|---|---|---|---|---|
| Immunization Incidence$^a$ | Total Sequences | Unique peptides | Fraction unique | Corrected Fold enrichment/RD |
| Naïve | 730261 | 423290 | 0.579642073 | 1 |
| RD1 | 339453 | 148333 | 0.436976548 | 1.326483255 |
| RD2 | 344611 | 17238 | 0.050021619 | 11.58783121 |
| RD3 | 383700 | 557 | 0.001451655 | 399.297421 |
| RD4 | 317153 | 29 | 9.14385E−05 | 6339.145601 |
| EAE6-CD8 TCR | | | | |
| Naïve | 435087 | 201808 | 0.46383367 | 1 |
| RD1 | 110427 | 70893 | 0.641989731 | 0.722493909 |
| RD2 | 65165 | 21848 | 0.335272002 | 1.383454829 |
| RD3 | 81996 | 87 | 0.001061027 | 437.1552369 |
| RD4 | 60005 | 48 | 0.000799933 | 579.8404036 |
| 6218-CD8 TCR | | | | |
| Naïve | 435087 | 201808 | 0.46383367 | 1 |
| RD1 | 64312 | 48978 | 0.761568603 | 0.60905041 |
| RD2 | 322526 | 59975 | 0.185954001 | 2.494346282 |
| RD3 | 336894 | 293 | 0.00086971 | 533.3200698 |
| RD4 | 336315 | 144 | 0.00042817 | 1083.2932 |

Enrichment of unique peptides per round (RD) for 6218, EAE6, and EAE7-CD8 TCR selections of H2-D$^b$ Library.

Summary of total number of Illumina reads by round for 6218, EAE6, and EAE7-CD8 TCR selections. Unique peptide sequences corresponded to reads that were in-frame with no stop codons. Fraction of unique peptides refers to total sequencing reads per RD divided by unique peptide sequences for that RD. Corrected fold enrichment refers to fold enrichment of peptides per RD selection normalized to the total number of reads from naïve RD.

TABLE 6

EAE clinical traits associated with MOG, MOG + SP, SP immunization

|  |  |  |  |  |  |
|---|---|---|---|---|---|
| MOG$_{35\text{-}55}$ | 10/10 (100) | 46.3 ± 5.9 | 16.3 ± 0.7 | 3 ± 0.4 | 3.2 ± 0.4 | 13.8 ± 0.2 |
| MOG$_{35\text{-}55}$ + SP | 3/10 (30) | 8.5 ± 4.8 | 4.7 ± 2.4 | 0.5 ± 0.3 | 0.7 ± 0.4 | 15 ± 0.1 |
| Pathways upregulated in Ly49* cell | | | | | |

Overall, $\chi^3$ = 21.45, 2, P < 0.0001     P < 0.0001  P < 0.0006  P < 0.0001  P < 0.0001  P < 0.0082

TABLE 7

EAE clinical traits associated with MOG, SP challenge, and MOG challenge

| Immunization | Incidence[a] | CDS | DA | SI | PS | DO |
|---|---|---|---|---|---|---|
| MOG$_{35\text{-}55}$ | 10/10, 100 | 55.8 ± 3.9 | 17 ± 0.3 | 3.14 ± 0.2 | 4 ± 0.1 | 13.3 ± 0.3 |
| SP challenge | 6/10, 60 | 43.3 ± 6.8 | 9 ± 2.5 | 1.67 ± 0.5 | 2.1 ± 0.6 | 8.7 ± 2.5 |
| MOG challenge | 6/10, 60 | 43.3 ± 5.3 | 8.2 ± 2.5 | 1.29 ± 0.3 | 1.5 ± 0.4 | 10 ± 2.8 |
|  | Overall, $\chi^3$ = 5.455, 2, P < 0.0654 | MOG$_{35\text{-}55}$ > PPT Challenge > MOG$_{35\text{-}55}$ Challenge P = 0.0004 | MOG$_{35\text{-}55}$ > PPT Challenge > MOG$_{35\text{-}55}$ Challenge P = 0.0055 | MOG$_{35\text{-}55}$ > PPT Challenge > MOG$_{35\text{-}55}$ Challenge P = 0.0052 | MOG$_{35\text{-}55}$ > PPT Challenge > MOG$_{35\text{-}55}$ Challenge P = 0 0054 | NS P = 0.5333 |

CDS, cumulative disease score over 30 days of experiment; DA, days affected; SI, severity index (cumulative disease score/days affected); SP, surrogate peptides; PS, peak score; DO, day of onset in affected animals; NS, not significant. Values are shown as means ± SEM. Significance of differences for the trait values among the experimental conditions was assessed by I$_2$ analysis (overall incidence) or One-ANOVA analysis, followed by Tukey's post hoc multiple comparisons; P values are as indicated.
[a]Percentage affected. Animals were considered affected if clinical scores ε 1 were apparent for ε 2 consecutive days.

TABLE 8

Differentially expressed genes between Ly49$_+$ and Ly49$_-$ CD8$_+$ cells sorted based on geneontology

| T cell activation | Il18r1, Nck2, Cd28, Bcl2, Lax1, Ptprc, Xcl1, Fcer1g, Psen2, Stx11, Myb, Fyn, Adora2a, Ifng, Ncor1, Ccl5, Tbx21, Adam17, Sos2, Zbtb1, Ctla2a, F2rl1, Zmiz1, Lgals3, Il7r, Nlrc3, Prkdc, Tfrc, Tigit, Btla, Cblb, Runx2, Tnfsf14, Zfp36l2, Malt1, Ptpn2, Socs6, Gata3, Il2ra, Rc3h2, Cd44, Rasgrp1, Zbtb7b, Ptpn22, Chd7, Wwp1, Clec2i, Nfkbid, Itgal, Itgad, Adam8, 5830411N06Rik, Casp3, Il12rb1, Smad3, Rab27a, Eomes, Ccr2 |
|---|---|
| Leukocyte migration | Xcl1, Fcer1g, Ifng, Ccl5, Ccl4, Epx, Tbx21, Itgb3, Prkca, Adam17, Pik3cg, Lyst, F2rl1, Itga2, Lgals3, Pdgfb, Gpr15, Tnfsf14, Rock1, Camk1d, Gata3, Ptpn22, Lyn, Padi2, Swap70, Adam8, Itgb1, Cxcr5, Dapk2, Adam10, Cx3cr1, Ccr2, Cxcr3 |
| T cell differentiation | Il18r1, Cd28, Bcl2, Ptprc, Fcer1g, Myb, Ifng, Ncor1, Tbx21, Adam17, Sos2, Zbtb1, Ctla2a, Zmiz1, Il7r, Prkdc, Runx2, Zfp36l2, Ptpn2, Gata3, Il2ra, Rc3h2, Cd44, Rasgrp1, Zbtb7b, Ptpn22, Chd7, Wwp1, Nfkbid, Adam8, 5830411N06Rik, Eomes, Ccr2 |
| T cell chemotaxis | Xcl1, Ccl5, Adam17, Pik3cg, Tnfsf14, Adam10, Ccr2, Cxcr3 |

TABLE 8-continued

Differentially expressed genes between Ly49$_+$ and Ly49$_-$ CD8$_+$ cells sorted based on geneontology

| Negative regulation of immune system process | Inpp5d, Traf3ip1, Lax1, Ptprc, Xcl1, Fcgr2b, Fcer1g, Adora2a, Ifng, Tbx21, Id2, Serpinb9, F2rl1, Pik3r1, Lgals3, Il7r, Nlrc3, Prkdc, Tigit, Btla, Cblb, Samsn1, Pdpk1, Ptpn2, Socs6, Tjp2, Pik3ap1, Il2ra, Cd44, Zbtb7b, Pias3, Ptpn22, |
|---|---|

TABLE 8-continued

Differentially expressed genes between Ly49$_+$ and Ly49$_-$ CD8$_+$ cells sorted based on geneontology

|  | Fam19a3, Lyn, Smpdl3b, Padi2, Pilrb1, Nod1, Clec2i, Klre1, Pglyrp1, Nfkbid, Casp3, Otud4, Zfpm1, Ubash3b, Ccr2 |
|---|---|
| Lymphocyte differentiation | Il18r1, Cd28, Dock10, Inpp5d, Bcl2, Ptprc, Fcer1g, Myb, fng, Ncor1, Tbx21, Ikzf3, Adam17, Id2, Hectd1, Sos2, Zbtb1, Ctla2a, Pik3r1, Zmiz1, Il7r, Ep300, Prkdc, Runx2, Zfp36l2, Malt1, Ptpn2, Hhex, Hells, Gata3, Il2ra, Il15ra, Rc3h2, Cd44, Rasgrp1, Zbtb7b, Ptpn22, Chd7, Wwp1, Pglyrp1, Nfkbid, Adam8, 5830411N06Rik, Eomes, Ccr2, Itm2a |
| Regulation of leukocyte differentiation | Cd28, Inpp5d, Ptprc, Myb, Ifng, Ccl5, Tbx21, Ikzf3, Itgb3, Prkca, Asxl2, Id2, Sos2, Zbtb1, Fos, Ctla2a, Pik3r1, Zmiz1, Il7r, Zfp36l2, Ptpn2, Tjp2, Gata3, Il2ra, Il15ra, Cd44, Rasgrp1, Zbtb7b, Pias3, Lyn, Pilrb1, Clec2i, Pglyrp1, Nfkbid, Adam8, Zfpm1, Ubash3b, Ccr2 |
| Regulation of T cell activation | Nck2, Cd28, Lax1, Ptprc, Xcl1, Myb, Adora2a, Ifng, Ccl5, Tbx21, Sos2, Zbtb1, Ctla2a, Zmiz1, Lgals3, Il7r, Tfrc, Tigit, Btla, Cblb, Tnfsf14, Malt1, Ptpn2, Socs6, Gata3, Il2ra, Cd44, Rasgrp1, Zbtb7b, Ptpn22, Clec2i, Nfkbid, Itgal, Adam8, Casp3, Il12rb1, Ccr2 |

TABLE 8-continued

Differentially expressed genes between
Ly49+ and Ly49_ CD8+ cells sorted based on geneontology

| Pathways down-regulated in Lv49[+] | |
|---|---|
| T cell activation | Slamf1, Dusp10, Ccl2, Ccr7, Sox4, Gadd45g, H2-Oa, H2-DMa, Gsn, Rorc, Tnfaip8l2, Sit1, Ddost, Rhoh, Dtx1, Ephb6, Cd8a, Bcl3, Rps3, Lat, Coro1a, Psmb10, Ccr9 |
| Leukocyte migration | Slamf1, Ccl2, Ccr7, Itgb7, Rps19, Rpl13a, Coro1a |
| T cell differentiation | Dusp10, Ccr7, Sox4, Gadd45g, H2-Oa, H2-DMa, Rorc, Rhoh, Dtx1, Cd8a, Bcl3, Ccr9 |
| T cell chemotaxis | Ccr7 |
| Negative regulation of immune system process | Slamf1, Dusp10, Gpr68, Hist1h4d, Hist1h4c, H2-Oa, Tap1, Nfkbil1, Tnfaip8l2, Dtx1, Hist4h4, Nlrp4e, Rps19, Inpp4b, Ldlr, Tsc22d3 |
| Lymphocyte differentiation | Slamf1, Dusp10, Ccr7, Hdac5, Sox4, Gadd45g, Ly6d, Nfam1, H2-Oa, H2-DMa, Rorc, Rhoh, Dtx1, Cd8a, Bcl3, Cmtm7, Ccr9 |
| Regulation of leukocyte differentiation | Dusp10, Ccr7, Gpr68, Nfam1, H2-Oa, H2-DMa, Car2, Hax1, Rorc, Tesc, Dtx1, Inpp4b |
| Regulation of T cell activation | Slamf1, Dusp10, Ccl2, Ccr7, H2-Oa, H2-DMa, Gsn, Rorc, Tnfaip8l2, Sit1, Dtx1, Ephb6, Rps3, Lat, Coro1a |

TABLE 9

Demographic and clinical features of the multiple sclerosis dataset

| Patient ID | Sex | Ethnicity/ Ancestry | Age at exam | MS subtype at exam |
|---|---|---|---|---|
| MS1 | F | 1 | 23 | CIS |
| MS2 | F | 1 | 32 | RR |
| MS3 | F | 1 | 22 | Unknown |
| MS4 | F | 1, 4 | 40 | RR |
| MS5 | F | 1 | 38 | RR |
| MS6 | F | 1 | 47 | RR |
| MS7 | F | 1 | 24 | CIS |
| MS8 | F | 1 | 26 | CIS |
| MS9 | M | 3 | 33 | RR |
| MS10 | F | 1 | 40 | RR |
| MS11 | F | 3 | 31 | CIS |
| MS12 | F | 1 | 25 | RR |
| MS13 | M | 2 | 43 | Unknown |
| MS14 | F | 2 | 31 | RR |
| MS15 | F | 1 | 43 | CIS |
| MS16 | F | 1 | 36 | RR |
| MS17 | F | 1 | 38 | RR |
| MS18 | F | 1 | 38 | RR |

| HC ID | Sex | Ethnicity | Age at blood drawn |
|---|---|---|---|
| HC1 | F | 3 | 26 |
| HC2 | F | 3 | 30 |
| HC3 | F | 3 | 32 |
| HC4 | F | 3 | 23 |
| HC5 | M | 4 | 28 |
| HC6 | F | 4 | 35 |
| HV7 | F | 4 | 36 |
| HC8 | M | 4 | 40 |
| HC9 | F | 2 | 28 |
| HC10 | F | 2 | 47 |

Study participants form an on-going prospective observational study at the University of California, San Francisco, CA Multiple Sclerosis Center. Patients were recruited when suspected of having MS or presented with an initial event indicative of MS within 24 hours and no later than 90 days. Patients with Clinically Isolated Syndromes (CIS) were also included if they fulfilled the Magnetic Resonance Imaging in Multiple Sclerosis (MAG-NIMS) criteria (Polman et al., 2011). Eligibility criteria also included no prior treatment with MS disease modifying therapies or board spectrum immune suppressants and no treatment with corticosteroids within the last 30 days. Peripheral blood lymphocytes were prepared by ficol gradient and frozen in liquid nitrogen within 2 hours of phlebotomy. Age matched and sex matched healthy control PBMCs were obtained from Stanford Blood Center, Stanford University, Stanford, CA. Ancestry; 1-European American, 2-African American, 3-Hispanic, 4-Asian. HLA-DRB1*15:01; 1-carrier and 2-non-carrier. PP primary progressive MS, RR relapsing remitting MS, CIS clinical isolated syndrome. HC, healthy control.

Related Publications

International Multiple Sclerosis Genetics Consortium et al. Genetic risk and a primary role for cell-mediated immune mechanisms in multiple sclerosis. Nature 476, 214-219 (2011).

Fallang, L.-E. et al. Nat. Immunol. 10, 1096-1101 (2009).

Sollid, et al. Immunogenetics 64, 455-460 (2012).

Zamvil, S. et al. Nature 317, 355-358 (1985).

Blankenhorn, E. P. et al. Ann. Neurol. 70, 887-896 (2011).

Skulina, C. et al. PNAS 101, 2428-2433 (2004).

Babbe, H. et al. J. Exp. Med. 192, 393-404 (2000).

Blink, S. E. & Miller, S. D. Curr. Mol. Med. 9, 15-22 (2009).

Han, A. et al. Proc. Natl. Acad. Sci. U.S.A. 110, 13073-13078 (2013).

Birnbaum, M. E. et al. Cell 157, 1073-1087 (2014).

Gee, M. H. et al. Cell 172, 549-556.e16 (2018).

Han, et al. Nat. Biotechnol. 32, 684-692 (2014).

Wei, Y.-L. et al. Front Immunol 6, 118 (2015).

Langrish, C. L. et al. J. Exp. Med. 201, 233-240 (2005).

Kroenke et al. J. Exp. Med. 205, 1535-1541 (2008).

Ben Nun et al. European Journal of Immunology 11, 195-199 (1981).

Jäger et al. The Journal of Immunology 183, 7169-7177 (2009).

Denton, A. E. et al. The Journal of Immunology 187, 5733-5744 (2011).

Day, E. B. et al. PNAS 108, 9536-9541 (2011).

Moon, J. J. et al. Immunity 27, 203-213 (2007).

Kim, H.-J. & Cantor, H. Semin. Immunol. 23, 446-452 (2011).

Lu, et al. Proc. Natl. Acad. Sci. U.S.A. 105, 19420-19425 (2008).

Kim, H.-J. et al. Proc. Natl. Acad. Sci. U.S.A. 108, 2010-2015 (2011).

Agarwal, R. K. & Caspi, R. R. Methods Mol. Med. 102, 395-419 (2004).

Zemmour, D. et al. Nat. Immunol. 19, 291-301 (2018).

Hvas, et al. J. Neuroimmunol. 46, 225-234 (1993).

Wucherpfennig, K. W. et al. PNAS 89, 4588-4592 (1992).

Gandhi, R., Laroni, A. & Weiner, H. L J. Neuroimmunol. 221, 7-14 (2010).

Caccamo, N. et al. Blood 118, 129-138 (2011).

Moens, E. et al. J. Leukoc. Biol. 89, 743-752 (2011).

Sutton, C. E. et al. Immunity 31, 331-341 (2009).

Price et al. PLOS ONE 7, e39750 (2012).

Harrington, L. E. et al. Nat. Immunol. 6, 1123-1132 (2005).

Elias, et al. Int Immunol 11, 957-966 (1999).

Kumar et al. J. Exp. Med. 184, 1609-1617 (1996).

Hu, D. et al. Nat. Immunol. 5, 516-523 (2004).

Panoutsakopoulou, V. et al. J. Clin. Invest. 113, 1218-1224 (2004).

Davis & Brodin Rebooting Human Immunology. Annual Review of Immunology 36, 843-864 (2018).

O'Shea, et al. Current Biology 3, 658-667 (1993).

Birnbaum, M. E. et al. Cell 157, 1073-1087 (2014).

Adams, J. J. et al. Immunity 35, 681-693 (2011).

Nelson, R. W. et al. Immunity 42, 95-107 (2015).

Stadinski, B. D. et al. PNAS 107, 10978-10983 (2010).

Altman, J. D. et al. Science 274, 94-96 (1996).

Grotenbreg, G. M. et al. PNAS 105, 3831-3836 (2008).

Krementsov, D. N. et al. Ann. Neurol. 75, 50-66 (2014).

Tennakoon, D. K. et al. J. Immunol. 176, 7119-7129 (2006).

Bian, Y. et al. PLOS Pathogens 13, e1006384 (2017).

Mahajan et al. J Vis Exp e3184-e3184 (2011). doi: 10.3791/3184

Mamedov, M. R. et al. Immunity 48, 350-363.e7 (2018).

Love, M. I., Huber, W. & Anders, S. Genome Biol. 15, 31 (2014).

Li, B. & Dewey, C. N. BMC Bioinformatics 12, 323 (2011).

Kolde, R. R package version 1.0.8. (2015).

Yu, G. clusterProfiler: An universal enrichment tool for functional and comparative study. doi:10.1101/256784

Example 2

CD8+KIR+ Cells in Human Disease

A small subset of CD8+ T cells expressing Ly49 proteins in mice can suppress autoimmunity in a model of demyelinating disease. It is shown herein that there is a markedly increased frequency of $CD8^+$ T cells expressing Killer cell Immunoglobulin like Receptors (KIR), the functional counterparts of the Ly49 family, in the blood and inflamed tissues in patients with a wide variety of autoimmune diseases. In Celiac disease (CeD) we show that $KIR^+$ but not KIR $CD8^+$ T cells are able to eliminate pathogenic gliadin-specific $CD4^+$ T cells from patients' leukocytes in vitro. Together with gene expression data, this shows that these cells are the likely equivalent of the mouse $Ly49^+CD8^+$ T cells. Furthermore, in COVID-19 patients, who can suffer from serious clinical problems that are suggestive of autoimmunity, we find elevated levels of $KIR^+CD8^+$ T cells are correlated with disease severity and onset of vasculitis, a common complication of COVID-19, whereas CD4+ regulatory T cells do not show this trend. In addition, we also find increases in $CD4^+$ T cells with phenotypes unique to gliadin-specific cells in CeD, which are also elevated in some autoimmune diseases. These results define and characterize a regulatory $CD8^+$ T cell subset in humans, which we speculate is a common feature of infectious disease responses, as well as in autoimmunity, and which functions to control self-reactive or otherwise pathogenic T cells. These data also suggest that many of the complications of COVID-19 are the results of various types of autoimmunity.

While most CD8+ T cells are geared towards the control of pathogen-infected or cancerous cells, there have been long standing evidence in mice that some can also suppress autoimmune response. This potentially regulatory function of CD8+ T cells was first implicated by the depletion of CD8+ T cells in experimental autoimmune encephalomyelitis (EAE), a mouse model of human Multiple Sclerosis (MS). The inhibitory C-type lectin-like family of receptors, Ly49, which are ubiquitous on natural killer (NK) cells, were identified as unique surface markers for this regulatory CD8+ T cell subset, and the transcription factor Helios as an essential control element for their differentiation and function in mice. Recently, we showed that clonally expanded CD8+ T cells in EAE recognized peptides bound to H2-D$^b$ and that these peptides stimulated Ly49+CD8+ regulatory T cells and suppressed disease. This extends the original observations beyond Qa-1 to encompass classical class I MHC interactions, showing a general mechanism of peripheral tolerance. Here, we identify CD8+ T cells expressing Killer cell Immunoglobulin like Receptors (KIR), the functional counterpart of the mouse Ly49 family in humans, as a novel CD8+ T cell subset that targets pathogenic CD4+ T cells in Celiac disease (CeD), and other autoimmune disorders and infectious diseases.

Figure 17:
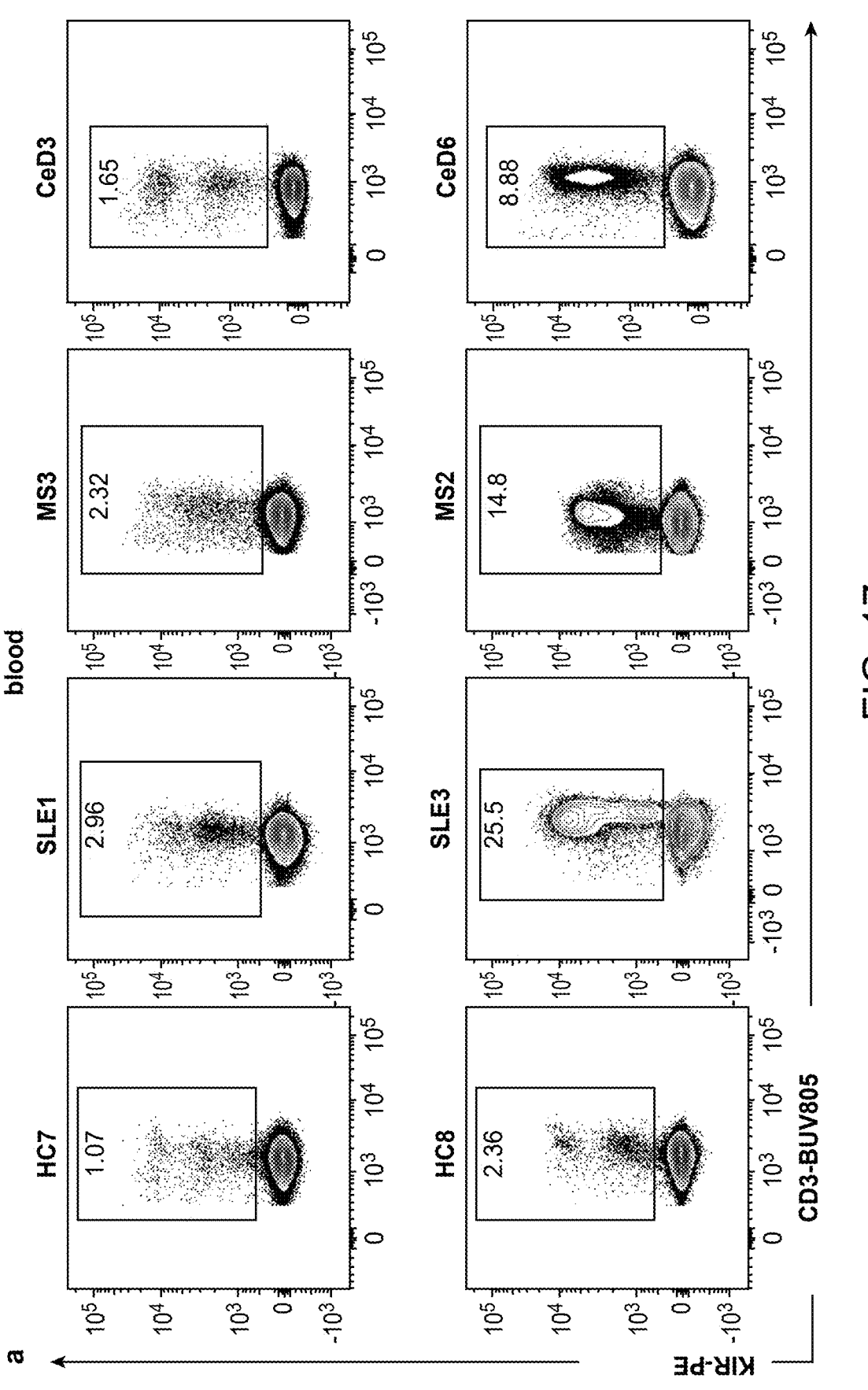
FIG. 17. Frequency of KIR+ CD8+ T cells in human autoimmune diseases. a, Representative contour plots (left) and summary histogram (right) showing frequency of KIR+ CD8+ T cells (CD3+CD56−) in the peripheral blood of healthy controls (HC, N=16) and patients with systemic lupus erythematous (SLE, N=22), multiple sclerosis (MS, N=10) or celiac disease (CeD, N=14) analyzed by flow cytometry. KIR+ cells were detected by PE-conjugated antibodies against KIR2DL1 (clone #143211), KIR2DL2/L3 (Dx27), KIR2DL5 (UP-R1), KIR3DL1 (Dx9) and KIR3DL2 (clone #539304). *P<0.05, one-way ANOVA corrected for multiple comparisons. b, Correlation between frequency of KIR+ CD8+ T cells and autoimmune CD4+ T cells (CD45RA−, CD62L−, PD-1+, CXCR3+, CD39+, CD38+, CD127−, CD25low, CD161+ and ICOS+ CD4+ T cells) in the blood of SLE patients (N=11). R2=0.8479, P=0.0002***. c, Expression of KIR transcripts (KIR3DL1, KIR2DL3 and KIR2DL2) in CD8+ T cells from control healthy kidneys versus SLE nephritis kidneys is shown. d, Expression of KIR transcripts (KIR3DL1, KIR2DL3 and KIR2DL2) in synovial CD8+ T cells and expression of FOXP3 in synovial CD4+ T cells from rheumatoid arthritis (RA) and osteoarthritis (OA) are shown.

Increased KIR+CD8+ T cells in human autoimmune diseases. Both mouse Ly49 and human KIR receptors bind to class I MHC molecules, typically having the inhibitory tyrosine-based inhibition motifs (ITIM) in their cytoplasmic tails, and are ubiquitously expressed on NK cells, as well as a small subset (1~5%) of CD8+ T cells. We analyzed CD8+ T cells expressing inhibitory KIRs in the peripheral blood of patients with autoimmune diseases and age/gender-matched healthy controls (HC). In particular, we found that KIR3DL1 and KIR2DL3 are the two major KIR subtypes expressed by a small subset of human CD8+ T cells. We found that KIR+CD8+ T cells were significantly increased, as much as ten-fold, in a subset of patients with MS, and Systemic Lupus Erythematosus (SLE), and to a lesser degree in CeD, as compared to healthy controls (FIG. 17a). Moreover, the frequency of KIR+CD8+ T cells in the blood of SLE patients positively correlated with that of the potentially autoreactive CD4+ T cells with phenotypes previously found to be unique to gliadin-specific CD4+ T cells in CeD (CD45RA−CD62L−PD-1+CXCR3+CD39+CD38+CD127−CD25lowCD161+ICOS+) (FIG. 17b), indicating a synchronous expansion of KIR+CD8+ T cells with the intensity of autoimmune responses by CD4+ T cells. Next, we investigated whether KIR+CD8+ T cells are also present in the inflamed tissues of autoimmune diseases. We took advantage of publicly available single cell RNA-seq data from SLE kidneys and Rheumatoid Arthritis (RA) synovia previously generated by the Accelerating Medicines Partnership RA/SLE program. First, we identified CD8+ T cells that express KIR transcripts (KIR3DL1, KIR2DL3 and KIR2DL2) in kidneys and synovia. In particular, a markedly increased number of KIR+CD8+ T cells was observed in the kidneys of patients with SLE compared to healthy kidneys (FIG. 17c). In addition, we detected a higher frequency of KIR+CD8+ T cells in the synovial tissues of RA patients compared to those with Osteoarthritis (OA), while the percentage of synovial FOXP3+CD4+ Treg cells was similar between RA and OA (FIG. 17d). Although both RA and OA cause joint inflammation, RA is a classic autoimmune disease, whereas OA is not, suggesting that KIR+CD8+ T cells might be more important in the suppression of autoimmune inflammation than CD4+ Tregs.

KIR+CD8+ T cells are the functional and phenotypic equivalent of mouse Ly49+CD8+ T cells. Next we sought to investigate whether KIR+CD8+ T cells are the functional counterpart of mouse Ly49+ regulatory CD8+ T cells. Previously we found that Ly49+ CD8+ T cells suppress myelin oligodendrocyte glycoprotein (MOG)-specific CD4+ T cells in a perforin-dependent manner, indicating cytotoxicity as the mechanism of suppression. Deamidated gliadin derived from dietary gluten is the antigen for CD4+ T cells that drive autoimmune enteropathy in human CeD. Therefore, we explored whether KIR+CD8+ T cells can suppress gliadin-specific CD4+ T cells from CeD patients. CD8+ T cells were purified from peripheral blood mononuclear cells (PBMCs) of HLA-DQ2.5+ CeD patients; from these KIR+CD8+ and KIR-CD8+ T cells were sorted, activated with anti-CD3/CD28 microbeads overnight, and then cultured with the CD8-depleted fraction of PBMCs at a 1:30 ratio in the presence of 250 µg/mL deamidated gluten. The cultures were harvested on Day 6, and the gliadin-specific CD4+ T cells were enriched and quantified using PE-labeled HLA-DQ2.5 tetramers complexed with different gliadin peptides (FIG. 18a). In the absence of KIR+CD8+ T cells, deamidated gluten profoundly stimulated the expansion of gliadin-specific CD4+ T cells. Importantly, stimulated KIR+CD8+ T cells significantly reduced the number of gliadin-specific CD4+ T cells without affecting the number of total CD4+ T cells, whereas KIR-CD8+ T cells did not (FIG. 18b). We also measured Annexin V binding on Day 3 (FIG. 18a), and found increased staining of gliadin-specific CD4+ T cells in the presence of KIR+CD8+ T cells (FIG. 18c), indicating these T cells suppress the pathogenic CD4+ T cells by direct killing. This effect of KIR+CD8+ T cells targets only a small fraction of the CD4+ T cells, since they had no discernible effect on the proliferation of CD4+ T cells responding to anti-CD3 stimulation.

To further investigate whether KIR+CD8+ T cells are the phenotypic equivalent of mouse Ly49+ T cells in humans, we performed RNA sequencing (RNA-seq) analysis on KIR+ versus KIR-CD8+ T cells from patients with MS to compare with mouse Ly49+CD8+ T cells in EAE (mouse model of human MS). There were 778 differentially expressed genes (adjusted P<0.05, fold change>2) between KIR+ and KIR-CD8+ T cells, among them 300 were up-regulated and 478 were down-regulated in KIR+CD8+ T cells. Notably, KIR+CD8+ T cells showed a marked up-regulation of cytotoxic molecules (e.g. GZMH, GZMB, PRF1 and GNLY), NK-associated genes (e.g. NKG7, NCR1 and the KLR family) and cell-trafficking molecules (such as CX3CR1, which mediates migration of leukocyte to inflamed tissues and is involved in tissue injury-mediated brain inflammation, and brain-homing receptor ITGB1), in addition to inhibitory KIR receptor genes. In addition, KIR+CD8+ T cells had higher transcript levels for Helios (encoded by Ikzf2), a transcription factor associated with regulatory functions of both CD4+ and CD8+ T cells. On the other hand, KIR+CD8+ T cells down-regulated naïve/memory T cell-associated molecules, e.g. CCR7, SELL, TCF7 and IL7R, indicating they might have entered the program for effector T cell differentiation. Interestingly, KIR+CD8+ T cells had a lower expression of the co-stimulatory receptor CD28, which is one of the key features for regulatory CD8+ T cell populations in mice and humans. Gene Ontology enrichment analysis of these differentially expressed genes showed enrichment for T cell activation, proliferation, migration and differentiation. Moreover, gene set enrichment analysis (GSEA) revealed that about half of the top 200 genes up-regulated in Ly49+CD8+ T cells (including cytotoxic molecule GZMB, KLRC family genes, CX3CR1, ITGB1 and IKZF2) were also higher in KIR+CD8+ T cells. Previously, we found Ly49+CD8+ T cells expressed 16 out of 60 of the genes conserved in CD4+ regulatory T cells (Tregs), and these same Treg signature genes23 were also enriched in KIR+CD8+ T cells in GSEA analysis. Overall, RNA-seq analysis indicates that KIR+CD8+ T cells from MS patients share many similarities with Ly49+CD8+ T cells from EAE mice.

Furthermore, we also performed RNA-seq on KIR+ and KIR-CD8+ T cells from healthy subjects and patients with other autoimmune disease, specifically CeD and SLE, to determine whether there are common features shared by KIR+CD8+ T cells across different circumstances. We identified a set of 963 genes that were differentially expressed (adjusted P<0.05, fold change>2) between KIR+ and KIR-CD8+ T cells from all subjects, including HC, MS, CeD, and SLE patients. Many of them overlapped with the differentially expressed genes previously defined in MS. However, larger fold changes of these genes were observed in patients with higher frequencies of KIR+CD8+ T cells. Consistent with the transcript profiles, KIR+CD8+ T cells had higher protein expression levels for granzyme B, perforin, CX3CR1, KLRG1, CD244, TIGIT, T-bet and Helios proteins and lower levels of CCR7, CD27 and CD28, as measured by flow cytometry. In addition, we compared KIR+ and KIR-CD8+ T cells in kidneys or synovia for expression of the same genes enriched in circulating KIR+CD8+ T cells. Similar to those cells, both kidney and synovial KIR+CD8+ T cells up-regulated KLRG1, CD244, TIGIT, CX3CR1, PRF1, GZMB and IKZF2, while down-regulating CD28 and CCR7. Overall, our results show that KIR+CD8+ T cells are the functional and phenotypic equivalent of mouse Ly49+CD8+ T cells in humans, with conserved features in both healthy subjects and those with autoimmune conditions.

Increased KIR+CD8+ T cells correlate with immune dysregulation in COVID-19 patients. While previously it had been thought that most self-specific T cells were eliminated in the thymus, recent work shows that this is not the case, and that many such cells survive and populate the periphery of both humans and mice. We have speculated that this is because the constant threat of infectious diseases throughout human history necessitates a complete T cell repertoire such that even self-reactive T cells might be needed in the response to a particular pathogen. Consistent with this are classic experiments showing that infectious diseases or treatments that mimic them (such as complete Freund's adjuvant) can activate self-specific T cells. There is also anecdotal evidence that many patients cite an infection immediately preceding the onset of their disease. Thus, we were interested in analyzing patients with an infectious disease to see whether KIR+CD8+ T cells were induced as part of the response.

In particular, emerging reports show that infection with Severe Acute Respiratory Syndrome Coronavirus 2 (SARS-CoV-2) can lead to excessive production of pro-inflammatory cytokines and the appearance of autoimmune-related complications, especially in patients with more severe disease. Therefore, we analyzed the frequency of both KIR+CD8+ T cells and autoimmune CD4+ T cells with phenotypes unique to gliadin-specific cells from CeD in the peripheral blood of patients with Coronavirus Disease 2019 (COVID-19) compared to age/gender-matched healthy subjects collected before the pandemic. Similar to our previous finding in influenza-infected patients, the frequency of autoimmune CD4+ T cells was increased in COVID-19 patients, especially those with moderate or severe disease (FIG. 19a). The percentage of KIR+CD8+ T cells was also elevated in COVID-19 patients and correlated with disease severity (FIG. 19b), as well as with the frequency of autoimmune CD4+ T cells (FIG. 19c). Moreover, both autoimmune CD4+ T cells and KIR+CD8+ T cells were increased in COVID-19 patients with vasculitis or embolism and to a lesser extent in those with acute respiratory distress syndrome (ARDS) (FIG. 19d), which are common complications of this disease and likely caused by excessive inflammation. These two T cell subsets are associated with autoimmune-related immunopathology during SARS-CoV-2 infection. However, we did not observe a significant difference in the levels of $CD25^{hi}CD127^{low}CD4^+$ Treg in COVID-19 patients compared to healthy donors, or COVID-19 patients with different disease severities or complications, suggesting $KIR^+CD8^+$ T cells are a unique regulatory mechanism up-regulated during SARS-CoV-2 infection to specifically control cross-reactivity to self antigens.

We also utilized the publicly available single cell RNA-seq data of bronchoalveolar immune cells from COVID-19 patients and healthy people to investigate whether KIR+CD8+ T cells are also present in the bronchoalveolar lavage fluid (BALF) of COVID-19 patients. CD8+ T cells expressing KIR transcripts (KIR3DL1, KIR3DL2, KIR2DL3 or KIR2DL1) were detected in the BALF of COVID-19 patients with moderate or severe disease, but not in the BALF from healthy controls (FIG. 19e), which indicates KIR+CD8+ T cells are induced at the local site of infection as well.

Commonality and heterogeneity of KIR+CD8+ T cells. In order to better understand the functional properties of this type of cells under different circumstances, we integrated the single cell RNA-seq data of peripheral blood CD8+ T cells from healthy subjects, MS patients and COVID-19 patients (generated with the 10× Genomics platform) using the Seurat package. Total CD8+ T cells were projected onto a two-dimensional UMAP and unsupervised clustering identified 8 subpopulations based on gene expression. KIR+ CD8+ T cells from different conditions (healthy, MS and COVID-19) formed a distinct cluster with high expression of effector genes (GZMB and PRF1) as well as KIR transcripts (FIG. 20a-b), revealing the commonality of KIR+ CD8+ T cells across physiological and diseased status and their uniqueness relative to other CD8+ T cells.

In order to better understand the similarity and heterogeneity of KIR+CD8+ T cells under different circumstances and to probe the mechanism for their suppressive activity to pathogenic CD4+ T cells, we performed single cell RNA-seq on 4,512 KIR+CD8+ T cells sorted from the blood of age- and gender-matched healthy subjects (N=10) and patients with MS (N=2), SLE (N=6) or CeD (N=5) using the Smart-seq2 protocol. In parallel, we also analyzed their TCR α and β sequences. Unsupervised clustering of these KIR+ CD8+ T cells by Seurat identified 6 clusters, with Clusters 1 to 3 mostly containing expanded KIR+CD8+ T cells (≥2 cells expressing same TCR) and Clusters 5 and 6 consisting of unexpanded cells expressing unique TCRs (FIG. 20c). Expanded KIR+ cells in Clusters 1 to 3 had higher transcripts for cytotoxic molecules (e.g., GZMH, GZMB and PRF1) and genes associated with effector T cells (e.g., FCGR3A, FGFBP2 and CX3CR1). Cluster 2, which was more restricted to expanded KIR+ cells from MS patients, showed higher levels of Type I IFN responding genes (including IFIT1, IFIT2, IFIT3, MX1, RSAD2 and ISG15). Cluster 3, specific to expanded KIR+ cells from a subset of HC and SLE patients, displayed higher expression of genes involved in glycolysis (e.g., GAPDH, GPI, ENO1 and PGK1) (FIG. 20d-e). Cells in Cluster 4 were in a transitional state with a loss of memory-associated features. Clusters 5 and 6 (restricted to unexpanded KIR+CD8+ T cells) displayed memory and naïve signatures, respectively (FIG. 20e), and accounted for a small proportion of total KIR+ CD8+ T cells. T cell clones expressing identical TCRs can be found in different clusters, indicating possible lineage relationships. In addition, clonally expanded KIR+CD8+ T cells in COVID-19 patients (identified from the previous 10× Genomics scRNA-seq) displayed a higher expression of cytotoxic genes while down-regulating naïve- or memory-associated genes compared to unexpanded KIR+CD8+ T cells. Thus, in parallel with clonal expansion, KIR+CD8+ T cells might lose their naïve or memory attributes, enter the differentiation program for effector T cells and then suppress autoreactive CD4+ T cells via cytotoxicity. There are common features shared by KIR+CD8+ T cells from healthy subjects and different diseases, yet there is also heterogeneity (i.e., up-regulated Type I IFN signaling and glycolysis in Clusters 2 and 3) associated with different diseases or treatments.

Discussion

Here we characterize KIR+CD8+ T cells as a novel regulatory CD8+ T cell subset in humans, which suppress pathogenic CD4+ T cells arising from self-reactivity in autoimmune disorders or cross-reactivity to autoantigens in infectious diseases via cytotoxicity (FIG. 20f). Similar to the perforin- or Fas/FasL-dependent suppression of self-reactive CD4+ T cells by murine Ly49+CD8+ T cells, human KIR+

CD8+ T cells target pathogenic CD4+ T cells via their cytolytic activity, since expanded KIR+CD8+ T cells significantly up-regulated cytotoxic molecules and increased apoptosis in gliadin-specific CD4+ T cells was observed in the presence of KIR+CD8+ T cells. We often observed an increased frequency of KIR+CD8+ T cells in the blood and also in the inflamed tissues of patients with autoimmune disease, and this positively correlates with the potentially autoreactive CD4+ T cells with a rare phenotype unique to gliadin-specific cells from CeD in the case of SLE. This expansion of KIR+CD8+ T cells correlating with the incidence of these autoimmune responses might act as a negative feedback mechanism to ameliorate pathogenesis by killing autoreactive T cells.

Increased KIR+CD8+ T cells together with CD4+ T cells with the same phenotype as gliadin-specific cells in CeD, which may represent self-reactive clones that cross-react with pathogens, were found in COVID-19 patients, and were associated with autoimmune-related complications. Therefore, a primary role of KIR+CD8+ T cells can be to control self-reactive T cells that arise in the course of an infectious disease, owing to their cross-reactivity to antigens expressed by a particular pathogen. This would allow an organism to maintain as complete a peripheral T cell repertoire as possible to protect itself against potential infection by pathogens, yet still be able to precisely control T cell clones with cross-reactivity to self antigens.

Interestingly, clonally expanded KIR+CD8+ T cells are also found in the peripheral blood of healthy subjects and share gene expression signatures with those from patients with autoimmune diseases or COVID-19. This indicates that at least some T cells of this type are continually active, although not at the very high levels seen in COVID-19 patients or in some subjects with autoimmunity. The activation of KIR+CD8+ T cells can be a specific regulatory mechanism to maintain peripheral tolerance, even in healthy people. The fact that CD4+ regulatory T cells are not elevated in COVID-19 patients indicates that their role in peripheral tolerance is quite distinct, and perhaps more general, whereas the KIR+CD8+ T cells can be particularly geared towards maintaining tolerance during an infection.

In summary, we identify KIR+CD8+ T cells as a novel human CD8+ T cell subset that is able to kill pathogenic T cells, while sparing others, analogous to Ly49+CD8+ T cells in mice. They are active across a broad spectrum of autoimmune diseases (e.g., MS, SLE and CeD), in at least some infectious diseases (e.g., COVID-19) and to a lesser extent in healthy adults. This type of peripheral tolerance is distinct from and likely complementary to CD4+ regulatory T cells, which represent a separate lineage of T cells and does not appear to be generally active in COVID-19 patients. Thus, the KIR+CD8+ T cells and the properties described here are useful in both understanding key dynamics in the phenomenon of immune dysregulation and in therapeutic applications. We also note an increase in a rare phenotype of CD4+ T cells that is characteristic of the gliadin-specific cells that are pathogenic in celiac disease, and elevated in other autoimmune diseases, in COVID-19 patients. Taken together, these data indicate that many of the sequelae in COVID-19 patients may be autoimmune in nature.

Human samples. Our study cohort of patients with autoimmune disorders met classification criteria for systemic lupus erythematosus (SLE) 43, celiac diseases (CeD) 44 or Multiple sclerosis (MS), respectively. Collection of blood from patients with SLE, CeD or MS was covered by IRB-14734 (Stanford University Immunological and Rheumatic Disease Database: Disease Activity and Biomarker Study), IRB-20362 (Studying the Molecular Factors Involved in Celiac Disease Pathogenesis) and IRB-8629 (Understanding Mechanisms of Allergy and Immunology Study). Blood from healthy subjects was requested from Stanford Blood Center or drawn from healthy volunteers under IRB-40146. The protocols mentioned above have been approved by the Research Compliance Office of Stanford University. PBMCs from MS patients were also obtained from the Multiple Sclerosis Center at the University of California, San Francisco (UCSF) with the protocol approved by the committee on Human Research at UCSF. Informed written consent was obtained from all participants.

PBMCs were isolated from the blood through density gradient centrifugation (Ficoll-Paque, GE Healthcare). COVID-19 patients and sample collection. Enrollment included any adult with RT-PCR positive COVID-19. Informed consent was obtained from each patient or from the patient's legally authorized representative if the patient was unable to provide consent. Participants were excluded if they were taking any experimental medications (i.e. those medications not approved by a regulatory agency for use in COVID-19). COVID-19 severity of illness was defined as described in the literature. Collection of blood from COVID-19 patients was covered by IRB-14734 and NCT04373148. Handling of COVID-19 PBMCs for flow cytometric analysis was covered under APB-3343-MD0620. The IRB and APB protocols mentioned above have been approved by the Research Compliance Office of Stanford University. Clinical metadata was obtained from Stanford clinical data electronic medical record system as per consented participant permission and definitions and diagnoses of disease were used according to Harrison's Principles of Internal Medicine, 20e.

Flow cytometric analysis. The following fluorescent dye-conjugated anti-human antibodies were used for staining: CD8a (RPA-T8), CD56 (5.1H11), KIR3DL1 (Dx9), KIR2DL2/L3 (Dx27), KIR2DL5 (UP-R1), TIGIT (A15153G), KLRG1 (SA231A2), CD244 (C1.7), CX3CR1 (2A9-1), CD28 (CD28.2), CD27 (O323), CCR7 (G043H7), T-bet (4B10), Helios (22F6), Granzyme B (QA16A02), Perforin (B-D48), PD-1 (EH12.2H7), CD25 (M-A251), CD39 (A1), CD161 (HP-3G10), CD38 (HIT2), ICOS (C398.4A), CXCR3 (G025H7), CD45RA (HI100), CD4 (RPA-T4) and CD62L (DREG-56) (Biolegend); CD3 (UCHT-1), TCRB (IP26) and CD127 (HIL-7R-M21) (BD); KIR2DL1 (clone #143211) and KIR3DL2 (clone #539304) (R&D). Frozen cell samples were thawed and washed in 10% FBS with Benzonase (Sigma-Aldrich, 1:10,000) in RPMI. After 450 g centrifugation, cells were treated with 1:20 diluted FcR block (BD) in FACS buffer (0.5% BSA, 2 mM EDTA in PBS) for 10 min followed by staining with antibodies against surface molecules (30 min, 4° C.). For intracellular staining, cells were fixed and permeabilized with the Intracellular Fixation & Permeabilization Buffer Set (eBioscience), followed by staining with antibodies against intracellular antigens (30 min, 4° C.). Cells were acquired on an LSR II flow cytometer (BD), and data was analyzed using FlowJo X. Dead cells were excluded based on viability dye staining (LIVE/DEAD™ Fixable Near-IR Dead Cell Stain, ThermoFisher).

Functional assay. Chymotryptic gluten digests were deamidated with recombinant human transglutaminase 2, as described previously. PBMCs were isolated from blood of HLA-DQ2.5+CeD patients on Day 0. CD8+ T cells were purified from PBMCs using CD8 microbeads (Miltenyi) per manufacturer's instructions, stained with flow antibodies, and live CD3+CD56− CD8+KIR+ or KIR− T cells were sorted out by FACSAria Fusion flow cytometer (BD). The sorted KIR+ or KIR− CD8+ T cells were stimulated with anti-CD3/CD28 beads (Gibco) at 1:1 ratio (1 μL beads per 4×104 cells) supplemented with 50 U/mL IL-2 in 96-well plates for 18 hours. The CD8-PBMCs were stimulated with 250 μg/mL deamidated gluten or left unstimulated at 3×105~1×106/100 μL per well supplemented with 50 U/mL IL-2. X-VIVO 15 with Gentamicin L-Gln (Lonza) supplemented with 10% human AB serum (Sigma-Aldrich) was used as culture medium. After 18 hours, anti-CD3/CD28 beads were removed from CD8+ T cells by a magnet and KIR+ or KIR− CD8+ T cells were added to the culture of CD8-PBMCs at 1:30 ratio. 50 U/mL IL-2 was added to the cultures on Day 3. Cells were harvested on Day 6 and stained with 10 μg/mL HLA-DQ2.5 tetramers complexed with four disease-relevant and immunodominant gliadin T cell epitopes (DQ2.5-glia-α1a, QLQPFPQPELPY (SEQ ID NO: 513); DQ2.5-glia-α2, PQPELPYPQPE (SEQ ID NO: 514); DQ2.5-glia-ω1, QQPFPQPEQPFP (SEQ ID NO: 515); DQ2.5-glia-ω2, FPQPEQPFPWQP (SEQ ID NO: 516) for 5 min at room temperature.

Magnetic bead enrichment of tetramer-positive CD4+ T cells was done as previously described. Cells were washed with FACS buffer and then stained with antibodies against surface molecules for 30 min at 4° C. After two washes with FACS buffer, 10% of the cells were reserved for FACS analysis while 90% were labeled with anti-PE microbeads and subjected to magnetic bead enrichment of PE-conjugated tetramer-positive cells using a single MACS column according to the manufacturer's protocol (Miltenyi). Cells were also harvested on Day 3 to measure Annexin V binding (BD) on gliadin-specific CD4+ T cells. All cells were acquired on an LSR II flow cytometer (BD), gated on live CD3+CD4+CD8− TCRαβ+ cells, and analyzed using FlowJo X software. The frequency of tetramer-positive cells was calculated by dividing the number of post-enrichment tetramer+ CD4+ T cells by the number of CD4+ T cells in the pre-enrichment sample multiplied by 9 (to account for the fact that 90% of the cells were used for the enrichment).

Bulk RNA-seq gene expression quantification and data analysis. Bulk RNA sequencing was done as previously described. Live KIR+ or KIR− CD8+ T cells were bulk sorted directly into 350 μL TRIzol (Qiagen) by FACSAria Fusion flow cytometer (BD). Total RNA was extracted from TRIzol samples using chloroform separation and isopropanol precipitation and then RNAeasy Plus Mini kit (Qiagen) for clean-up. After analysis on the 2100 Bioanalyzer, the sequencing libraries were prepared using the RiboGone Mammalian rRNA Depletion Kit (Clontech) and the SMARTer Stranded RNA-seq Kit (Clontech). The resulting library was sequenced on the HiSeq 4000 platform (Illumina) in Stanford Functional Genomics Facility. For each sample in the bulk RNA sequencing library, 75-base-pair paired-end reads were acquired from the sequencer. We aligned the reads to the human reference genome (NCBI GRCh38) using STAR v2.7.0e50. Gene counts were quantified and normalized (TPM) with Salmon51. Differential gene expression analysis was determined via the DESeq function in the DESeq2 R package.

Heatmaps were generated with seaborn.clustermap in python. Gene Ontology analysis plots were generated with the R package 'clusterProfiler'. To generate gene sets for gene set enrichment analysis (GSEA), we selected the top 200 genes up-regulated in Ly49+ CD8+ T cells compared to Ly49− CD8+ T cells in EAE mice, and the previously reported CD4+ Treg signature genes identified in mice. These mouse genes were converted to homologue genes in humans and constituted as gene sets for the subsequent GSEA analysis in human KIR+ versus KIR-CD8+ T cells.

Analysis of single cell RNA-seq of kidneys and synovial tissues. The Unique Molecular Identifier (UMI) count matrixes of cells in kidneys (accession code SDY997) or synovial tissues (accession code SDY998) generated by CEL-Seq2 were downloaded from the ImmPort repository and downstream analysis was performed using the Seurat 3.0 package. Cells with fewer than 1,000 detected genes, more than 5,000 detected genes or more than 25% mitochondrial genes were discarded. CD8+ T cells (expressing CD3D, CD3E, CD8A and CD8B transcripts) and CD4+ T cells (expressing CD3D, CD3E and CD4 transcripts) were selected for standard downstream procedures of log-normalization, variable gene selection and data scaling.

Analysis of single cell RNA-seq of bronchoalveolar immune cells. Filtered expression matrix of single-cell RNA-seq of immune cells from the bronchoalveolar lavage fluid of 6 severe and 3 moderate COVID-19 patients and 3 healthy controls generated by 10x Genomics36 were downloaded from Gene Expression Omnibus under the accession number GSE145926. CD8+ T cells were identified for downstream analysis using the Seurat 3.0 package.

Analysis of single cell RNA-seq generated by 10x Genomics. Single cell RNA-seq of T cells from the blood of healthy subjects (N=10), MS patients (N=6) and COVID-19 patients (N=25) from the microfluidic droplet platform (10x Genomics Chromium Single Cell 5' paired-end chemistry) were de-multiplexed, aligned to the GRCh38 reference genome, and converted into gene counts matrices using CellRanger 3.1.0. Downstream analysis was performed using the Seurat 3.0 package. Cells with fewer than 800 detected genes, more than 3,000 detected genes or more than 10% mitochondrial genes were discarded. CD8+ T cells (expressing CD8A and CD8B but not TRDC transcripts) from each individual were selected for further analysis. To make counts comparable among cells, gene counts were normalized to 10,000 reads per cell, then log-transformed. We identified highly-variable genes for each individual, then integrated gene expression data from all individuals using Seurat's integration anchor discovery algorithm. We performed PCA dimensionality reduction on the integrated data, then clustered cells with the Louvain algorithm and visualized the data using UMAP. We identified canonical cell type marker genes that were conserved across conditions using the Wilcoxon rank-sum test implemented in the Seurat package's 'FindConservedMarkers' function.

Single cell RNA-seq gene expression quantification by Smart-seq2 and data analysis. Single cell RNA-seq of blood KIR+ CD8+ T cells (Live CD3+CD56–CD8+TCRαβ+ KIR+ cells) was performed using the Smart-seq2 protocol with some modifications40,53. In brief, single cells were sorted into 96-well plates containing 5 μL lysis buffer (0.8 U/μL RNase Inhibitor (Clontech), ~5,000 molecules of ERCC (External RNA Controls Consortium) spike-in RNAs (Ambion), 0.08% BioUltra Triton X-100 (Sigma-Aldrich), 2 μM oligo-dT30VN (Integrated DNA Technologies, 5'-AAGCAGTGGTATCAACGCAGAGTACT30VN-3'; SEQ ID NO: 517), 2 mM Qiagen dNTP mix) in each well. Immediately after sorting, plates were sealed with aluminium seal (Axygen), centrifuged, flash frozen on dry ice and then stored at −80° C. Before reverse transcription, the plates were thawed on ice and lysed at 72° C. for 3 min. 5 μL reaction mix containing 10 mM DTT, 2 μM TSO (Exiqon, 5'-AAGCAGTGGTATCAACGCAGAGTGAATr-GrGrG-3; SEQ ID NO: 518; 20 U/μL SMARTScribe Reverse Transcriptase (Takara), 2 U/μL RNase Inhibitor (Clontech) and 2× First Strand Buffer was added to each well and reverse transcription was carried out by incubating wells on a thermal-cycler (Eppendorf) at 42° C. for 90 min, 10 cycles of 50° C. for 2 min, 42° C. for 2 min, and stopped by heating at 70° C. for 15 min. Subsequently, 15 μL of PCR mix containing 1.67×KAPA HiFi HotStart ReadyMix (Kapa Biosystems, KK2602) and 0.17 μM IS PCR primer (IDT, 5'-AAGCAGTGGTATCAACGCAGAGT-3'; SEQ ID NO: 519) was added to each well and second-strand synthesis was performed on a thermal-cycler (Eppendorf) by using the following program: 1) 98° C. for 3 min, 2) 22 cycles of 98° C. for 20 s, 67° C. for 15 s and 72° C. for 6 min, and 3) 72° C. for 5 min. 1 μL of the cDNA products were used for TCR PCR reaction. The remaining 24 μL cDNA products were subjected to purification by AMPure XP beads (Beckman Coulter) on the Biomek FXP Automated Workstation (Beckman Coulter): 15.6 μL of Ampure XP beads (0.65×) were added to each sample and mixed by pipetting up and down thirty times; the mixture were incubated at room temperature for 5 min to let the DNA bind to the beads; then the 96-well plate was placed on the magnet for 5 min, and the liquid was removed while samples were on the magnet; the beads were wash with 180 μL of 80% (vol/vol) ethanol solution twice and air dried on the magnet for 6 min; 25 μL of water was added to each well, mixed by pipetting up and down ten times, and incubated at room temperature for 3 min; the plate was placed on the magnet for 3 min and the supernatants were transferred to a new 96-well plate; finally, 2 μL of the supernatants were subjected to quality control using capillary electrophoresis on a Fragment Analyzer (Agilent Technologies) by Stanford Protein and Nucleic Acid Facility.

cDNA in 96-well plates was transferred into 384-well Low Volume Serial Dil. (LVSD) plates (TTP Labtech) and diluted to 0.16 ng/μL using a Mosquito X1 liquid handler (TTP Labtech). Illumina sequencing libraries were prepared as described previously54 using a Mosquito HTS liquid handler (TTP Labtech). In brief, tagmentation was carried out on 0.4 μL double-stranded cDNA using the Nextera XT DNA Library Preparation Kit (Illumina, FC-131-1096). Each well was mixed with 0.8 μL Nextera tagmentation DNA buffer (Illumina) and 0.4 μL Amplicon Tagment Mix (Illumina), then incubated at 55° C. for 10 min. The reaction was stopped by adding 0.4 μL Neutralize Tagment Buffer (Illumina) and centrifuging at room temperature at 3,000 g for 5 min. Indexing PCR reactions were performed by adding 0.8 μL of pre-mixed 5 μM i5 and i7 unique dual indexing primers (IDT, customized) and 1.2 μL of Nextera NPM mix (Illumina). PCR amplification was carried out on a C1000 Touch™ Thermal Cycler with 384-Well Reaction Module (Bio-rad) using the following program: 1) 72° C. for 3 min, 2) 95° C. for 30 s, 3) 12 cycles of 95° C. for 10 s, 55° C. for 30 s and 72° C. for 1 min, and 4) 72° C. for 5 min. After library preparation, wells of each library plate were pooled using a Mosquito HTS liquid handler (TTP labtech). Pooling was followed by two purifications using 0.65× and 1×AMPure XP beads (Beckman Coulter), respectively. Library quality was assessed by Agilent 2100 Bioanalyzer and normalized to 5 nM. Libraries were sequenced on the Hiseq4000 Sequencing System (Illumina) in Stanford Functional Genomics Facility, acquiring 150-bp paired-end reads.

Stanford Functional Genomics Facility extracted and generated FASTQ files for each cell, distinguished by the unique dual index adaptors. Reads were aligned to the GRCh38 genome using STAR v2.6.1d. Transcript abundance was quantified using HTSeq v0.5.4p5.

Standard procedures for filtering, log-normalization, variable gene selection, dimensionality reduction and clustering were performed using the Seurat 3.0 package. Briefly, cells with fewer than 800 detected genes, more than 5,000 detected genes or more than 15% mitochondrial genes were discarded. To make counts comparable among cells, gene counts were normalized to 10,000 reads per cell, then log-transformed. Following PCA dimensionality reduction, cells were clustered by running the Louvain algorithm and visualized using UMAP. Differential expression analysis was performed using the Wilcoxon rank-sum test implemented in the Seurat package's 'FindAllMarkers' function. Significantly differentially expressed genes were defined as those with log fold change>0.5 and Bonferroni-corrected p-value<0.05.

Single cell TCR-seq. TCR-seq was performed using our previously developed single-cell paired TCR sequencing method with some modifications. Briefly, for the first TCR reaction, 1 µL of the cDNA products of Smart-seq2 was preamplified with HotStarTaq DNA polymerase (Qiagen) using multiplex PCR with multiple Vα and VB region primers, Cα and CB region primers. A 25-cycle first PCR reaction was done per manufacturer's instructions using the following cycling conditions: 95° C. 15 min; 94° C. 30 s, 62° C. 1 min, 72° C. 1 min×25 cycles; 72° C. 10 min; 4° C. Next, 1 µL aliquot of the first reaction was used as a template for second 12 µL PCR using HotStarTaq DNA polymerase (Qiagen) with multiple internally nested TCRVα, TCRVβ, TCRCα and Cβ primers. The cycling conditions were: 95° C. 15 min; 94° C. 30 s, 64° C. 1 min, 72° C. 1 min×25 cycles; 72° C. 7 min; 4° C. 1 µL aliquot of the second PCR product was used as a template for the third 20 µL PCR reaction, which incorporates barcodes and enables sequencing on the Illumina MiSeq platform. For the third and final PCR reaction for TCR sequencing, amplification was performed with HotStarTaq DNA polymerase for 36 cycles using a 5' barcoding primer (0.05 µM) containing the common 23-base sequence and a 3' barcoding primer (0.05 µM) containing sequence of a third internally nested Ca and/or CB primer, and Illumina Paired-End primers. The cycling conditions were: 95° C. 15 min; 94° C. 30 s, 66° C. 30 s, 72° C. 1 min×36 cycles; 72° C. 10 min; 4° C. The PCR products were combined at equal proportion by volume, run on a 1.2% agarose gel, and a band around 350 to 380 bp was excised and gel purified using a Qiaquick gel extraction kit (Qiagen). This purified product was then sequenced on a Miseq platform (Illumina) acquiring 2×250 bp reads.

In vitro cell proliferation assay. CD8+ T cells were purified from PBMCs of healthy donors using CD8 microbeads (Miltenyi) per manufacturer's instructions, stained with flow antibodies, and live CD3+CD56-CD8+KIR+ or KIR-T cells were sorted out by FACSAria Fusion flow cytometer (BD). The sorted KIR+ or KIR− CD8+ T cells were stimulated with anti-CD3/CD28 beads (Gibco) at 1:1 ratio (1 µL beads per 4×104 cells) supplemented with 50 U/mL IL-2 in 96-well plates for 18 hours. The CD8-PBMCs were labeled with CellTrace Violet (CTV, ThermoFisher) per manufacturer's instruction. 1 µg/mL anti-CD3 (UCHT-1) was coated on 96-well plate in 50 µL PBS per well at 4° C. overnight. After removal of anti-CD3/CD28 microbeads, KIR+ and KIR-CD8+ T cells were mixed with CTV-labelled CD8-PBMCs at 1:30 ratio and cultured in 96-well plate pre-coated with 1 µg/mL anti-CD3. After 4 or 6 days, cells were harvested and dilution of CTV in CD4+ T cells was analyzed by flow cytometry.

Statistical analysis. No specific statistical methods were used to predetermine sample size. All results are presented as the mean±SEM. The significance of the difference between groups was analyzed as described in the figure legends. Pearson's correlation coefficients with two-tailed P values were determined in the correlation analysis. P values<0.05 were considered statistically significant. All statistical analyses were performed using GraphPad Prism Software version.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of expanding in an individual in vivo a population of CD8$^+$ KIR$^+$ human suppressor T cells that selectively suppress activity of CD4$^+$ T cells responsive to a target antigen; but are not themselves activated by the target antigen, the method comprising:

immunizing the individual with a surrogate peptide of any of SEQ ID NO:1-4.

2. A method of obtaining a population of human regulatory T cells, the method comprising enriching or expanding from an individual for a human cell population of CD8$^+$ KIR$^+$ human regulatory T cells that selectively suppress activity of CD4$^+$ T cells responsive to an initiating antigen; the method comprising selecting for cells that express CD8, express one or more of KIR3DL1, KIR2DL3 and KIR2DL2, are restricted to an MHC class I antigen, and express low levels of CD28, to obtain a population of human regulatory T cells.

3. A method of screening a population of regulatory T cells obtained by the method of claim 2, for antigen specificity, the method comprising:

expressing T cell receptors (TCR) of the regulatory T cell as a soluble multimer;

contacting the soluble multimer in a binding assay against a library of diverse peptides in an MHC context and selecting for an MHC-peptide that binds to the T cell receptor;

performing multiple rounds of selection;

identifying the antigenic specificity of the regulatory T cell by sequencing the selected peptide antigen, and comparing the antigen specificity of the regulatory T cell to the CD4$^+$ T cells responsive to the initiating antigen.

4. A method of decreasing a CD4$^+$ T cell response to a target antigen in a subject, the method comprising administering an effective dose of CD8$^+$ KIR$^+$ human regulatory T cells that express CD8, express one or more of KIR3DL1, KIR2DL3 and KIR2DL2, are restricted to an MHC class I antigen, and express low levels of CD28.

5. The method of claim 4, wherein the target antigen is a self antigen.

6. The method of claim 4, wherein the CD8$^+$ KIR$^+$ human regulatory T cells are restricted to an MHC class I antigen associated with an autoimmune disease.

7. The method of claim 4, wherein the CD8$^+$ KIR$^+$ human regulatory T cells are restricted to an MHC class I antigen other than an MHC associated with an autoimmune disease.

8. The method of claim 4, wherein the CD8$^+$ KIR$^+$ human regulatory T cells express a TCR other than the native TCR.

9. The method of claim 4, wherein the CD8$^+$ KIR$^+$ human regulatory T cells are formulated in a therapeutically effective unit dose.

10. The method of claim 4, wherein the CD8$^+$ KIR$^+$ human regulatory T cells have been obtained from a sample from an individual following (a) immunization with an initiating antigen; (b) a flare of an autoimmune disease; or (c) an infection.

11. The method of claim 10, wherein the sample is peripheral blood, CSF, synovial fluid, or a biopsy sample.

12. The method of claim 10, wherein the sample has been obtained from the individual from 10-20 days following immunization or the autoimmune disease flare.

13. The method of claim 10, wherein the initiating antigen is an autoantigen or a surrogate peptide of any of SEQ ID NO:1-4.

14. The method of claim 10, wherein the infection is SARS-CoV-2 infection.

15. The method of claim 4, wherein the CD8$^+$ KIR$^+$ human regulatory T cells have been enriched by affinity selection for CD8 and an inhibitory KIR protein or expanded in vitro.

16. The method of claim 4, wherein the CD8$^+$ KIR$^+$ human regulatory T cells have been generated by contact with an immunogen in vitro.

17. The method of claim 16, wherein the immunogen is a surrogate peptide of any of SEQ ID NO:1-4.

* * * * *